United States Patent
Curtis

(10) Patent No.: US 6,518,398 B1
(45) Date of Patent: Feb. 11, 2003

(54) ERG POTASSIUM CHANNEL

(75) Inventor: Rory A. J. Curtis, Southborough, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/358,383

(22) Filed: Jul. 21, 1999

Related U.S. Application Data

(63) Continuation-in-part of application No. 09/119,855, filed on Jul. 21, 1998.

(51) Int. Cl.⁷ ............... C07K 14/525; C07K 14/52; C07K 14/435
(52) U.S. Cl. ............ 530/300; 530/350; 536/23.5
(58) Field of Search ................. 530/350, 300; 536/23.5

(56) References Cited

U.S. PATENT DOCUMENTS 5,508,164 A   4/1996   Kausch et al.

OTHER PUBLICATIONS

Ludwig, J. et al., "Functional Expression of ″Rat Homologue of the Voltage Gated Ether a go–go Potassium Channel Reveals Differences in Selectivity and Activation Kinetics Between the *Drosophila* Channel and its Mammalian Counterpart," *EMBO J.*, vol. 13, No. 19, pp. 4451–4458 (1994).

Shi, W. et al. "Identification of Two Nervous System–Specific Members of the erg Potassium Channel Gene Family" *The Journal of Neuroscience* 17(24):9423–9432 (Dec. 15, 1997).

Wang, H–S. et al., "Electrophysiological analysis of two erg–related channels, erg2 and erg3," *Soc. Neurosci.* 23:476.2 (1997).

*Primary Examiner*—Michael Pak
(74) *Attorney, Agent, or Firm*—Amy E. Mandragouras; Maria C. Laccotripe; Lahive & Cockfield, LLP

(57) ABSTRACT

The invention provides isolated nucleic acids molecules, designated ERG-LP nucleic acid molecules, which encode proteins involved in potassium channel mediated activities. The invention also provides antisense nucleic acid molecules, recombinant expression vectors containing ERG-LP nucleic acid molecules, host cells into which the expression vectors have been introduced, and nonhuman transgenic animals in which an ERG-LP gene has been introduced or disrupted. The invention still further provides isolated ERG-LP proteins, fusion proteins, antigenic pertides and anti-ERG-LP antibodies. Diagnostic methods utilizing compositions of the invention are also provided.

14 Claims, 32 Drawing Sheets gggagcgcgg ggcccggcgg ggggcggccg agctgggcgc cctccccgg cgcggagtcc 60 ccgcaccccg gagggatggg gccggcagcc gcgggcgcct aag atg ccg gcc atg 115
                                                Met Pro Ala Met
                                                 1 cgg ggc ctc ctg gcg ccg cag aac acc ttc ctg gac acc atc gct acg   163
Arg Gly Leu Leu Ala Pro Gln Asn Thr Phe Leu Asp Thr Ile Ala Thr
 5              10              15              20 cgc ttc gac ggc acg cac agt aac ttc gtg ctg ggc aac gcc cag gtg   211
Arg Phe Asp Gly Thr His Ser Asn Phe Val Leu Gly Asn Ala Gln Val
             25              30              35 gcg ggg ctc ttc ccc gtg gtc tac tgc tct gat ggc ttc tgt gac ctc   259
Ala Gly Leu Phe Pro Val Val Tyr Cys Ser Asp Gly Phe Cys Asp Leu
         40              45              50 acg ggc ttc tcc cgg gct gag gtc atg cag cgg ggc tgt gcc tgc tcc   307
Thr Gly Phe Ser Arg Ala Glu Val Met Gln Arg Gly Cys Ala Cys Ser
     55              60              65 ttc ctt tat ggg cca gac acc agt gag ctc gtc cgc caa cag atc cgc   355
Phe Leu Tyr Gly Pro Asp Thr Ser Glu Leu Val Arg Gln Gln Ile Arg
 70              75              80 aag gcc ctg gac gag cac aag gag ttc aag gct gag ctg atc ctg tac   403
Lys Ala Leu Asp Glu His Lys Glu Phe Lys Ala Glu Leu Ile Leu Tyr
 85              90              95             100 cgg aag agc ggg ctc ccg ttc tgg tgt ctc ctg gat gtg ata ccc ata   451
Arg Lys Ser Gly Leu Pro Phe Trp Cys Leu Leu Asp Val Ile Pro Ile
             105             110             115 aag aat gag aaa ggg gag gtg gct ctc ttc cta gtc tct cac aag gac   499
Lys Asn Glu Lys Gly Glu Val Ala Leu Phe Leu Val Ser His Lys Asp
         120             125             130 atc agt gaa acc aag aac cga ggg ggc cct gac aga tgg aag gag aca   547
Ile Ser Glu Thr Lys Asn Arg Gly Gly Pro Asp Arg Trp Lys Glu Thr
     135             140             145 ggt agt ggc cgg cgc cga tat ggc cgg gca cga tcc aaa ggc ttc aat   595
Gly Ser Gly Arg Arg Arg Tyr Gly Arg Ala Arg Ser Lys Gly Phe Asn
 150             155             160 gcc aac cgg cgg cgg agc cgg gct gtg ctc tac cac ctg tcc ggg cac   643
Ala Asn Arg Arg Arg Ser Arg Ala Val Leu Tyr His Leu Ser Gly His
165             170             175             180 ctg cag aag cag ccc aag ggc aag cac aag ctc aat aag ggg gtg ttt   691
Leu Gln Lys Gln Pro Lys Gly Lys His Lys Leu Asn Lys Gly Val Phe
         185             190             195 ggg gag aag cca aac ttg cct gag tac aaa gta gct gcc atc cgg aag   739
Gly Glu Lys Pro Asn Leu Pro Glu Tyr Lys Val Ala Ala Ile Arg Lys
     200             205             210

Fig. 1

```
tcg cct ttc atc ctg ttg cac tgt ggg gcg ctg agg gcc acc tgg gat  787
Ser Pro Phe Ile Leu Leu His Cys Gly Ala Leu Arg Ala Thr Trp Asp
        215                 220                 225 ggc ttc atc ctg ctc gcc acg ctc tat gtg gct gtc acc gtg ccc tac  835
Gly Phe Ile Leu Leu Ala Thr Leu Tyr Val Ala Val Thr Val Pro Tyr
    230                 235                 240 agc gtg tgt gtg agc aca gca cgg gag ccc agt gcc gcc cgc ggc cca  883
Ser Val Cys Val Ser Thr Ala Arg Glu Pro Ser Ala Ala Arg Gly Pro
245                 250                 255                 260 ccc agc gtc tgt gac ctg gct gtg gag gtc ctc ttc atc ctt gac att  931
Pro Ser Val Cys Asp Leu Ala Val Glu Val Leu Phe Ile Leu Asp Ile
            265                 270                 275 gtg ctg aat ttc cgt acc aca ttc gtg tcc aag tcg ggc cag gtg gtg  979
Val Leu Asn Phe Arg Thr Thr Phe Val Ser Lys Ser Gly Gln Val Val
        280                 285                 290 ttt gcc cca aag tcc att tgc ctc cac tac gtc acc acc tgg ttc ctg  1027
Phe Ala Pro Lys Ser Ile Cys Leu His Tyr Val Thr Thr Trp Phe Leu
    295                 300                 305 ctg gat gtc atc gca gcg ctg ccc ttt gac ctg ctg cat gcc ttc aag  1075
Leu Asp Val Ile Ala Ala Leu Pro Phe Asp Leu Leu His Ala Phe Lys
310                 315                 320 gtc aac gtg tac ttc ggg gcc cac ctg ctg aag acg gtg cgc ctg ctg  1123
Val Asn Val Tyr Phe Gly Ala His Leu Leu Lys Thr Val Arg Leu Leu
325                 330                 335                 340 cgc ctg ctg cgc ctg ctt ccg cgg ctg gac cgg tac tcg cag tac agc  1171
Arg Leu Leu Arg Leu Leu Pro Arg Leu Asp Arg Tyr Ser Gln Tyr Ser
            345                 350                 355 gcc gtg gtg ctg aca ctg ctc atg gcc gtg ttt gcc ctg ctt gcg cac  1219
Ala Val Val Leu Thr Leu Leu Met Ala Val Phe Ala Leu Leu Ala His
        360                 365                 370 tgg gtt gcc tgc gtc tgg ttt tac att ggt cag cgg gag atc gag agc  1267
Trp Val Ala Cys Val Trp Phe Tyr Ile Gly Gln Arg Glu Ile Glu Ser
    375                 380                 385 agc gaa tcc gag ctg cct gag att ggc tgg ctg cag gag ctg gcc cgc  1315
Ser Glu Ser Glu Leu Pro Glu Ile Gly Trp Leu Gln Glu Leu Ala Arg
390                 395                 400 cga ctg gag acc ccc tac tac ttg gtg ggc cgg aga cca gcc gga ggg  1363
Arg Leu Glu Thr Pro Tyr Tyr Leu Val Gly Arg Arg Pro Ala Gly Gly
405                 410                 415                 420 aac agc tct ggc cag agt gac aac tgc agc agc agc gag gcc aac  1411
Asn Ser Ser Gly Gln Ser Asp Asn Cys Ser Ser Ser Glu Ala Asn
            425                 430                 435 ggg acg ggg ctg gag ctg cta ggc ggc ccg tcg ctg cgc agc gcc tac  1459
Gly Thr Gly Leu Glu Leu Leu Gly Gly Pro Ser Leu Arg Ser Ala Tyr
        440                 445                 450
```

Fig. 1 (cont'd)

```
atc acc tcc ctc tac ttc gca ctc agc agc ctc acc agc gtg ggc ttc  1507
Ile Thr Ser Leu Tyr Phe Ala Leu Ser Ser Leu Thr Ser Val Gly Phe
        455                 460                 465 ggc aac gtg tcc gcc aac acg gac act gag aag atc ttc tcc atc tgc  1555
Gly Asn Val Ser Ala Asn Thr Asp Thr Glu Lys Ile Phe Ser Ile Cys
        470                 475                 480 acc atg ctc atc ggc gcc ctg atg cac gcg gtg gtg ttc ggg aac gtg  1603
Thr Met Leu Ile Gly Ala Leu Met His Ala Val Val Phe Gly Asn Val
485                 490                 495                 500 acg gcc atc atc cag cgc atg tac gcc cgc cgc ttt ctg tac cac agc  1651
Thr Ala Ile Ile Gln Arg Met Tyr Ala Arg Arg Phe Leu Tyr His Ser
                505                 510                 515 cgc acg cgc gac ctg cgc gac tac atc cgc atc cac cgt atc ccc aag  1699
Arg Thr Arg Asp Leu Arg Asp Tyr Ile Arg Ile His Arg Ile Pro Lys
            520                 525                 530 ccc ctc aag cag cgc atg ctg gag tac ttc cag gcc acc tgg gcg gtg  1747
Pro Leu Lys Gln Arg Met Leu Glu Tyr Phe Gln Ala Thr Trp Ala Val
        535                 540                 545 aac aat ggc atc gac acc acc gag ctg ctg cag agc ctc cct gac gag  1795
Asn Asn Gly Ile Asp Thr Thr Glu Leu Leu Gln Ser Leu Pro Asp Glu
550                 555                 560 ctg cgc gca gac atc gcc atg cac ctg cac aag gag gtc ctg cag ctg  1843
Leu Arg Ala Asp Ile Ala Met His Leu His Lys Glu Val Leu Gln Leu
565                 570                 575                 580 ccg ctg ttt gag gca gcc agc cgc ggc tgc ctg cgg gca ctg tct ctg  1891
Pro Leu Phe Glu Ala Ala Ser Arg Gly Cys Leu Arg Ala Leu Ser Leu
                585                 590                 595 gcc ctg cgg ccc gcc ttc tgc acg ccg ggc gag tac ctc atc cac caa  1939
Ala Leu Arg Pro Ala Phe Cys Thr Pro Gly Glu Tyr Leu Ile His Gln
            600                 605                 610 ggc gat gcc ctg cag gcc ctc tac ttt gtc tgc tct ggc tcc atg gag  1987
Gly Asp Ala Leu Gln Ala Leu Tyr Phe Val Cys Ser Gly Ser Met Glu
        615                 620                 625 gtg ctc aag ggt ggc acc gtg ctc gcc atc cta ggg aag ggt gac ctg  2035
Val Leu Lys Gly Gly Thr Val Leu Ala Ile Leu Gly Lys Gly Asp Leu
630                 635                 640 atc ggc tgt gag ctg ccc cgg agg gag cag gtg gta aag gcc aac gcc  2083
Ile Gly Cys Glu Leu Pro Arg Arg Glu Gln Val Val Lys Ala Asn Ala
645                 650                 655                 660 gat gtg aag ggg ctg acg tac tgc gtc ctg cag tgt ctg cag ctg gct  2131
Asp Val Lys Gly Leu Thr Tyr Cys Val Leu Gln Cys Leu Gln Leu Ala
                665                 670                 675 ggc ctg cac gac agc ctt gcg ctc tac ccc gag ttt gcc ccg cgc ttc  2179
Gly Leu His Asp Ser Leu Ala Leu Tyr Pro Glu Phe Ala Pro Arg Phe
            680                 685                 690
```

Fig. 1 (cont'd)

```
agc cgt ggc ctc cga ggg gag ctc agc tac aac ctg ggt gct ggg gga    2227
Ser Arg Gly Leu Arg Gly Glu Leu Ser Tyr Asn Leu Gly Ala Gly Gly
    695                 700                 705 ggc tct gca gag gtg gac acc agc tcc ctg agc ggc gac aat acc ctt    2275
Gly Ser Ala Glu Val Asp Thr Ser Ser Leu Ser Gly Asp Asn Thr Leu
    710                 715                 720 atg tcc acg ctg gag gag aag gag aca gat ggg gag cag ggc ccc aca    2323
Met Ser Thr Leu Glu Glu Lys Glu Thr Asp Gly Glu Gln Gly Pro Thr
725                 730                 735                 740 gtc tcc cca gcc cca gct gat gag ccc tcc agc ccc cta ctg tcc cct    2371
Val Ser Pro Ala Pro Ala Asp Glu Pro Ser Ser Pro Leu Leu Ser Pro
            745                 750                 755 ggt tgc acc tcc tca tcc tcg gct gcc aag ctg cta tcc cca cgt cga    2419
Gly Cys Thr Ser Ser Ser Ser Ala Ala Lys Leu Leu Ser Pro Arg Arg
                760                 765                 770 aca gca ccc cgg cct cgt cta ggt ggc aga ggg aga cca ggc agg gca    2467
Thr Ala Pro Arg Pro Arg Leu Gly Gly Arg Gly Arg Pro Gly Arg Ala
        775                 780                 785 ggg gct ttg aag gct gag gct ggc ccc tct gct ccc cca cgg gcc cta    2515
Gly Ala Leu Lys Ala Glu Ala Gly Pro Ser Ala Pro Pro Arg Ala Leu
    790                 795                 800 gag ggg cta cgg ctg ccc ccc atg cca tgg aat gtg ccc cca gat ctg    2563
Glu Gly Leu Arg Leu Pro Pro Met Pro Trp Asn Val Pro Pro Asp Leu
805                 810                 815                 820 agc ccc agg gta gta gat ggc att gaa gac ggc tgt ggc tcg gac cag    2611
Ser Pro Arg Val Val Asp Gly Ile Glu Asp Gly Cys Gly Ser Asp Gln
            825                 830                 835 ccc aag ttc tct ttc cgc atg ggc cag tct ggc ccg gaa tgt agc agc    2659
Pro Lys Phe Ser Phe Arg Met Gly Gln Ser Gly Pro Glu Cys Ser Ser
                840                 845                 850 agc ccc tcc cct gga cca gag agt ggc ctg ctc act gtc ccc cat ggg    2707
Ser Pro Ser Pro Gly Pro Glu Ser Gly Leu Leu Thr Val Pro His Gly
        855                 860                 865 ccc agc gag gca agg aac aca gac aca ctg gac aag ctt cgg cag gcg    2755
Pro Ser Glu Ala Arg Asn Thr Asp Thr Leu Asp Lys Leu Arg Gln Ala
    870                 875                 880 gtg atg gag ctg tca gaa cag gtg ctg cag atg cgg gaa gga cta cag    2803
Val Met Glu Leu Ser Glu Gln Val Leu Gln Met Arg Glu Gly Leu Gln
885                 890                 895                 900 tca ctt cgc cag gct gtg cag ctt gtc ctg gca ccc cat agg gag ggt    2851
Ser Leu Arg Gln Ala Val Gln Leu Val Leu Ala Pro His Arg Glu Gly
            905                 910                 915 cca tgc cct cgg gcc tca gga gag ggg cca tgc cca gcc agc acc tcc    2899
Pro Cys Pro Arg Ala Ser Gly Glu Gly Pro Cys Pro Ala Ser Thr Ser
        920                 925                 930
```

Fig. 1 (cont'd)

```
ggg ctt ctg cag cct ctg tgt gtg gac act ggg gca tcc tcc tac tgc   2947
Gly Leu Leu Gln Pro Leu Cys Val Asp Thr Gly Ala Ser Ser Tyr Cys
        935             940             945 ctg cag ccc cca gct ggc tct gtc ttg agt ggg act tgg ccc cac cct   2995
Leu Gln Pro Pro Ala Gly Ser Val Leu Ser Gly Thr Trp Pro His Pro
    950             955             960 cgt ccg ggg cct cct ccc ctc atg gca ccc tgg ccc tgg ggt ccc cca   3043
Arg Pro Gly Pro Pro Pro Leu Met Ala Pro Trp Pro Trp Gly Pro Pro
965             970             975             980 gca tct cag agc tcc ccc tgg cct cga gcc aca gct ttc tgg acc tcc   3091
Ala Ser Gln Ser Ser Pro Trp Pro Arg Ala Thr Ala Phe Trp Thr Ser
            985             990             995 acc tca gac tca gag ccc cct gcc tca gga gac ctc tgc tct gag ccc   3139
Thr Ser Asp Ser Glu Pro Pro Ala Ser Gly Asp Leu Cys Ser Glu Pro
                1000            1005            1010 agc acc cct gcc tca cct cct cct tct gag gaa ggg gct agg act ggg   3187
Ser Thr Pro Ala Ser Pro Pro Pro Ser Glu Glu Gly Ala Arg Thr Gly
        1015            1020            1025 ccc cca gag cct gtg agc cag gct gag gct acc agc act gga gag ccc   3235
Pro Pro Glu Pro Val Ser Gln Ala Glu Ala Thr Ser Thr Gly Glu Pro
    1030            1035            1040 ccg cca gtg tca ggg ggc ctg gcc ttg ccc tgg gac ccc cac agc ctg   3283
Pro Pro Val Ser Gly Gly Leu Ala Leu Pro Trp Asp Pro His Ser Leu
1045            1050            1055            1060 gag atg gtg ctt att ggc tgc cac ggc tct ggc aca gtc cag tgg acc   3331
Glu Met Val Leu Ile Gly Cys His Gly Ser Gly Thr Val Gln Trp Thr
            1065            1070            1075 cag gaa gaa ggc aca ggg gtc tga                                    3355
Gln Glu Glu Gly Thr Gly Val
        1080
```

Fig. 1 (cont'd)

```
GTCGACCCACGCGTCCGCTCCTGCCACAGCCGGGGCGGCTGGAACTCTCTCCCTTTCTCCCTCCATCCTTCCACTTCCC

CTGCTCGGCCCCGCCGTCAGGCCGGGTCCCCCTTCCCTGCCGTCATCAGGTTCCCCTTCTCCCTTCTTGGCACTTTCCT
                                                     M   P   V   M   K        5
TTCGAACCATCCTTCTGGACAAACTTTGATGGAGAATTTCACACCACGCTGGAAAA ATG CCG GTT ATG AAA     15

G   L   L   A   P   Q   N   T   F   L   D   T   I   A   T   R   F   D   G   T   25
GGA TTA CTG GCG CCG CAA AAC ACC TTC CTG GAC ACC ATC GCC ACC CGT TTT GAC GGA ACA   75

H   S   N   F   I   L   A   N   A   Q   V   A   K   G   F   P   I   V   Y   C   45
CAT AGC AAC TTC ATC CTT GCC AAT GCC CAG GTG GCT AAG GGT TTC CCC ATA GTC TAC TGT   135

S   D   G   F   C   E   L   A   G   F   A   R   T   E   V   M   Q   K   S   C   65
TCC GAT GGC TTC TGC GAG CTT GCT GGA TTT GCC CGA ACT GAA GTC ATG CAG AAG AGT TGT   195

S   C   K   F   L   F   G   V   E   T   N   E   Q   L   M   L   Q   I   E   K   85
AGC TGC AAG TTC TTA TTT GGG GTT GAA ACC AAT GAG CAA CTG ATG CTT CAA ATA GAA AAG   255

S   L   E   E   K   T   E   F   K   G   E   I   M   F   Y   K   K   N   G   S   105
TCA CTG GAG GAG AAA ACA GAA TTC AAA GGA GAA ATT ATG TTC TAC AAG AAA AAC GGG TCT   315

P   F   W   C   L   L   D   I   V   P   I   K   N   E   K   G   D   V   V   L   125
CCA TTT TGG TGC CTA CTG GAT ATT GTT CCC ATA AAG AAT GAA AAA GGA GAT GTA GTA CTT   375

F   L   A   S   F   K   D   I   T   D   T   K   V   K   I   T   P   E   D   K   145
TTT CTG GCC TCG TTC AAA GAT ATA ACA GAT ACA AAA GTG AAG ATT ACT CCA GAA GAT AAA   435

K   E   D   K   V   K   G   R   S   R   A   G   T   H   F   D   S   A   R   R   165
AAA GAA GAC AAA GTC AAA GGA AGA TCA AGA GCA GGG ACC CAC TTT GAC TCA GCC CGG AGA   495

R   S   R   A   V   L   Y   H   I   S   G   H   L   Q   R   R   E   K   N   K   185
CGG AGT CGA GCA GTC CTT TAT CAC ATC TCT GGG CAC CTG CAA AGA AGA GAA AAG AAC AAA   555

L   K   I   N   N   N   V   F   V   D   K   P   A   F   P   E   Y   K   V   S   205
TTG AAA ATA AAT AAC AAT GTT TTT GTA GAT AAA CCA GCA TTT CCG GAG TAT AAA GTT TCT   615

D   A   K   K   S   K   F   I   L   L   H   F   S   T   F   K   A   G   W   D   225
GAT GCA AAA AAG TCC AAA TTC ATA CTT CTG CAT TTT AGC ACT TTT AAA GCT GGC TGG GAC   675

W   L   I   L   L   A   T   F   Y   V   A   V   T   V   P   Y   N   V   C   F   245
TGG CTT ATT TTG TTG GCA ACG TTT TAT GTT GCT GTG ACT GTA CCT TAC AAC GTT TGC TTT   735

I   G   N   D   D   L   S   T   T   R   S   T   T   V   S   D   I   A   V   E   265
ATT GGC AAT GAC GAC CTG TCC ACA ACT CGG AGC ACA ACC GTC AGT GAC ATT GCA GTG GAG   795

I   L   F   I   I   D   I   I   L   N   F   R   T   T   Y   V   S   K   S   G   285
ATT CTT TTT ATT ATA GAT ATT ATT TTA AAT TTC CGA ACA ACT TAT GTC AGC AAG TCT GGC   855

Q   V   I   F   E   A   R   S   I   C   I   H   Y   V   T   T   W   F   I   I   305
CAA GTT ATC TTT GAA GCA AGA TCA ATT TGC ATC CAC TAT GTC ACA ACC TGG TTC ATC ATT   915

D   L   I   A   A   L   P   F   D   L   L   Y   A   F   N   V   T   V   V   S   325
GAT TTA ATC GCT GCC CTG CCT TTT GAT CTT CTG TAT GCT TTC AAC GTC ACA GTG GTG TCT   975
```

Fig. 2

```
          L   V   H   L   L   K   T   V   R   L   L   R   L   L   R   L   L   Q   K   L   345
         CTC GTG CAT CTT CTA AAG ACA GTG CGC CTC TTG CGT CTT TTG CGT CTG CTG CAG AAG TTA 1035

D   R   Y   S   Q   H   S   T   I   V   L   T   L   L   M   S   M   F   A   L   365
         GAC CGC TAT TCC CAA CAC AGT ACT ATC GTC CTG ACT CTG CTC ATG TCC ATG TTT GCA CTC 1095

L   A   H   W   M   A   C   I   W   Y   V   I   G   K   M   E   R   E   D   N   385
         CTT GCA CAC TGG ATG GCG TGT ATC TGG TAC GTC ATT GGA AAA ATG GAG AGG GAA GAC AAC 1155

S   L   L   K   W   E   V   G   W   L   H   E   L   G   K   R   L   E   S   P   405
         AGC CTT CTG AAG TGG GAA GTT GGT TGG CTT CAT GAG TTG GGA AAG AGA CTG GAA TCT CCA 1215

Y   Y   G   N   N   T   L   G   G   P   S   I   R   S   A   Y   I   A   A   L   425
         TAC TAT GGC AAC AAT ACC TTG GGG GGC CCG TCG ATC CGA AGT GCC TAT ATT GCC GCT CTG 1275

Y   F   T   L   S   S   L   T   S   V   G   F   G   N   V   S   A   N   T   D   445
         TAC TTC ACG CTG AGC AGC CTC ACC AGC GTG GGT TTT GGG AAC GTC TCT GCT AAT ACA GAT 1335

A   E   K   I   F   S   I   C   T   M   L   I   G   A   L   M   H   A   L   V   465
         GCA GAA AAG ATC TTC TCC ATC TGC ACC ATG CTG ATT GGT GCC TTG ATG CAC GCC TTG GTG 1395

F   G   N   V   T   A   I   I   Q   R   M   Y   S   R   W   S   L   Y   H   T   485
         TTT GGA AAC GTG ACA GCA ATC ATA CAG AGG ATG TAC TCC AGA TGG TCC CTC TAT CAC ACT 1455

R   T   K   D   L   K   D   F   I   R   V   H   H   L   P   Q   Q   L   K   Q   505
         AGA ACT AAG GAT CTG AAA GAT TTC ATC CGT GTC CAT CAC TTG CCC CAA CAA CTC AAG CAG 1515

R   M   L   E   Y   F   Q   T   T   W   S   V   N   N   G   I   D   S   N   E   525
         AGG ATG CTC GAA TAT TTT CAA ACA ACC TGG TCA GTC AAC AAT GGA ATA GAT TCA AAT GAG 1575

V   M   F   I   S   H   V   V   F   R   Q   K   A   H   I   L   R   *           543
         GTA ATG TTC ATT TCT CAT GTT GTT TTC AGG CAG AAA GCA CAT ATT CTA AGG TAA          1629

ACGCAAGATGTTCTAATGCAGGTATCAGAAGTGAAAAGCATACCAACTTCTTTATTCCTTTACATTTTTAATTATTCAT

GAATCCCAATCCATCTTCTTTCACTTGCTTTGGCTTGTGTTTTCACAATGCCAATTTGGATTGACCGAAGTTTTATATT

AACTTGCTGCTTATTCGATCAGGTGGATTTATTTTCCTTCTTATTGTCTCTTTTCAAAGGAATCAATTCTTACGATAAT

TTAACAGTGTAATCTGGGATAATTATATTAATCAAGTTTCTGTTTCCCTTAACATCAATAAAGTTAAAAAATTCCATCA

AAGGGGTTATCTTTATACTTCCAGAAACACCCCAGACTGCCACTATAAAAACAGTATTATATAAATCAACGAACCATTT

CATCAACCCACCAGCCAAACCTGTAACCAACATTTAGTAGTGATTAATTGGTTTCTCCTCTCTTCGCATAATCACCAGT

GGGTCCAAATTCCATATCTTCTGTCCTGACTAGGACTCTCTGTGAGAAGGAAGTCACAATGAGTTATATGTTTTCCTGC

TAGAGGCTTTTTTAATTTGTTCTGTTTCTCCAGACTTCTTATCAGCTGATTATTCAGTAGCACATAATTCACAGTCACT

GAAAAATCTCTCCAGGATTATACATACTTAGATTTCCTCTTCTGTATGCTGGATGGCCAAACAGCAGGAGACAGTAGGA

AGAGCATCCCTGCTGTCTTGCAAAGTAAATCAGTTAGACTACACTTACCCCAATTTGATTTCCTCCTTCATCTTCTCTG

ACAGCTTTTGAAAGACTTTCCAGATGAACCTGCGTTCTGACATCACTATGCACTTGAACAA
```

Fig. 2 (cont'd)

```
Human.erg    MPVRRGHVAPQNTFLDTIIRKFEGQSRKFIIANARVENCA-VIYCNDGFCELCGYSRAEV
1kba251dl0orf MPAMRGLLAPQNTFLDTIATRFDGTHSNFVLGNAQVAGLFPVVYCSDGFCDLTGFSRAEV
             **. ** :********** :*:*   :*::.**:* .   *:**.****:* *:*****

Human.erg    MQRPCTCDFLHGPRTQRRAAAQIAQALLGAEERKVEIAFYRKDGSCFLCLVDVVPVKNED
1kba251dl0orf MQRGCACSFLYGPDTSELVRQQIRKALDEHKEFKAELILYRKSGLPFWCLLDVIPIKNEK
             *** *:*.**:** *... . ** :** :* *.*: :***.*  * **:**:*:***.

Human.erg    GAVIMFILNFEVVMEKDMVGSPAHDTNHRGPPTSWLAPGRAKTFRLKLPALLALTARESS
1kba251dl0orf GEVALFL-----VSHKDIS-----ETKNRGGPDRWKETG---------------------
             * * :*:   ,  *  .**:     :*::** *   * .*

Human.erg    VRSGGAGGAGAPGAVVVDVDLTPAAPSSESLALDEVTAMDNHVAGLGPAEERRALVGPGS
1kba251dl0orf ---------SG---------------------------------------RR-------
                      :*                                        **

Human.erg    PPRSAPGQLPSPRAHSLNPDASGSSCSLARTRSRESCASVRRASSADDIEAMRAGVLPPP
1kba251dl0orf --R-----------Y-------G------RARSKGFNANRRRS---------RA-VL---
               *           :       *       *.:**:   *.. **:         ** **

Human.erg    PRHASTGAMHPLRSGLLNSTSDSDLVRYRTISKIPQITLNFVDLKGDPFLASPTSDREII
1kba251dl0orf -YHLS-G--H-LQ--------------KQ-----P---------KG-------------
              * * * **:                 :     *         **
                                                                       S1
Human.erg    APKIKERTHNVTEKVTQVLSLG-ADVLPEYKLQAPRIHRWTILHYSPFKAVWDWLILLLV
1kba251dl0orf -K------HKLNKGV-----FGEKPNLPEYKVAAIRKSPFILLHCGALRATWDGFILLAT
              *::.: *    :*      *     ***** * *  :  :** ..::*.** :***  .
                                            S2
Human.erg    IYTAVFTPYSAAFLLKETEEGPPATECGYACQPLAVVDLIVDIMFIVDILINFRTTYVNA
1kba251dl0orf LYVAVTVPYS--VCVSTARE--PSAARG----PPSVCDLAVEVLFILDIVLNFRTTFVSK
             :*.** .***  . :. :.* *::   *    * :* ** *:::**:**::*****:*.
                             S3                          S4
Human.erg    NEEVVSHPGRIAVHYFKGWFLIDMVAAIPFDLL-IFGSGSEELIGLLKTARLLRLVRVAR
1kba251dl0orf SGQVVFAPKSICLHYVTTWFLLDVIAALPFDLLHAFKVNVYFGAHLLKTVRLLRLLRLLP
             . :** *  *.:**.. ***:*:.:**:***** *          **** .****:*:
                              S5
Human.erg    KLDRYSEYGAAVLFLLMCTFALIAHWLACIWYAIGNMEQPHMDS---RIGWLHNLGDQIG
1kba251dl0orf RLDRYSQYSAVVLTLLMAVFALLAHWVACVWFYIGQREIESSESELPEIGWLQELARRLE
             :*****:*.*.** ***..***:***:**:*:.**: **: *      :* .****::*. ::
                                                                     P-LOOP
Human.erg    KPY---------NSSG------------------LGGPSIKDKYVTALYFTFSSLTSVG
1kba251dl0orf TPYYLVGRRPAGGNSSGQSDNCSSSSEANGTGLELLGGPSLRSAYITSLYFALSSLTSVG
             .**           ****                 *****::. *:*:***::*******
                              S6
Human.erg    FGNVSPNTNSEKIFSICVMLIGSLMYASIFGNVSAIIQRLYSGTARYHTQMLRVREFIRF
1kba251dl0orf FGNVSANTDTEKIFSICTMLIGALMHAVVFGNVTAIIQRMYARRFLYHSRTRDLRDYIRI
             *****.**::*******.****:**:*::****:*****:*:   **::   :*::**:

Human.erg    HQIPNPLRQRLEEYFQHAWSYTNGIDMNAVLKGFPECLQADICLHLNRSLLQHCKPFRGA
1kba251dl0orf HRIPKPLKQRMLEYFQATWAVNNGIDTTELLQSLPDELRADIAMHLHKEVLQ-LPLFEAA
             *:**:**:**: ****: **: ****  . :*..*:.*:***.:**::: :** *..*
                                                      CYCLIC NUCLEOTIDE-BINDING DOMAIN
Human.erg    TKGCLRALAMKFKTTHAPPGDTLVHAGDLLTALYFISRGSIEILRGDVVVAILGKNDIFG
1kba251dl0orf SRGCLRALSLALRPAFCTPGEYLIHQGDALQALYFVCSGSMEVLKGGTVLAILGKGDLIG
             ::******:: :: :..  **: *:* ** **  *:*:*:*.**:**.*:****.*::*

Human.erg    EPLNLYARPGKSNGDVRALTYCDLHKIHRDDLLEVLDMYPEFSDHFWSSL--EITFNL--
```

Fig. 3

```
Lkba251d10orf    CELPRREQVVKANADVKGLTYCVLQCLQLAGLHDSLALYPEFAPRFSRGLRGELSYNLGA
                  *   : *:*.**:.**** *: ::  .* : * :**** :*  .*  *:::**

Human.erg        ------RDTNMIPG--SPGSTELEGGFSRQRKRKLSFRRRTDKDTE---QPGEVSA---
Lkba251d10orf    GGGSAEVDTSSLSGDNTLMSTLEEKETDGEQGPTVS-PAPADEPSSPLLSPGCTSSSSAA
                       **. :.* : ** *  . :: .:*   :*: :.  .** .*:

Human.erg        -------------LG----PGRAG-----AGPSS--R---G-R-PGGPWGESPSSGPSSP
Lkba251d10orf    KLLSPRRTAPRPRLGGRGRPGRAGALKAEAGPSAPPRALEGLRLPPMPWNVPPDLSPRVV
                              **  ***** ****: *  * * **. .*. .*

Human.erg        ESSED-EGPGRSSSPLRL---VPFSSPRP-PGEPPGGE--PLMEDCEKSSDTCNPLSGAF
Lkba251d10orf    DGIEDGCGSDQPKFSFRMGQSGPECSSSPSPGPESGLLTVPHGPSEARNTDTLDKLRQAV
                 :. ** *..:.. .:*:   *.*. * **  .*     .  .:.:** : *  *.

Human.erg        SGVSN-IFS-FWGDSRGRQ-YQEL--P-R---CP-----APTP---SLLNIPLSS-PG--
Lkba251d10orf    MELSEQVLQMREGLQSLRQAVQLVLAPHREGPCPRASGEGPCPASTSGLLQPLCVDTGAS
                  :*: ::.. *. ** *:: * *  **     .* *  * * **. .*

Human.erg        ----RRPRGDVESRLDALQRQLNRLETRLSADMATVLQLLQR-QMTLVPPAYSAVTTPGP
Lkba251d10orf    SYCLQPPAGSVLSGTWPHPRPGPPPLMAPWPWGPPASQSSPWPRATAFWTSTSDSEPPAS
                     : *.*.**  . *   . ...*    :*..: *  .*..

Human.erg        GPTSTSPLLPVSPLPTLTLDSLS---QVSQFMACE--ELPP--GAPELPQEGPTRRLSLP
Lkba251d10orf    GDLCSEPSTPASPPPSEEGARTGPPEPVSQAEATSTGEPPPVSGGLALPWDPHSLEMVLI
                 *  .:.* *.** *:    .    *** *. * ** *. ** : : .: *

Human.erg        GQLGALTSQPLHRHGSDPGS
Lkba251d10orf    GCHGSGTVQWTQEEGT--GV
                 * *: * *  :..*: *
```

Fig. 3 (cont'd)

```
Dros.elk      MPARKGLLAPQNTFLDTIATRFDGTHSNFVLGNAQAN-GNPIVYCSDGFVDLTGYSRAQI
1hba042h05    MPVMKGLLAPQNTFLDTIATRFDGTHSNFILANAQVAKGFPIVYCSDGFCELAGFARTEV
              **.********************.***. * ********* :*:*::*:::

Dros.elk      MQKGCSCHFLYGPDTKEEHKQQIEKSLSNKMELKLEVIFYKKEGAPFWCLFDIVPIKNEK
1hba042h05    MQKSCSCKFLFGVETNEQLMLQIEKSLEEKTEFKGEIMFYKKNGSPFWCLLDIVPIKNEK
              ***.***:**:* :*:*:    ******.:* *:* *::****:*:****:*********

Dros.elk      RDVVLFLASHKDITHTKMLEMNVNEECDSVFALTAALLGARFRAGSNAGMLGLGGLPGLG
1hba042h05    GDVVLFLASFKDITDTKVKITPEDKKEDKVK--------GRSRAGT--------------
              ******** .****.**:    :::  *.*         .* ***:

Dros.elk      GPAASDGDTEAGEGNNLDVPAGCNMGRRRSRAVLYQLSGHYKPEKGGVKTKLKLGNNFMH
1hba042h05    ----------------HFDS------ARRRSRAVLYHISGHLQRRE---KNKLKINNNVFV
                              ::*       .*********::***  : .:  *.***:.**.:

Dros.elk      STEAPFPEYKTQSIKKSRLILPHYGVFKGIWDVVILVATFYVALMVPYNAAFAKAD----
1hba042h05    DKPA-FPEYKVSDAKKSKFILHFSTFKAGWDWLILLATFYVAVTVPYNVCFIGNDDLST
              .. * *****.., ***:** *:..**. ***:**.******: ****..*    *

Dros.elk      -RQTKVSDVIVEALFIVDILLNFRTTFVSRKGEVVSNSKQIAINYLRGWFALDLLAALPF
1hba042h05    TRSTTVSDIAVEILFIIDIILNFRTTYVSKSGQVIFEARSICIHYVTTWFIIDLIAALPF
               *.*.***: ** ***:**:******:**:.*:*: :.:.*:*: ** :**:*****

Dros.elk      DHLYASDLYDGEDSHIHLVKLTRLLRLARLLQKIDRYSQHTAMILTLLMFSFTLAAHWLA
1hba042h05    DLLYAFNVT--VVSLVHLLKTVRLLRLLRLLQKLDRYSQHSTIVLTLLMSMFALIAHWMA
              * *** ::   * :**:* .***** **** *:*******:::::*****  *:* ***:*

Dros.elk      CIWYVIAVKEYEWFP--ESNIGWLQLLAER------KNASVAILTTAETYSTALYFTFTS
1hba042h05    CIWYVIGKMEREDNSLLKWEVGWLHELGKRLESPYYGNNTLGGPSIRSAYIAALYFTLSS
              ******.  *  . : ::***:  *..*       *  ::.  : .:* :*****::*

Dros.elk      LTSVGFGNVSANTTAEKVFTIIMMLIGALMHAVVFGNVTAIIQRMYSRRSLYESKWRDLK
1hba042h05    LTSVGFGNVSANTDAEKIFSICTMLIGALMHALVFGNVTAIIQRMYSRWSLYHTRTKDLK
              ************* ***:*:*  .********:**************** **.:: :***

Dros.elk      DFVALHNMPKELKQRIEDYFQTSWSLSHGIDIYETLREFPEELRGDVSMHLHREILQLPI
1hba042h05    DFIRVHHLPQQLKQRMLEYFQTTWSVNNGIDSNEVMFISHVVFR--QKAHILR-------
              **: :*::*:: ****: ****:**:..*** :*  .: *      :* . *: *

Dros.elk      FEAASQGCLKLLSLHIKTNFCAPGEYLIHKGDALNYIYYLCNGSMEVIKDDMVVAILGKG
1hba042h05    ------------------------------------------------------------

Dros.elk      DLVGSDINVHLVATSNGQMTATTNSAGQDVVVRSSSDIKALTYCDLKCIHMGGLVEVLRL
1hba042h05    ------------------------------------------------------------

Dros.elk      YPEYQQQFANDIQHDLTCNLREGYENQDSDIGPSFPLPSISEDDENREEAEEGGKGEKEN
1hba042h05    ------------------------------------------------------------

Dros.elk      GGGPPSGASPLHNISNSPLHATRSPLLGMGSPRNQRLHQRGRSLITLRETNKRHRTLNAA
1hba042h05    ------------------------------------------------------------

Dros.elk      CSLDRGSFEEPEPLEEEQSSGGKRPSLERLDSQVSTLHQDVAQLSAEVRNAISALQEMTF
```

Fig. 4

```
lhba042h05    ------------------------------------------------------------
Dros.elk      TSNAMTSHSSLKFPPARSIPNISGVAGTRSGVAVEHGLMGGVLAAAELAAMQRSSSHPPE
lhba042h05    ------------------------------------------------------------
Dros.elk      VWGRDVQLPTSNTASSKAPSPVEPKKTMTSRSSQTDFYRIDFPTFERFVLANPRLVLGLL
lhba042h05    ------------------------------------------------------------
Dros.elk      GIEPAIKNEMDLLQQKQTLQISPLNTIDECVSPSDHNLASSKERLITSSAVPTPGRIYPP
lhba042h05    ------------------------------------------------------------
Dros.elk      LDDENSNDFRWTMKHSASHHSCCKSTDALLSPEEQPPISILPVDATPAPSVQEVRSSKRS
lhba042h05    ------------------------------------------------------------
Dros.elk      IRKSTSGSNSSLSSSSSSSNSCLVSQSTGNLTTTNASVHCSNSSQSVASVATTRRASWKL
lhba042h05    ------------------------------------------------------------
Dros.elk      QHSRSGEYRRLSEATAEYSPPAKTPLPVAGVSYGGDEEESVELLGPRRNSRPILLGVSQN
lhba042h05    ------------------------------------------------------------
Dros.elk      QGQGQAMNFRFSAGDADKLEKGLRGLPSTRSLRDPSSK
lhba042h05    --------------------------------------
```

Fig. 4 (cont'd)

```
GCGGCCGCGGGGCCTGGAGCCCGGGATTTGTGGGCGGCGAGGGCGCGAGGGGCCGCGCGCCA
TGCTCCGGGCCCCGACGGCGCGGACGCCCCCTCGCGCGCCAGCGTCCGGCGCGACCCCGGAT
CCCGGTCTGCGCATTGCCCCCCGACGGCTGCGCTAGGGAGCGCGGGGCCCGGCGGGGGGCGG
CCGAGCTGGGCGCCCTCCCCCGGCGCGGAGTCCCCGCACCCCGGAGGGATGGGGCGGGCAGC
CGCGGGCGCCTAAGATGCCGGCCATGCGGGGCCTCCTGGCGCCGCAGAACACCTTCCTGGAC
ACCATCGCTACGCGCTTCGACGGCACGCACAGTAACTTCGTGCTGGGCAACGCCCAGGTGGC
GGGGCTCTTCCCCGTGGTCTACTGCTCTGATGGCTTCTGTGACCTCACGGGCTTCTCCCGGG
CTGAGGTCATGCAGCGGGGCTGTGCCTGCTCCTTCCTTTATGGGCCAGACACCAGTGAGCTC
GTCCGCCAACAGATCCGCAAGGCCCTGGACGAGCACAAGGAGTTCAAGGCTGAGCTGATCCT
GTACCGGAAGAGCGGGCTCCCGTTCTGGTGTCTCCTGGATGTGATACCCATAAAGAATGAGA
AAGGGGAGGTGGCTCTCTTCCTAGTCTCTCACAAGGACATCAGCGAAACCAAGAACCGAGGG
GGCCCCGACAGATGGAAGGAGACAGGTGGTGGCCGGCGCCGATATGGCCGGGCACGATCCAA
AGGCTTCAATGCCAACCGGCGGCGGAGCCGGGCCGTGCTCTACCACCTGTCCGGGCACCTGC
AGAAGCAGCCCAAGGGCAAGCACAAGCTCAATAAGGGGGTGTTTGGGGAGAAACCAAACTTG
CCTGAGTACAAAGTAGCCGCCATCCGGAAGTCGCCCTTCATCCTGTTGCACTGTGGGGCACT
GAGAGCCACCTGGGATGGCTTCATCCTGCTCGCCACACTCTATGTGGCTGTCACTGTGCCCT
ACAGCGTGTGTGTGAGCACAGCACGGGAGCCCAGTGCCGCCCGCGGCCCGCCCAGCGTCTGT
GACCTGGCCGTGGAGGTCCTCTTCATCCTTGACATTGTGCTGAATTTCCGTACCCTCGTGCC
ACCTCGTGCCAAGCTT
```

MPAMRGLLAPQNTFLDTIATRFDGTHSNFVLGN
AQVAGLFPVVYCSDGFCDLTGFSRAEVMQRGCACSFLYGPDTSELVRQQIRKALDEHKEF
KAELILYRKSGLPFWCLLDVIPIKNEKGEVALFLVSHKDISETKNRGGPDRWKETGGGRR
RYGRARSKGFNANRRRSRAVLYHLSGHLQKQPKGKHKLNKGVFGEKPNLPEYKVAAIRKS
PFILLHCGALRATWDGFILLATLYVAVTVPYSVCVSTAREPSARRGPPSVCDLAVEVLFI
LDIVLNFRTLVPPRAKL

Fig. 5

```
cctgccacag ccggggcggc tggaactctc tcccttcctc cctccatcct tccacttccc    60
ctgctcggcc ccgccgtcag gccgggtccc ccttccctgc cgtcatcagg ttccccttct   120
cccttcttgg cactttcctt tcgaaccatc cttctggaca aactttgatg gagaatttca   180
caccacgctg gaaaa atg ccg gtt atg aaa gga tta ctg gcg ccg caa aac    231
              Met Pro Val Met Lys Gly Leu Leu Ala Pro Gln Asn
                1           5                  10 acc ttc ctg gac acc atc gcc acc cgt ttt gac gga aca cat agc aac    279
Thr Phe Leu Asp Thr Ile Ala Thr Arg Phe Asp Gly Thr His Ser Asn
         15              20                  25 ttc atc ctt gcc aat gcc cag gtg gct aag ggt ttc ccc ata gtc tac    327
Phe Ile Leu Ala Asn Ala Gln Val Ala Lys Gly Phe Pro Ile Val Tyr
     30              35                  40 tgt tcc gat ggc ttc tgc gag ctt gct gga ttt gcc cga act gaa gtc    375
Cys Ser Asp Gly Phe Cys Glu Leu Ala Gly Phe Ala Arg Thr Glu Val
 45              50                  55                      60 atg cag aag agt tgt agc tgc aag ttc tta ttt ggg gtt gaa acc aat    423
Met Gln Lys Ser Cys Ser Cys Lys Phe Leu Phe Gly Val Glu Thr Asn
                 65                  70                  75 gag caa ctg atg ctt caa ata gaa aag tca ctg gag gag aaa aca gaa    471
Glu Gln Leu Met Leu Gln Ile Glu Lys Ser Leu Glu Glu Lys Thr Glu
             80                  85                  90 ttc aaa gga gaa att atg ttc tac aag aaa aac ggg tct cca ttt tgg    519
Phe Lys Gly Glu Ile Met Phe Tyr Lys Lys Asn Gly Ser Pro Phe Trp
         95                  100                 105 tgc cta ctg gat att gtt ccc ata aag aat gaa aaa gga gat gta gta    567
Cys Leu Leu Asp Ile Val Pro Ile Lys Asn Glu Lys Gly Asp Val Val
     110                 115                 120 ctt ttt ctg gcc tcg ttc aaa gat ata aca gat aca aaa gtg aag att    615
Leu Phe Leu Ala Ser Phe Lys Asp Ile Thr Asp Thr Lys Val Lys Ile
125                 130                 135                 140 act cca gaa gat aaa aaa gaa gac aaa gtc aaa gga aga tca aga gca    663
Thr Pro Glu Asp Lys Lys Glu Asp Lys Val Lys Gly Arg Ser Arg Ala
                 145                 150                 155 ggg acc cac ttt gac tca gcc cgg aga cgg agt cga gca gtc ctt tat    711
Gly Thr His Phe Asp Ser Ala Arg Arg Arg Ser Arg Ala Val Leu Tyr
             160                 165                 170 cac atc tct ggg cac ctg caa aga aga gaa aag aac aaa ttg aaa ata    759
His Ile Ser Gly His Leu Gln Arg Arg Glu Lys Asn Lys Leu Lys Ile
         175                 180                 185 aat aac aat gtt ttt gta gat aaa cca gca ttt ccg gag tat aaa gtt    807
Asn Asn Asn Val Phe Val Asp Lys Pro Ala Phe Pro Glu Tyr Lys Val
     190                 195                 200 tct gat gca aaa aag tcc aaa ttc ata ctt ctg cat ttt agc act ttt    855
Ser Asp Ala Lys Lys Ser Lys Phe Ile Leu Leu His Phe Ser Thr Phe
205                 210                 215                 220
```

Fig. 8

```
aaa gct ggc tgg gac tgg ctt att ttg ttg gca acg ttt tat gtt gct    903
Lys Ala Gly Trp Asp Trp Leu Ile Leu Leu Ala Thr Phe Tyr Val Ala
            225             230                 235 gtg act gta cct tac aac gtt tgc ttt att ggc aat gac gac ctg tcc    951
Val Thr Val Pro Tyr Asn Val Cys Phe Ile Gly Asn Asp Asp Leu Ser
            240             245                 250 aca act cgg agc aca acc gtc agt gac att gca gtg gag att ctt ttt    999
Thr Thr Arg Ser Thr Thr Val Ser Asp Ile Ala Val Glu Ile Leu Phe
            255             260                 265 att ata gat att att tta aat ttc cga aca act tat gtc agc aag tct   1047
Ile Ile Asp Ile Ile Leu Asn Phe Arg Thr Thr Tyr Val Ser Lys Ser
        270             275                 280 ggc caa gtt atc ttt gaa gca aga tca att tgc atc cac tat gtc aca   1095
Gly Gln Val Ile Phe Glu Ala Arg Ser Ile Cys Ile His Tyr Val Thr
285             290             295                 300 acc tgg ttc atc att gat tta atc gct gcc ctg cct ttt gat ctt ctg   1143
Thr Trp Phe Ile Ile Asp Leu Ile Ala Ala Leu Pro Phe Asp Leu Leu
            305             310                 315 tat gct ttc aac gtc aca gtg gtg tct ctc gtg cat ctt cta aag aca   1191
Tyr Ala Phe Asn Val Thr Val Val Ser Leu Val His Leu Leu Lys Thr
            320             325                 330 gtg cgc ctc ttg cgt ctt ttg cgt ctg ctg cag aag tta gac cgc tat   1239
Val Arg Leu Leu Arg Leu Leu Arg Leu Leu Gln Lys Leu Asp Arg Tyr
            335             340                 345 tcc caa cac agt act atc gtc ctg act ctg ctc atg tcc atg ttt gca   1287
Ser Gln His Ser Thr Ile Val Leu Thr Leu Leu Met Ser Met Phe Ala
            350             355                 360 ctc ctt gca cac tgg atg gcg tgt atc tgg tac gtc att gga aaa atg   1335
Leu Leu Ala His Trp Met Ala Cys Ile Trp Tyr Val Ile Gly Lys Met
365             370             375                 380 gag agg gaa gac aac agc ctt ctg aag tgg gaa gtt ggt tgg ctt cat   1383
Glu Arg Glu Asp Asn Ser Leu Leu Lys Trp Glu Val Gly Trp Leu His
            385             390                 395 gag ttg gga aag aga ctg gaa tct cca tac tat ggc aac aat acc ttg   1431
Glu Leu Gly Lys Arg Leu Glu Ser Pro Tyr Tyr Gly Asn Asn Thr Leu
            400             405                 410 ggg ggc ccg tcg atc cga agt gcc tat att gcc gct ctg tac ttc acg   1479
Gly Gly Pro Ser Ile Arg Ser Ala Tyr Ile Ala Ala Leu Tyr Phe Thr
            415             420                 425 ctg agc agc ctc acc agc gtg ggt ttt ggg aac gtc tct gct aat aca   1527
Leu Ser Ser Leu Thr Ser Val Gly Phe Gly Asn Val Ser Ala Asn Thr
            430             435                 440 gat gca gaa aag atc ttc tcc atc tgc acc atg ctg att ggt gcc ttg   1575
Asp Ala Glu Lys Ile Phe Ser Ile Cys Thr Met Leu Ile Gly Ala Leu
445             450             455                 460
```

Fig. 8 (cont'd)

```
atg cac gcc ttg gtg ttt gga aac gtg aca gca atc ata cag agg atg      1623
Met His Ala Leu Val Phe Gly Asn Val Thr Ala Ile Ile Gln Arg Met
            465             470             475 tac tcc aga tgg tcc ctc tat cac act aga act aag gat ctg aaa gat      1671
Tyr Ser Arg Trp Ser Leu Tyr His Thr Arg Thr Lys Asp Leu Lys Asp
            480             485             490 ttc atc cgt gtc cat cac ttg ccc caa caa ctc aag cag agg atg ctc      1719
Phe Ile Arg Val His His Leu Pro Gln Gln Leu Lys Gln Arg Met Leu
            495             500             505 gaa tat ttt caa aca acc tgg tca gtc aac aat gga ata gat tca aat      1767
Glu Tyr Phe Gln Thr Thr Trp Ser Val Asn Asn Gly Ile Asp Ser Asn
            510             515             520 gag ctt ttg aaa gac ttt cca gat gaa ctg cgt tct gac atc act atg      1815
Glu Leu Leu Lys Asp Phe Pro Asp Glu Leu Arg Ser Asp Ile Thr Met
525             530             535             540 cac ttg aac aag gag atc tta cag ttg tcc ctt ttt gaa tgt gcc agc      1863
His Leu Asn Lys Glu Ile Leu Gln Leu Ser Leu Phe Glu Cys Ala Ser
            545             550             555 cgg ggc tgc ctc agg tct ctg tct cta cac atc aaa acc tct ttc tgt      1911
Arg Gly Cys Leu Arg Ser Leu Ser Leu His Ile Lys Thr Ser Phe Cys
            560             565             570 gct ccg ggg gag tat ctg ctg cgt caa ggg gat gct ttg cag gcc atc      1959
Ala Pro Gly Glu Tyr Leu Leu Arg Gln Gly Asp Ala Leu Gln Ala Ile
            575             580             585 tac ttt gta tgc tcg ggc tcc atg gaa gtt ctt aaa gac agc atg gtg      2007
Tyr Phe Val Cys Ser Gly Ser Met Glu Val Leu Lys Asp Ser Met Val
            590             595             600 ctg gct att ctt ggg aaa ggg gat tta att gga gca aat cta tca att      2055
Leu Ala Ile Leu Gly Lys Gly Asp Leu Ile Gly Ala Asn Leu Ser Ile
605             610             615             620 aag gac caa gtg atc aag acc aat gca gat gta aag gct tta acc tac      2103
Lys Asp Gln Val Ile Lys Thr Asn Ala Asp Val Lys Ala Leu Thr Tyr
            625             630             635 tgt gat ctc cag tgt atc atc ctc aaa gga ctc ttt gaa gtg cta gac      2151
Cys Asp Leu Gln Cys Ile Ile Leu Lys Gly Leu Phe Glu Val Leu Asp
            640             645             650 ctt tac cca gaa tat gct cac aaa ttc gtg gaa gac att cag cat gac      2199
Leu Tyr Pro Glu Tyr Ala His Lys Phe Val Glu Asp Ile Gln His Asp
            655             660             665 ctc aca tac aac ctc cga gaa ggt cat gag agt gat gtg ata tca aga      2247
Leu Thr Tyr Asn Leu Arg Glu Gly His Glu Ser Asp Val Ile Ser Arg
670             675             680 cta tca aac aaa tct atg gtc tca cag tca gag ccc aag gga aat ggc      2295
Leu Ser Asn Lys Ser Met Val Ser Gln Ser Glu Pro Lys Gly Asn Gly
685             690             695             700
```

Fig. 8 (cont'd)

```
aac atc aac aag cga ctc cca tcc att gtg gaa gat gag gaa gag gag    2343
Asn Ile Asn Lys Arg Leu Pro Ser Ile Val Glu Asp Glu Glu Glu Glu
            705                 710                 715 gag gag ggg gag gaa gag gag gca gtc tcc ctc tct ccc atc tgc aca    2391
Glu Glu Gly Glu Glu Glu Glu Ala Val Ser Leu Ser Pro Ile Cys Thr
            720                 725                 730 agg gga tct tct tcg cgc aac aag aag gtt gga agc aat aaa gcc tac    2439
Arg Gly Ser Ser Ser Arg Asn Lys Lys Val Gly Ser Asn Lys Ala Tyr
            735                 740                 745 ctg ggc tta agc tta aag caa ctg gcc tcg gga acg gtg ccc ttt cac    2487
Leu Gly Leu Ser Leu Lys Gln Leu Ala Ser Gly Thr Val Pro Phe His
            750                 755                 760 tcg cct atc aga gtc tcc agg tca aat tcc ccc aaa acc aag cag gaa    2535
Ser Pro Ile Arg Val Ser Arg Ser Asn Ser Pro Lys Thr Lys Gln Glu
765                 770                 775                 780 att gac ccc ccc aac cat aat aaa agg aaa gag aag aac ttg aaa ttg    2583
Ile Asp Pro Pro Asn His Asn Lys Arg Lys Glu Lys Asn Leu Lys Leu
                    785                 790                 795 caa ctt tca act ttg aat aat gct gga ccc cca gac ctc agt cca agg    2631
Gln Leu Ser Thr Leu Asn Asn Ala Gly Pro Pro Asp Leu Ser Pro Arg
                800                 805                 810 att gtt gat gga att gaa gat gga aac agc agt gaa gaa agt cag act    2679
Ile Val Asp Gly Ile Glu Asp Gly Asn Ser Ser Glu Glu Ser Gln Thr
            815                 820                 825 ttt gat ttt ggc tct gaa cga atc aga tca gag ccc aga att tct cct    2727
Phe Asp Phe Gly Ser Glu Arg Ile Arg Ser Glu Pro Arg Ile Ser Pro
830                 835                 840 cct ctt gga gat cca gag att gga gct gct gtt ctc ttc atc aaa gca    2775
Pro Leu Gly Asp Pro Glu Ile Gly Ala Ala Val Leu Phe Ile Lys Ala
845                 850                 855                 860 gag gag acc aag cag cag ata aac aaa ctc aac agt gag gta aca aca    2823
Glu Glu Thr Lys Gln Gln Ile Asn Lys Leu Asn Ser Glu Val Thr Thr
                865                 870                 875 ttg act cag gaa gtt tct cag ttg ggt aaa gac atg aga aat gtg atc    2871
Leu Thr Gln Glu Val Ser Gln Leu Gly Lys Asp Met Arg Asn Val Ile
            880                 885                 890 cgg ctt ctg gaa aac gtt ctg tca cct cag cag cca tca cgg ttt tgc    2919
Arg Leu Leu Glu Asn Val Leu Ser Pro Gln Gln Pro Ser Arg Phe Cys
            895                 900                 905 tct ttg cac agc acc tct gtg tgt ccc tcc agg gag agc tta cag acc    2967
Ser Leu His Ser Thr Ser Val Cys Pro Ser Arg Glu Ser Leu Gln Thr
910                 915                 920 aga acg agc tgg agt gca cac cag cct tgc cta cac ttg caa aca ggc    3015
Arg Thr Ser Trp Ser Ala His Gln Pro Cys Leu His Leu Gln Thr Gly
925                 930                 935                 940
```

Fig. 8 (cont'd)

```
ggg gct gct tat acc caa gca caa ctt tgt agc agt aat atc acc tca    3063
Gly Ala Ala Tyr Thr Gln Ala Gln Leu Cys Ser Ser Asn Ile Thr Ser
            945                 950                 955 gac att tgg agt gtg gat ccc tcc tct gtg ggg agc agc ccc caa cga    3111
Asp Ile Trp Ser Val Asp Pro Ser Ser Val Gly Ser Ser Pro Gln Arg
            960                 965                 970 act gga gct cat gag caa aat cct gca gac agt gaa ctt tat cat tct    3159
Thr Gly Ala His Glu Gln Asn Pro Ala Asp Ser Glu Leu Tyr His Ser
            975                 980                 985 cca agc ctt gat tat tca cct tcc cac tac cag gtt gtc caa gaa ggt    3207
Pro Ser Leu Asp Tyr Ser Pro Ser His Tyr Gln Val Val Gln Glu Gly
            990                 995                 1000 cat ttg caa ttt tta agg tgc atc tct cca cat tca gat tct acg ttg    3255
His Leu Gln Phe Leu Arg Cys Ile Ser Pro His Ser Asp Ser Thr Leu
1005            1010                1015                1020 acg cct ctg cag tcc att tca gca act ctc tca tct tct gtc tgc tcc    3303
Thr Pro Leu Gln Ser Ile Ser Ala Thr Leu Ser Ser Ser Val Cys Ser
            1025                1030                1035 tct tcg gaa aca tct ttg cac cta gtt ctc cca agc aga tca gag gag    3351
Ser Ser Glu Thr Ser Leu His Leu Val Leu Pro Ser Arg Ser Glu Glu
            1040                1045                1050 ggc agc ttc agt cag gga act gtg agt tcc ttc agt ctg gaa aac tta    3399
Gly Ser Phe Ser Gln Gly Thr Val Ser Ser Phe Ser Leu Glu Asn Leu
            1055                1060                1065 cca gga tct tgg aac cag gaa gga atg gca tca gct tct aca aaa cct    3447
Pro Gly Ser Trp Asn Gln Glu Gly Met Ala Ser Ala Ser Thr Lys Pro
            1070                1075                1080 ttg gag aac ctt cca ctg gaa gtt gtc aca agc aca gca gaa gtg aaa    3495
Leu Glu Asn Leu Pro Leu Glu Val Val Thr Ser Thr Ala Glu Val Lys
1085            1090                1095                1100 gat aac aaa gcc ata aat gta tgatattagt gcccatgatg cagcagctaa      3546
Asp Asn Lys Ala Ile Asn Val
            1105 tttcaaacct accactgcat gacagtttta gtttgccttt ttgcctctgg tgggcatgaa  3606 gactgagcaa agctgggaat cctgcagaaa agagtgtgag gagccaggga aaggcagaac  3666 cacctccatg ctgtagcaaa caatttctag atactagaag cataatagaa acatttttct  3726 gtacaggtat taaactactg gtctgtttga cagactttgg taacaatcca aagaccctga  3786 gggtctgagc agctagaagt cctagacaaa gaacttgtgg atgactttg tcccatgtgg   3846 cttttgtgaa gtatggcaaa ggttttcat gagtgcctga ttgttattcc tgaacaatat   3906 ccatagcact gttggcctca ggagtgcaca gctcctgctg atgtattttt cttttgtga   3966 aggcaaaggg acaattatca ctgcatgtca tctcctagac aatcagtcaa atagagctgg  4026 tggccagtgg ttagctattc gcacgttatt tgccatgtaa atgaaaacgt ctttatttat  4086
```

Fig. 8 (cont'd)

```
caaaaaaaca cagaggctat ttttatatcc ttggtatgaa atatgtattt aaactattta    4146
aatatttata aagaaatgaa tgttttcttt tcattttggt aaaaaaaaag cttgctgttt    4206
taacaagaaa tgcactactg ttgtgtatag tagatcaaaa attatttatt actaagagga    4266
tgtagtttcc aaaggaatcc cccattttt ctgcatgcag tttgcaacaa atgtattctc    4326
atgcttctgg attataaaag aaaagtgaag tcatattttg ttaatgaaat aaaaacatgg    4386
actgagtgtc aactacatga gctttggcat ggggatagag aggctccatc taggctctgc    4446
caactcatgt caatgacatg atttaaggtc cgttgtgcca gcagaaatgt ctctcctcta    4506
ggtatcgtat tttgttgctc aagaatccaa aatgggtctg tggacatagg gcaatttggg    4566
gctcaaagtg agggagaaaa cctgggtgtg tcctttccca gtgcttttct tttacaagag    4626
gtagtagact agtggaaatc cccaaatgga gccaagactt ctgagctata acttgtggga    4686
gtaataccag cttgcaatgg gtcagcactt tacctttttt ctttaaggct cccaacaatg    4746
ctatacagcg cagttgtttc cattcctatt nttaataaat ctcaggggaa gcctcagaga    4806
ttacacagtt aggatgctga cacagtctag aatccataat gctccctaca tctcacacta    4866
acaggcaaat tcagatgctg ggattggcaa tgatttaagc accttcacta aagtcttatt    4926
ttatgtttta gaacagttac agtctaattg tcttggacat tttgggaaga tatattgggt    4986
tcacattctg gagttctctt tatttccac cacaaaaaat aatctgagaa ttgtatcatt    5046
aaaagtatct aaacacacaa aaaaaaaaaa aaaaaaaaaa aaaaaaaaaa aaaaaaaaa    5106
a                                                                    5107
```

Fig. 8 (cont'd)

Protein Family / Domain Matches, HMMer version 2

```
Searching for complete domains
hmmpfam - search a single seq against HMM database
HMMER 2.1.1 (Dec 1998)
Copyright (C) 1992-1998 Washington University School of Medicine
HMMER is freely distributed under the GNU General Public License (GPL).
- - - - - - - - - - - - - - - - - - - - - - - - - - - - - - - - - - -
HMM file:        /prod/ddm/seqanal/PFAM/pfam4.1/Pfam
Sequence file:   /usr/ns-home/docs/seqanal/orfanal/oa-script.20137.seq
- - - - - - - - - - - - - - - - - - - - - - - - - - - - - - - - - - -
    Query: humanERG-LP2

Scores for sequence family classification (score includes all domains):
Model       Description                                  Score     E-value    N
--------    -----------                                  -----     -------    ---
CNG membrane Transmembrane region cyclic Nucleotide G    332.4     5.2e-96    1

Parsed for domains:
Model         Domain     seq-f    seq-t    hmm-f    hmm-t       score    E-value
--------      ------     -----    -----    -----    -----       -----    -------

CNG_membrane  1/1        295      535 ..     1      259 []      332.4    5.2e-96

Alignments of top-scoring domains:
CNG_membrane: domain 1 of 1, from 295 to 535: score 332.4, E = 5.2e-96
                *->YlkstwFllDvlStlPfDllyiffgsdegsgggslfplLrlnRLLRlr
                   Y+  twF++D++++lPfDlly+f            sl++lL+++RLLRl
   humanERG-L  295 YVT-TWFIIDLIAALPFDLLYAFNVTVV----SLVHLLKTVRLLRLL 336

RvaelfdRlekdtafnyfairlikLvcvtllliiHwnACvfdiliyYlisd
                   R+  +++dR++       ++ +i+l++L++  + l++Hw+AC     i+Y i++
   humanERG-L  337 RLLQKLDRYS-----QHSTIVLTLLMSMFALLAHWMAC-----IWYVIGK 376

Yd.veaerygfgtdtWlyalnndfeepslwtrgitgGPslkrqYitSlYW
                   ++ + +     ++ +W1+ 1 ++ e p+++++  +gGPs++++Yi +1Y+
   humanERG-L  377 MErEDNSLLKWEV-GWLHELGKRLESPYYGNN-TLGGPSIRSAYIAALYF 424

SitTLTTvGyGdpaPvttrEkiFvifdmLfGvllFAyiiGnvtsivvnmn
                   +  +LT+vG+G+++++t++EkiF i+  mL+G+l++A  ++Gnvt+i+++m+
   humanERG-L  425 TLSSLTSVGFGNVSANTDAEKIFSICTMLIGALMHALVFGNVTAIIQRMY 474 srtaefrtkmdavkefmkfrklpkrLqeRVlkyfeytWsnksDegldeee
                   sr + ++t+  ++k+f++  ++lp  +L++R+l+yf+   tWs     +g+d +e
   humanERG-L  475 SRWSLYHTRTKDLKDFIRVHHLPQQLKQRMLEYFQTTWSVN--NGIDSNE 522 vleqLPkkLraeI<-*
                   +l+  +P++Lr++I
   humanERG-L  523 LLKDFPDELRSDI 535
```

Fig. 10

ProDom Matches

```
ProDom entry 1039      Match length 205
Keywords: CHANNEL IONIC CATION CYCLIC-NUCLEOTIDE-GATED ION TRANSPORT POTASSIUM PROTEIN
          CYCLIC CNG Expect 3.0e-17  Score 215      Bits 88.2      Identical 0.31  Conserved 0.51
query 165 RAVLYHISGHLQRREKNKLKINNNVFVDKPAFPEYKVSDAKKSKFILLHFS--------T
              R + YH+ H+    +    +++ +      PEYK  K+ + L HFS
sbjct   4 RDIFYHL--HVGEEFRTDSITSSSTSLGADILPEYKAQAPKRHR--LRHFSGWVIDPYGN query 217 FKAGWDWLILLATFYVAVTVPYNVCFIGNDDLSTTRSTTVSDIAVEILFIIDIILNFRTT
            F  WD+ I+L  Y A VPY CF     +       + D V+I+++IDII+NFRT
sbjct  60 FYYIWDFFIVLLVMYNAWMVPYRACFDELQSDNYLEPWLIIDYIVDIIYLIDIIINFRTG query 277 YVSKSGQVIF-EARSICIHYVTTW-FIIDLIAALPFDLLYAFNVTVV---SLVHLLKTVR
          Y+ +  +++   + +  I +Y+ TW F +D+++ +PFDLLY  +        + LL+  R
sbjct 120 YLDQGSELLVKDPKKIRKNYLKTWQFKLDILSVIPFDLLYFISNDEKIGWNYPELLRLNR query 332 LLRLLRLLQKLDR
          LLR+  R+ + LDR
sbjct 180 LLRISRMFEFLDR ProDom entry 2152      Match length 184
Keywords: CHANNEL CATION CYCLIC-NUCLEOTIDE-GATED ION CYCLIC IONIC CNG TRANSPORT
          PROTEIN CAMP-BINDING Expect 4.0e-17  Score 214      Bits 87.8      Identical 0.24  Conserved 0.55
query 365 HWMACIWYVIGKMEREDNSLLKWEVGWLHELGKRLESPYYGNNTLGGPSIRSAYIAALYF
          HW AC++Y I K +    +       W++  G  + ++ + T   +   YI   Y+
sbjct   1 HWNACLYYWISKYQGFGSD------AWVY--GNYNKPNHWISVT---DNFGRQYIYCFYW query 425 TLSSLTSVGFGNVSANTDAEKIFSICTMLIGALMHALVFGNVTAIIQRMYSRWSLYHTRT
          + +LT++G    S  T  E +F +   L+G L+ A +  GNV ++I  M + + +
sbjct  50 STLTLTTIGQEMPSPTTSFEYVFEVFDFLVGVLIFATIIGNVGSMISNMNAARTEFQNKM query 485 KDLKDFIRVHHLPQQLKQRMLEYFQTTWSVNNGIDSNELLKDFPDELRSDITMHLNKEIL
          +K +++    +P++L++R++++F+  W+    +D  E+L++  PD+LR++I  ++++ + L
sbjct 110 DGVKQYMKYRKIPKELQKRVIKWFEYLWANQGAVDEEEILEELPDKLRAEIAINIHMDTL query 545 Q
          +
sbjct 170 K
```

Fig. 10 (cont'd)

ProDom entry 110620 Match length 58
Keywords: VENTRICULAR ERG K+ CHANNEL SUBUNIT. IONIC CHANNEL Expect 7.0e-14 Score 186      Bits 76.9   Identical 0.47    Conserved 0.63
query 39 IVYCSDGFCELAGFARTEVMQKSCSCKFLFGVETNEQLMLQIEKSLEEKTEFKGEIMFYK
         ++YC+DGFCEL G++R EVMQ+ C+C FL G E                 E K EI FY+
sbjct  1 VIYCNDGFCELCGYSRAEVMQRPCTCDFLLGAE----------------ERKVEIAFYR query 99 KNGSPFWCLLDIVPI
         K+GS F CL+D+VP+
sbjct 44 KDGSCFLCLVDVVPV ProDom entry 33035       Match length 90
Keywords: CHANNEL POTASSIUM PROTEIN EAG IONIC TRANSMEMBRANE ION TRANSPORT
         VOLTAGE-GATED GLYCOPROTEIN Expect 3.0e-13  Score 181      Bits 74.9    Identical 0.33  Conserved 0.69
query 471 QRMYSRWSLYHTRTKDLKDFIRVHHLPQQLKQRMLEYFQTTWSVNNGIDSNELLKDFPDE
          Q+M S  + YH     ++++F+++H +P++L +R+++Y  +TW++  GID+ ++L  P +
sbjct   1 QQMTSATARYHDMINNVREFMKLHEIPKELAERVMDYVVSTWAMTKGIDTEKVLNCCPKD query 531 LRSDITMHLNKEIL-QLSLFECASRGCLRS
          +++DI +HLN+++ +    F  AS GCLR+
sbjct  61 MKADICVHLNRKVFNEHPCFRLASDGCLRA ProDom entry 88814      Match length 40
Keywords: PUTATIVE POTASSIUM CHANNEL SUBUNIT. IONIC CHANNEL Expect 2.0e-10 Score 156      Bits 65.2     Identical 0.86  Conserved 0.89
query 2 KGLLAPQNTFLDTIATRFDGTHSNFILANAQVAKGFP
        KGLLAPQNTFLDTIATRFDGTHSNF+L NAQ A G P
sbjct 5 KGLLAPQNTFLDTIATRFDGTHSNFVLGNAQ-ANGNP ProDom entry 4561     Match length 54
Keywords: CHANNEL IONIC POTASSIUM SUBUNIT PUTATIVE MERG1A ERG K+ ISOFORM EAG Expect 3.0e-09 Score 147     Bits 61.7    Identical 0.56  Conserved 0.71
query 506 EYFQTTWSVNNGIDSNELLKDFPDELRSDITMHLNKEILQ-LSLFECASRGC
          +YFQ  WS  NGID N++LK FP+ LR+DI +HLN++ILQ    F  AS GC
sbjct   3 DYFQHAWSYTNGIDMNKVLKGFPECLRADICLHLNRKILQHCPAFRAASDGC

Fig. 10 (cont'd)

```
GAP of: ratelkl.pep  check: 5875  from: 1  to: 1102 ratELK1 | AF061957 Rattus norvegicus potassium channel (elk1) mRNA, complete
cds.

to: Flhba042h05.pep  check: 6895  from: 1  to: 1107

Flhba42h5orf - Import - complete

Symbol comparison table:
/ddm_local/gcg/gcg_9.1/gcgcore/data/rundata/blosum62.cmp
CompCheck: 6430

Gap Weight:       12      Average Match:    2.912
    Length Weight:        4      Average Mismatch: -2.003

Quality:     5220           Length:     1108
             Ratio:    4.737             Gaps:        3
Percent Similarity:   93.551  Percent Identity:   92.552

Match display thresholds for the alignment(s):
                      | = IDENTITY
                      : = 2
                      . = 1 ratelkl.pep x Flhba042h05.pep.
```

```
  1 MPVMKGLLAPQNTFLDTIATRFDGTHSNFILANAQVAKGFPIVYCSDGFC  50 ratelk1
    ||||||||||||||||||||||||||||||||||||||||||||||||||
  1 MPVMKGLLAPQNTFLDTIATRFDGTHSNFILANAQVAKGFPIVYCSDGFC  50 Flhba042h05

51 ELAGFARTEVMQKSCSCKFLFGVETNEQLMLQIEKSLEEKVEFKGEIMFY 100
    |||||||||||||||||||||||||||||||||||||| |||||||||||
 51 ELAGFARTEVMQKSCSCKFLFGVETNEQLMLQIEKSLEEKTEFKGEIMFY 100

101 KKNGAPFWCLLDIVPIKNEKGDVVLFLASFKDITDTKVKITSEDKKEDRA 150
    ||||.|||||||||||||||||||||||||||||||||||| ||||||:
101 KKNGSPFWCLLDIVPIKNEKGDVVLFLASFKDITDTKVKITPEDKKEDKV 150

151 KGRSRAGSHFDSARRRSRAVLYHISGHLQRREKNKLKINNNVFVDKPAFP 200
    |||||||.||||||||||||||||||||||||||||||||||||||||||
151 KGRSRAGTHFDSARRRSRAVLYHISGHLQRREKNKLKINNNVFVDKPAFP 200

. S1      .       .
201 EYKVSDAKKSKFILLHFSTFKAGWDWLILLATFYVAVTVPYNVCFIGNED 250
    |||||||||||||||||||||||||||||||||||||||||||||||:|
201 EYKVSDAKKSKFILLHFSTFKAGWDWLILLATFYVAVTVPYNVCFIGNDD 250
           . S2
251 LSTTRSTTVSDIAVEILFIIDIILNFRTTYVSKSGQVIFEARSICIHYVT 300
    ||||||||||||||||||||||||||||||||||||||||||||||||||
251 LSTTRSTTVSDIAVEILFIIDIILNFRTTYVSKSGQVIFEARSICIHYVT 300
```

Fig. 11

```
       S3              S4
301 TWFIIDLIAALPFDLLYAFNVTVVSLVHLLKTVRLLRLLRLLQKLDRYSQ 350
    ||||||||||||||||||||||||||||||||||||||||||||||||||
301 TWFIIDLIAALPFDLLYAFNVTVVSLVHLLKTVRLLRLLRLLQKLDRYSQ 350
         S5
351 HSTIVLTLLMSMFALLAHWMACIWYVIGKMEREDNSLLKWEVGWLHELGK 400
    ||||||||||||||||||||||||||||||||||||||||||||||||||
351 HSTIVLTLLMSMFALLAHWMACIWYVIGKMEREDNSLLKWEVGWLHELGK 400
                          pore   loop
401 RLESPYYGNNTLGGPSIRSAYIAALYFTLSSLTSVGFGNVSANTDAEKIF 450
    ||||||||||||||||||||||||||||||||||||||||||||||||||
401 RLESPYYGNNTLGGPSIRSAYIAALYFTLSSLTSVGFGNVSANTDAEKIF 450
      S6
451 SICTMLIGALMHALVFGNVTAIIQRMYSRWSLYHTRTKDLKDFIRVHHLP 500
    ||||||||||||||||||||||||||||||||||||||||||||||||||
451 SICTMLIGALMHALVFGNVTAIIQRMYSRWSLYHTRTKDLKDFIRVHHLP 500

501 QQLKQRMLEYFQTTWSVNNGIDSNELLKDFPDELRSDITMHLNKEILQLS 550
    ||||||||||||||||||||||||||||||||||||||||||||||||||
501 QQLKQRMLEYFQTTWSVNNGIDSNELLKDFPDELRSDITMHLNKEILQLS 550
                               cyclic
551 LFECASRGCLRSLSLHIKTSFCAPGEYLLRQGDALQAIYFVCSGSMEVLK 600
    ||||||||||||||||||||||||||||||||||||||||||||||||||
551 LFECASRGCLRSLSLHIKTSFCAPGEYLLRQGDALQAIYFVCSGSMEVLK 600
   nucloetide . binding . domain
601 DSMVLAILGKGDLIGANLSIKDQVIKTNADVKALTYCDLQCIILKGLFEV 650
    ||||||||||||||||||||||||||||||||||||||||||||||||||
601 DSMVLAILGKGDLIGANLSIKDQVIKTNADVKALTYCDLQCIILKGLFEV 650

651 LGLYPEYAHKFVEDIQHDLTYNLREGHESDVISRLSNKSTVPQAEPKGNG 700
    |.||||||||||||||||||||||||||||||||||||||.|.|.||||
651 LDLYPEYAHKFVEDIQHDLTYNLREGHESDVISRLSNKSMVSQSEPKGNG 700

701 SIKKRLPSIVEDEEEEV.EEEETTSLSPIYTRGSSVSHSKKTGSSKSYL 749
    .|.|||||||||||||| .|||| |||||.||||.  .|.||.|.|.||
701 NINKRLPSIVEDEEEEEGEEEEAVSLSPICTRGSS.SRNKKVGSNKAYL 749

750 GLSLKQLTSGTVPFHSPIRVSSANSPKTKQEADPPNHGTRKEKNLKVQLC 799
    |||||||.||||||||||||.|.|||||||||.||||.|.|||||.|.|
750 GLSLKQLASGTVPFHSPIRVSRSNSPKTKQEIDPPNHNKRKEKNLKLQLS 799

800 SLGTAGTPELSPRIVDGIEDGNSSEETQTFDFGSEQIRPEPRISPSLGES 849
    .|.||.|||||||||||||||||||||.|||||||||||||||||.|.|
800 TLNNAGPPDLSPRIVDGIEDGNSSEESQTFDFGSERIRSEPRISPPLGDP 849

850 EIGAAFLFIKAEETKQQINKLNSEVTTLTQEVSQLGKDMRSIMQLLENIL 899
    ||||| ||||||||||||||||||||||||||||||||||| . . . |
850 EIGAAVLFIKAEETKQQINKLNSEVTTLTQEVSQLGKDMRNVIRLLENVL 899

900 SPQQPSQFCSLHPTSICPSRESFQTRVSWSAHQPCLHLQANG.....AHL 944
    ||||||.|||| .|.|||||||.|||||||||||||||| ...  ..|.
900 SPQQPSRFCSLHSTSVCPSRESLQTRTSWSAHQPCLHLQTGGAAYTQAQL 949
```

Fig. 11 (cont'd)

```
995  YHGNVTSDIWSVDPSLVGSNPQRTEAHEQSPVDSELHHSPNLAYSPSHCQ  994
     |:|||||||||| |||.|||| ||||.| ||||:|||.| ||||||
950  CSSNITSDIWSVDPSSVGSSPQRTGAHEQNPADSELYHSPSLDYSPSHYQ  999

995  VIQEGHLQFLRCISPHSDTTLTPLQSISATLSSSVCSSSETSLHLVLPSR  1044
     |:||||||||||||||||.||||||||||||||||||||||||||||||
1000 VVQEGHLQFLRCISPHSDSTLTPLQSISATLSSSVCSSSETSLHLVLPSR  1049

1045 SEEGSITHGPVSSFSLENLPGSWDREGMMSASTEPLENFPVEVVTSTADV  1094
     ||||| . | |||||||||||||..||| ||||.|||| |.||||||:|
1050 SEEGSFSQGTVSSFSLENLPGSWNQEGMASASTKPLENLPLEVVTSTAEV  1099

1095 KDSKAINV  1102
     ||.|||||
1100 KDNKAINV  1107
```

Fig. 11 (cont'd)

(End-weighted) GAP of: Flhba042h05.pep check: 6895 from: 1 to: 1107

Flhba42h5orf - Import - complete to: human.erg.pep check: 9836 from: 1 to: 1159 human.erg | U04270 Human putative potassium channel subunit (h-erg) mRNA, complete Symbol comparison table:
/ddm local/gcg/gcg_9.1/gcgcore/data/rundata/blosum62.cmp
CompCheck: 6430

```
        Gap Weight:    12        Average Match:   2.912
     Length Weight:     4        Average Mismatch: -2.003

Quality:   262                Length:   1304
             Ratio:  0.237                 Gaps:     24
Percent Similarity: 50.520      Percent Identity:  40.852
```

Match display thresholds for the alignment(s):
    | = IDENTITY
    : = 2
    . = 1

Flhba042h05.pep x human.erg.pep

```
  1 MPVMKGLLAPQNTFLDTIATRFDGTHSNFILANAQVAKGFPIVYCSDGFC  50 Flhba042h05
    ||| : .||||||||||  :|:|    ||:|||.|  ::|| ||||
  1 MPVRRGHVAPQNTFLDTIIRKFEGQSRKFIIANARV.ENCAVIYCNDGFC  49 human.erg 51 ELAGFARTEVMQKSCSCKFLFGVETNEQLMLQIEKSLEEKTEFKGEIMFY 100
    || |:.|||||:|.|||   |||.  .|| ||..|   ||||||
 50 ELCGYSRAEVMQRPCTCDFLHGPRTQRRAAAQIAQALLGAEERKVEIAFY  99

101 KKNGSPFWCLLDIVPIKNEKGDVVLFLASFKDITD.............. 135
    :|.|| ||.:||:||| | |::|: .|.:  : :
100 RKDGSCFLCLVDVVPVKNEDGAVIMFILNFEVVMEKDMVGSPAHDTNHRG 149

136 ..........................................TKVK   139
                                                |
150 PPTSWLAPGRAKTFRLKLPALLALTARESSVRSGGAGGAGAPGAVVVDVD 199

140 ITPEDKKEDKVK...................................  151
    :||       :  .
200 LTPAAPSSESLALDEVTAMDNHVAGLGPAEERRALVGPGSPPRSAPGQLP 249

152 ................GRSRAGTHFDSARRRSRA...............  169
                    |.|.  |||||:|
250 SPRAHSLNPDASGSSCSLARTRSRESCASVRRASSADDIEAMRAGVLPPP 299
```

Fig. 12

```
170 ........................VLYHISGHLQRREKNKLKINNNVFV 194
                           || : |..  |.
300 PRHASTGAMHPLRSGLLNSTSDSDLVRYRTISKIPQITLNFVDLKGDPFL 349

195 DKP.........................AFPEYKVSDAKKSKFI 213
    |                            ||||.   : :.
350 ASPTSDREIIAPKIKERTHNVTEKVTQVLSLGADVLPEYKLQAPRIHRWT 399

214 LLHFSTFKAGWDWLILLATFYVAVTVPYNVCFIGNDDLSTTRST...... 257
    :||:||| |||||||  ||  ||. |: .       .|
400 ILHYSPFKAVWDWLILLLVIYTAVFTPYSAAFLLKETEEGPPATECGYAC 449

258 ...TVSDIAVEILFIIDIILNFRTTYVSKSGQVIFEARSICIHYVTTWFI 304
       || : |:|:||:||::|||||| ..:|:     |:||    ||:
450 QPLAVVDLIVDIMFIVDILINFRTTYVNANEEVVSHPGRIAVHYFKGWFL 499

305 IDLIAALPFDLLYAFNVTVVSLVHLLKTVRLLRLLRLLQKLDRYSQHSTI 354
    ||::||:|||||  |    |: ||||  |||||.|. .||||||::
500 IDMVAAIPFDLL.IFGSGSEELIGLLKTARLLRLVRVARKLDRYSEYGAA 548

355 VLTLLMSMFALLAHWMACIWYVIGKMEREDNSLLKWEVGWLHELGKRLES 404
    || |||  |||:|||| ||||||:|:|||||. :  :||||| |  .:
549 VLFLLMCTFALIAHWLACIWYAIGNMEQPH...MDSRIGWLHNLGDQIGK 595

405 PYYGNNTLGGPSIRSAYIAALYFTLSSLTSVGFGNVSANTDAEKIFSICT 454
    |   | .. ||||||:  |: ||||| ||||||||||||  ..|||||||
596 P.YNSSGLGGPSIKDKYVTALYFTFSSLTSVGFGNVSPNTNSEKIFSICV 644

455 MLIGALMHALVFGNVTAIIQRMYSRWSLYHTRTKDLKDFIRVHHLPQQLK 504
    ||||.||:| :||||.|||||||:||  .|||.     .::|||  |  |:
645 MLIGSLMYASIFGNVSAIIQRLYSGTARYHTQMLRVREFIRFHQIPNPLR 694

505 QRMLEYFQTTWSVNNGIDSNELLKDFPDELRSDITMHLNKEILQ.LSLFE 553
    ||:||||| || |||||||:|..||  |: |..|| :|||:||  |
695 QRLEEYFQHAWSYTNGIDMNAVLKGFPECLQADICLHLNRSLLQHCKPFR 744

554 CASRGCLRSLSLHIKTSFCAPGEYLLRQGDALQAIYFVCSGSMEVLKDSM 603
    |.:|||||.|.:  ||.  ||  |:  |:||  ||:||   ||.|:||
745 GATKGCLRALAMKFKTTHAPPGDTLVHAGDLLTALYFISRGSIEILRGDV 794

604 VLAILGKGDLIGANLSIKDQVIKTNADVKALTYCDLQCIILKGLFEVLDL 653
    |.||||||:|||||  |.: ||.|  |.:||||||||:|||  ||||| ||
795 VVAILGKNDIFGEPLNLYARPGKSNGDVRALTYCDLHKIHRDDLLEVLDM 844

654 YPEYAHKFVEDIQHDLTYNLREGHESDVISRLSNKSMVSQSEPKGNGNIN 703
    |||:.  |   :  ::|:|||:      . :     |. :|    |
845 YPEFSDHFWSSL..EITFNLRD.......TNMIPGSPGSTELEGGFSRQR 885

704 KRLPSIVEDEEEEEGEEEEAVSLSPICTRGSSSRNKKVGSNKAYLGLSL 753
    || ||    :.:||||  |.           ||||:  |
886 KRKLSFRRRTDKDTEQPGEVSALGPGRAGAGPSSRGRPGG.......... 925
```

Fig. 12 (cont'd)

```
 754 KQLASGTVPFHSPIRVSRSNSPKTKQEIDPPNHNKRKEKNLKLQLSTLNN  803
         |  |   |        .||..  ::    |
 926 ...PWGESPSSGP......SSPESSEDEGP....................  946

804 AGPPDLSPRIVDGIEDGNSSEESQTFDFGSERIRSEPRISPPLGDPEIGA  853
              |||   .        |||       |    ||  |:|
 947 ..............GRSSSPLRLVPFSSPR....PPGEPPGGEP....   972

854 AVLFIKAEETKQQINKLNSEVTTLTQEVSQLGKDMRNVIRLLENVLSPQQ  903
          |  |..   |.  |   ..    |         |       .|
 973 ..LMEDCEKSSDTCNPLSGAFSGVSNIFSFWGDSRGRQYQELPRCPAPTP 1020

904 PSRFCSLHSTSVCPSRESLQTRTSWSAHQPCLHLQTGGAAYTQAQLCSSN  953
         |||   |  |     .:.|                |
1021 SLLNIPLSSPGRRP.RGDVESRLD.............ALQRQLNRLETR 1055

954 ITSDIWSVDPSSVGSSPQRTGAHEQNPADSELYHSPSLDYSPSHYQVVQE 1003
     :..|..|.                     :|        |.: |
1056 LSADMATV....................LQLLQRQMTLVPPAYSAVTTP 1084

1004 GHLQFLRCISPHSDSTLTPLQSISATLSSSVCSSSETSLHLVLPSRSEEG 1053
       |     ||||| : | .    |.  |:    ||  .|
1085 GP.......GPTSTSPLLPVSPLPTLTLDSLSQVSQFMACEELPPGAPE. 1126

1054 SFSQGTVSSFSLENLPGSWNQEGMASASTKPLENLPLEVVTSTAEVKDNK 1103
        ||  |||    .|   :    |||   . ||
1127 ..............LP....QEGPTRRLSLPGQ...LGALTSQPLHRHGS 1155

1104 AINV 1107

1156 DPGS 1159
```

Fig. 12 (cont'd)

SEQUENCE LISTING

<160> NUMBER OF SEQ ID NOS: 36

<210> SEQ ID NO 1
<211> LENGTH: 3355
<212> TYPE: DNA
<213> ORGANISM: Macaca sp.
<220> FEATURE:
<221> NAME/KEY: CDS
<222> LOCATION: (104)..(3352)

<400> SEQUENCE: 1

```
gggagcgcgg ggcccggcgg ggggcggccg agctgggcgc cctcccccgg cgcggagtcc      60
ccgcaccccg gagggatggg gccggcagcc gcgggcgcct aag atg ccg gcc atg     115
                                              Met Pro Ala Met
                                              1 cgg ggc ctc ctg gcg ccg cag aac acc ttc ctg gac acc atc gct acg    163
Arg Gly Leu Leu Ala Pro Gln Asn Thr Phe Leu Asp Thr Ile Ala Thr
  5                  10                  15                  20 cgc ttc gac ggc acg cac agt aac ttc gtg ctg ggc aac gcc cag gtg    211
Arg Phe Asp Gly Thr His Ser Asn Phe Val Leu Gly Asn Ala Gln Val
                 25                  30                  35 gcg ggg ctc ttc ccc gtg gtc tac tgc tct gat ggc ttc tgt gac ctc    259
Ala Gly Leu Phe Pro Val Val Tyr Cys Ser Asp Gly Phe Cys Asp Leu
```

| | | |
|---|---|---|
| acg ggc ttc tcc cgg gct gag gtc atg cag cgg ggc tgt gcc tgc tcc<br>Thr Gly Phe Ser Arg Ala Glu Val Met Gln Arg Gly Cys Ala Cys Ser<br>        55                       60                  65 | 307 |
| ttc ctt tat ggg cca gac acc agt gag ctc gtc cgc caa cag atc cgc<br>Phe Leu Tyr Gly Pro Asp Thr Ser Glu Leu Val Arg Gln Gln Ile Arg<br>70                       75                    80 | 355 |
| aag gcc ctg gac gag cac aag gag ttc aag gct gag ctg atc ctg tac<br>Lys Ala Leu Asp Glu His Lys Glu Phe Lys Ala Glu Leu Ile Leu Tyr<br>85                     90                  95                  100 | 403 |
| cgg aag agc ggg ctc ccg ttc tgg tgt ctc ctg gat gtg ata ccc ata<br>Arg Lys Ser Gly Leu Pro Phe Trp Cys Leu Leu Asp Val Ile Pro Ile<br>                    105                 110              115 | 451 |
| aag aat gag aaa ggg gag gtg gct ctc ttc cta gtc tct cac aag gac<br>Lys Asn Glu Lys Gly Glu Val Ala Leu Phe Leu Val Ser His Lys Asp<br>              120                   125               130 | 499 |
| atc agt gaa acc aag aac cga ggg ggc cct gac aga tgg aag gag aca<br>Ile Ser Glu Thr Lys Asn Arg Gly Gly Pro Asp Arg Trp Lys Glu Thr<br>       135                  140                 145 | 547 |
| ggt agt ggc cgg cgc cga tat ggc cgg gca cga tcc aaa ggc ttc aat<br>Gly Ser Gly Arg Arg Arg Tyr Gly Arg Ala Arg Ser Lys Gly Phe Asn<br>150                    155                 160 | 595 |
| gcc aac cgg cgg cgg agc cgg gct gtg ctc tac cac ctg tcc ggg cac<br>Ala Asn Arg Arg Arg Ser Arg Ala Val Leu Tyr His Leu Ser Gly His<br>165                   170                 175               180 | 643 |
| ctg cag aag cag ccc aag ggc aag cac aag ctc aat aag ggg gtg ttt<br>Leu Gln Lys Gln Pro Lys Gly Lys His Lys Leu Asn Lys Gly Val Phe<br>                    185                 190              195 | 691 |
| ggg gag aag cca aac ttg cct gag tac aaa gta gct gcc atc cgg aag<br>Gly Glu Lys Pro Asn Leu Pro Glu Tyr Lys Val Ala Ala Ile Arg Lys<br>              200                   205               210 | 739 |
| tcg cct ttc atc ctg ttg cac tgt ggg gcg ctg agg gcc acc tgg gat<br>Ser Pro Phe Ile Leu Leu His Cys Gly Ala Leu Arg Ala Thr Trp Asp<br>       215                  220                 225 | 787 |
| ggc ttc atc ctg ctc gcc acg ctc tat gtg gct gtc acc gtg ccc tac<br>Gly Phe Ile Leu Leu Ala Thr Leu Tyr Val Ala Val Thr Val Pro Tyr<br>230                    235                 240 | 835 |
| agc gtg tgt gtg agc aca gca cgg gag ccc agt gcc gcc cgc ggc cca<br>Ser Val Cys Val Ser Thr Ala Arg Glu Pro Ser Ala Ala Arg Gly Pro<br>245                    250                 255               260 | 883 |
| ccc agc gtc tgt gac ctg gct gtg gag gtc ctc ttc atc ctt gac att<br>Pro Ser Val Cys Asp Leu Ala Val Glu Val Leu Phe Ile Leu Asp Ile<br>                    265                 270              275 | 931 |
| gtg ctg aat ttc cgt acc aca ttc gtg tcc aag tcg ggc cag gtg gtg<br>Val Leu Asn Phe Arg Thr Thr Phe Val Ser Lys Ser Gly Gln Val Val<br>              280                   285               290 | 979 |
| ttt gcc cca aag tcc att tgc ctc cac tac gtc acc acc tgg ttc ctg<br>Phe Ala Pro Lys Ser Ile Cys Leu His Tyr Val Thr Thr Trp Phe Leu<br>       295                  300                 305 | 1027 |
| ctg gat gtc atc gca gcg ctg ccc ttt gac ctg ctg cat gcc ttc aag<br>Leu Asp Val Ile Ala Ala Leu Pro Phe Asp Leu Leu His Ala Phe Lys<br>310                    315                 320 | 1075 |
| gtc aac gtg tac ttc ggg gcc cac ctg ctg aag acg gtg cgc ctg ctg<br>Val Asn Val Tyr Phe Gly Ala His Leu Leu Lys Thr Val Arg Leu Leu<br>325                    330                 335               340 | 1123 |
| cgc ctg ctg cgc ctg ctt ccg cgg ctg gac cgg tac tcg cag tac agc<br>Arg Leu Leu Arg Leu Leu Pro Arg Leu Asp Arg Tyr Ser Gln Tyr Ser<br>                    345                 350              355 | 1171 |
| gcc gtg gtg ctg aca ctg ctc atg gcc gtg ttt gcc ctg ctt gcg cac | 1219 |

```
                Ala Val Val Leu Thr Leu Leu Met Ala Val Phe Ala Leu Leu Ala His
                            360                 365                 370 tgg gtt gcc tgc gtc tgg ttt tac att ggt cag cgg gag atc gag agc         1267
Trp Val Ala Cys Val Trp Phe Tyr Ile Gly Gln Arg Glu Ile Glu Ser
            375                 380                 385 agc gaa tcc gag ctg cct gag att ggc tgg ctg cag gag ctg gcc cgc         1315
Ser Glu Ser Glu Leu Pro Glu Ile Gly Trp Leu Gln Glu Leu Ala Arg
    390                 395                 400 cga ctg gag acc ccc tac tac ttg gtg ggc cgg aga cca gcc gga ggg         1363
Arg Leu Glu Thr Pro Tyr Tyr Leu Val Gly Arg Arg Pro Ala Gly Gly
405                 410                 415                 420 aac agc tct ggc cag agt gac aac tgc agc agc agc gag gcc aac             1411
Asn Ser Ser Gly Gln Ser Asp Asn Cys Ser Ser Ser Glu Ala Asn
                425                 430                 435 ggg acg ggg ctg gag ctg cta ggc ggc ccg tcg ctg cgc agc gcc tac         1459
Gly Thr Gly Leu Glu Leu Leu Gly Gly Pro Ser Leu Arg Ser Ala Tyr
            440                 445                 450 atc acc tcc ctc tac ttc gca ctc agc agc ctc acc agc gtg ggc ttc         1507
Ile Thr Ser Leu Tyr Phe Ala Leu Ser Ser Leu Thr Ser Val Gly Phe
        455                 460                 465 ggc aac gtg tcc gcc aac acg gac act gag aag atc ttc tcc atc tgc         1555
Gly Asn Val Ser Ala Asn Thr Asp Thr Glu Lys Ile Phe Ser Ile Cys
    470                 475                 480 acc atg ctc atc ggc gcc ctg atg cac gcg gtg gtg ttc ggg aac gtg         1603
Thr Met Leu Ile Gly Ala Leu Met His Ala Val Val Phe Gly Asn Val
485                 490                 495                 500 acg gcc atc atc cag cgc atg tac gcc cgc cgc ttt ctg tac cac agc         1651
Thr Ala Ile Ile Gln Arg Met Tyr Ala Arg Arg Phe Leu Tyr His Ser
                505                 510                 515 cgc acg cgc gac ctg cgc gac tac atc cgc atc cac cgt atc ccc aag         1699
Arg Thr Arg Asp Leu Arg Asp Tyr Ile Arg Ile His Arg Ile Pro Lys
            520                 525                 530 ccc ctc aag cag cgc atg ctg gag tac ttc cag gcc acc tgg gcg gtg         1747
Pro Leu Lys Gln Arg Met Leu Glu Tyr Phe Gln Ala Thr Trp Ala Val
        535                 540                 545 aac aat ggc atc gac acc acc gag ctg ctg cag agc ctc cct gac gag         1795
Asn Asn Gly Ile Asp Thr Thr Glu Leu Leu Gln Ser Leu Pro Asp Glu
    550                 555                 560 ctg cgc gca gac atc gcc atg cac ctg cac aag gag gtc ctg cag ctg         1843
Leu Arg Ala Asp Ile Ala Met His Leu His Lys Glu Val Leu Gln Leu
565                 570                 575                 580 ccg ctg ttt gag gca gcc agc cgc ggc tgc ctg cgg gca ctg tct ctg         1891
Pro Leu Phe Glu Ala Ala Ser Arg Gly Cys Leu Arg Ala Leu Ser Leu
                585                 590                 595 gcc ctg cgg ccc gcc ttc tgc acg ccg ggc gag tac ctc atc cac caa         1939
Ala Leu Arg Pro Ala Phe Cys Thr Pro Gly Glu Tyr Leu Ile His Gln
            600                 605                 610 ggc gat gcc ctg cag gcc ctc tac ttt gtc tgc tct ggc tcc atg gag         1987
Gly Asp Ala Leu Gln Ala Leu Tyr Phe Val Cys Ser Gly Ser Met Glu
        615                 620                 625 gtg ctc aag ggt ggc acc gtg ctc gcc atc cta ggg aag ggt gac ctg         2035
Val Leu Lys Gly Gly Thr Val Leu Ala Ile Leu Gly Lys Gly Asp Leu
    630                 635                 640 atc ggc tgt gag ctg ccc cgg agg gag cag gtg gta aag gcc aac gcc         2083
Ile Gly Cys Glu Leu Pro Arg Arg Glu Gln Val Val Lys Ala Asn Ala
645                 650                 655                 660 gat gtg aag ggg ctg acg tac tgc gtc ctg cag tgt ctg cag ctg gct         2131
Asp Val Lys Gly Leu Thr Tyr Cys Val Leu Gln Cys Leu Gln Leu Ala
                665                 670                 675
```

```
ggc ctg cac gac agc ctt gcg ctc tac ccc gag ttt gcc ccg cgc ttc        2179
Gly Leu His Asp Ser Leu Ala Leu Tyr Pro Glu Phe Ala Pro Arg Phe
        680                 685                 690 agc cgt ggc ctc cga ggg gag ctc agc tac aac ctg ggt gct ggg gga        2227
Ser Arg Gly Leu Arg Gly Glu Leu Ser Tyr Asn Leu Gly Ala Gly Gly
    695                 700                 705 ggc tct gca gag gtg gac acc agc tcc ctg agc ggc gac aat acc ctt        2275
Gly Ser Ala Glu Val Asp Thr Ser Ser Leu Ser Gly Asp Asn Thr Leu
710                 715                 720 atg tcc acg ctg gag gag aag gag aca gat ggg gag cag ggc ccc aca        2323
Met Ser Thr Leu Glu Glu Lys Glu Thr Asp Gly Glu Gln Gly Pro Thr
725                 730                 735                 740 gtc tcc cca gcc cca gct gat gag ccc tcc agc ccc cta ctg tcc cct        2371
Val Ser Pro Ala Pro Ala Asp Glu Pro Ser Ser Pro Leu Leu Ser Pro
            745                 750                 755 ggt tgc acc tcc tca tcc tcg gct gcc aag ctg cta tcc cca cgt cga        2419
Gly Cys Thr Ser Ser Ser Ser Ala Ala Lys Leu Leu Ser Pro Arg Arg
        760                 765                 770 aca gca ccc cgg cct cgt cta ggt ggc aga ggg aga cca ggc agg gca        2467
Thr Ala Pro Arg Pro Arg Leu Gly Gly Arg Gly Arg Pro Gly Arg Ala
    775                 780                 785 ggg gct ttg aag gct gag gct ggc ccc tct gct ccc cca cgg gcc cta        2515
Gly Ala Leu Lys Ala Glu Ala Gly Pro Ser Ala Pro Pro Arg Ala Leu
790                 795                 800 gag ggg cta cgg ctg ccc ccc atg cca tgg aat gtg ccc cca gat ctg        2563
Glu Gly Leu Arg Leu Pro Pro Met Pro Trp Asn Val Pro Pro Asp Leu
805                 810                 815                 820 agc ccc agg gta gta gat ggc att gaa gac ggc tgt ggc tcg gac cag        2611
Ser Pro Arg Val Val Asp Gly Ile Glu Asp Gly Cys Gly Ser Asp Gln
            825                 830                 835 ccc aag ttc tct ttc cgc atg ggc cag tct ggc ccg gaa tgt agc agc        2659
Pro Lys Phe Ser Phe Arg Met Gly Gln Ser Gly Pro Glu Cys Ser Ser
        840                 845                 850 agc ccc tcc cct gga cca gag agt ggc ctg ctc act gtc ccc cat ggg        2707
Ser Pro Ser Pro Gly Pro Glu Ser Gly Leu Leu Thr Val Pro His Gly
    855                 860                 865 ccc agc gag gca agg aac aca gac aca ctg gac aag ctt cgg cag gcg        2755
Pro Ser Glu Ala Arg Asn Thr Asp Thr Leu Asp Lys Leu Arg Gln Ala
870                 875                 880 gtg atg gag ctg tca gaa cag gtg ctg cag atg cgg gaa gga cta cag        2803
Val Met Glu Leu Ser Glu Gln Val Leu Gln Met Arg Glu Gly Leu Gln
885                 890                 895                 900 tca ctt cgc cag gct gtg cag ctt gtc ctg gca ccc cat agg gag ggt        2851
Ser Leu Arg Gln Ala Val Gln Leu Val Leu Ala Pro His Arg Glu Gly
            905                 910                 915 cca tgc cct cgg gcc tca gga gag ggg cca tgc cca gcc agc acc tcc        2899
Pro Cys Pro Arg Ala Ser Gly Glu Gly Pro Cys Pro Ala Ser Thr Ser
        920                 925                 930 ggg ctt ctg cag cct ctg tgt gtg gac act ggg gca tcc tcc tac tgc        2947
Gly Leu Leu Gln Pro Leu Cys Val Asp Thr Gly Ala Ser Ser Tyr Cys
    935                 940                 945 ctg cag ccc cca gct ggc tct gtc ttg agt ggg act tgg ccc cac cct        2995
Leu Gln Pro Pro Ala Gly Ser Val Leu Ser Gly Thr Trp Pro His Pro
950                 955                 960 cgt ccg ggg cct cct ccc ctc atg gca ccc tgg ccc tgg ggt ccc cca        3043
Arg Pro Gly Pro Pro Pro Leu Met Ala Pro Trp Pro Trp Gly Pro Pro
965                 970                 975                 980 gca tct cag agc tcc ccc tgg cct cga gcc aca gct ttc tgg acc tcc        3091
Ala Ser Gln Ser Ser Pro Trp Pro Arg Ala Thr Ala Phe Trp Thr Ser
            985                 990                 995
```

-continued

```
acc tca gac tca gag ccc cct gcc tca gga gac ctc tgc tct gag ccc    3139
Thr Ser Asp Ser Glu Pro Pro Ala Ser Gly Asp Leu Cys Ser Glu Pro
            1000                1005                1010 agc acc cct gcc tca cct cct cct tct gag gaa ggg gct agg act ggg    3187
Ser Thr Pro Ala Ser Pro Pro Pro Ser Glu Glu Gly Ala Arg Thr Gly
        1015                1020                1025 ccc cca gag cct gtg agc cag gct gag gct acc agc act gga gag ccc    3235
Pro Pro Glu Pro Val Ser Gln Ala Glu Ala Thr Ser Thr Gly Glu Pro
    1030                1035                1040 ccg cca gtg tca ggg ggc ctg gcc ttg ccc tgg gac ccc cac agc ctg    3283
Pro Pro Val Ser Gly Gly Leu Ala Leu Pro Trp Asp Pro His Ser Leu
1045                1050                1055                1060 gag atg gtg ctt att ggc tgc cac ggc tct ggc aca gtc cag tgg acc    3331
Glu Met Val Leu Ile Gly Cys His Gly Ser Gly Thr Val Gln Trp Thr
                1065                1070                1075 cag gaa gaa ggc aca ggg gtc tga                                    3355
Gln Glu Glu Gly Thr Gly Val
            1080
```

<210> SEQ ID NO 2
<211> LENGTH: 1083
<212> TYPE: PRT
<213> ORGANISM: Macaca sp.

<400> SEQUENCE: 2

```
Met Pro Ala Met Arg Gly Leu Leu Ala Pro Gln Asn Thr Phe Leu Asp
  1               5                  10                  15

Thr Ile Ala Thr Arg Phe Asp Gly Thr His Ser Asn Phe Val Leu Gly
                 20                  25                  30

Asn Ala Gln Val Ala Gly Leu Phe Pro Val Val Tyr Cys Ser Asp Gly
             35                  40                  45

Phe Cys Asp Leu Thr Gly Phe Ser Arg Ala Glu Val Met Gln Arg Gly
 50                  55                  60

Cys Ala Cys Ser Phe Leu Tyr Gly Pro Asp Thr Ser Glu Leu Val Arg
 65                  70                  75                  80

Gln Gln Ile Arg Lys Ala Leu Asp Glu His Lys Glu Phe Lys Ala Glu
                 85                  90                  95

Leu Ile Leu Tyr Arg Lys Ser Gly Leu Pro Phe Trp Cys Leu Leu Asp
                100                 105                 110

Val Ile Pro Ile Lys Asn Glu Lys Gly Glu Val Ala Leu Phe Leu Val
            115                 120                 125

Ser His Lys Asp Ile Ser Glu Thr Lys Asn Arg Gly Gly Pro Asp Arg
130                 135                 140

Trp Lys Glu Thr Gly Ser Gly Arg Arg Arg Tyr Gly Arg Ala Arg Ser
145                 150                 155                 160

Lys Gly Phe Asn Ala Asn Arg Arg Arg Ser Arg Ala Val Leu Tyr His
                165                 170                 175

Leu Ser Gly His Leu Gln Lys Gln Pro Lys Gly Lys His Lys Leu Asn
            180                 185                 190

Lys Gly Val Phe Gly Glu Lys Pro Asn Leu Pro Glu Tyr Lys Val Ala
        195                 200                 205

Ala Ile Arg Lys Ser Pro Phe Ile Leu Leu His Cys Gly Ala Leu Arg
    210                 215                 220

Ala Thr Trp Asp Gly Phe Ile Leu Leu Ala Thr Leu Tyr Val Ala Val
225                 230                 235                 240

Thr Val Pro Tyr Ser Val Cys Val Ser Thr Ala Arg Glu Pro Ser Ala
```

```
                    245                 250                 255
        Ala Arg Gly Pro Pro Ser Val Cys Asp Leu Ala Val Glu Val Leu Phe
                        260                 265                 270
        Ile Leu Asp Ile Val Leu Asn Phe Arg Thr Thr Phe Val Ser Lys Ser
                    275                 280                 285
        Gly Gln Val Val Phe Ala Pro Lys Ser Ile Cys Leu His Tyr Val Thr
                290                 295                 300
        Thr Trp Phe Leu Leu Asp Val Ile Ala Ala Leu Pro Phe Asp Leu Leu
        305                 310                 315                 320
        His Ala Phe Lys Val Asn Val Tyr Phe Gly Ala His Leu Leu Lys Thr
                        325                 330                 335
        Val Arg Leu Leu Arg Leu Leu Arg Leu Leu Pro Arg Leu Asp Arg Tyr
                    340                 345                 350
        Ser Gln Tyr Ser Ala Val Val Leu Thr Leu Leu Met Ala Val Phe Ala
                355                 360                 365
        Leu Leu Ala His Trp Val Ala Cys Val Trp Phe Tyr Ile Gly Gln Arg
            370                 375                 380
        Glu Ile Glu Ser Ser Glu Ser Glu Leu Pro Glu Ile Gly Trp Leu Gln
        385                 390                 395                 400
        Glu Leu Ala Arg Arg Leu Glu Thr Pro Tyr Tyr Leu Val Gly Arg Arg
                        405                 410                 415
        Pro Ala Gly Gly Asn Ser Ser Gly Gln Ser Asp Asn Cys Ser Ser Ser
                    420                 425                 430
        Ser Glu Ala Asn Gly Thr Gly Leu Glu Leu Leu Gly Gly Pro Ser Leu
                435                 440                 445
        Arg Ser Ala Tyr Ile Thr Ser Leu Tyr Phe Ala Leu Ser Ser Leu Thr
        450                 455                 460
        Ser Val Gly Phe Gly Asn Val Ser Ala Asn Thr Asp Thr Glu Lys Ile
        465                 470                 475                 480
        Phe Ser Ile Cys Thr Met Leu Ile Gly Ala Leu Met His Ala Val Val
                        485                 490                 495
        Phe Gly Asn Val Thr Ala Ile Ile Gln Arg Met Tyr Ala Arg Arg Phe
                    500                 505                 510
        Leu Tyr His Ser Arg Thr Arg Asp Leu Arg Asp Tyr Ile Arg Ile His
                515                 520                 525
        Arg Ile Pro Lys Pro Leu Lys Gln Arg Met Leu Glu Tyr Phe Gln Ala
            530                 535                 540
        Thr Trp Ala Val Asn Asn Gly Ile Asp Thr Thr Glu Leu Leu Gln Ser
        545                 550                 555                 560
        Leu Pro Asp Glu Leu Arg Ala Asp Ile Ala Met His Leu His Lys Glu
                        565                 570                 575
        Val Leu Gln Leu Pro Leu Phe Glu Ala Ala Ser Arg Gly Cys Leu Arg
                    580                 585                 590
        Ala Leu Ser Leu Ala Leu Arg Pro Ala Phe Cys Thr Pro Gly Glu Tyr
                595                 600                 605
        Leu Ile His Gln Gly Asp Ala Leu Gln Ala Leu Tyr Phe Val Cys Ser
            610                 615                 620
        Gly Ser Met Glu Val Leu Lys Gly Gly Thr Val Leu Ala Ile Leu Gly
        625                 630                 635                 640
        Lys Gly Asp Leu Ile Gly Cys Glu Leu Pro Arg Arg Glu Gln Val Val
                        645                 650                 655
        Lys Ala Asn Ala Asp Val Lys Gly Leu Thr Tyr Cys Val Leu Gln Cys
                    660                 665                 670
```

```
Leu Gln Leu Ala Gly Leu His Asp Ser Leu Ala Leu Tyr Pro Glu Phe
        675                 680                 685

Ala Pro Arg Phe Ser Arg Gly Leu Arg Gly Glu Leu Ser Tyr Asn Leu
    690                 695                 700

Gly Ala Gly Gly Ser Ala Glu Val Asp Thr Ser Ser Leu Ser Gly
705                 710                 715                 720

Asp Asn Thr Leu Met Ser Thr Leu Glu Glu Lys Glu Thr Asp Gly Glu
                725                 730                 735

Gln Gly Pro Thr Val Ser Pro Ala Pro Ala Asp Glu Pro Ser Ser Pro
            740                 745                 750

Leu Leu Ser Pro Gly Cys Thr Ser Ser Ser Ala Ala Lys Leu Leu
    755                 760                 765

Ser Pro Arg Arg Thr Ala Pro Arg Pro Arg Leu Gly Arg Gly Arg
    770                 775                 780

Pro Gly Arg Ala Gly Ala Leu Lys Ala Glu Ala Gly Pro Ser Ala Pro
785                 790                 795                 800

Pro Arg Ala Leu Glu Gly Leu Arg Leu Pro Pro Met Pro Trp Asn Val
                805                 810                 815

Pro Pro Asp Leu Ser Pro Arg Val Val Asp Gly Ile Glu Asp Gly Cys
            820                 825                 830

Gly Ser Asp Gln Pro Lys Phe Ser Phe Arg Met Gly Gln Ser Gly Pro
        835                 840                 845

Glu Cys Ser Ser Pro Ser Pro Gly Pro Glu Ser Gly Leu Leu Thr
    850                 855                 860

Val Pro His Gly Pro Ser Glu Ala Arg Asn Thr Asp Thr Leu Asp Lys
865                 870                 875                 880

Leu Arg Gln Ala Val Met Glu Leu Ser Glu Gln Val Leu Gln Met Arg
                885                 890                 895

Glu Gly Leu Gln Ser Leu Arg Gln Ala Val Gln Leu Val Leu Ala Pro
            900                 905                 910

His Arg Glu Gly Pro Cys Pro Arg Ala Ser Gly Glu Gly Pro Cys Pro
        915                 920                 925

Ala Ser Thr Ser Gly Leu Leu Gln Pro Leu Cys Val Asp Thr Gly Ala
    930                 935                 940

Ser Ser Tyr Cys Leu Gln Pro Pro Ala Gly Ser Val Leu Ser Gly Thr
945                 950                 955                 960

Trp Pro His Pro Arg Pro Gly Pro Pro Leu Met Ala Pro Trp Pro
                965                 970                 975

Trp Gly Pro Pro Ala Ser Gln Ser Ser Pro Trp Pro Arg Ala Thr Ala
            980                 985                 990

Phe Trp Thr Ser Thr Ser Asp Ser Glu Pro Pro Ala Ser Gly Asp Leu
        995                 1000                1005

Cys Ser Glu Pro Ser Thr Pro Ala Ser Pro Pro Ser Glu Glu Gly
    1010                1015                1020

Ala Arg Thr Gly Pro Pro Glu Pro Val Ser Gln Ala Glu Ala Thr Ser
1025                1030                1035                1040

Thr Gly Glu Pro Pro Pro Val Ser Gly Gly Leu Ala Leu Pro Trp Asp
                1045                1050                1055

Pro His Ser Leu Glu Met Val Leu Ile Gly Cys His Gly Ser Gly Thr
            1060                1065                1070

Val Gln Trp Thr Gln Glu Glu Gly Thr Gly Val
    1075                1080
```

-continued

```
<210> SEQ ID NO 3
<211> LENGTH: 3249
<212> TYPE: DNA
<213> ORGANISM: Macaca sp.
<220> FEATURE:
<221> NAME/KEY: CDS
<222> LOCATION: (1)..(3249)

<400> SEQUENCE: 3
```

| | | | | | | | | | | | | | | | | |
|---|---|---|---|---|---|---|---|---|---|---|---|---|---|---|---|---|
| atg | ccg | gcc | atg | cgg | ggc | ctc | ctg | gcg | ccg | cag | aac | acc | ttc | ctg | gac | 48 |
| Met | Pro | Ala | Met | Arg | Gly | Leu | Leu | Ala | Pro | Gln | Asn | Thr | Phe | Leu | Asp | |
| 1 | | | | 5 | | | | | 10 | | | | | 15 | | |
| acc | atc | gct | acg | cgc | ttc | gac | ggc | acg | cac | agt | aac | ttc | gtg | ctg | ggc | 96 |
| Thr | Ile | Ala | Thr | Arg | Phe | Asp | Gly | Thr | His | Ser | Asn | Phe | Val | Leu | Gly | |
| | | | 20 | | | | | 25 | | | | | 30 | | | |
| aac | gcc | cag | gtg | gcg | ggg | ctc | ttc | ccc | gtg | gtc | tac | tgc | tct | gat | ggc | 144 |
| Asn | Ala | Gln | Val | Ala | Gly | Leu | Phe | Pro | Val | Val | Tyr | Cys | Ser | Asp | Gly | |
| | | 35 | | | | | 40 | | | | | 45 | | | | |
| ttc | tgt | gac | ctc | acg | ggc | ttc | tcc | cgg | gct | gag | gtc | atg | cag | cgg | ggc | 192 |
| Phe | Cys | Asp | Leu | Thr | Gly | Phe | Ser | Arg | Ala | Glu | Val | Met | Gln | Arg | Gly | |
| | 50 | | | | | 55 | | | | | 60 | | | | | |
| tgt | gcc | tgc | tcc | ttc | ctt | tat | ggg | cca | gac | acc | agt | gag | ctc | gtc | cgc | 240 |
| Cys | Ala | Cys | Ser | Phe | Leu | Tyr | Gly | Pro | Asp | Thr | Ser | Glu | Leu | Val | Arg | |
| 65 | | | | | 70 | | | | | 75 | | | | | 80 | |
| caa | cag | atc | cgc | aag | gcc | ctg | gac | gag | cac | aag | gag | ttc | aag | gct | gag | 288 |
| Gln | Gln | Ile | Arg | Lys | Ala | Leu | Asp | Glu | His | Lys | Glu | Phe | Lys | Ala | Glu | |
| | | | | 85 | | | | | 90 | | | | | 95 | | |
| ctg | atc | ctg | tac | cgg | aag | agc | ggg | ctc | ccg | ttc | tgg | tgt | ctc | ctg | gat | 336 |
| Leu | Ile | Leu | Tyr | Arg | Lys | Ser | Gly | Leu | Pro | Phe | Trp | Cys | Leu | Leu | Asp | |
| | | | 100 | | | | | 105 | | | | | 110 | | | |
| gtg | ata | ccc | ata | aag | aat | gag | aaa | ggg | gag | gtg | gct | ctc | ttc | cta | gtc | 384 |
| Val | Ile | Pro | Ile | Lys | Asn | Glu | Lys | Gly | Glu | Val | Ala | Leu | Phe | Leu | Val | |
| | | 115 | | | | | 120 | | | | | 125 | | | | |
| tct | cac | aag | gac | atc | agt | gaa | acc | aag | aac | cga | ggg | ggc | cct | gac | aga | 432 |
| Ser | His | Lys | Asp | Ile | Ser | Glu | Thr | Lys | Asn | Arg | Gly | Gly | Pro | Asp | Arg | |
| | 130 | | | | | 135 | | | | | 140 | | | | | |
| tgg | aag | gag | aca | ggt | agt | ggc | cgg | cgc | cga | tat | ggc | cgg | gca | cga | tcc | 480 |
| Trp | Lys | Glu | Thr | Gly | Ser | Gly | Arg | Arg | Arg | Tyr | Gly | Arg | Ala | Arg | Ser | |
| 145 | | | | | 150 | | | | | 155 | | | | | 160 | |
| aaa | ggc | ttc | aat | gcc | aac | cgg | cgg | cgg | agc | cgg | gct | gtg | ctc | tac | cac | 528 |
| Lys | Gly | Phe | Asn | Ala | Asn | Arg | Arg | Arg | Ser | Arg | Ala | Val | Leu | Tyr | His | |
| | | | | 165 | | | | | 170 | | | | | 175 | | |
| ctg | tcc | ggg | cac | ctg | cag | aag | cag | ccc | aag | ggc | aag | cac | aag | ctc | aat | 576 |
| Leu | Ser | Gly | His | Leu | Gln | Lys | Gln | Pro | Lys | Gly | Lys | His | Lys | Leu | Asn | |
| | | | 180 | | | | | 185 | | | | | 190 | | | |
| aag | ggg | gtg | ttt | ggg | gag | aag | cca | aac | ttg | cct | gag | tac | aaa | gta | gct | 624 |
| Lys | Gly | Val | Phe | Gly | Glu | Lys | Pro | Asn | Leu | Pro | Glu | Tyr | Lys | Val | Ala | |
| | | 195 | | | | | 200 | | | | | 205 | | | | |
| gcc | atc | cgg | aag | tcg | cct | ttc | atc | ctg | ttg | cac | tgt | ggg | gcg | ctg | agg | 672 |
| Ala | Ile | Arg | Lys | Ser | Pro | Phe | Ile | Leu | Leu | His | Cys | Gly | Ala | Leu | Arg | |
| | 210 | | | | | 215 | | | | | 220 | | | | | |
| gcc | acc | tgg | gat | ggc | ttc | atc | ctg | ctc | gcc | acg | ctc | tat | gtg | gct | gtc | 720 |
| Ala | Thr | Trp | Asp | Gly | Phe | Ile | Leu | Leu | Ala | Thr | Leu | Tyr | Val | Ala | Val | |
| 225 | | | | | 230 | | | | | 235 | | | | | 240 | |
| acc | gtg | ccc | tac | agc | gtg | tgt | gtg | agc | aca | gca | cgg | gag | ccc | agt | gcc | 768 |
| Thr | Val | Pro | Tyr | Ser | Val | Cys | Val | Ser | Thr | Ala | Arg | Glu | Pro | Ser | Ala | |
| | | | 245 | | | | | 250 | | | | | 255 | | | |
| gcc | cgc | ggc | cca | ccc | agc | gtc | tgt | gac | ctg | gct | gtg | gag | gtc | ctc | ttc | 816 |
| Ala | Arg | Gly | Pro | Pro | Ser | Val | Cys | Asp | Leu | Ala | Val | Glu | Val | Leu | Phe | |
| | | 260 | | | | | 265 | | | | | 270 | | | | |

```
atc ctt gac att gtg ctg aat ttc cgt acc aca ttc gtg tcc aag tcg      864
Ile Leu Asp Ile Val Leu Asn Phe Arg Thr Thr Phe Val Ser Lys Ser
        275                 280                 285 ggc cag gtg gtg ttt gcc cca aag tcc att tgc ctc cac tac gtc acc      912
Gly Gln Val Val Phe Ala Pro Lys Ser Ile Cys Leu His Tyr Val Thr
290                 295                 300 acc tgg ttc ctg ctg gat gtc atc gca gcg ctg ccc ttt gac ctg ctg      960
Thr Trp Phe Leu Leu Asp Val Ile Ala Ala Leu Pro Phe Asp Leu Leu
305                 310                 315                 320 cat gcc ttc aag gtc aac gtg tac ttc ggg gcc cac ctg ctg aag acg     1008
His Ala Phe Lys Val Asn Val Tyr Phe Gly Ala His Leu Leu Lys Thr
                325                 330                 335 gtg cgc ctg ctg cgc ctg ctg cgc ctg ctt ccg cgg ctg gac cgg tac     1056
Val Arg Leu Leu Arg Leu Leu Arg Leu Leu Pro Arg Leu Asp Arg Tyr
        340                 345                 350 tcg cag tac agc gcc gtg gtg ctg aca ctg ctc atg gcc gtg ttt gcc     1104
Ser Gln Tyr Ser Ala Val Val Leu Thr Leu Leu Met Ala Val Phe Ala
Ser Gln Tyr Ser Ala Val Val Leu Thr Leu Leu Met Ala Val Phe Ala
355                 360                 365 ctg ctt gcg cac tgg gtt gcc tgc gtc tgg ttt tac att ggt cag cgg     1152
Leu Leu Ala His Trp Val Ala Cys Val Trp Phe Tyr Ile Gly Gln Arg
370                 375                 380 gag atc gag agc agc gaa tcc gag ctg cct gag att ggc tgg ctg cag     1200
Glu Ile Glu Ser Ser Glu Ser Glu Leu Pro Glu Ile Gly Trp Leu Gln
385                 390                 395                 400 gag ctg gcc cgc cga ctg gag acc ccc tac tac ttg gtg ggc cgg aga     1248
Glu Leu Ala Arg Arg Leu Glu Thr Pro Tyr Tyr Leu Val Gly Arg Arg
                405                 410                 415 cca gcc gga ggg aac agc tct ggc cag agt gac aac tgc agc agc agc     1296
Pro Ala Gly Gly Asn Ser Ser Gly Gln Ser Asp Asn Cys Ser Ser Ser
            420                 425                 430 agc gag gcc aac ggg acg ggg ctg gag ctg cta ggc ggc ccg tcg ctg     1344
Ser Glu Ala Asn Gly Thr Gly Leu Glu Leu Leu Gly Gly Pro Ser Leu
        435                 440                 445 cgc agc gcc tac atc acc tcc ctc tac ttc gca ctc agc agc ctc acc     1392
Arg Ser Ala Tyr Ile Thr Ser Leu Tyr Phe Ala Leu Ser Ser Leu Thr
    450                 455                 460 agc gtg ggc ttc ggc aac gtg tcc gcc aac acg gac act gag aag atc     1440
Ser Val Gly Phe Gly Asn Val Ser Ala Asn Thr Asp Thr Glu Lys Ile
465                 470                 475                 480 ttc tcc atc tgc acc atg ctc atc ggc gcc ctg atg cac gcg gtg gtg     1488
Phe Ser Ile Cys Thr Met Leu Ile Gly Ala Leu Met His Ala Val Val
                485                 490                 495 ttc ggg aac gtg acg gcc atc atc cag cgc atg tac gcc cgc cgc ttt     1536
Phe Gly Asn Val Thr Ala Ile Ile Gln Arg Met Tyr Ala Arg Arg Phe
            500                 505                 510 ctg tac cac agc cgc acg cgc gac ctg cgc gac tac atc cgc atc cac     1584
Leu Tyr His Ser Arg Thr Arg Asp Leu Arg Asp Tyr Ile Arg Ile His
        515                 520                 525 cgt atc ccc aag ccc ctc aag cag cgc atg ctg gag tac ttc cag gcc     1632
Arg Ile Pro Lys Pro Leu Lys Gln Arg Met Leu Glu Tyr Phe Gln Ala
    530                 535                 540 acc tgg gcg gtg aac aat ggc atc gac acc acc gag ctg ctg cag agc     1680
Thr Trp Ala Val Asn Asn Gly Ile Asp Thr Thr Glu Leu Leu Gln Ser
545                 550                 555                 560 ctc cct gac gag ctg cgc gca gac atc gcc atg cac ctg cac aag gag     1728
Leu Pro Asp Glu Leu Arg Ala Asp Ile Ala Met His Leu His Lys Glu
                565                 570                 575 gtc ctg cag ctg ccg ctg ttt gag gca gcc agc cgc ggc tgc ctg cgg     1776
Val Leu Gln Leu Pro Leu Phe Glu Ala Ala Ser Arg Gly Cys Leu Arg
            580                 585                 590
```

```
gca ctg tct ctg gcc ctg cgg ccc gcc ttc tgc acg ccg ggc gag tac      1824
Ala Leu Ser Leu Ala Leu Arg Pro Ala Phe Cys Thr Pro Gly Glu Tyr
        595                 600                 605 ctc atc cac caa ggc gat gcc ctg cag gcc ctc tac ttt gtc tgc tct      1872
Leu Ile His Gln Gly Asp Ala Leu Gln Ala Leu Tyr Phe Val Cys Ser
610                 615                 620 ggc tcc atg gag gtg ctc aag ggt ggc acc gtg ctc gcc atc cta ggg      1920
Gly Ser Met Glu Val Leu Lys Gly Gly Thr Val Leu Ala Ile Leu Gly
625                 630                 635                 640 aag ggt gac ctg atc ggc tgt gag ctg ccc cgg agg gag cag gtg gta      1968
Lys Gly Asp Leu Ile Gly Cys Glu Leu Pro Arg Arg Glu Gln Val Val
                645                 650                 655 aag gcc aac gcc gat gtg aag ggg ctg acg tac tgc gtc ctg cag tgt      2016
Lys Ala Asn Ala Asp Val Lys Gly Leu Thr Tyr Cys Val Leu Gln Cys
            660                 665                 670 ctg cag ctg gct ggc ctg cac gac agc ctt gcg ctc tac ccc gag ttt      2064
Leu Gln Leu Ala Gly Leu His Asp Ser Leu Ala Leu Tyr Pro Glu Phe
        675                 680                 685 gcc ccg cgc ttc agc cgt ggc ctc cga ggg gag ctc agc tac aac ctg      2112
Ala Pro Arg Phe Ser Arg Gly Leu Arg Gly Glu Leu Ser Tyr Asn Leu
690                 695                 700 ggt gct ggg gga ggc tct gca gag gtg gac acc agc tcc ctg agc ggc      2160
Gly Ala Gly Gly Gly Ser Ala Glu Val Asp Thr Ser Ser Leu Ser Gly
705                 710                 715                 720 gac aat acc ctt atg tcc acg ctg gag gag aag gag aca gat ggg gag      2208
Asp Asn Thr Leu Met Ser Thr Leu Glu Glu Lys Glu Thr Asp Gly Glu
                725                 730                 735 cag ggc ccc aca gtc tcc cca gcc cca gct gat gag ccc tcc agc ccc      2256
Gln Gly Pro Thr Val Ser Pro Ala Pro Ala Asp Glu Pro Ser Ser Pro
            740                 745                 750 cta ctg tcc cct ggt tgc acc tcc tca tcc tcg gct gcc aag ctg cta      2304
Leu Leu Ser Pro Gly Cys Thr Ser Ser Ser Ser Ala Ala Lys Leu Leu
        755                 760                 765 tcc cca cgt cga aca gca ccc cgg cct cgt cta ggt ggc aga ggg aga      2352
Ser Pro Arg Arg Thr Ala Pro Arg Pro Arg Leu Gly Gly Arg Gly Arg
770                 775                 780 cca ggc agg gca ggg gct ttg aag gct gag gct ggc ccc tct gct ccc      2400
Pro Gly Arg Ala Gly Ala Leu Lys Ala Glu Ala Gly Pro Ser Ala Pro
785                 790                 795                 800 cca cgg gcc cta gag ggg cta cgg ctg ccc ccc atg cca tgg aat gtg      2448
Pro Arg Ala Leu Glu Gly Leu Arg Leu Pro Pro Met Pro Trp Asn Val
                805                 810                 815 ccc cca gat ctg agc ccc agg gta gta gat ggc att gaa gac ggc tgt      2496
Pro Pro Asp Leu Ser Pro Arg Val Val Asp Gly Ile Glu Asp Gly Cys
            820                 825                 830 ggc tcg gac cag ccc aag ttc tct ttc cgc atg ggc cag tct ggc ccg      2544
Gly Ser Asp Gln Pro Lys Phe Ser Phe Arg Met Gly Gln Ser Gly Pro
        835                 840                 845 gaa tgt agc agc agc ccc tcc cct gga cca gag agt ggc ctg ctc act      2592
Glu Cys Ser Ser Ser Pro Ser Pro Gly Pro Glu Ser Gly Leu Leu Thr
850                 855                 860 gtc ccc cat ggg ccc agc gag gca agg aac aca gac aca ctg gac aag      2640
Val Pro His Gly Pro Ser Glu Ala Arg Asn Thr Asp Thr Leu Asp Lys
865                 870                 875                 880 ctt cgg cag gcg gtg atg gag ctg tca gaa cag gtg ctg cag atg cgg      2688
Leu Arg Gln Ala Val Met Glu Leu Ser Glu Gln Val Leu Gln Met Arg
                885                 890                 895 gaa gga cta cag tca ctt cgc cag gct gtg cag ctt gtc ctg gca ccc      2736
Glu Gly Leu Gln Ser Leu Arg Gln Ala Val Gln Leu Val Leu Ala Pro
```

```
cat agg gag ggt cca tgc cct cgg gcc tca gga gag ggg cca tgc cca      2784
His Arg Glu Gly Pro Cys Pro Arg Ala Ser Gly Glu Gly Pro Cys Pro
            915                 920                 925 gcc agc acc tcc ggg ctt ctg cag cct ctg tgt gtg gac act ggg gca      2832
Ala Ser Thr Ser Gly Leu Leu Gln Pro Leu Cys Val Asp Thr Gly Ala
930                 935                 940 tcc tcc tac tgc ctg cag ccc cca gct ggc tct gtc ttg agt ggg act      2880
Ser Ser Tyr Cys Leu Gln Pro Pro Ala Gly Ser Val Leu Ser Gly Thr
945                 950                 955                 960 tgg ccc cac cct cgt ccg ggg cct cct ccc ctc atg gca ccc tgg ccc      2928
Trp Pro His Pro Arg Pro Gly Pro Pro Pro Leu Met Ala Pro Trp Pro
                965                 970                 975 tgg ggt ccc cca gca tct cag agc tcc ccc tgg cct cga gcc aca gct      2976
Trp Gly Pro Pro Ala Ser Gln Ser Ser Pro Trp Pro Arg Ala Thr Ala
            980                 985                 990 ttc tgg acc tcc acc tca gac tca gag ccc cct gcc tca gga gac ctc      3024
Phe Trp Thr Ser Thr Ser Asp Ser Glu Pro Pro Ala Ser Gly Asp Leu
            995                 1000                1005 tgc tct gag ccc agc acc cct gcc tca cct cct cct tct gag gaa ggg      3072
Cys Ser Glu Pro Ser Thr Pro Ala Ser Pro Pro Pro Ser Glu Glu Gly
        1010                1015                1020 gct agg act ggg ccc cca gag cct gtg agc cag gct gag gct acc agc      3120
Ala Arg Thr Gly Pro Pro Glu Pro Val Ser Gln Ala Glu Ala Thr Ser
1025                1030                1035                1040 act gga gag ccc ccg cca gtg tca ggg ggc ctg gcc ttg ccc tgg gac      3168
Thr Gly Glu Pro Pro Pro Val Ser Gly Gly Leu Ala Leu Pro Trp Asp
                    1045                1050                1055 ccc cac agc ctg gag atg gtg ctt att ggc tgc cac ggc tct ggc aca      3216
Pro His Ser Leu Glu Met Val Leu Ile Gly Cys His Gly Ser Gly Thr
                1060                1065                1070 gtc cag tgg acc cag gaa gaa ggc aca ggg gtc                          3249
Val Gln Trp Thr Gln Glu Glu Gly Thr Gly Val
        1075                1080

<210> SEQ ID NO 4
<211> LENGTH: 2694
<212> TYPE: DNA
<213> ORGANISM: Homo sapiens
<220> FEATURE:
<221> NAME/KEY: CDS
<222> LOCATION: (215)..(1840)

<400> SEQUENCE: 4
gtcgacccac gcgtccgctc ctgccacagc cggggcggct ggaactctct cccttttctcc      60 ctccatcctt ccacttcccc tgctcggccc cgccgtcagg ccgggtcccc cttccctgcc     120
gtcatcaggt tccccttctc ccttcttggc actttccttt cgaaccatcc ttctggacaa     180
actttgatgg agaatttcac accacgctgg aaaa atg ccg gtt atg aaa gga tta     235
                                     Met Pro Val Met Lys Gly Leu
                                       1               5 ctg gcg ccg caa aac acc ttc ctg gac acc atc gcc acc cgt ttt gac        283
Leu Ala Pro Gln Asn Thr Phe Leu Asp Thr Ile Ala Thr Arg Phe Asp
            10                  15                  20 gga aca cat agc aac ttc atc ctt gcc aat gcc cag gtg gct aag ggt        331
Gly Thr His Ser Asn Phe Ile Leu Ala Asn Ala Gln Val Ala Lys Gly
25                  30                  35 ttc ccc ata gtc tac tgt tcc gat ggc ttc tgc gag ctt gct gga ttt        379
Phe Pro Ile Val Tyr Cys Ser Asp Gly Phe Cys Glu Leu Ala Gly Phe
40                  45                  50                  55
```

| | |
|---|---|
| gcc cga act gaa gtc atg cag aag agt tgt agc tgc aag ttc tta ttt<br>Ala Arg Thr Glu Val Met Gln Lys Ser Cys Ser Cys Lys Phe Leu Phe<br>               60                     65                 70 | 427 |
| ggg gtt gaa acc aat gag caa ctg atg ctt caa ata gaa aag tca ctg<br>Gly Val Glu Thr Asn Glu Gln Leu Met Leu Gln Ile Glu Lys Ser Leu<br>             75                    80                 85 | 475 |
| gag gag aaa aca gaa ttc aaa gga gaa att atg ttc tac aag aaa aac<br>Glu Glu Lys Thr Glu Phe Lys Gly Glu Ile Met Phe Tyr Lys Lys Asn<br>        90                   95                100 | 523 |
| ggg tct cca ttt tgg tgc cta ctg gat att gtt ccc ata aag aat gaa<br>Gly Ser Pro Phe Trp Cys Leu Leu Asp Ile Val Pro Ile Lys Asn Glu<br>105                   110                 115 | 571 |
| aaa gga gat gta gta ctt ttt ctg gcc tcg ttc aaa gat ata aca gat<br>Lys Gly Asp Val Val Leu Phe Leu Ala Ser Phe Lys Asp Ile Thr Asp<br>120                   125                 130                 135 | 619 |
| aca aaa gtg aag att act cca gaa gat aaa aaa gaa gac aaa gtc aaa<br>Thr Lys Val Lys Ile Thr Pro Glu Asp Lys Lys Glu Asp Lys Val Lys<br>             140                   145                 150 | 667 |
| gga aga tca aga gca ggg acc cac ttt gac tca gcc cgg aga cgg agt<br>Gly Arg Ser Arg Ala Gly Thr His Phe Asp Ser Ala Arg Arg Arg Ser<br>                 155                 160                 165 | 715 |
| cga gca gtc ctt tat cac atc tct ggg cac ctg caa aga aga gaa aag<br>Arg Ala Val Leu Tyr His Ile Ser Gly His Leu Gln Arg Arg Glu Lys<br>             170                   175                 180 | 763 |
| aac aaa ttg aaa ata aat aac aat gtt ttt gta gat aaa cca gca ttt<br>Asn Lys Leu Lys Ile Asn Asn Asn Val Phe Val Asp Lys Pro Ala Phe<br>185                   190                 195 | 811 |
| ccg gag tat aaa gtt tct gat gca aaa aag tcc aaa ttc ata ctt ctg<br>Pro Glu Tyr Lys Val Ser Asp Ala Lys Lys Ser Lys Phe Ile Leu Leu<br>200                   205                 210                 215 | 859 |
| cat ttt agc act ttt aaa gct ggc tgg gac tgg ctt att ttg ttg gca<br>His Phe Ser Thr Phe Lys Ala Gly Trp Asp Trp Leu Ile Leu Leu Ala<br>             220                   225                 230 | 907 |
| acg ttt tat gtt gct gtg act gta cct tac aac gtt tgc ttt att ggc<br>Thr Phe Tyr Val Ala Val Thr Val Pro Tyr Asn Val Cys Phe Ile Gly<br>                 235                 240                 245 | 955 |
| aat gac gac ctg tcc aca act cgg agc aca acc gtc agt gac att gca<br>Asn Asp Asp Leu Ser Thr Thr Arg Ser Thr Thr Val Ser Asp Ile Ala<br>             250                   255                 260 | 1003 |
| gtg gag att ctt ttt att ata gat att att tta aat ttc cga aca act<br>Val Glu Ile Leu Phe Ile Ile Asp Ile Ile Leu Asn Phe Arg Thr Thr<br>265                   270                 275 | 1051 |
| tat gtc agc aag tct ggc caa gtt atc ttt gaa gca aga tca att tgc<br>Tyr Val Ser Lys Ser Gly Gln Val Ile Phe Glu Ala Arg Ser Ile Cys<br>280                   285                 290                 295 | 1099 |
| atc cac tat gtc aca acc tgg ttc atc att gat tta atc gct gcc ctg<br>Ile His Tyr Val Thr Thr Trp Phe Ile Ile Asp Leu Ile Ala Ala Leu<br>             300                   305                 310 | 1147 |
| cct ttt gat ctt ctg tat gct ttc aac gtc aca gtg gtg tct ctc gtg<br>Pro Phe Asp Leu Leu Tyr Ala Phe Asn Val Thr Val Val Ser Leu Val<br>             315                   320                 325 | 1195 |
| cat ctt cta aag aca gtg cgc ctc ttg cgt ctt ttg cgt ctg ctg cag<br>His Leu Leu Lys Thr Val Arg Leu Leu Arg Leu Leu Arg Leu Leu Gln<br>             330                   335                 340 | 1243 |
| aag tta gac cgc tat tcc caa cac agt act atc gtc ctg act ctg ctc<br>Lys Leu Asp Arg Tyr Ser Gln His Ser Thr Ile Val Leu Thr Leu Leu<br>345                   350                 355 | 1291 |
| atg tcc atg ttt gca ctc ctt gca cac tgg atg gcg tgt atc tgg tac<br>Met Ser Met Phe Ala Leu Leu Ala His Trp Met Ala Cys Ile Trp Tyr<br>360                   365                 370                 375 | 1339 |

-continued

```
gtc att gga aaa atg gag agg gaa gac aac agc ctt ctg aag tgg gaa      1387
Val Ile Gly Lys Met Glu Arg Glu Asp Asn Ser Leu Leu Lys Trp Glu
                380                 385                 390 gtt ggt tgg ctt cat gag ttg gga aag aga ctg gaa tct cca tac tat      1435
Val Gly Trp Leu His Glu Leu Gly Lys Arg Leu Glu Ser Pro Tyr Tyr
            395                 400                 405 ggc aac aat acc ttg ggg ggc ccg tcg atc cga agt gcc tat att gcc      1483
Gly Asn Asn Thr Leu Gly Gly Pro Ser Ile Arg Ser Ala Tyr Ile Ala
        410                 415                 420 gct ctg tac ttc acg ctg agc agc ctc acc agc gtg ggt ttt ggg aac      1531
Ala Leu Tyr Phe Thr Leu Ser Ser Leu Thr Ser Val Gly Phe Gly Asn
    425                 430                 435 gtc tct gct aat aca gat gca gaa aag atc ttc tcc atc tgc acc atg      1579
Val Ser Ala Asn Thr Asp Ala Glu Lys Ile Phe Ser Ile Cys Thr Met
440                 445                 450                 455 ctg att ggt gcc ttg atg cac gcc ttg gtg ttt gga aac gtg aca gca      1627
Leu Ile Gly Ala Leu Met His Ala Leu Val Phe Gly Asn Val Thr Ala
                460                 465                 470 atc ata cag agg atg tac tcc aga tgg tcc ctc tat cac act aga act      1675
Ile Ile Gln Arg Met Tyr Ser Arg Trp Ser Leu Tyr His Thr Arg Thr
            475                 480                 485 aag gat ctg aaa gat ttc atc cgt gtc cat cac ttg ccc caa caa ctc      1723
Lys Asp Leu Lys Asp Phe Ile Arg Val His His Leu Pro Gln Gln Leu
        490                 495                 500 aag cag agg atg ctc gaa tat ttt caa aca acc tgg tca gtc aac aat      1771
Lys Gln Arg Met Leu Glu Tyr Phe Gln Thr Thr Trp Ser Val Asn Asn
    505                 510                 515 gga ata gat tca aat gag gta atg ttc att tct cat gtt gtt ttc agg      1819
Gly Ile Asp Ser Asn Glu Val Met Phe Ile Ser His Val Val Phe Arg
520                 525                 530                 535 cag aaa gca cat att cta agg taaacgcaag atgttctaat gcaggtatca         1870
Gln Lys Ala His Ile Leu Arg
                540 gaagtgaaaa gcataccaac ttctttattc ctttacattt ttaattattc atgaatccca    1930 atccatcttc tttcacttgc tttggcttgt gttttcacaa tgccaatttg gattgaccga    1990 agttttatat taacttgctg cttattcgat caggtggatt tattttcctt cttattgtct    2050 ctttttcaaag gaatcaattc ttacgataat ttaacagtgt aatctgggat aattatatta   2110 atcaagtttc tgtttccctt aacatcaata aagttaaaaa attccatcaa aggggttatc    2170 tttatacttc cagaaacacc ccagactgcc actataaaaa cagtattata taaatcaacg    2230 aaccatttca tcaacccacc agccaaacct gtaaccaaca tttagtagtg attaattggt    2290 ttctcctctc ttcgcataat caccagtggg tccaaattcc atatcttctg tcctgactag    2350 gactctctgt gagaaggaag tcacaatgag ttatatgttt tcctgctaga ggcttttta    2410 atttgttctg tttctccaga cttcttatca gctgattatt cagtagcaca taattcacag    2470 tcactgaaaa atctctccag gattatacat acttagattt cctcttctgt atgctggatg    2530 gccaaacagc aggagacagt aggaagagca tccctgctgt cttgcaaagt aaatcagtta    2590 gactacactt accccaattt gatttcctcc ttcatcttct ctgacagctt ttgaaagact    2650 ttccagatga acctgcgttc tgacatcact atgcacttga acaa                     2694
```

<210> SEQ ID NO 5
<211> LENGTH: 542
<212> TYPE: PRT
<213> ORGANISM: Homo sapiens -continued

```
<400> SEQUENCE: 5

Met Pro Val Met Lys Gly Leu Leu Ala Pro Gln Asn Thr Phe Leu Asp
  1               5                  10                  15

Thr Ile Ala Thr Arg Phe Asp Gly Thr His Ser Asn Phe Ile Leu Ala
             20                  25                  30

Asn Ala Gln Val Ala Lys Gly Phe Pro Ile Val Tyr Cys Ser Asp Gly
         35                  40                  45

Phe Cys Glu Leu Ala Gly Phe Ala Arg Thr Glu Val Met Gln Lys Ser
     50                  55                  60

Cys Ser Cys Lys Phe Leu Phe Gly Val Glu Thr Asn Glu Gln Leu Met
 65                  70                  75                  80

Leu Gln Ile Glu Lys Ser Leu Glu Glu Lys Thr Glu Phe Lys Gly Glu
                 85                  90                  95

Ile Met Phe Tyr Lys Lys Asn Gly Ser Pro Phe Trp Cys Leu Leu Asp
                100                 105                 110

Ile Val Pro Ile Lys Asn Glu Lys Gly Asp Val Val Leu Phe Leu Ala
            115                 120                 125

Ser Phe Lys Asp Ile Thr Asp Thr Lys Val Lys Ile Thr Pro Glu Asp
130                 135                 140

Lys Lys Glu Asp Lys Val Lys Gly Arg Ser Arg Ala Gly Thr His Phe
145                 150                 155                 160

Asp Ser Ala Arg Arg Ser Arg Ala Val Leu Tyr His Ile Ser Gly
                165                 170                 175

His Leu Gln Arg Arg Glu Lys Asn Lys Leu Lys Ile Asn Asn Asn Val
                180                 185                 190

Phe Val Asp Lys Pro Ala Phe Pro Glu Tyr Lys Val Ser Asp Ala Lys
            195                 200                 205

Lys Ser Lys Phe Ile Leu Leu His Phe Ser Thr Phe Lys Ala Gly Trp
210                 215                 220

Asp Trp Leu Ile Leu Leu Ala Thr Phe Tyr Val Ala Val Thr Val Pro
225                 230                 235                 240

Tyr Asn Val Cys Phe Ile Gly Asn Asp Asp Leu Ser Thr Thr Arg Ser
                245                 250                 255

Thr Thr Val Ser Asp Ile Ala Val Glu Ile Leu Phe Ile Ile Asp Ile
            260                 265                 270

Ile Leu Asn Phe Arg Thr Thr Tyr Val Ser Lys Ser Gly Gln Val Ile
275                 280                 285

Phe Glu Ala Arg Ser Ile Cys Ile His Tyr Val Thr Thr Trp Phe Ile
290                 295                 300

Ile Asp Leu Ile Ala Ala Leu Pro Phe Asp Leu Leu Tyr Ala Phe Asn
305                 310                 315                 320

Val Thr Val Val Ser Leu Val His Leu Leu Lys Thr Val Arg Leu Leu
            325                 330                 335

Arg Leu Leu Arg Leu Leu Gln Lys Leu Asp Arg Tyr Ser Gln His Ser
                340                 345                 350

Thr Ile Val Leu Thr Leu Leu Met Ser Met Phe Ala Leu Leu Ala His
            355                 360                 365

Trp Met Ala Cys Ile Trp Tyr Val Ile Gly Lys Met Glu Arg Glu Asp
            370                 375                 380

Asn Ser Leu Leu Lys Trp Glu Val Gly Trp Leu His Glu Leu Gly Lys
385                 390                 395                 400

Arg Leu Glu Ser Pro Tyr Tyr Gly Asn Asn Thr Leu Gly Gly Pro Ser
                405                 410                 415
```

```
Ile Arg Ser Ala Tyr Ile Ala Ala Leu Tyr Phe Thr Leu Ser Ser Leu
            420                 425                 430

Thr Ser Val Gly Phe Gly Asn Val Ser Ala Asn Thr Asp Ala Glu Lys
        435                 440                 445

Ile Phe Ser Ile Cys Thr Met Leu Ile Gly Ala Leu Met His Ala Leu
        450                 455                 460

Val Phe Gly Asn Val Thr Ala Ile Ile Gln Arg Met Tyr Ser Arg Trp
465                 470                 475                 480

Ser Leu Tyr His Thr Arg Thr Lys Asp Leu Lys Asp Phe Ile Arg Val
            485                 490                 495

His His Leu Pro Gln Gln Leu Lys Gln Arg Met Leu Glu Tyr Phe Gln
                500                 505                 510

Thr Thr Trp Ser Val Asn Asn Gly Ile Asp Ser Asn Glu Val Met Phe
            515                 520                 525

Ile Ser His Val Val Phe Arg Gln Lys Ala His Ile Leu Arg
            530                 535                 540
```

<210> SEQ ID NO 6
<211> LENGTH: 1626
<212> TYPE: DNA
<213> ORGANISM: Homo sapiens
<220> FEATURE:
<221> NAME/KEY: CDS
<222> LOCATION: (1)..(1626)

<400> SEQUENCE: 6

```
atg ccg gtt atg aaa gga tta ctg gcg ccg caa aac acc ttc ctg gac      48
Met Pro Val Met Lys Gly Leu Leu Ala Pro Gln Asn Thr Phe Leu Asp
 1               5                  10                  15 acc atc gcc acc cgt ttt gac gga aca cat agc aac ttc atc ctt gcc      96
Thr Ile Ala Thr Arg Phe Asp Gly Thr His Ser Asn Phe Ile Leu Ala
             20                  25                  30 aat gcc cag gtg gct aag ggt ttc ccc ata gtc tac tgt tcc gat ggc     144
Asn Ala Gln Val Ala Lys Gly Phe Pro Ile Val Tyr Cys Ser Asp Gly
         35                  40                  45 ttc tgc gag ctt gct gga ttt gcc cga act gaa gtc atg cag aag agt     192
Phe Cys Glu Leu Ala Gly Phe Ala Arg Thr Glu Val Met Gln Lys Ser
     50                  55                  60 tgt agc tgc aag ttc tta ttt ggg gtt gaa acc aat gag caa ctg atg     240
Cys Ser Cys Lys Phe Leu Phe Gly Val Glu Thr Asn Glu Gln Leu Met
 65                  70                  75                  80 ctt caa ata gaa aag tca ctg gag gag aaa aca gaa ttc aaa gga gaa     288
Leu Gln Ile Glu Lys Ser Leu Glu Glu Lys Thr Glu Phe Lys Gly Glu
                 85                  90                  95 att atg ttc tac aag aaa aac ggg tct cca ttt tgg tgc cta ctg gat     336
Ile Met Phe Tyr Lys Lys Asn Gly Ser Pro Phe Trp Cys Leu Leu Asp
            100                 105                 110 att gtt ccc ata aag aat gaa aaa gga gat gta gta ctt ttt ctg gcc     384
Ile Val Pro Ile Lys Asn Glu Lys Gly Asp Val Val Leu Phe Leu Ala
        115                 120                 125 tcg ttc aaa gat ata aca gat aca aaa gtg aag att act cca gaa gat     432
Ser Phe Lys Asp Ile Thr Asp Thr Lys Val Lys Ile Thr Pro Glu Asp
    130                 135                 140 aaa aaa gaa gac aaa gtc aaa gga aga tca aga gca ggg acc cac ttt     480
Lys Lys Glu Asp Lys Val Lys Gly Arg Ser Arg Ala Gly Thr His Phe
145                 150                 155                 160 gac tca gcc cgg aga cgg agt cga gca gtc ctt tat cac atc tct ggg     528
Asp Ser Ala Arg Arg Arg Ser Arg Ala Val Leu Tyr His Ile Ser Gly
                165                 170                 175
```

```
cac ctg caa aga aga gaa aag aac aaa ttg aaa ata aat aac aat gtt      576
His Leu Gln Arg Arg Glu Lys Asn Lys Leu Lys Ile Asn Asn Val
            180                 185                 190 ttt gta gat aaa cca gca ttt ccg gag tat aaa gtt tct gat gca aaa      624
Phe Val Asp Lys Pro Ala Phe Pro Glu Tyr Lys Val Ser Asp Ala Lys
                195                 200                 205 aag tcc aaa ttc ata ctt ctg cat ttt agc act ttt aaa gct ggc tgg      672
Lys Ser Lys Phe Ile Leu Leu His Phe Ser Thr Phe Lys Ala Gly Trp
        210                 215                 220 gac tgg ctt att ttg ttg gca acg ttt tat gtt gct gtg act gta cct      720
Asp Trp Leu Ile Leu Leu Ala Thr Phe Tyr Val Ala Val Thr Val Pro
225                 230                 235                 240 tac aac gtt tgc ttt att ggc aat gac gac ctg tcc aca act cgg agc      768
Tyr Asn Val Cys Phe Ile Gly Asn Asp Asp Leu Ser Thr Thr Arg Ser
                245                 250                 255 aca acc gtc agt gac att gca gtg gag att ctt ttt att ata gat att      816
Thr Thr Val Ser Asp Ile Ala Val Glu Ile Leu Phe Ile Ile Asp Ile
                260                 265                 270 att tta aat ttc cga aca act tat gtc agc aag tct ggc caa gtt atc      864
Ile Leu Asn Phe Arg Thr Thr Tyr Val Ser Lys Ser Gly Gln Val Ile
        275                 280                 285 ttt gaa gca aga tca att tgc atc cac tat gtc aca acc tgg ttc atc      912
Phe Glu Ala Arg Ser Ile Cys Ile His Tyr Val Thr Thr Trp Phe Ile
290                 295                 300 att gat tta atc gct gcc ctg cct ttt gat ctt ctg tat gct ttc aac      960
Ile Asp Leu Ile Ala Ala Leu Pro Phe Asp Leu Leu Tyr Ala Phe Asn
305                 310                 315                 320 gtc aca gtg gtg tct ctc gtg cat ctt cta aag aca gtg cgc ctc ttg     1008
Val Thr Val Val Ser Leu Val His Leu Leu Lys Thr Val Arg Leu Leu
                325                 330                 335 cgt ctt ttg cgt ctg ctg cag aag tta gac cgc tat tcc caa cac agt     1056
Arg Leu Leu Arg Leu Leu Gln Lys Leu Asp Arg Tyr Ser Gln His Ser
                340                 345                 350 act atc gtc ctg act ctg ctc atg tcc atg ttt gca ctc ctt gca cac     1104
Thr Ile Val Leu Thr Leu Leu Met Ser Met Phe Ala Leu Leu Ala His
                355                 360                 365 tgg atg gcg tgt atc tgg tac gtc att gga aaa atg gag agg gaa gac     1152
Trp Met Ala Cys Ile Trp Tyr Val Ile Gly Lys Met Glu Arg Glu Asp
        370                 375                 380 aac agc ctt ctg aag tgg gaa gtt ggt tgg ctt cat gag ttg gga aag     1200
Asn Ser Leu Leu Lys Trp Glu Val Gly Trp Leu His Glu Leu Gly Lys
385                 390                 395                 400 aga ctg gaa tct cca tac tat ggc aac aat acc ttg ggg ggc ccg tcg     1248
Arg Leu Glu Ser Pro Tyr Tyr Gly Asn Asn Thr Leu Gly Gly Pro Ser
                405                 410                 415 atc cga agt gcc tat att gcc gct ctg tac ttc acg ctg agc agc ctc     1296
Ile Arg Ser Ala Tyr Ile Ala Ala Leu Tyr Phe Thr Leu Ser Ser Leu
                420                 425                 430 acc agc gtg ggt ttt ggg aac gtc tct gct aat aca gat gca gaa aag     1344
Thr Ser Val Gly Phe Gly Asn Val Ser Ala Asn Thr Asp Ala Glu Lys
                435                 440                 445 atc ttc tcc atc tgc acc atg ctg att ggt gcc ttg atg cac gcc ttg     1392
Ile Phe Ser Ile Cys Thr Met Leu Ile Gly Ala Leu Met His Ala Leu
450                 455                 460 gtg ttt gga aac gtg aca gca atc ata cag agg atg tac tcc aga tgg     1440
Val Phe Gly Asn Val Thr Ala Ile Ile Gln Arg Met Tyr Ser Arg Trp
465                 470                 475                 480 tcc ctc tat cac act aga act aag gat ctg aaa gat ttc atc cgt gtc     1488
Ser Leu Tyr His Thr Arg Thr Lys Asp Leu Lys Asp Phe Ile Arg Val
```

-continued

```
                   485                 490                 495
cat cac ttg ccc caa caa ctc aag cag agg atg ctc gaa tat ttt caa    1536
His His Leu Pro Gln Gln Leu Lys Gln Arg Met Leu Glu Tyr Phe Gln
            500                 505                 510 aca acc tgg tca gtc aac aat gga ata gat tca aat gag gta atg ttc    1584
Thr Thr Trp Ser Val Asn Asn Gly Ile Asp Ser Asn Glu Val Met Phe
            515                 520                 525 att tct cat gtt gtt ttc agg cag aaa gca cat att cta agg            1626
Ile Ser His Val Val Phe Arg Gln Lys Ala His Ile Leu Arg
            530                 535                 540

<210> SEQ ID NO 7
<211> LENGTH: 1132
<212> TYPE: DNA
<213> ORGANISM: Homo sapiens
<220> FEATURE:
<221> NAME/KEY: CDS
<222> LOCATION: (263)..(1132)

<400> SEQUENCE: 7
gcggccgcgg ggcctggagc ccgggatttg tgggcggcga gggcgcgagg ggccgcgcgc     60
catgctccgg gccccgacgg cgcggacgcc ccctcgcgcg ccagcgtccg gcgcgacccc    120
ggatcccggt ctgcgcattg ccccccgacg gctgcgctag ggagcgcggg gcccggcggg    180
gggcggccga gctgggcgcc ctcccccggc gcggagtccc cgcaccccgg agggatgggg    240
cgggcagccg cgggcgccta ag atg ccg gcc atg cgg ggc ctc ctg gcg ccg     292
                        Met Pro Ala Met Arg Gly Leu Leu Ala Pro
                          1               5                  10 cag aac acc ttc ctg gac acc atc gct acg cgc ttc gac ggc acg cac     340
Gln Asn Thr Phe Leu Asp Thr Ile Ala Thr Arg Phe Asp Gly Thr His
                15                  20                  25 agt aac ttc gtg ctg ggc aac gcc cag gtg gcg ggg ctc ttc ccc gtg     388
Ser Asn Phe Val Leu Gly Asn Ala Gln Val Ala Gly Leu Phe Pro Val
            30                  35                  40 gtc tac tgc tct gat ggc ttc tgt gac ctc acg ggc ttc tcc cgg gct     436
Val Tyr Cys Ser Asp Gly Phe Cys Asp Leu Thr Gly Phe Ser Arg Ala
        45                  50                  55 gag gtc atg cag cgg ggc tgt gcc tgc tcc ttc ctt tat ggg cca gac     484
Glu Val Met Gln Arg Gly Cys Ala Cys Ser Phe Leu Tyr Gly Pro Asp
    60                  65                  70 acc agt gag ctc gtc cgc caa cag atc cgc aag gcc ctg gac gag cac     532
Thr Ser Glu Leu Val Arg Gln Gln Ile Arg Lys Ala Leu Asp Glu His
75                  80                  85                  90 aag gag ttc aag gct gag ctg atc ctg tac cgg aag agc ggg ctc ccg     580
Lys Glu Phe Lys Ala Glu Leu Ile Leu Tyr Arg Lys Ser Gly Leu Pro
                95                 100                 105 ttc tgg tgt ctc ctg gat gtg ata ccc ata aag aat gag aaa ggg gag     628
Phe Trp Cys Leu Leu Asp Val Ile Pro Ile Lys Asn Glu Lys Gly Glu
            110                 115                 120 gtg gct ctc ttc cta gtc tct cac aag gac atc agc gaa acc aag aac     676
Val Ala Leu Phe Leu Val Ser His Lys Asp Ile Ser Glu Thr Lys Asn
        125                 130                 135 cga ggg ggc ccc gac aga tgg aag gag aca ggt ggt ggc cgg cgc cga     724
Arg Gly Gly Pro Asp Arg Trp Lys Glu Thr Gly Gly Gly Arg Arg Arg
    140                 145                 150 tat ggc cgg gca cga tcc aaa ggc ttc aat gcc aac cgg cgg cgg agc     772
Tyr Gly Arg Ala Arg Ser Lys Gly Phe Asn Ala Asn Arg Arg Arg Ser
155                 160                 165                 170 cgg gcc gtg ctc tac cac ctg tcc ggg cac ctg cag aag cag ccc aag     820
Arg Ala Val Leu Tyr His Leu Ser Gly His Leu Gln Lys Gln Pro Lys
```

```
                        175                 180                 185
ggc aag cac aag ctc aat aag ggg gtg ttt ggg gag aaa cca aac ttg      868
Gly Lys His Lys Leu Asn Lys Gly Val Phe Gly Glu Lys Pro Asn Leu
            190                 195                 200 cct gag tac aaa gta gcc gcc atc cgg aag tcg ccc ttc atc ctg ttg      916
Pro Glu Tyr Lys Val Ala Ala Ile Arg Lys Ser Pro Phe Ile Leu Leu
        205                 210                 215 cac tgt ggg gca ctg aga gcc acc tgg gat ggc ttc atc ctg ctc gcc      964
His Cys Gly Ala Leu Arg Ala Thr Trp Asp Gly Phe Ile Leu Leu Ala
    220                 225                 230 aca ctc tat gtg gct gtc act gtg ccc tac agc gtg tgt gtg agc aca     1012
Thr Leu Tyr Val Ala Val Thr Val Pro Tyr Ser Val Cys Val Ser Thr
235                 240                 245                 250 gca cgg gag ccc agt gcc gcc cgc ggc ccg ccc agc gtc tgt gac ctg     1060
Ala Arg Glu Pro Ser Ala Ala Arg Gly Pro Pro Ser Val Cys Asp Leu
                255                 260                 265 gcc gtg gag gtc ctc ttc atc ctt gac att gtg ctg aat ttc cgt acc     1108
Ala Val Glu Val Leu Phe Ile Leu Asp Ile Val Leu Asn Phe Arg Thr
            270                 275                 280 ctc gtg cca cct cgt gcc aag ctt                                      1132
Leu Val Pro Pro Arg Ala Lys Leu
        285                 290
```

<210> SEQ ID NO 8
<211> LENGTH: 290
<212> TYPE: PRT
<213> ORGANISM: Homo sapiens

<400> SEQUENCE: 8

```
Met Pro Ala Met Arg Gly Leu Leu Ala Pro Gln Asn Thr Phe Leu Asp
 1               5                  10                  15

Thr Ile Ala Thr Arg Phe Asp Gly Thr His Ser Asn Phe Val Leu Gly
            20                  25                  30

Asn Ala Gln Val Ala Gly Leu Phe Pro Val Val Tyr Cys Ser Asp Gly
        35                  40                  45

Phe Cys Asp Leu Thr Gly Phe Ser Arg Ala Glu Val Met Gln Arg Gly
    50                  55                  60

Cys Ala Cys Ser Phe Leu Tyr Gly Pro Asp Thr Ser Glu Leu Val Arg
65                  70                  75                  80

Gln Gln Ile Arg Lys Ala Leu Asp Glu His Lys Glu Phe Lys Ala Glu
                85                  90                  95

Leu Ile Leu Tyr Arg Lys Ser Gly Leu Pro Phe Trp Cys Leu Leu Asp
            100                 105                 110

Val Ile Pro Ile Lys Asn Glu Lys Gly Glu Val Ala Leu Phe Leu Val
        115                 120                 125

Ser His Lys Asp Ile Ser Glu Thr Lys Asn Arg Gly Gly Pro Asp Arg
    130                 135                 140

Trp Lys Glu Thr Gly Gly Gly Arg Arg Tyr Gly Arg Ala Arg Ser
145                 150                 155                 160

Lys Gly Phe Asn Ala Asn Arg Arg Ser Arg Ala Val Leu Tyr His
                165                 170                 175

Leu Ser Gly His Leu Gln Lys Gln Pro Lys Gly Lys His Lys Leu Asn
            180                 185                 190

Lys Gly Val Phe Gly Glu Lys Pro Asn Leu Pro Glu Tyr Lys Val Ala
        195                 200                 205

Ala Ile Arg Lys Ser Pro Phe Ile Leu Leu His Cys Gly Ala Leu Arg
    210                 215                 220
```

```
Ala Thr Trp Asp Gly Phe Ile Leu Leu Ala Thr Leu Tyr Val Ala Val
225                 230                 235                 240

Thr Val Pro Tyr Ser Val Cys Val Ser Thr Ala Arg Glu Pro Ser Ala
            245                 250                 255

Ala Arg Gly Pro Pro Ser Val Cys Asp Leu Ala Val Glu Val Leu Phe
            260                 265                 270

Ile Leu Asp Ile Val Leu Asn Phe Arg Thr Leu Val Pro Pro Arg Ala
            275                 280                 285

Lys Leu
    290

<210> SEQ ID NO 9
<211> LENGTH: 870
<212> TYPE: DNA
<213> ORGANISM: Homo sapiens
<220> FEATURE:
<221> NAME/KEY: CDS
<222> LOCATION: (1)..(870)

<400> SEQUENCE: 9 atg ccg gcc atg cgg ggc ctc ctg gcg ccg cag aac acc ttc ctg gac      48
Met Pro Ala Met Arg Gly Leu Leu Ala Pro Gln Asn Thr Phe Leu Asp
1               5                   10                  15 acc atc gct acg cgc ttc gac ggc acg cac agt aac ttc gtg ctg ggc      96
Thr Ile Ala Thr Arg Phe Asp Gly Thr His Ser Asn Phe Val Leu Gly
                20                  25                  30 aac gcc cag gtg gcg ggg ctc ttc ccc gtg gtc tac tgc tct gat ggc     144
Asn Ala Gln Val Ala Gly Leu Phe Pro Val Val Tyr Cys Ser Asp Gly
            35                  40                  45 ttc tgt gac ctc acg ggc ttc tcc cgg gct gag gtc atg cag cgg ggc     192
Phe Cys Asp Leu Thr Gly Phe Ser Arg Ala Glu Val Met Gln Arg Gly
        50                  55                  60 tgt gcc tgc tcc ttc ctt tat ggg cca gac acc agt gag ctc gtc cgc     240
Cys Ala Cys Ser Phe Leu Tyr Gly Pro Asp Thr Ser Glu Leu Val Arg
65                  70                  75                  80 caa cag atc cgc aag gcc ctg gac gag cac aag gag ttc aag gct gag     288
Gln Gln Ile Arg Lys Ala Leu Asp Glu His Lys Glu Phe Lys Ala Glu
                85                  90                  95 ctg atc ctg tac cgg aag agc ggg ctc ccg ttc tgg tgt ctc ctg gat     336
Leu Ile Leu Tyr Arg Lys Ser Gly Leu Pro Phe Trp Cys Leu Leu Asp
            100                 105                 110 gtg ata ccc ata aag aat gag aaa ggg gag gtg gct ctc ttc cta gtc     384
Val Ile Pro Ile Lys Asn Glu Lys Gly Glu Val Ala Leu Phe Leu Val
        115                 120                 125 tct cac aag gac atc agc gaa acc aag aac cga ggg ggc ccc gac aga     432
Ser His Lys Asp Ile Ser Glu Thr Lys Asn Arg Gly Gly Pro Asp Arg
130                 135                 140 tgg aag gag aca ggt ggt ggc cgg cgc cga tat ggc cgg gca cga tcc     480
Trp Lys Glu Thr Gly Gly Gly Arg Arg Arg Tyr Gly Arg Ala Arg Ser
145                 150                 155                 160 aaa ggc ttc aat gcc aac cgg cgg cgg agc cgg gcc gtg ctc tac cac     528
Lys Gly Phe Asn Ala Asn Arg Arg Arg Ser Arg Ala Val Leu Tyr His
                165                 170                 175 ctg tcc ggg cac ctg cag aag cag ccc aag ggc aag cac aag ctc aat     576
Leu Ser Gly His Leu Gln Lys Gln Pro Lys Gly Lys His Lys Leu Asn
            180                 185                 190 aag ggg gtg ttt ggg gag aaa cca aac ttg cct gag tac aaa gta gcc     624
Lys Gly Val Phe Gly Glu Lys Pro Asn Leu Pro Glu Tyr Lys Val Ala
        195                 200                 205
```

```
gcc atc cgg aag tcg ccc ttc atc ctg ttg cac tgt ggg gca ctg aga        672
Ala Ile Arg Lys Ser Pro Phe Ile Leu Leu His Cys Gly Ala Leu Arg
    210                 215                 220 gcc acc tgg gat ggc ttc atc ctg ctc gcc aca ctc tat gtg gct gtc        720
Ala Thr Trp Asp Gly Phe Ile Leu Leu Ala Thr Leu Tyr Val Ala Val
225                 230                 235                 240 act gtg ccc tac agc gtg tgt gtg agc aca gca cgg gag ccc agt gcc        768
Thr Val Pro Tyr Ser Val Cys Val Ser Thr Ala Arg Glu Pro Ser Ala
                245                 250                 255 gcc cgc ggc ccg ccc agc gtc tgt gac ctg gcc gtg gag gtc ctc ttc        816
Ala Arg Gly Pro Pro Ser Val Cys Asp Leu Ala Val Glu Val Leu Phe
            260                 265                 270 atc ctt gac att gtg ctg aat ttc cgt acc ctc gtg cca cct cgt gcc        864
Ile Leu Asp Ile Val Leu Asn Phe Arg Thr Leu Val Pro Pro Arg Ala
        275                 280                 285 aag ctt                                                                 870
Lys Leu
    290

<210> SEQ ID NO 10
<211> LENGTH: 1159
<212> TYPE: PRT
<213> ORGANISM: Homo sapiens

<400> SEQUENCE: 10

Met Pro Val Arg Arg Gly His Val Ala Pro Gln Asn Thr Phe Leu Asp
 1               5                  10                  15

Thr Ile Ile Arg Lys Phe Glu Gly Gln Ser Arg Lys Phe Ile Ile Ala
                20                  25                  30

Asn Ala Arg Val Glu Asn Cys Ala Val Ile Tyr Cys Asn Asp Gly Phe
            35                  40                  45

Cys Glu Leu Cys Gly Tyr Ser Arg Ala Glu Val Met Gln Arg Pro Cys
        50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
               100                 105                 110

Val Pro Val Lys Asn Glu Asp Gly Ala Val Ile Met Phe Ile Leu Asn
           115                 120                 125

Phe Glu Val Val Met Glu Lys Asp Met Val Gly Ser Pro Ala His Asp
       130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
               165                 170                 175

Glu Ser Ser Val Arg Ser Gly Gly Ala Gly Gly Ala Gly Ala Pro Gly
           180                 185                 190

Ala Val Val Val Asp Val Asp Leu Thr Pro Ala Ala Pro Ser Ser Glu
       195                 200                 205

Ser Leu Ala Leu Asp Glu Val Thr Ala Met Asp Asn His Val Ala Gly
   210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
               245                 250                 255
```

-continued

```
Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
        290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365

Asn Val Thr Glu Lys Val Thr Gln Val Leu Ser Leu Gly Ala Asp Val
        370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
                420                 425                 430

Leu Lys Glu Thr Glu Glu Gly Pro Pro Ala Thr Glu Cys Gly Tyr Ala
            435                 440                 445

Cys Gln Pro Leu Ala Val Val Asp Leu Ile Val Asp Ile Met Phe Ile
        450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
                500                 505                 510

Phe Gly Ser Gly Ser Glu Glu Leu Ile Gly Leu Leu Lys Thr Ala Arg
        515                 520                 525

Leu Leu Arg Leu Val Arg Val Ala Arg Lys Leu Asp Arg Tyr Ser Glu
530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Gly Pro Ser Ile Lys
        595                 600                 605

Asp Lys Tyr Val Thr Ala Leu Tyr Phe Thr Phe Ser Ser Leu Thr Ser
        610                 615                 620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
            660                 665                 670
```

```
Tyr His Thr Gln Met Leu Arg Val Arg Glu Phe Ile Arg Phe His Gln
        675                 680                 685

Ile Pro Asn Pro Leu Arg Gln Arg Leu Glu Glu Tyr Phe Gln His Ala
        690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735

Leu Gln His Cys Lys Pro Phe Arg Gly Ala Thr Lys Gly Cys Leu Arg
                740                 745                 750

Ala Leu Ala Met Lys Phe Lys Thr Thr His Ala Pro Pro Gly Asp Thr
                755                 760                 765

Leu Val His Ala Gly Asp Leu Leu Thr Ala Leu Tyr Phe Ile Ser Arg
                770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
                820                 825                 830

Ile His Arg Asp Asp Leu Leu Glu Val Leu Asp Met Tyr Pro Glu Phe
                835                 840                 845

Ser Asp His Phe Trp Ser Ser Leu Glu Ile Thr Phe Asn Leu Arg Asp
850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Val Ser Ala Leu Gly Pro Gly Arg
                900                 905                 910

Ala Gly Ala Gly Pro Ser Ser Arg Gly Arg Pro Gly Gly Pro Trp Gly
                915                 920                 925

Glu Ser Pro Ser Ser Gly Pro Ser Ser Pro Glu Ser Ser Glu Asp Glu
                930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                965                 970                 975

Cys Glu Lys Ser Ser Asp Thr Cys Asn Pro Leu Ser Gly Ala Phe Ser
                980                 985                 990

Gly Val Ser Asn Ile Phe Ser Phe Trp Gly Asp Ser Arg Gly Arg Gln
                995                 1000                1005

Tyr Gln Glu Leu Pro Arg Cys Pro Ala Pro Thr Pro Ser Leu Leu Asn
        1010                1015                1020

Ile Pro Leu Ser Ser Pro Gly Arg Arg Pro Arg Gly Asp Val Glu Ser
1025                1030                1035                1040

Arg Leu Asp Ala Leu Gln Arg Gln Leu Asn Arg Leu Glu Thr Arg Leu
                1045                1050                1055

Ser Ala Asp Met Ala Thr Val Leu Gln Leu Leu Gln Arg Gln Met Thr
                1060                1065                1070

Leu Val Pro Pro Ala Tyr Ser Ala Val Thr Thr Pro Gly Pro Gly Pro
        1075                1080                1085

Thr Ser Thr Ser Pro Leu Leu Pro Val Ser Pro Leu Pro Thr Leu Thr
```

-continued

```
                1090                1095                1100

Leu Asp Ser Leu Ser Gln Val Ser Gln Phe Met Ala Cys Glu Glu Leu
1105                1110                1115                1120

Pro Pro Gly Ala Pro Glu Leu Pro Gln Glu Gly Pro Thr Arg Arg Leu
                1125                1130                1135

Ser Leu Pro Gly Gln Leu Gly Ala Leu Thr Ser Gln Pro Leu His Arg
                1140                1145                1150

His Gly Ser Asp Pro Gly Ser
        1155

<210> SEQ ID NO 11
<211> LENGTH: 1284
<212> TYPE: PRT
<213> ORGANISM: Drosophila melanogaster

<400> SEQUENCE: 11

Met Pro Ala Arg Lys Gly Leu Leu Ala Pro Gln Asn Thr Phe Leu Asp
  1               5                  10                  15

Thr Ile Ala Thr Arg Phe Asp Gly Thr His Ser Asn Phe Val Leu Gly
             20                  25                  30

Asn Ala Gln Ala Asn Gly Asn Pro Ile Val Tyr Cys Ser Asp Gly Phe
         35                  40                  45

Val Asp Leu Thr Gly Tyr Ser Arg Ala Gln Ile Met Gln Lys Gly Cys
     50                  55                  60

Ser Cys His Phe Leu Tyr Gly Pro Asp Thr Lys Glu Glu His Lys Gln
 65                  70                  75                  80

Gln Ile Glu Lys Ser Leu Ser Asn Lys Met Glu Leu Lys Leu Glu Val
                 85                  90                  95

Ile Phe Tyr Lys Lys Glu Gly Ala Pro Phe Trp Cys Leu Phe Asp Ile
            100                 105                 110

Val Pro Ile Lys Asn Glu Lys Arg Asp Val Val Leu Phe Leu Ala Ser
        115                 120                 125

His Lys Asp Ile Thr His Thr Lys Met Leu Glu Met Asn Val Asn Glu
    130                 135                 140

Glu Cys Asp Ser Val Phe Ala Leu Thr Ala Ala Leu Leu Gly Ala Arg
145                 150                 155                 160

Phe Arg Ala Gly Ser Asn Ala Gly Met Leu Gly Leu Gly Leu Pro
                165                 170                 175

Gly Leu Gly Gly Pro Ala Ala Ser Asp Gly Asp Thr Glu Ala Gly Glu
            180                 185                 190

Gly Asn Asn Leu Asp Val Pro Ala Gly Cys Asn Met Gly Arg Arg Arg
        195                 200                 205

Ser Arg Ala Val Leu Tyr Gln Leu Ser Gly His Tyr Lys Pro Glu Lys
    210                 215                 220

Gly Gly Val Lys Thr Lys Leu Lys Leu Gly Asn Asn Phe Met His Ser
225                 230                 235                 240

Thr Glu Ala Pro Phe Pro Glu Tyr Lys Thr Gln Ser Ile Lys Lys Ser
                245                 250                 255

Arg Leu Ile Leu Pro His Tyr Gly Val Phe Lys Gly Ile Trp Asp Trp
            260                 265                 270

Val Ile Leu Val Ala Thr Phe Tyr Val Ala Leu Met Val Pro Tyr Asn
        275                 280                 285

Ala Ala Phe Ala Lys Ala Asp Arg Gln Thr Lys Val Ser Asp Val Ile
    290                 295                 300
```

-continued

```
Val Glu Ala Leu Phe Ile Val Asp Ile Leu Leu Asn Phe Arg Thr Thr
305                 310                 315                 320

Phe Val Ser Arg Lys Gly Glu Val Val Ser Asn Ser Lys Gln Ile Ala
            325                 330                 335

Ile Asn Tyr Leu Arg Gly Trp Phe Ala Leu Asp Leu Leu Ala Ala Leu
            340                 345                 350

Pro Phe Asp His Leu Tyr Ala Ser Asp Leu Tyr Asp Gly Glu Asp Ser
            355                 360                 365

His Ile His Leu Val Lys Leu Thr Arg Leu Leu Arg Leu Ala Arg Leu
370                 375                 380

Leu Gln Lys Ile Asp Arg Tyr Ser Gln His Thr Ala Met Ile Leu Thr
385                 390                 395                 400

Leu Leu Met Phe Ser Phe Thr Leu Ala Ala His Trp Leu Ala Cys Ile
                405                 410                 415

Trp Tyr Val Ile Ala Val Lys Glu Tyr Glu Trp Phe Pro Glu Ser Asn
            420                 425                 430

Ile Gly Trp Leu Gln Leu Leu Ala Glu Arg Lys Asn Ala Ser Val Ala
            435                 440                 445

Ile Leu Thr Thr Ala Glu Thr Tyr Ser Thr Ala Leu Tyr Phe Thr Phe
450                 455                 460

Thr Ser Leu Thr Ser Val Gly Phe Gly Asn Val Ser Ala Asn Thr Thr
465                 470                 475                 480

Ala Glu Lys Val Phe Thr Ile Ile Met Met Leu Ile Gly Ala Leu Met
                485                 490                 495

His Ala Val Val Phe Gly Asn Val Thr Ala Ile Ile Gln Arg Met Tyr
            500                 505                 510

Ser Arg Arg Ser Leu Tyr Glu Ser Lys Trp Arg Asp Leu Lys Asp Phe
            515                 520                 525

Val Ala Leu His Asn Met Pro Lys Glu Leu Lys Gln Arg Ile Glu Asp
530                 535                 540

Tyr Phe Gln Thr Ser Trp Ser Leu Ser His Gly Ile Asp Ile Tyr Glu
545                 550                 555                 560

Thr Leu Arg Glu Phe Pro Glu Glu Leu Arg Gly Asp Val Ser Met His
                565                 570                 575

Leu His Arg Glu Ile Leu Gln Leu Pro Ile Phe Glu Ala Ala Ser Gln
            580                 585                 590

Gly Cys Leu Lys Leu Leu Ser Leu His Ile Lys Thr Asn Phe Cys Ala
            595                 600                 605

Pro Gly Glu Tyr Leu Ile His Lys Gly Asp Ala Leu Asn Tyr Ile Tyr
610                 615                 620

Tyr Leu Cys Asn Gly Ser Met Glu Val Ile Lys Asp Asp Met Val Val
625                 630                 635                 640

Ala Ile Leu Gly Lys Gly Asp Leu Val Gly Ser Asp Ile Asn Val His
                645                 650                 655

Leu Val Ala Thr Ser Asn Gly Gln Met Thr Ala Thr Asn Ser Ala
            660                 665                 670

Gly Gln Asp Val Val Arg Ser Ser Asp Ile Lys Ala Leu Thr
            675                 680                 685

Tyr Cys Asp Leu Lys Cys Ile His Met Gly Gly Leu Val Glu Val Leu
            690                 695                 700

Arg Leu Tyr Pro Glu Tyr Gln Gln Phe Ala Asn Asp Ile Gln His
705                 710                 715                 720

Asp Leu Thr Cys Asn Leu Arg Glu Gly Tyr Glu Asn Gln Asp Ser Asp
```

-continued

```
                    725                 730                 735
Ile Gly Pro Ser Phe Pro Leu Pro Ser Ile Ser Glu Asp Asp Glu Asn
                740                 745                 750

Arg Glu Ala Glu Glu Gly Gly Lys Gly Lys Glu Asn Gly Gly
            755                 760                 765

Gly Pro Pro Ser Gly Ala Ser Pro Leu His Asn Ile Ser Asn Ser Pro
        770                 775                 780

Leu His Ala Thr Arg Ser Pro Leu Leu Gly Met Gly Ser Pro Arg Asn
785                 790                 795                 800

Gln Arg Leu His Gln Arg Gly Arg Ser Leu Ile Thr Leu Arg Glu Thr
                805                 810                 815

Asn Lys Arg His Arg Thr Leu Asn Ala Ala Cys Ser Leu Asp Arg Gly
                820                 825                 830

Ser Phe Glu Glu Pro Glu Pro Leu Glu Glu Gln Ser Ser Gly Gly
                835                 840                 845

Lys Arg Pro Ser Leu Glu Arg Leu Asp Ser Gln Val Ser Thr Leu His
850                 855                 860

Gln Asp Val Ala Gln Leu Ser Ala Glu Val Arg Asn Ala Ile Ser Ala
865                 870                 875                 880

Leu Gln Glu Met Thr Phe Thr Ser Asn Ala Met Thr Ser His Ser Ser
                885                 890                 895

Leu Lys Phe Pro Pro Ala Arg Ser Ile Pro Asn Ile Ser Gly Val Ala
                900                 905                 910

Gly Thr Arg Ser Gly Val Ala Val Glu His Gly Leu Met Gly Gly Val
                915                 920                 925

Leu Ala Ala Ala Glu Leu Ala Ala Met Gln Arg Ser Ser Ser His Pro
                930                 935                 940

Pro Glu Val Trp Gly Arg Asp Val Gln Leu Pro Thr Ser Asn Thr Ala
945                 950                 955                 960

Ser Ser Lys Ala Pro Ser Pro Val Glu Pro Lys Lys Thr Met Thr Ser
                965                 970                 975

Arg Ser Ser Gln Thr Asp Phe Tyr Arg Ile Asp Phe Pro Thr Phe Glu
                980                 985                 990

Arg Phe Val Leu Ala Asn Pro Arg Leu Val Leu Gly Leu Leu Gly Ile
                995                 1000                1005

Glu Pro Ala Ile Lys Asn Glu Met Asp Leu Leu Gln Gln Lys Gln Thr
        1010                1015                1020

Leu Gln Ile Ser Pro Leu Asn Thr Ile Asp Glu Cys Val Ser Pro Ser
1025                1030                1035                1040

Asp His Asn Leu Ala Ser Ser Lys Glu Arg Leu Ile Thr Ser Ser Ala
                1045                1050                1055

Val Pro Thr Pro Gly Arg Ile Tyr Pro Pro Leu Asp Asp Glu Asn Ser
                1060                1065                1070

Asn Asp Phe Arg Trp Thr Met Lys His Ser Ala Ser His His Ser Cys
                1075                1080                1085

Cys Lys Ser Thr Asp Ala Leu Leu Ser Pro Glu Glu Gln Pro Pro Ile
                1090                1095                1100

Ser Ile Leu Pro Val Asp Ala Thr Pro Ala Pro Ser Val Gln Glu Val
1105                1110                1115                1120

Arg Ser Ser Lys Arg Ser Ile Arg Lys Ser Thr Ser Gly Ser Asn Ser
                1125                1130                1135

Ser Leu Ser Ser Ser Ser Ser Ser Asn Ser Cys Leu Val Ser Gln
                1140                1145                1150
```

```
Ser Thr Gly Asn Leu Thr Thr Thr Asn Ala Ser Val His Cys Ser Asn
        1155                1160                1165
Ser Ser Gln Ser Val Ala Ser Val Ala Thr Thr Arg Arg Ala Ser Trp
        1170                1175                1180
Lys Leu Gln His Ser Arg Ser Gly Glu Tyr Arg Arg Leu Ser Glu Ala
1185                1190                1195                1200
Thr Ala Glu Tyr Ser Pro Pro Ala Lys Thr Pro Leu Pro Val Ala Gly
                1205                1210                1215
Val Ser Tyr Gly Gly Asp Glu Glu Glu Ser Val Glu Leu Leu Gly Pro
                1220                1225                1230
Arg Arg Asn Ser Arg Pro Ile Leu Leu Gly Val Ser Gln Asn Gln Gly
        1235                1240                1245
Gln Gly Gln Ala Met Asn Phe Arg Phe Ser Ala Gly Asp Ala Asp Lys
        1250                1255                1260
Leu Glu Lys Gly Leu Arg Gly Leu Pro Ser Thr Arg Ser Leu Arg Asp
1265                1270                1275                1280

Pro Ser Ser Lys

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Consensus
      sequence for the p-loop
<223> OTHER INFORMATION: Xaa at positions 4, 5 and 15 may be Phe, Tyr
      or Val
<223> OTHER INFORMATION: Trp
<223> OTHER INFORMATION: Xaa at positions 7, 10, or 18 may be Met, Ile,
      Leu or Val
<223> OTHER INFORMATION: Xaa at positions 19, 21, and 23 through 25 may
      be any amino acid
<223> OTHER INFORMATION: Xaa at positions 8, 9, and 12 may be either Ser
      or Val
<223> OTHER INFORMATION: Thr
<221> NAME/KEY: PEPTIDE
<222> LOCATION: (1)
<223> OTHER INFORMATION: Xaa = Asp or Thr
<221> NAME/KEY: PEPTIDE
<222> LOCATION: (2)
<223> OTHER INFORMATION: Xaa = Ala or Ser
<221> NAME/KEY: PEPTIDE
<222> LOCATION: (3)
<223> OTHER INFORMATION: Xaa = Leu or Phe
<221> NAME/KEY: PEPTIDE
<222> LOCATION: (6)
<223> OTHER INFORMATION: Xaa = Ala or Thr
<221> NAME/KEY: PEPTIDE
<222> LOCATION: (17)
<223> OTHER INFORMATION: Xaa = Asn or Asp
<221> NAME/KEY: PEPTIDE
<222> LOCATION: (20)
<223> OTHER INFORMATION: Xaa = Ala or Pro

<400> SEQUENCE: 12

Xaa Xaa Xaa Xaa Xaa Xaa Xaa Xaa Xaa Xaa Thr Xaa Val Gly Xaa Gly
1               5                   10                  15
Xaa Xaa Xaa Xaa Xaa Thr Xaa Xaa Xaa
            20                  25

<210> SEQ ID NO 13
<211> LENGTH: 80
<212> TYPE: PRT
<213> ORGANISM: Artificial Sequence
<220> FEATURE:
<223> OTHER INFORMATION: Description of Artificial Sequence: Consensus
```

```
         sequence for the cyclic nucleotide-binding domain
<223> OTHER INFORMATION: Xaas at positions 1 through 3, 8 through 10,
      25, 28, 30, 45 through 50, and 68 through 69 may be
      any amino acid
<221> NAME/KEY: PEPTIDE
<222> LOCATION: (5)
<223> OTHER INFORMATION: Xaa = Glu or Asp
<221> NAME/KEY: PEPTIDE
<222> LOCATION: (6)
<223> OTHER INFORMATION: Xaa = Thr, Tyr, Leu or Cys
<221> NAME/KEY: PEPTIDE
<222> LOCATION: (7)
<223> OTHER INFORMATION: Xaa = Leu or any amino acid
<221> NAME/KEY: PEPTIDE
<222> LOCATION: (12)
<223> OTHER INFORMATION: Xaa = Asp, Ser or Arg
<221> NAME/KEY: PEPTIDE
<222> LOCATION: (13)..(22)
<223> OTHER INFORMATION: Any 3 of the Xaas at positions 13 through 22
      may be absent - intended to equal a range of 7-10 amino acids
<221> NAME/KEY: PEPTIDE
<222> LOCATION: (24)
<223> OTHER INFORMATION: Xaa = Ser or Lys
<221> NAME/KEY: PEPTIDE
<222> LOCATION: (26)
<223> OTHER INFORMATION: Xaa = Glu, Ala or Asn
<221> NAME/KEY: PEPTIDE
<222> LOCATION: (27)
<223> OTHER INFORMATION: Xaa = Val or Ile
<221> NAME/KEY: PEPTIDE
<222> LOCATION: (29)
<223> OTHER INFORMATION: Xaa = Arg or Lys
<221> NAME/KEY: PEPTIDE
<222> LOCATION: (31)
<223> OTHER INFORMATION: Xaa = Asp or Glu
<221> NAME/KEY: PEPTIDE
<222> LOCATION: (32)..(43)
<223> OTHER INFORMATION: Any 5 of the Xaas at positions 32 through 43
      may be absent - intended to equal a range of 7-12 amino acids
<221> NAME/KEY: PEPTIDE
<222> LOCATION: (51)
<223> OTHER INFORMATION: Xaa = Asp or Glu
<221> NAME/KEY: PEPTIDE
<222> LOCATION: (52)..(66)
<223> OTHER INFORMATION: Any 7 of the Xaas in positions 52 through 66
      may be absent - intended to equal a range of 9-15 amino acids
<221> NAME/KEY: PEPTIDE
<222> LOCATION: (67)
<223> OTHER INFORMATION: Xaa = Ala or Thr
<221> NAME/KEY: PEPTIDE
<222> LOCATION: (70)
<223> OTHER INFORMATION: Xaa = Asp, Ala or Val
<221> NAME/KEY: PEPTIDE
<222> LOCATION: (71)..(80)
<223> OTHER INFORMATION: Any 5 of the Xaas at positions 71 through 80
      may be absent - intended to equal a range of 5-10 amino acids

<400> SEQUENCE: 13

Xaa Xaa Xaa Gly Xaa Xaa Xaa Xaa Xaa Xaa Gly Xaa Xaa Xaa Xaa Xaa
 1               5                  10                  15

Xaa Xaa Xaa Xaa Xaa Xaa Gly Xaa Xaa Xaa Xaa Xaa Xaa Xaa Xaa
             20                  25                  30

Xaa Xaa Xaa Xaa Xaa Xaa Xaa Xaa Xaa Xaa Xaa Gly Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

<210> SEQ ID NO 14
<211> LENGTH: 5955
<212> TYPE: DNA
<213> ORGANISM: Homo sapiens
```

```
<220> FEATURE:
<221> NAME/KEY: exon
<222> LOCATION: (196)..(1770)
<221> NAME/KEY: intron
<222> LOCATION: (1771)..(2618)
<221> NAME/KEY: exon
<222> LOCATION: (2619)..(4364)
<223> OTHER INFORMATION: At position 5625, n=any nucleic acid

<400> SEQUENCE: 14
cctgccacag ccggggcggc tggaactctc tcccttctc cctccatcct tccacttccc      60
ctgctcggcc ccgccgtcag gccgggtccc ccttccctgc cgtcatcagg ttccccttct    120
cccttcttgg cactttcctt tcgaaccatc cttctggaca aactttgatg gagaatttca    180
caccacgctg gaaaa atg ccg gtt atg aaa gga tta ctg gcg ccg caa aac    231
acc ttc ctg gac acc atc gcc acc cgt ttt gac gga aca cat agc aac      279
ttc atc ctt gcc aat gcc cag gtg gct aag ggt ttc ccc ata gtc tac      327
tgt tcc gat ggc ttc tgc gag ctt gct gga ttt gcc cga act gaa gtc      375
atg cag aag agt tgt agc tgc aag ttc tta ttt ggg gtt gaa acc aat      423
gag caa ctg atg ctt caa ata gaa aag tca ctg gag gag aaa aca gaa      471
ttc aaa gga gaa att atg ttc tac aag aaa aac ggg tct cca ttt tgg      519
tgc cta ctg gat att gtt ccc ata aag aat gaa aaa gga gat gta gta      567
ctt ttt ctg gcc tcg ttc aaa gat ata aca gat aca aaa gtg aag att      615
act cca gaa gat aaa aaa gaa gac aaa gtc aaa gga aga tca aga gca      663
ggg acc cac ttt gac tca gcc cgg aga cgg agt cga gca gtc ctt tat      711
cac atc tct ggg cac ctg caa aga aga gaa aag aac aaa ttg aaa ata      759
aat aac aat gtt ttt gta gat aaa cca gca ttt ccg gag tat aaa gtt      807
tct gat gca aaa aag tcc aaa ttc ata ctt ctg cat ttt agc act ttt      855
aaa gct ggc tgg gac tgg ctt att ttg ttg gca acg ttt tat gtt gct      903
gtg act gta cct tac aac gtt tgc ttt att ggc aat gac gac ctg tcc      951
aca act cgg agc aca acc gtc agt gac att gca gtg gag att ctt ttt      999
att ata gat att att tta aat ttc cga aca act tat gtc agc aag tct     1047
ggc caa gtt atc ttt gaa gca aga tca att tgc atc cac tat gtc aca     1095
acc tgg ttc atc att gat tta atc gct gcc ctg cct ttt gat ctt ctg     1143
tat gct ttc aac gtc aca gtg gtg tct ctc gtg cat ctt cta aag aca     1191
gtg cgc ctc ttg cgt ctt ttg cgt ctg ctg cag aag tta gac cgc tat     1239
tcc caa cac agt act atc gtc ctg act ctg ctc atg tcc atg ttt gca     1287
ctc ctt gca cac tgg atg gcg tgt atc tgg tac gtc att gga aaa atg     1335
gag agg gaa gac aac agc ctt ctg aag tgg gaa gtt ggt tgg ctt cat     1383
gag ttg gga aag aga ctg gaa tct cca tac tat ggc aac aat acc ttg     1431
ggg ggc ccg tcg atc cga agt gcc tat att gcc gct ctg tac ttc acg     1479
ctg agc agc ctc acc agc gtg ggt ttt ggg aac gtc tct gct aat aca     1527
gat gca gaa aag atc ttc tcc atc tgc acc atg ctg att ggt gcc ttg     1575
atg cac gcc ttg gtg ttt gga aac gtg aca gca atc ata cag agg atg     1623
tac tcc aga tgg tcc ctc tat cac act aga act aag gat ctg aaa gat     1671
```

```
ttc atc cgt gtc cat cac ttg ccc caa caa ctc aag cag agg atg ctc    1719 gaa tat ttt caa aca acc tgg tca gtc aac aat gga ata gat tca aat    1767 gag gtaatgttca tttctcatgt tgttttcagg cagaaagcac atattctaag         1820
gtaaacgcaa gatgttctaa tgcaggtatc agaagtgaaa agcataccaa cttctttatt  1880
cctttacatt tttaattatt catgaatccc aatccatctt ctttcacttg ctttggcttg  1940
tgttttcaca atgccaattt ggattgaccg aagttttata ttaacttgct gcttattcga  2000
tcaggtggat ttattttcct tcttattgtc tcttttcaaa ggaatcaatt cttacgataa  2060
tttaacagtg taatctggga taattatatt aatcaagttt ctgtttccct aacatcaat   2120 aaagttaaaa aattccatca aagggttat ctttatactt ccagaaacac cccagactgc   2180
cactataaaa acagtattat ataaatcaac gaaccatttc atcaacccac cagccaaacc  2240
tgtaaccaac atttagtagt gattaattgg tttctcctct cttcgcataa tcaccagtgg  2300
gtccaaattc catatcttct gtcctgacta ggactctctg tgagaaggaa gtcacaatga  2360
gttatatgtt ttcctgctag aggctttttt aatttgttct gtttctccag acttcttatc  2420
agctgattat tcagtagcac ataattcaca gtcactgaaa aatctctcca ggattataca  2480
tacttagatt tcctcttctg tatgctggat ggccaaacag caggagacag taggaagagc  2540
atccctgctg tcttgcaaag taaatcagtt agactacact taccccaatt tgatttcctc  2600
cttcatcttc tctgacag ctt ttg aaa gac ttt cca gat gaa ctg cgt tct   2651 gac atc act atg cac ttg aac aag gag atc tta cag ttg tcc ctt ttt   2699 gaa tgt gcc agc cgg ggc tgc ctc agg tct ctg tct cta cac atc aaa   2747 acc tct ttc tgt gct ccg ggg gag tat ctg ctg cgt caa ggg gat gct   2795 ttg cag gcc atc tac ttt gta tgc tcg ggc tcc atg gaa gtt ctt aaa   2843 gac agc atg gtg ctg gct att ctt ggg aaa ggg gat tta att gga gca   2891 aat cta tca att aag gac caa gtg atc aag acc aat gca gat gta aag   2939 gct tta acc tac tgt gat ctc cag tgt atc atc ctc aaa gga ctc ttt   2987 gaa gtg cta gac ctt tac cca gaa tat gct cac aaa ttc gtg gaa gac   3035 att cag cat gac ctc aca tac aac ctc cga gaa ggt cat gag agt gat   3083 gtg ata tca aga cta tca aac aaa tct atg gtc tca cag tca gag ccc   3131 aag gga aat ggc aac atc aac aag cga ctc cca tcc att gtg gaa gat   3179 gag gaa gag gag gag gag ggg gag gaa gag gag gca gtc tcc ctc tct   3227 ccc atc tgc aca agg gga tct tct tcg cgc aac aag aag gtt gga agc   3275 aat aaa gcc tac ctg ggc tta agc tta aag caa ctg gcc tcg gga acg   3323 gtg ccc ttt cac tcg cct atc aga gtc tcc agg tca aat tcc ccc aaa   3371 acc aag cag gaa att gac ccc ccc aac cat aat aaa agg aaa gag aag   3419 aac ttg aaa ttg caa ctt tca act ttg aat aat gct gga ccc cca gac   3467 ctc agt cca agg att gtt gat gga att gaa gat gga aac agc agt gaa   3515 gaa agt cag act ttt gat ttt ggc tct gaa cga atc aga tca gag ccc   3563 aga att tct cct cct ctt gga gat cca gag att gga gct gct gtt ctc   3611 ttc atc aaa gca gag gag acc aag cag cag ata aac aaa ctc aac agt   3659 gag gta aca aca ttg act cag gaa gtt tct cag ttg ggt aaa gac atg   3707 aga aat gtg atc cgg ctt ctg gaa aac gtt ctg tca cct cag cag cca   3755
```

```
tca cgg ttt tgc tct ttg cac agc acc tct gtg tgt ccc tcc agg gag    3803 agc tta cag acc aga acg agc tgg agt gca cac cag cct tgc cta cac    3851 ttg caa aca ggc ggg gct gct tat acc caa gca caa ctt tgt agc agt    3899 aat atc acc tca gac att tgg agt gtg gat ccc tcc tct gtg ggg agc    3947 agc ccc caa cga act gga gct cat gag caa aat cct gca gac agt gaa    3995 ctt tat cat tct cca agc ctt gat tat tca cct tcc cac tac cag gtt    4043 gtc caa gaa ggt cat ttg caa ttt tta agg tgc atc tct cca cat tca    4091 gat tct acg ttg acg cct ctg cag tcc att tca gca act ctc tca tct    4139 tct gtc tgc tcc tct tcg gaa aca tct ttg cac cta gtt ctc cca agc    4187 aga tca gag gag ggc agc ttc agt cag gga act gtg agt tcc ttc agt    4235 ctg gaa aac tta cca gga tct tgg aac cag gaa gga atg gca tca gct    4283 tct aca aaa cct ttg gag aac ctt cca ctg gaa gtt gtc aca agc aca    4331 gca gaa gtg aaa gat aac aaa gcc ata aat gta tgatattagt gcccatgatg  4384
cagcagctaa tttcaaacct accactgcat gacagtttta gtttgccttt tgcctctgg   4444 tgggcatgaa gactgagcaa agctgggaat cctgcagaaa agagtgtgag gagccaggga  4504
aaggcagaac cacctccatg ctgtagcaaa caatttctag atactagaag cataatagaa  4564
acatttttct gtacaggtat taaactactg gtctgtttga cagactttgg taacaatcca  4624
aagaccctga gggtctgagc agctagaagt cctagacaaa gaacttgtgg atgactttg   4684 tcccatgtgg ctttttgtgaa gtatggcaaa ggttttcat gagtgcctga ttgttattcc  4744
tgaacaatat ccatagcact gttggcctca ggagtgcaca gctcctgctg atgtattttt  4804
ctttttgtga aggcaaaggg acaattatca ctgcatgtca tctcctagac aatcagtcaa  4864
atagagctgg tggccagtgg ttagctattc gcacgttatt tgccatgtaa atgaaaacgt  4924
ctttatttat caaaaaaaca cagaggctat ttttatatcc ttggtatgaa atatgtattt  4984
aaactattta atatttata aagaaatgaa tgttttcttt tcattttggt aaaaaaaag    5044 cttgctgttt taacaagaaa tgcactactg ttgtgtatag tagatcaaaa attatttatt  5104
actaagagga tgtagtttcc aaaggaatcc cccattttt ctgcatgcag tttgcaacaa   5164
atgtattctc atgcttctgg attataaaag aaaagtgaag tcatattttg ttaatgaaat  5224
aaaaacatgg actgagtgtc aactacatga gctttggcat ggggatagag aggctccatc  5284
taggctctgc caactcatgt caatgacatg atttaaggtc cgttgtgcca gcagaaatgt  5344
ctctcctcta ggtatcgtat tttgttgctc aagaatccaa aatgggtctg tggacatagg  5404
gcaatttggg gctcaaagtg agggagaaaa cctgggtgtg tcctttccca gtgcttttct  5464
tttacaagag gtagtagact agtggaaatc cccaaatgga gccaagactt ctgagctata  5524
acttgtggga gtaataccag cttgcaatgg gtcagcactt tacctttttt ctttaaggct  5584
cccaacaatg ctatacagcg cagttgtttc cattcctatt nttaataaat ctcaggggaa  5644
gcctcagaga ttacacagtt aggatgctga cacagtctag aatccataat gctccctaca  5704
tctcacacta acaggcaaat tcagatgctg ggattggcaa tgatttaagc accttcacta  5764
aagtcttatt ttatgtttta gaacagttac agtctaattg tcttggacat tttgggaaga  5824
tatattgggt tcacattctg gagttctctt tattttccac cacaaaaaat aatctgagaa  5884
ttgtatcatt aaaagtatct aaacacacaa aaaaaaaaaa aaaaaaaaaa aaaaaaaaa   5944
```

-continued

```
aaaaaaaaaa a                                                          5955

<210> SEQ ID NO 15
<211> LENGTH: 5107
<212> TYPE: DNA
<213> ORGANISM: Homo sapiens
<220> FEATURE:
<221> NAME/KEY: CDS
<222> LOCATION: (196)..(3516)
<221> NAME/KEY: misc_feature
<222> LOCATION: 4777
<223> OTHER INFORMATION: n = a,g,t or c

<400> SEQUENCE: 15
cctgccacag ccggggcggc tggaactctc tcccttctc cctccatcct tccacttccc        60
ctgctcggcc ccgccgtcag gccgggtccc ccttccctgc cgtcatcagg ttccccttct      120
cccttcttgg cactttcctt tcgaaccatc cttctggaca aactttgatg gagaatttca      180
caccacgctg gaaaa atg ccg gtt atg aaa gga tta ctg gcg ccg caa aac      231
              Met Pro Val Met Lys Gly Leu Leu Ala Pro Gln Asn
                1               5                  10 acc ttc ctg gac acc atc gcc acc cgt ttt gac gga aca cat agc aac      279
Thr Phe Leu Asp Thr Ile Ala Thr Arg Phe Asp Gly Thr His Ser Asn
         15                  20                  25 ttc atc ctt gcc aat gcc cag gtg gct aag ggt ttc ccc ata gtc tac      327
Phe Ile Leu Ala Asn Ala Gln Val Ala Lys Gly Phe Pro Ile Val Tyr
     30                  35                  40 tgt tcc gat ggc ttc tgc gag ctt gct gga ttt gcc cga act gaa gtc      375
Cys Ser Asp Gly Phe Cys Glu Leu Ala Gly Phe Ala Arg Thr Glu Val
 45                  50                  55                  60 atg cag aag agt tgt agc tgc aag ttc tta ttt ggg gtt gaa acc aat      423
Met Gln Lys Ser Cys Ser Cys Lys Phe Leu Phe Gly Val Glu Thr Asn
                 65                  70                  75 gag caa ctg atg ctt caa ata gaa aag tca ctg gag gag aaa aca gaa      471
Glu Gln Leu Met Leu Gln Ile Glu Lys Ser Leu Glu Glu Lys Thr Glu
             80                  85                  90 ttc aaa gga gaa att atg ttc tac aag aaa aac ggg tct cca ttt tgg      519
Phe Lys Gly Glu Ile Met Phe Tyr Lys Lys Asn Gly Ser Pro Phe Trp
         95                 100                 105 tgc cta ctg gat att gtt ccc ata aag aat gaa aaa gga gat gta gta      567
Cys Leu Leu Asp Ile Val Pro Ile Lys Asn Glu Lys Gly Asp Val Val
    110                 115                 120 ctt ttt ctg gcc tcg ttc aaa gat ata aca gat aca aaa gtg aag att      615
Leu Phe Leu Ala Ser Phe Lys Asp Ile Thr Asp Thr Lys Val Lys Ile
125                 130                 135                 140 act cca gaa gat aaa aaa gaa gac aaa gtc aaa gga aga tca aga gca      663
Thr Pro Glu Asp Lys Lys Glu Asp Lys Val Lys Gly Arg Ser Arg Ala
                145                 150                 155 ggg acc cac ttt gac tca gcc cgg aga cgg agt cga gca gtc ctt tat      711
Gly Thr His Phe Asp Ser Ala Arg Arg Arg Ser Arg Ala Val Leu Tyr
            160                 165                 170 cac atc tct ggg cac ctg caa aga aga gaa aag aac aaa ttg aaa ata      759
His Ile Ser Gly His Leu Gln Arg Arg Glu Lys Asn Lys Leu Lys Ile
        175                 180                 185 aat aac aat gtt ttt gta gat aaa cca gca ttt ccg gag tat aaa gtt      807
Asn Asn Asn Val Phe Val Asp Lys Pro Ala Phe Pro Glu Tyr Lys Val
    190                 195                 200 tct gat gca aaa aag tcc aaa ttc ata ctt ctg cat ttt agc act ttt      855
Ser Asp Ala Lys Lys Ser Lys Phe Ile Leu Leu His Phe Ser Thr Phe
205                 210                 215                 220 aaa gct ggc tgg gac tgg ctt att ttg ttg gca acg ttt tat gtt gct      903
```

```
                                                                -continued

Lys Ala Gly Trp Asp Trp Leu Ile Leu Leu Ala Thr Phe Tyr Val Ala
                      225                 230                 235 gtg act gta cct tac aac gtt tgc ttt att ggc aat gac gac ctg tcc          951
Val Thr Val Pro Tyr Asn Val Cys Phe Ile Gly Asn Asp Asp Leu Ser
            240                 245                 250 aca act cgg agc aca acc gtc agt gac att gca gtg gag att ctt ttt          999
Thr Thr Arg Ser Thr Thr Val Ser Asp Ile Ala Val Glu Ile Leu Phe
                255                 260                 265 att ata gat att att tta aat ttc cga aca act tat gtc agc aag tct         1047
Ile Ile Asp Ile Ile Leu Asn Phe Arg Thr Thr Tyr Val Ser Lys Ser
        270                 275                 280 ggc caa gtt atc ttt gaa gca aga tca att tgc atc cac tat gtc aca         1095
Gly Gln Val Ile Phe Glu Ala Arg Ser Ile Cys Ile His Tyr Val Thr
285                 290                 295                 300 acc tgg ttc atc att gat tta atc gct gcc ctg cct ttt gat ctt ctg         1143
Thr Trp Phe Ile Ile Asp Leu Ile Ala Ala Leu Pro Phe Asp Leu Leu
                    305                 310                 315 tat gct ttc aac gtc aca gtg gtg tct ctc gtg cat ctt cta aag aca         1191
Tyr Ala Phe Asn Val Thr Val Val Ser Leu Val His Leu Leu Lys Thr
                320                 325                 330 gtg cgc ctc ttg cgt ctt ttg cgt ctg ctg cag aag tta gac cgc tat         1239
Val Arg Leu Leu Arg Leu Leu Arg Leu Leu Gln Lys Leu Asp Arg Tyr
            335                 340                 345 tcc caa cac agt act atc gtc ctg act ctg ctc atg tcc atg ttt gca         1287
Ser Gln His Ser Thr Ile Val Leu Thr Leu Leu Met Ser Met Phe Ala
350                 355                 360 ctc ctt gca cac tgg atg gcg tgt atc tgg tac gtc att gga aaa atg         1335
Leu Leu Ala His Trp Met Ala Cys Ile Trp Tyr Val Ile Gly Lys Met
365                 370                 375                 380 gag agg gaa gac aac agc ctt ctg aag tgg gaa gtt ggt tgg ctt cat         1383
Glu Arg Glu Asp Asn Ser Leu Leu Lys Trp Glu Val Gly Trp Leu His
                385                 390                 395 gag ttg gga aag aga ctg gaa tct cca tac tat ggc aac aat acc ttg         1431
Glu Leu Gly Lys Arg Leu Glu Ser Pro Tyr Tyr Gly Asn Asn Thr Leu
            400                 405                 410 ggg ggc ccg tcg atc cga agt gcc tat att gcc gct ctg tac ttc acg         1479
Gly Gly Pro Ser Ile Arg Ser Ala Tyr Ile Ala Ala Leu Tyr Phe Thr
        415                 420                 425 ctg agc agc ctc acc agc gtg ggt ttt ggg aac gtc tct gct aat aca         1527
Leu Ser Ser Leu Thr Ser Val Gly Phe Gly Asn Val Ser Ala Asn Thr
        430                 435                 440 gat gca gaa aag atc ttc tcc atc tgc acc atg ctg att ggt gcc ttg         1575
Asp Ala Glu Lys Ile Phe Ser Ile Cys Thr Met Leu Ile Gly Ala Leu
445                 450                 455                 460 atg cac gcc ttg gtg ttt gga aac gtg aca gca atc ata cag agg atg         1623
Met His Ala Leu Val Phe Gly Asn Val Thr Ala Ile Ile Gln Arg Met
                465                 470                 475 tac tcc aga tgg tcc ctc tat cac act aga act aag gat ctg aaa gat         1671
Tyr Ser Arg Trp Ser Leu Tyr His Thr Arg Thr Lys Asp Leu Lys Asp
            480                 485                 490 ttc atc cgt gtc cat cac ttg ccc caa caa ctc aag cag agg atg ctc         1719
Phe Ile Arg Val His His Leu Pro Gln Gln Leu Lys Gln Arg Met Leu
        495                 500                 505 gaa tat ttt caa aca acc tgg tca gtc aac aat gga ata gat tca aat         1767
Glu Tyr Phe Gln Thr Thr Trp Ser Val Asn Asn Gly Ile Asp Ser Asn
        510                 515                 520 gag ctt ttg aaa gac ttt cca gat gaa ctg cgt tct gac atc act atg         1815
Glu Leu Leu Lys Asp Phe Pro Asp Glu Leu Arg Ser Asp Ile Thr Met
525                 530                 535                 540
```

| | |
|---|---|
| cac ttg aac aag gag atc tta cag ttg tcc ctt ttt gaa tgt gcc agc<br>His Leu Asn Lys Glu Ile Leu Gln Leu Ser Leu Phe Glu Cys Ala Ser<br>              545                550                  555 | 1863 |
| cgg ggc tgc ctc agg tct ctg tct cta cac atc aaa acc tct ttc tgt<br>Arg Gly Cys Leu Arg Ser Leu Ser Leu His Ile Lys Thr Ser Phe Cys<br>560                  565                570 | 1911 |
| gct ccg ggg gag tat ctg ctg cgt caa ggg gat gct ttg cag gcc atc<br>Ala Pro Gly Glu Tyr Leu Leu Arg Gln Gly Asp Ala Leu Gln Ala Ile<br>              575                580                585 | 1959 |
| tac ttt gta tgc tcg ggc tcc atg gaa gtt ctt aaa gac agc atg gtg<br>Tyr Phe Val Cys Ser Gly Ser Met Glu Val Leu Lys Asp Ser Met Val<br>590                  595                600 | 2007 |
| ctg gct att ctt ggg aaa ggg gat tta att gga gca aat cta tca att<br>Leu Ala Ile Leu Gly Lys Gly Asp Leu Ile Gly Ala Asn Leu Ser Ile<br>605                  610                615                620 | 2055 |
| aag gac caa gtg atc aag acc aat gca gat gta aag gct tta acc tac<br>Lys Asp Gln Val Ile Lys Thr Asn Ala Asp Val Lys Ala Leu Thr Tyr<br>              625                630                635 | 2103 |
| tgt gat ctc cag tgt atc atc ctc aaa gga ctc ttt gaa gtg cta gac<br>Cys Asp Leu Gln Cys Ile Ile Leu Lys Gly Leu Phe Glu Val Leu Asp<br>640                  645                650 | 2151 |
| ctt tac cca gaa tat gct cac aaa ttc gtg gaa gac att cag cat gac<br>Leu Tyr Pro Glu Tyr Ala His Lys Phe Val Glu Asp Ile Gln His Asp<br>              655                660                665 | 2199 |
| ctc aca tac aac ctc cga gaa ggt cat gag agt gat gtg ata tca aga<br>Leu Thr Tyr Asn Leu Arg Glu Gly His Glu Ser Asp Val Ile Ser Arg<br>670                  675                680 | 2247 |
| cta tca aac aaa tct atg gtc tca cag tca gag ccc aag gga aat ggc<br>Leu Ser Asn Lys Ser Met Val Ser Gln Ser Glu Pro Lys Gly Asn Gly<br>685                  690                695                700 | 2295 |
| aac atc aac aag cga ctc cca tcc att gtg gaa gat gag gaa gag gag<br>Asn Ile Asn Lys Arg Leu Pro Ser Ile Val Glu Asp Glu Glu Glu Glu<br>              705                710                715 | 2343 |
| gag gag ggg gag gaa gag gag gca gtc tcc ctc tct ccc atc tgc aca<br>Glu Glu Gly Glu Glu Glu Glu Ala Val Ser Leu Ser Pro Ile Cys Thr<br>720                  725                730 | 2391 |
| agg gga tct tct tcg cgc aac aag aag gtt gga agc aat aaa gcc tac<br>Arg Gly Ser Ser Ser Arg Asn Lys Lys Val Gly Ser Asn Lys Ala Tyr<br>              735                740                745 | 2439 |
| ctg ggc tta agc tta aag caa ctg gcc tcg gga acg gtg ccc ttt cac<br>Leu Gly Leu Ser Leu Lys Gln Leu Ala Ser Gly Thr Val Pro Phe His<br>750                  755                760 | 2487 |
| tcg cct atc aga gtc tcc agg tca aat tcc ccc aaa acc aag cag gaa<br>Ser Pro Ile Arg Val Ser Arg Ser Asn Ser Pro Lys Thr Lys Gln Glu<br>765                  770                775                780 | 2535 |
| att gac ccc ccc aac cat aat aaa agg aaa gag aag aac ttg aaa ttg<br>Ile Asp Pro Pro Asn His Asn Lys Arg Lys Glu Lys Asn Leu Lys Leu<br>              785                790                795 | 2583 |
| caa ctt tca act ttg aat aat gct gga ccc cca gac ctc agt cca agg<br>Gln Leu Ser Thr Leu Asn Asn Ala Gly Pro Pro Asp Leu Ser Pro Arg<br>800                  805                810 | 2631 |
| att gtt gat gga att gaa gat gga aac agc agt gaa gaa agt cag act<br>Ile Val Asp Gly Ile Glu Asp Gly Asn Ser Ser Glu Glu Ser Gln Thr<br>              815                820                825 | 2679 |
| ttt gat ttt ggc tct gaa cga atc aga tca gag ccc aga att tct cct<br>Phe Asp Phe Gly Ser Glu Arg Ile Arg Ser Glu Pro Arg Ile Ser Pro<br>830                  835                840 | 2727 |
| cct ctt gga gat cca gag att gga gct gct gtt ctc ttc atc aaa gca<br>Pro Leu Gly Asp Pro Glu Ile Gly Ala Ala Val Leu Phe Ile Lys Ala<br>845                  850                855                860 | 2775 |

```
gag gag acc aag cag cag ata aac aaa ctc aac agt gag gta aca aca    2823
Glu Glu Thr Lys Gln Gln Ile Asn Lys Leu Asn Ser Glu Val Thr Thr
                865                 870                 875 ttg act cag gaa gtt tct cag ttg ggt aaa gac atg aga aat gtg atc    2871
Leu Thr Gln Glu Val Ser Gln Leu Gly Lys Asp Met Arg Asn Val Ile
        880                 885                 890 cgg ctt ctg gaa aac gtt ctg tca cct cag cag cca tca cgg ttt tgc    2919
Arg Leu Leu Glu Asn Val Leu Ser Pro Gln Gln Pro Ser Arg Phe Cys
            895                 900                 905 tct ttg cac agc acc tct gtg tgt ccc tcc agg gag agc tta cag acc    2967
Ser Leu His Ser Thr Ser Val Cys Pro Ser Arg Glu Ser Leu Gln Thr
                910                 915                 920 aga acg agc tgg agt gca cac cag cct tgc cta cac ttg caa aca ggc    3015
Arg Thr Ser Trp Ser Ala His Gln Pro Cys Leu His Leu Gln Thr Gly
925                 930                 935                 940 ggg gct gct tat acc caa gca caa ctt tgt agc agt aat atc acc tca    3063
Gly Ala Ala Tyr Thr Gln Ala Gln Leu Cys Ser Ser Asn Ile Thr Ser
                945                 950                 955 gac att tgg agt gtg gat ccc tcc tct gtg ggg agc agc ccc caa cga    3111
Asp Ile Trp Ser Val Asp Pro Ser Ser Val Gly Ser Ser Pro Gln Arg
            960                 965                 970 act gga gct cat gag caa aat cct gca gac agt gaa ctt tat cat tct    3159
Thr Gly Ala His Glu Gln Asn Pro Ala Asp Ser Glu Leu Tyr His Ser
        975                 980                 985 cca agc ctt gat tat tca cct tcc cac tac cag gtt gtc caa gaa ggt    3207
Pro Ser Leu Asp Tyr Ser Pro Ser His Tyr Gln Val Val Gln Glu Gly
    990                 995                 1000 cat ttg caa ttt tta agg tgc atc tct cca cat tca gat tct acg ttg    3255
His Leu Gln Phe Leu Arg Cys Ile Ser Pro His Ser Asp Ser Thr Leu
1005                1010                1015                1020 acg cct ctg cag tcc att tca gca act ctc tca tct tct gtc tgc tcc    3303
Thr Pro Leu Gln Ser Ile Ser Ala Thr Leu Ser Ser Ser Val Cys Ser
                1025                1030                1035 tct tcg gaa aca tct ttg cac cta gtt ctc cca agc aga tca gag gag    3351
Ser Ser Glu Thr Ser Leu His Leu Val Leu Pro Ser Arg Ser Glu Glu
            1040                1045                1050 ggc agc ttc agt cag gga act gtg agt tcc ttc agt ctg gaa aac tta    3399
Gly Ser Phe Ser Gln Gly Thr Val Ser Ser Phe Ser Leu Glu Asn Leu
        1055                1060                1065 cca gga tct tgg aac cag gaa gga atg gca tca gct tct aca aaa cct    3447
Pro Gly Ser Trp Asn Gln Glu Gly Met Ala Ser Ala Ser Thr Lys Pro
    1070                1075                1080 ttg gag aac ctt cca ctg gaa gtt gtc aca agc aca gca gaa gtg aaa    3495
Leu Glu Asn Leu Pro Leu Glu Val Val Thr Ser Thr Ala Glu Val Lys
1085                1090                1095                1100 gat aac aaa gcc ata aat gta tgatattagt gcccatgatg cagcagctaa      3546
Asp Asn Lys Ala Ile Asn Val
                1105 tttcaaacct accactgcat gacagtttta gtttgccttt ttgcctctgg tgggcatgaa 3606 gactgagcaa agctgggaat cctgcagaaa agagtgtgag gagccaggga aaggcagaac 3666 cacctccatg ctgtagcaaa caatttctag atactagaag cataatagaa acatttttct 3726 gtacaggtat taaactactg gtctgtttga cagactttgg taacaatcca aagaccctga 3786 gggtctgagc agctagaagt cctagacaaa gaacttgtgg atgactttg tcccatgtgg 3846 cttttgtgaa gtatggcaaa ggttttttcat gagtgcctga ttgttattcc tgaacaatat 3906 ccatagcact gttggcctca ggagtgcaca gctcctgctg atgtattttt cttttttgtga 3966
```

```
aggcaaaggg acaattatca ctgcatgtca tctcctagac aatcagtcaa atagagctgg    4026
tggccagtgg ttagctattc gcacgttatt tgccatgtaa atgaaaacgt ctttatttat    4086
caaaaaaaca cagaggctat ttttatatcc ttggtatgaa atatgtattt aaactattta    4146
aatatttata aagaaatgaa tgttttcttt tcattttggt aaaaaaaaag cttgctgttt    4206
taacaagaaa tgcactactg ttgtgtatag tagatcaaaa attatttatt actaagagga    4266
tgtagtttcc aaaggaatcc cccattttt ctgcatgcag tttgcaacaa atgtattctc    4326
atgcttctgg attataaaag aaaagtgaag tcatattttg ttaatgaaat aaaaacatgg    4386
actgagtgtc aactacatga gctttggcat ggggatagag aggctccatc taggctctgc    4446
caactcatgt caatgacatg atttaaggtc cgttgtgcca gcagaaatgt ctctcctcta    4506
ggtatcgtat tttgttgctc aagaatccaa atgggtctg tggacatagg gcaatttggg     4566
gctcaaagtg agggagaaaa cctgggtgtg tcctttccca gtgcttttct tttacaagag    4626
gtagtagact agtggaaatc cccaaatgga gccaagactt ctgagctata acttgtggga    4686
gtaataccag cttgcaatgg gtcagcactt tacctttttt ctttaaggct cccaacaatg    4746
ctatacagcg cagttgtttc cattcctatt nttaataaat ctcagggaa gcctcagaga      4806 ttacacagtt aggatgctga cacagtctag aatccataat gctccctaca tctcacacta    4866
acaggcaaat tcagatgctg ggattggcaa tgatttaagc accttcacta aagtcttatt    4926
ttatgtttta gaacagttac agtctaattg tcttggacat tttgggaaga tatattgggt    4986
tcacattctg gagttctctt tattttccac cacaaaaaat aatctgagaa ttgtatcatt    5046
aaaagtatct aaacacacaa aaaaaaaaaa aaaaaaaaa aaaaaaaaaa aaaaaaaaa     5106 a                                                                    5107
```

<210> SEQ ID NO 16
<211> LENGTH: 1107
<212> TYPE: PRT
<213> ORGANISM: Homo sapiens

<400> SEQUENCE: 16

Met Pro Val Met Lys Gly Leu Leu Ala Pro Gln Asn Thr Phe Leu Asp
 1               5                  10                  15

Thr Ile Ala Thr Arg Phe Asp Gly Thr His Ser Asn Phe Ile Leu Ala
            20                  25                  30

Asn Ala Gln Val Ala Lys Gly Phe Pro Ile Val Tyr Cys Ser Asp Gly
        35                  40                  45

Phe Cys Glu Leu Ala Gly Phe Ala Arg Thr Glu Val Met Gln Lys Ser
    50                  55                  60

Cys Ser Cys Lys Phe Leu Phe Gly Val Glu Thr Asn Glu Gln Leu Met
65                  70                  75                  80

Leu Gln Ile Glu Lys Ser Leu Glu Glu Lys Thr Glu Phe Lys Gly Glu
                85                  90                  95

Ile Met Phe Tyr Lys Lys Asn Gly Ser Pro Phe Trp Cys Leu Leu Asp
            100                 105                 110

Ile Val Pro Ile Lys Asn Glu Lys Gly Asp Val Val Leu Phe Leu Ala
        115                 120                 125

Ser Phe Lys Asp Ile Thr Asp Thr Lys Val Lys Ile Thr Pro Glu Asp
    130                 135                 140

Lys Lys Glu Asp Lys Val Lys Gly Arg Ser Arg Ala Gly Thr His Phe
145                 150                 155                 160

-continued

```
Asp Ser Ala Arg Arg Arg Ser Arg Ala Val Leu Tyr His Ile Ser Gly
            165                 170                 175
His Leu Gln Arg Arg Glu Lys Asn Lys Leu Lys Ile Asn Asn Asn Val
            180                 185                 190
Phe Val Asp Lys Pro Ala Phe Pro Glu Tyr Lys Val Ser Asp Ala Lys
            195                 200                 205
Lys Ser Lys Phe Ile Leu Leu His Phe Ser Thr Phe Lys Ala Gly Trp
    210                 215                 220
Asp Trp Leu Ile Leu Leu Ala Thr Phe Tyr Val Ala Val Thr Val Pro
225                 230                 235                 240
Tyr Asn Val Cys Phe Ile Gly Asn Asp Asp Leu Ser Thr Thr Arg Ser
                245                 250                 255
Thr Thr Val Ser Asp Ile Ala Val Glu Ile Leu Phe Ile Ile Asp Ile
            260                 265                 270
Ile Leu Asn Phe Arg Thr Thr Tyr Val Ser Lys Ser Gly Gln Val Ile
            275                 280                 285
Phe Glu Ala Arg Ser Ile Cys Ile His Tyr Val Thr Thr Trp Phe Ile
    290                 295                 300
Ile Asp Leu Ile Ala Ala Leu Pro Phe Asp Leu Leu Tyr Ala Phe Asn
305                 310                 315                 320
Val Thr Val Val Ser Leu Val His Leu Leu Lys Thr Val Arg Leu Leu
                325                 330                 335
Arg Leu Leu Arg Leu Leu Gln Lys Leu Asp Arg Tyr Ser Gln His Ser
            340                 345                 350
Thr Ile Val Leu Thr Leu Leu Met Ser Met Phe Ala Leu Leu Ala His
    355                 360                 365
Trp Met Ala Cys Ile Trp Tyr Val Ile Gly Lys Met Glu Arg Glu Asp
    370                 375                 380
Asn Ser Leu Leu Lys Trp Glu Val Gly Trp Leu His Glu Leu Gly Lys
385                 390                 395                 400
Arg Leu Glu Ser Pro Tyr Tyr Gly Asn Asn Thr Leu Gly Gly Pro Ser
                405                 410                 415
Ile Arg Ser Ala Tyr Ile Ala Ala Leu Tyr Phe Thr Leu Ser Ser Leu
            420                 425                 430
Thr Ser Val Gly Phe Gly Asn Val Ser Ala Asn Thr Asp Ala Glu Lys
    435                 440                 445
Ile Phe Ser Ile Cys Thr Met Leu Ile Gly Ala Leu Met His Ala Leu
    450                 455                 460
Val Phe Gly Asn Val Thr Ala Ile Ile Gln Arg Met Tyr Ser Arg Trp
465                 470                 475                 480
Ser Leu Tyr His Thr Arg Thr Lys Asp Leu Lys Asp Phe Ile Arg Val
                485                 490                 495
His His Leu Pro Gln Gln Leu Lys Gln Arg Met Leu Glu Tyr Phe Gln
            500                 505                 510
Thr Thr Trp Ser Val Asn Asn Gly Ile Asp Ser Asn Glu Leu Leu Lys
    515                 520                 525
Asp Phe Pro Asp Glu Leu Arg Ser Asp Ile Thr Met His Leu Asn Lys
    530                 535                 540
Glu Ile Leu Gln Leu Ser Leu Phe Glu Cys Ala Ser Arg Gly Cys Leu
545                 550                 555                 560
Arg Ser Leu Ser Leu His Ile Lys Thr Ser Phe Cys Ala Pro Gly Glu
                565                 570                 575
Tyr Leu Leu Arg Gln Gly Asp Ala Leu Gln Ala Ile Tyr Phe Val Cys
```

-continued

```
              580                 585                 590
Ser Gly Ser Met Glu Val Leu Lys Asp Ser Met Val Leu Ala Ile Leu
            595                 600             605

Gly Lys Gly Asp Leu Ile Gly Ala Asn Leu Ser Ile Lys Asp Gln Val
610                 615                 620

Ile Lys Thr Asn Ala Asp Val Lys Ala Leu Thr Tyr Cys Asp Leu Gln
625                 630                 635                 640

Cys Ile Ile Leu Lys Gly Leu Phe Glu Val Leu Asp Leu Tyr Pro Glu
                645                 650                 655

Tyr Ala His Lys Phe Val Glu Asp Ile Gln His Asp Leu Thr Tyr Asn
            660                 665                 670

Leu Arg Glu Gly His Glu Ser Asp Val Ile Ser Arg Leu Ser Asn Lys
            675                 680                 685

Ser Met Val Ser Gln Ser Glu Pro Lys Gly Asn Gly Asn Ile Asn Lys
690                 695                 700

Arg Leu Pro Ser Ile Val Glu Asp Glu Glu Glu Glu Glu Gly Glu
705                 710                 715                 720

Glu Glu Glu Ala Val Ser Leu Ser Pro Ile Cys Thr Arg Gly Ser Ser
                725                 730                 735

Ser Arg Asn Lys Lys Val Gly Ser Asn Lys Ala Tyr Leu Gly Leu Ser
            740                 745                 750

Leu Lys Gln Leu Ala Ser Gly Thr Val Pro Phe His Ser Pro Ile Arg
            755                 760                 765

Val Ser Arg Ser Asn Ser Pro Lys Thr Lys Gln Glu Ile Asp Pro Pro
770                 775                 780

Asn His Asn Lys Arg Lys Glu Lys Asn Leu Lys Leu Gln Leu Ser Thr
785                 790                 795                 800

Leu Asn Asn Ala Gly Pro Pro Asp Leu Ser Pro Arg Ile Val Asp Gly
                805                 810                 815

Ile Glu Asp Gly Asn Ser Ser Glu Glu Ser Gln Thr Phe Asp Phe Gly
                820                 825                 830

Ser Glu Arg Ile Arg Ser Glu Pro Arg Ile Ser Pro Pro Leu Gly Asp
            835                 840                 845

Pro Glu Ile Gly Ala Ala Val Leu Phe Ile Lys Ala Glu Glu Thr Lys
850                 855                 860

Gln Gln Ile Asn Lys Leu Asn Ser Glu Val Thr Thr Leu Thr Gln Glu
865                 870                 875                 880

Val Ser Gln Leu Gly Lys Asp Met Arg Asn Val Ile Arg Leu Leu Glu
                885                 890                 895

Asn Val Leu Ser Pro Gln Gln Pro Ser Arg Phe Cys Ser Leu His Ser
            900                 905                 910

Thr Ser Val Cys Pro Ser Arg Glu Ser Leu Gln Thr Arg Thr Ser Trp
            915                 920                 925

Ser Ala His Gln Pro Cys Leu His Leu Gln Thr Gly Gly Ala Ala Tyr
930                 935                 940

Thr Gln Ala Gln Leu Cys Ser Ser Asn Ile Thr Ser Asp Ile Trp Ser
945                 950                 955                 960

Val Asp Pro Ser Ser Val Gly Ser Ser Pro Gln Arg Thr Gly Ala His
                965                 970                 975

Glu Gln Asn Pro Ala Asp Ser Glu Leu Tyr His Ser Pro Ser Leu Asp
            980                 985                 990

Tyr Ser Pro Ser His Tyr Gln Val  Val Gln Glu Gly His  Leu Gln Phe
            995                 1000                1005
```

```
Leu Arg Cys Ile Ser Pro His  Ser Asp Ser Thr Leu  Thr Pro Leu Gln
    1010                1015               1020

Ser  Ile Ser Ala Thr Leu  Ser Ser Ser Val Cys  Ser Ser Ser Glu Thr
1025             1030                1035                1040

Ser Leu His Leu Val  Leu Pro Ser Arg Ser  Glu Glu Gly Ser Phe  Ser
                1045                1050                1055

Gln Gly Thr Val  Ser Ser Phe Ser Leu  Glu Asn Leu Pro Gly  Ser Trp
            1060                1065                1070

Asn Gln Glu  Gly Met Ala Ser Ala  Ser Thr Lys Pro Leu  Glu Asn Leu
        1075                1080                1085

Pro Leu Glu Val Val Thr Ser  Thr Ala Glu Val Lys  Asp Asn Lys Ala
    1090                1095                1100

Ile  Asn Val
1105
```

<210> SEQ ID NO 17
<211> LENGTH: 3321
<212> TYPE: DNA
<213> ORGANISM: Homo sapiens
<220> FEATURE:
<221> NAME/KEY: CDS
<222> LOCATION: (1)..(3321)

<400> SEQUENCE: 17

```
atg ccg gtt atg aaa gga tta ctg gcg ccg caa aac acc ttc ctg gac      48
Met Pro Val Met Lys Gly Leu Leu Ala Pro Gln Asn Thr Phe Leu Asp
 1               5                  10                  15 acc atc gcc acc cgt ttt gac gga aca cat agc aac ttc atc ctt gcc      96
Thr Ile Ala Thr Arg Phe Asp Gly Thr His Ser Asn Phe Ile Leu Ala
             20                  25                  30 aat gcc cag gtg gct aag ggt ttc ccc ata gtc tac tgt tcc gat ggc     144
Asn Ala Gln Val Ala Lys Gly Phe Pro Ile Val Tyr Cys Ser Asp Gly
         35                  40                  45 ttc tgc gag ctt gct gga ttt gcc cga act gaa gtc atg cag aag agt     192
Phe Cys Glu Leu Ala Gly Phe Ala Arg Thr Glu Val Met Gln Lys Ser
     50                  55                  60 tgt agc tgc aag ttc tta ttt ggg gtt gaa acc aat gag caa ctg atg     240
Cys Ser Cys Lys Phe Leu Phe Gly Val Glu Thr Asn Glu Gln Leu Met
 65                  70                  75                  80 ctt caa ata gaa aag tca ctg gag gag aaa aca gaa ttc aaa gga gaa     288
Leu Gln Ile Glu Lys Ser Leu Glu Glu Lys Thr Glu Phe Lys Gly Glu
                 85                  90                  95 att atg ttc tac aag aaa aac ggg tct cca ttt tgg tgc cta ctg gat     336
Ile Met Phe Tyr Lys Lys Asn Gly Ser Pro Phe Trp Cys Leu Leu Asp
            100                 105                 110 att gtt ccc ata aag aat gaa aaa gga gat gta gta ctt ttt ctg gcc     384
Ile Val Pro Ile Lys Asn Glu Lys Gly Asp Val Val Leu Phe Leu Ala
        115                 120                 125 tcg ttc aaa gat ata aca gat aca aaa gtg aag att act cca gaa gat     432
Ser Phe Lys Asp Ile Thr Asp Thr Lys Val Lys Ile Thr Pro Glu Asp
    130                 135                 140 aaa aaa gaa gac aaa gtc aaa gga aga tca aga gca ggg acc cac ttt     480
Lys Lys Glu Asp Lys Val Lys Gly Arg Ser Arg Ala Gly Thr His Phe
145                 150                 155                 160 gac tca gcc cgg aga cgg agt cga gca gtc ctt tat cac atc tct ggg     528
Asp Ser Ala Arg Arg Arg Ser Arg Ala Val Leu Tyr His Ile Ser Gly
                165                 170                 175 cac ctg caa aga aga gaa aag aac aaa ttg aaa ata aat aac aat gtt     576
His Leu Gln Arg Arg Glu Lys Asn Lys Leu Lys Ile Asn Asn Asn Val
```

```
                       180                 185                 190
ttt gta gat aaa cca gca ttt ccg gag tat aaa gtt tct gat gca aaa        624
Phe Val Asp Lys Pro Ala Phe Pro Glu Tyr Lys Val Ser Asp Ala Lys
            195                 200                 205 aag tcc aaa ttc ata ctt ctg cat ttt agc act ttt aaa gct ggc tgg        672
Lys Ser Lys Phe Ile Leu Leu His Phe Ser Thr Phe Lys Ala Gly Trp
        210                 215                 220 gac tgg ctt att ttg ttg gca acg ttt tat gtt gct gtg act gta cct        720
Asp Trp Leu Ile Leu Leu Ala Thr Phe Tyr Val Ala Val Thr Val Pro
225                 230                 235                 240 tac aac gtt tgc ttt att ggc aat gac gac ctg tcc aca act cgg agc        768
Tyr Asn Val Cys Phe Ile Gly Asn Asp Asp Leu Ser Thr Thr Arg Ser
                245                 250                 255 aca acc gtc agt gac att gca gtg gag att ctt ttt att ata gat att        816
Thr Thr Val Ser Asp Ile Ala Val Glu Ile Leu Phe Ile Ile Asp Ile
            260                 265                 270 att tta aat ttc cga aca act tat gtc agc aag tct ggc caa gtt atc        864
Ile Leu Asn Phe Arg Thr Thr Tyr Val Ser Lys Ser Gly Gln Val Ile
        275                 280                 285 ttt gaa gca aga tca att tgc atc cac tat gtc aca acc tgg ttc atc        912
Phe Glu Ala Arg Ser Ile Cys Ile His Tyr Val Thr Thr Trp Phe Ile
    290                 295                 300 att gat tta atc gct gcc ctg cct ttt gat ctt ctg tat gct ttc aac        960
Ile Asp Leu Ile Ala Ala Leu Pro Phe Asp Leu Leu Tyr Ala Phe Asn
305                 310                 315                 320 gtc aca gtg gtg tct ctc gtg cat ctt cta aag aca gtg cgc ctc ttg       1008
Val Thr Val Val Ser Leu Val His Leu Leu Lys Thr Val Arg Leu Leu
                325                 330                 335 cgt ctt ttg cgt ctg ctg cag aag tta gac cgc tat tcc caa cac agt       1056
Arg Leu Leu Arg Leu Leu Gln Lys Leu Asp Arg Tyr Ser Gln His Ser
            340                 345                 350 act atc gtc ctg act ctg ctc atg tcc atg ttt gca ctc ctt gca cac       1104
Thr Ile Val Leu Thr Leu Leu Met Ser Met Phe Ala Leu Leu Ala His
        355                 360                 365 tgg atg gcg tgt atc tgg tac gtc att gga aaa atg gag agg gaa gac       1152
Trp Met Ala Cys Ile Trp Tyr Val Ile Gly Lys Met Glu Arg Glu Asp
    370                 375                 380 aac agc ctt ctg aag tgg gaa gtt ggt tgg ctt cat gag ttg gga aag       1200
Asn Ser Leu Leu Lys Trp Glu Val Gly Trp Leu His Glu Leu Gly Lys
385                 390                 395                 400 aga ctg gaa tct cca tac tat ggc aac aat acc ttg ggg ggc ccg tcg       1248
Arg Leu Glu Ser Pro Tyr Tyr Gly Asn Asn Thr Leu Gly Gly Pro Ser
                405                 410                 415 atc cga agt gcc tat att gcc gct ctg tac ttc acg ctg agc agc ctc       1296
Ile Arg Ser Ala Tyr Ile Ala Ala Leu Tyr Phe Thr Leu Ser Ser Leu
            420                 425                 430 acc agc gtg ggt ttt ggg aac gtc tct gct aat aca gat gca gaa aag       1344
Thr Ser Val Gly Phe Gly Asn Val Ser Ala Asn Thr Asp Ala Glu Lys
        435                 440                 445 atc ttc tcc atc tgc acc atg ctg att ggt gcc ttg atg cac gcc ttg       1392
Ile Phe Ser Ile Cys Thr Met Leu Ile Gly Ala Leu Met His Ala Leu
    450                 455                 460 gtg ttt gga aac gtg aca gca atc ata cag agg atg tac tcc aga tgg       1440
Val Phe Gly Asn Val Thr Ala Ile Ile Gln Arg Met Tyr Ser Arg Trp
465                 470                 475                 480 tcc ctc tat cac act aga act aag gat ctg aaa gat ttc atc cgt gtc       1488
Ser Leu Tyr His Thr Arg Thr Lys Asp Leu Lys Asp Phe Ile Arg Val
                485                 490                 495 cat cac ttg ccc caa caa ctc aag cag agg atg ctc gaa tat ttt caa       1536
```

```
His His Leu Pro Gln Gln Leu Lys Gln Arg Met Leu Glu Tyr Phe Gln
            500                 505                 510 aca acc tgg tca gtc aac aat gga ata gat tca aat gag ctt ttg aaa        1584
Thr Thr Trp Ser Val Asn Asn Gly Ile Asp Ser Asn Glu Leu Leu Lys
            515                 520                 525 gac ttt cca gat gaa ctg cgt tct gac atc act atg cac ttg aac aag        1632
Asp Phe Pro Asp Glu Leu Arg Ser Asp Ile Thr Met His Leu Asn Lys
        530                 535                 540 gag atc tta cag ttg tcc ctt ttt gaa tgt gcc agc cgg ggc tgc ctc        1680
Glu Ile Leu Gln Leu Ser Leu Phe Glu Cys Ala Ser Arg Gly Cys Leu
545                 550                 555                 560 agg tct ctg tct cta cac atc aaa acc tct ttc tgt gct ccg ggg gag        1728
Arg Ser Leu Ser Leu His Ile Lys Thr Ser Phe Cys Ala Pro Gly Glu
                565                 570                 575 tat ctg ctg cgt caa ggg gat gct ttg cag gcc atc tac ttt gta tgc        1776
Tyr Leu Leu Arg Gln Gly Asp Ala Leu Gln Ala Ile Tyr Phe Val Cys
            580                 585                 590 tcg ggc tcc atg gaa gtt ctt aaa gac agc atg gtg ctg gct att ctt        1824
Ser Gly Ser Met Glu Val Leu Lys Asp Ser Met Val Leu Ala Ile Leu
                595                 600                 605 ggg aaa ggg gat tta att gga gca aat cta tca att aag gac caa gtg        1872
Gly Lys Gly Asp Leu Ile Gly Ala Asn Leu Ser Ile Lys Asp Gln Val
610                 615                 620 atc aag acc aat gca gat gta aag gct tta acc tac tgt gat ctc cag        1920
Ile Lys Thr Asn Ala Asp Val Lys Ala Leu Thr Tyr Cys Asp Leu Gln
625                 630                 635                 640 tgt atc atc ctc aaa gga ctc ttt gaa gtg cta gac ctt tac cca gaa        1968
Cys Ile Ile Leu Lys Gly Leu Phe Glu Val Leu Asp Leu Tyr Pro Glu
                645                 650                 655 tat gct cac aaa ttc gtg gaa gac att cag cat gac ctc aca tac aac        2016
Tyr Ala His Lys Phe Val Glu Asp Ile Gln His Asp Leu Thr Tyr Asn
            660                 665                 670 ctc cga gaa ggt cat gag agt gat gtg ata tca aga cta tca aac aaa        2064
Leu Arg Glu Gly His Glu Ser Asp Val Ile Ser Arg Leu Ser Asn Lys
        675                 680                 685 tct atg gtc tca cag tca gag ccc aag gga aat ggc aac atc aac aag        2112
Ser Met Val Ser Gln Ser Glu Pro Lys Gly Asn Gly Asn Ile Asn Lys
    690                 695                 700 cga ctc cca tcc att gtg gaa gat gag gaa gag gag gag gag ggg gag        2160
Arg Leu Pro Ser Ile Val Glu Asp Glu Glu Glu Glu Glu Glu Gly Glu
705                 710                 715                 720 gaa gag gag gca gtc tcc ctc tct ccc atc tgc aca agg gga tct tct        2208
Glu Glu Glu Ala Val Ser Leu Ser Pro Ile Cys Thr Arg Gly Ser Ser
                725                 730                 735 tcg cgc aac aag aag gtt gga agc aat aaa gcc tac ctg ggc tta agc        2256
Ser Arg Asn Lys Lys Val Gly Ser Asn Lys Ala Tyr Leu Gly Leu Ser
            740                 745                 750 tta aag caa ctg gcc tcg gga acg gtg ccc ttt cac tcg cct atc aga        2304
Leu Lys Gln Leu Ala Ser Gly Thr Val Pro Phe His Ser Pro Ile Arg
        755                 760                 765 gtc tcc agg tca aat tcc ccc aaa acc aag cag gaa att gac ccc ccc        2352
Val Ser Arg Ser Asn Ser Pro Lys Thr Lys Gln Glu Ile Asp Pro Pro
    770                 775                 780 aac cat aat aaa agg aaa gag aag aac ttg aaa ttg caa ctt tca act        2400
Asn His Asn Lys Arg Lys Glu Lys Asn Leu Lys Leu Gln Leu Ser Thr
785                 790                 795                 800 ttg aat aat gct gga ccc cca gac ctc agt cca agg att gtt gat gga        2448
Leu Asn Asn Ala Gly Pro Pro Asp Leu Ser Pro Arg Ile Val Asp Gly
                805                 810                 815
```

```
att gaa gat gga aac agc agt gaa gaa agt cag act ttt gat ttt ggc    2496
Ile Glu Asp Gly Asn Ser Ser Glu Glu Ser Gln Thr Phe Asp Phe Gly
            820                 825                 830 tct gaa cga atc aga tca gag ccc aga att tct cct cct ctt gga gat    2544
Ser Glu Arg Ile Arg Ser Glu Pro Arg Ile Ser Pro Pro Leu Gly Asp
        835                 840                 845 cca gag att gga gct gct gtt ctc ttc atc aaa gca gag gag acc aag    2592
Pro Glu Ile Gly Ala Ala Val Leu Phe Ile Lys Ala Glu Glu Thr Lys
    850                 855                 860 cag cag ata aac aaa ctc aac agt gag gta aca aca ttg act cag gaa    2640
Gln Gln Ile Asn Lys Leu Asn Ser Glu Val Thr Thr Leu Thr Gln Glu
865                 870                 875                 880 gtt tct cag ttg ggt aaa gac atg aga aat gtg atc cgg ctt ctg gaa    2688
Val Ser Gln Leu Gly Lys Asp Met Arg Asn Val Ile Arg Leu Leu Glu
                885                 890                 895 aac gtt ctg tca cct cag cag cca tca cgg ttt tgc tct ttg cac agc    2736
Asn Val Leu Ser Pro Gln Gln Pro Ser Arg Phe Cys Ser Leu His Ser
            900                 905                 910 acc tct gtg tgt ccc tcc agg gag agc tta cag acc aga acg agc tgg    2784
Thr Ser Val Cys Pro Ser Arg Glu Ser Leu Gln Thr Arg Thr Ser Trp
        915                 920                 925 agt gca cac cag cct tgc cta cac ttg caa aca ggg gct gct tat        2832
Ser Ala His Gln Pro Cys Leu His Leu Gln Thr Gly Gly Ala Ala Tyr
    930                 935                 940 acc caa gca caa ctt tgt agc agt aat atc acc tca gac att tgg agt    2880
Thr Gln Ala Gln Leu Cys Ser Ser Asn Ile Thr Ser Asp Ile Trp Ser
945                 950                 955                 960 gtg gat ccc tcc tct gtg ggg agc agc ccc caa cga act gga gct cat    2928
Val Asp Pro Ser Ser Val Gly Ser Ser Pro Gln Arg Thr Gly Ala His
                965                 970                 975 gag caa aat cct gca gac agt gaa ctt tat cat tct cca agc ctt gat    2976
Glu Gln Asn Pro Ala Asp Ser Glu Leu Tyr His Ser Pro Ser Leu Asp
            980                 985                 990 tat tca cct tcc cac tac cag gtt  gtc caa gaa ggt cat  ttg caa ttt  3024
Tyr Ser Pro Ser His Tyr Gln Val  Val Gln Glu Gly His  Leu Gln Phe
        995                 1000                 1005 tta agg tgc atc tct cca cat  tca gat tct acg ttg  acg cct ctg cag  3072
Leu Arg Cys Ile Ser Pro His  Ser Asp Ser Thr Leu  Thr Pro Leu Gln
    1010                1015                 1020 tcc att tca gca act ctc  tca tct tct gtc tgc  tcc tct tcg gaa aca  3120
Ser Ile Ser Ala Thr Leu  Ser Ser Ser Val Cys  Ser Ser Ser Glu Thr
1025                1030                 1035                 1040 tct ttg cac cta gtt  ctc cca agc aga tca  gag gag ggc agc ttc agt  3168
Ser Leu His Leu Val  Leu Pro Ser Arg Ser  Glu Glu Gly Ser Phe Ser
                1045                 1050                 1055 cag gga act gtg  agt tcc ttc agt ctg  gaa aac tta cca gga  tct tgg  3216
Gln Gly Thr Val  Ser Ser Phe Ser Leu  Glu Asn Leu Pro Gly  Ser Trp
            1060                 1065                 1070 aac cag gaa  gga atg gca tca gct  tct aca aaa cct ttg  gag aac ctt  3264
Asn Gln Glu  Gly Met Ala Ser Ala  Ser Thr Lys Pro Leu  Glu Asn Leu
        1075                 1080                 1085 cca ctg  gaa gtt gtc aca agc  aca gca gaa gtg aaa  gat aac aaa gcc  3312
Pro Leu  Glu Val Val Thr Ser  Thr Ala Glu Val Lys  Asp Asn Lys Ala
    1090                 1095                 1100 ata aat gta                                                        3321
Ile Asn Val
1105

<210> SEQ ID NO 18
<211> LENGTH: 21
```

-continued

```
<212> TYPE: DNA
<213> ORGANISM: Macaca sp.

<400> SEQUENCE: 18
cagagtgaag acagggtggc g                                          21

<210> SEQ ID NO 19
<211> LENGTH: 22
<212> TYPE: DNA
<213> ORGANISM: Macaca sp.

<400> SEQUENCE: 19
ttccttgtcc tcaggtctct gc                                             22

<210> SEQ ID NO 20
<211> LENGTH: 26
<212> TYPE: DNA
<213> ORGANISM: Homo sapiens

<400> SEQUENCE: 20
ttcacaatgc caatttggat tgaccg                                         26

<210> SEQ ID NO 21
<211> LENGTH: 20
<212> TYPE: DNA
<213> ORGANISM: Homo sapiens

<400> SEQUENCE: 21
gcagtctggg gtgtttctgg                                                20

<210> SEQ ID NO 22
<211> LENGTH: 319
<212> TYPE: PRT
<213> ORGANISM: Artificial Sequence
<220> FEATURE:
<223> OTHER INFORMATION: Description of Artificial Sequence: domain

<400> SEQUENCE: 22

Tyr Leu Lys Ser Thr Trp Phe Leu Leu Asp Val Leu Ser Thr Leu Pro
  1               5                  10                  15

Phe Asp Leu Leu Tyr Ile Phe Phe Gly Ser Asp Glu Gly Ser Gly Gly
                 20                  25                  30

Ser Leu Phe Pro Leu Leu Arg Leu Asn Arg Leu Leu Arg Leu Arg Arg
             35                  40                  45

Val Ala Glu Leu Phe Asp Arg Leu Glu Lys Asp Thr Ala Phe Asn Tyr
         50                  55                  60

Phe Ala Ile Arg Leu Ile Lys Leu Val Cys Val Thr Leu Leu Ile Ile
     65                  70                  75                  80

His Trp Asn Ala Cys Val Phe Asp Ile Leu Ile Tyr Tyr Leu Ile Ser
                 85                  90                  95

Asp Tyr Asp Val Glu Ala Glu Arg Tyr Gly Phe Gly Thr Asp Thr Trp
                100                 105                 110

Leu Tyr Ala Leu Asn Asn Asp Phe Glu Glu Pro Ser Leu Trp Thr Arg
            115                 120                 125

Gly Ile Thr Gly Gly Pro Ser Leu Lys Arg Gln Tyr Ile Thr Ser Leu
        130                 135                 140

Tyr Trp Ser Ile Thr Thr Leu Thr Thr Val Gly Tyr Gly Asp Pro Ala
145                 150                 155                 160

Pro Val Thr Thr Arg Glu Lys Ile Phe Val Ile Phe Asp Met Leu Phe
                165                 170                 175
```

```
Gly Val Leu Leu Phe Ala Tyr Ile Ile Gly Asn Val Thr Ser Ile Val
            180                 185                 190

Val Asn Met Asn Ser Arg Thr Ala Glu Phe Arg Thr Lys Met Asp Ala
        195                 200                 205

Val Lys Glu Phe Met Lys Phe Arg Lys Leu Pro Lys Arg Leu Gln Glu
    210                 215                 220

Arg Val Leu Lys Tyr Phe Glu Tyr Thr Trp Ser Asn Lys Ser Asp Glu
225                 230                 235                 240

Gly Leu Asp Glu Glu Val Leu Glu Gln Leu Pro Lys Lys Leu Arg
                245                 250                 255

Ala Glu Ile Ser Thr Leu Thr Leu Thr Thr Ile Gly Gln Glu Met Pro
            260                 265                 270

Ser Pro Thr Thr Ser Phe Glu Tyr Val Phe Glu Val Phe Asp Phe Leu
        275                 280                 285

Val Gly Val Leu Ile Phe Ala Thr Ile Ile Gly Asn Val Gly Ser Met
    290                 295                 300

Ile Ser Asn Met Asn Ala Ala Arg Thr Glu Phe Gln Asn Lys Met
305                 310                 315

<210> SEQ ID NO 23
<211> LENGTH: 241
<212> TYPE: PRT
<213> ORGANISM: Homo sapiens

<400> SEQUENCE: 23

Tyr Val Thr Thr Trp Phe Ile Ile Asp Leu Ile Ala Ala Leu Pro Phe
  1               5                  10                  15

Asp Leu Leu Tyr Ala Phe Asn Val Thr Val Val Ser Leu Val His Leu
                20                  25                  30

Leu Lys Thr Val Arg Leu Leu Arg Leu Leu Arg Leu Leu Gln Lys Leu
            35                  40                  45

Asp Arg Tyr Ser Gln His Ser Thr Ile Val Leu Thr Leu Leu Met Ser
    50                  55                  60

Met Phe Ala Leu Leu Ala His Trp Met Ala Cys Ile Trp Tyr Val Ile
65                  70                  75                  80

Gly Lys Met Glu Arg Glu Asp Asn Ser Leu Leu Lys Trp Glu Val Gly
                85                  90                  95

Trp Leu His Glu Leu Gly Lys Arg Leu Glu Ser Pro Tyr Tyr Gly Asn
                100                 105                 110

Asn Thr Leu Gly Gly Pro Ser Ile Arg Ser Ala Tyr Ile Ala Ala Leu
            115                 120                 125

Tyr Phe Thr Leu Ser Ser Leu Thr Ser Val Gly Phe Gly Asn Val Ser
    130                 135                 140

Ala Asn Thr Asp Ala Glu Lys Ile Phe Ser Ile Cys Thr Met Leu Ile
145                 150                 155                 160

Gly Ala Leu Met His Ala Leu Val Phe Gly Asn Val Thr Ala Ile Ile
                165                 170                 175

Gln Arg Met Tyr Ser Arg Trp Ser Leu Tyr His Thr Arg Thr Lys Asp
                180                 185                 190

Leu Lys Asp Phe Ile Arg Val His His Leu Pro Gln Gln Leu Lys Gln
            195                 200                 205

Arg Met Leu Glu Tyr Phe Gln Thr Thr Trp Ser Val Asn Asn Gly Ile
    210                 215                 220

Asp Ser Asn Glu Leu Leu Lys Asp Phe Pro Asp Glu Leu Arg Ser Asp
```

```
                    225                 230                 235                 240
Ile

<210> SEQ ID NO 24
<211> LENGTH: 180
<212> TYPE: PRT
<213> ORGANISM: Homo sapiens

<400> SEQUENCE: 24

Arg Ala Val Leu Tyr His Ile Ser Gly His Leu Gln Arg Arg Glu Lys
  1               5                  10                  15

Asn Lys Leu Lys Ile Asn Asn Val Phe Val Asp Lys Pro Ala Phe
             20                  25                  30

Pro Glu Tyr Lys Val Ser Asp Ala Lys Lys Ser Lys Phe Ile Leu Leu
             35                  40                  45

His Phe Ser Thr Phe Lys Ala Gly Trp Asp Trp Leu Ile Leu Leu Ala
         50                  55                  60

Thr Phe Tyr Val Ala Val Thr Val Pro Tyr Asn Val Cys Phe Ile Gly
 65                  70                  75                  80

Asn Asp Asp Leu Ser Thr Thr Arg Ser Thr Thr Val Ser Asp Ile Ala
                 85                  90                  95

Val Glu Ile Leu Phe Ile Ile Asp Ile Ile Leu Asn Phe Arg Thr Thr
                100                 105                 110

Tyr Val Ser Lys Ser Gly Gln Val Ile Phe Glu Ala Arg Ser Ile Cys
                115                 120                 125

Ile His Tyr Val Thr Thr Trp Phe Ile Ile Asp Leu Ile Ala Ala Leu
            130                 135                 140

Pro Phe Asp Leu Leu Tyr Ala Phe Asn Val Thr Val Val Ser Leu Val
145                 150                 155                 160

His Leu Leu Lys Thr Val Arg Leu Leu Arg Leu Leu Arg Leu Leu Gln
                165                 170                 175

Lys Leu Asp Arg
            180

<210> SEQ ID NO 25
<211> LENGTH: 189
<212> TYPE: PRT
<213> ORGANISM: Artificial Sequence
<220> FEATURE:
<223> OTHER INFORMATION: Description of Artificial Sequence: domain

<400> SEQUENCE: 25

Arg Asp Ile Phe Tyr His Leu His Val Gly Glu Glu Phe Arg Thr Asp
  1               5                  10                  15

Ser Ile Thr Ser Ser Thr Ser Leu Gly Ala Asp Ile Leu Pro Glu
             20                  25                  30

Tyr Lys Ala Gln Ala Pro Lys Arg His Arg Leu Arg His Phe Ser Gly
             35                  40                  45

Trp Val Ile Asp Pro Tyr Gly Asn Phe Tyr Tyr Ile Trp Asp Phe Phe
         50                  55                  60

Ile Val Leu Leu Val Met Tyr Asn Ala Trp Met Val Pro Tyr Arg Ala
 65                  70                  75                  80

Cys Phe Asp Glu Leu Gln Ser Asp Asn Tyr Leu Glu Pro Trp Leu Ile
                 85                  90                  95

Ile Asp Tyr Ile Val Asp Ile Ile Tyr Leu Ile Asp Ile Ile Asn
                100                 105                 110
```

```
Phe Arg Thr Gly Tyr Leu Asp Gln Gly Ser Glu Leu Leu Val Lys Asp
            115                 120                 125

Pro Lys Lys Ile Arg Lys Asn Tyr Leu Lys Thr Trp Gln Phe Lys Leu
        130                 135                 140

Asp Ile Leu Ser Val Ile Pro Phe Asp Leu Leu Tyr Phe Ile Ser Asn
145                 150                 155                 160

Asp Glu Lys Ile Gly Trp Asn Tyr Pro Glu Leu Leu Arg Leu Asn Arg
                165                 170                 175

Leu Leu Arg Ile Ser Arg Met Phe Glu Phe Leu Asp Arg
            180                 185

<210> SEQ ID NO 26
<211> LENGTH: 181
<212> TYPE: PRT
<213> ORGANISM: Homo sapiens

<400> SEQUENCE: 26

His Trp Met Ala Cys Ile Trp Tyr Val Ile Gly Lys Met Glu Arg Glu
 1               5                  10                  15

Asp Asn Ser Leu Leu Lys Trp Glu Val Gly Trp Leu His Glu Leu Gly
             20                  25                  30

Lys Arg Leu Glu Ser Pro Tyr Tyr Gly Asn Asn Thr Leu Gly Gly Pro
         35                  40                  45

Ser Ile Arg Ser Ala Tyr Ile Ala Leu Tyr Phe Thr Leu Ser Ser
     50                  55                  60

Leu Thr Ser Val Gly Phe Gly Asn Val Ser Ala Asn Thr Asp Ala Glu
 65                  70                  75                  80

Lys Ile Phe Ser Ile Cys Thr Met Leu Ile Gly Ala Leu Met His Ala
                 85                  90                  95

Leu Val Phe Gly Asn Val Thr Ala Ile Ile Gln Arg Met Tyr Ser Arg
            100                 105                 110

Trp Ser Leu Tyr His Thr Arg Thr Lys Asp Leu Lys Asp Phe Ile Arg
            115                 120                 125

Val His His Leu Pro Gln Gln Leu Lys Gln Arg Met Leu Glu Tyr Phe
        130                 135                 140

Gln Thr Thr Trp Ser Val Asn Asn Gly Ile Asp Ser Asn Glu Leu Leu
145                 150                 155                 160

Lys Asp Phe Pro Asp Glu Leu Arg Ser Asp Ile Thr Met His Leu Asn
                165                 170                 175

Lys Glu Ile Leu Gln
            180

<210> SEQ ID NO 27
<211> LENGTH: 170
<212> TYPE: PRT
<213> ORGANISM: Artificial Sequence
<220> FEATURE:
<223> OTHER INFORMATION: Description of Artificial Sequence: domain

<400> SEQUENCE: 27

His Trp Asn Ala Cys Leu Tyr Tyr Trp Ile Ser Lys Tyr Gln Gly Phe
 1               5                  10                  15

Gly Ser Asp Ala Trp Val Tyr Gly Asn Tyr Asn Lys Pro Asn His Trp
             20                  25                  30

Ile Ser Val Thr Asp Asn Phe Gly Arg Gln Tyr Ile Tyr Cys Phe Tyr
         35                  40                  45

Trp Ser Thr Leu Thr Leu Thr Thr Ile Gly Gln Glu Met Pro Ser Pro
```

```
                    50                  55                  60
Thr Thr Ser Phe Glu Tyr Val Phe Glu Val Phe Asp Phe Leu Val Gly
 65                  70                  75                  80

Val Leu Ile Phe Ala Thr Ile Ile Gly Asn Val Gly Ser Met Ile Ser
                 85                  90                  95

Asn Met Asn Ala Ala Arg Thr Glu Phe Gln Asn Lys Met Asp Gly Val
            100                 105                 110

Lys Gln Tyr Met Lys Tyr Arg Lys Ile Pro Lys Glu Leu Gln Lys Arg
        115                 120                 125

Val Ile Lys Trp Phe Glu Tyr Leu Trp Ala Asn Gln Gly Ala Val Asp
    130                 135                 140

Glu Glu Glu Ile Leu Glu Leu Pro Asp Lys Leu Arg Ala Glu Ile
145                 150                 155                 160

Ala Ile Asn Ile His Met Asp Thr Leu Lys
                165                 170

<210> SEQ ID NO 28
<211> LENGTH: 75
<212> TYPE: PRT
<213> ORGANISM: Homo sapiens

<400> SEQUENCE: 28

Ile Val Tyr Cys Ser Asp Gly Phe Cys Glu Leu Ala Gly Phe Ala Arg
  1               5                  10                  15

Thr Glu Val Met Gln Lys Ser Cys Ser Cys Lys Phe Leu Phe Gly Val
             20                  25                  30

Glu Thr Asn Glu Gln Leu Met Leu Gln Ile Glu Lys Ser Leu Glu Glu
         35                  40                  45

Lys Thr Glu Phe Lys Gly Glu Ile Met Phe Tyr Lys Lys Asn Gly Ser
     50                  55                  60

Pro Phe Trp Cys Leu Leu Asp Ile Val Pro Ile
 65                  70                  75

<210> SEQ ID NO 29
<211> LENGTH: 58
<212> TYPE: PRT
<213> ORGANISM: Artificial Sequence
<220> FEATURE:
<223> OTHER INFORMATION: Description of Artificial Sequence: domain

<400> SEQUENCE: 29

Val Ile Tyr Cys Asn Asp Gly Phe Cys Glu Leu Cys Gly Tyr Ser Arg
  1               5                  10                  15

Ala Glu Val Met Gln Arg Pro Cys Thr Cys Asp Phe Leu Leu Gly Ala
             20                  25                  30

Glu Glu Arg Lys Val Glu Ile Ala Phe Tyr Arg Lys Asp Gly Ser Cys
         35                  40                  45

Phe Leu Cys Leu Val Asp Val Val Pro Val
     50                  55

<210> SEQ ID NO 30
<211> LENGTH: 89
<212> TYPE: PRT
<213> ORGANISM: Homo sapiens

<400> SEQUENCE: 30

Gln Arg Met Tyr Ser Arg Trp Ser Leu Tyr His Thr Arg Thr Lys Asp
  1               5                  10                  15
```

```
Leu Lys Asp Phe Ile Arg Val His His Leu Pro Gln Gln Leu Lys Gln
             20                  25                  30

Arg Met Leu Glu Tyr Phe Gln Thr Thr Trp Ser Val Asn Asn Gly Ile
             35                  40                  45

Asp Ser Asn Glu Leu Leu Lys Asp Phe Pro Asp Glu Leu Arg Ser Asp
     50                  55                  60

Ile Thr Met His Leu Asn Lys Glu Ile Leu Gln Leu Ser Leu Phe Glu
 65                  70                  75                  80

Cys Ala Ser Arg Gly Cys Leu Arg Ser
                 85

<210> SEQ ID NO 31
<211> LENGTH: 90
<212> TYPE: PRT
<213> ORGANISM: Artificial Sequence
<220> FEATURE:
<223> OTHER INFORMATION: Description of Artificial Sequence: domain

<400> SEQUENCE: 31

Gln Gln Met Thr Ser Ala Thr Ala Arg Tyr His Asp Met Ile Asn Asn
  1               5                  10                  15

Val Arg Glu Phe Met Lys Leu His Glu Ile Pro Lys Glu Leu Ala Glu
             20                  25                  30

Arg Val Met Asp Tyr Val Val Ser Thr Trp Ala Met Thr Lys Gly Ile
         35                  40                  45

Asp Thr Glu Lys Val Leu Asn Cys Cys Pro Lys Asp Met Lys Ala Asp
     50                  55                  60

Ile Cys Val His Leu Asn Arg Lys Val Phe Asn Glu His Pro Cys Phe
 65                  70                  75                  80

Arg Leu Ala Ser Asp Gly Cys Leu Arg Ala
                 85                  90

<210> SEQ ID NO 32
<211> LENGTH: 37
<212> TYPE: PRT
<213> ORGANISM: Homo sapiens

<400> SEQUENCE: 32

Lys Gly Leu Leu Ala Pro Gln Asn Thr Phe Leu Asp Thr Ile Ala Thr
  1               5                  10                  15

Arg Phe Asp Gly Thr His Ser Asn Phe Ile Leu Ala Asn Ala Gln Val
             20                  25                  30

Ala Lys Gly Phe Pro
         35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: domain

<400> SEQUENCE: 33

Lys Gly Leu Leu Ala Pro Gln Asn Thr Phe Leu Asp Thr Ile Ala Thr
  1               5                  10                  15

Arg Phe Asp Gly Thr His Ser Asn Phe Val Leu Gly Asn Ala Gln Ala
             20                  25                  30

Asn Gly Asn Pro
         35
```

```
<210> SEQ ID NO 34
<211> LENGTH: 51
<212> TYPE: PRT
<213> ORGANISM: Homo sapiens

<400> SEQUENCE: 34

Glu Tyr Phe Gln Thr Thr Trp Ser Val Asn Asn Gly Ile Asp Ser Asn
 1               5                  10                  15

Glu Leu Leu Lys Asp Phe Pro Asp Glu Leu Arg Ser Asp Ile Thr Met
            20                  25                  30

His Leu Asn Lys Glu Ile Leu Gln Leu Ser Leu Phe Glu Cys Ala Ser
        35                  40                  45

Arg Gly Cys
    50

<210> SEQ ID NO 35
<211> LENGTH: 52
<212> TYPE: PRT
<213> ORGANISM: Artificial Sequence
<220> FEATURE:
<223> OTHER INFORMATION: Description of Artificial Sequence: domain

<400> SEQUENCE: 35

Asp Tyr Phe Gln His Ala Trp Ser Tyr Thr Asn Gly Ile Asp Met Asn
 1               5                  10                  15

Lys Val Leu Lys Gly Phe Pro Glu Cys Leu Arg Ala Asp Ile Cys Leu
            20                  25                  30

His Leu Asn Arg Lys Ile Leu Gln His Cys Pro Ala Phe Arg Ala Ala
        35                  40                  45

Ser Asp Gly Cys
    50

<210> SEQ ID NO 36
<211> LENGTH: 1102
<212> TYPE: PRT
<213> ORGANISM: Rattus norvegicus

<400> SEQUENCE: 36

Met Pro Val Met Lys Gly Leu Leu Ala Pro Gln Asn Thr Phe Leu Asp
 1               5                  10                  15

Thr Ile Ala Thr Arg Phe Asp Gly Thr His Ser Asn Phe Ile Leu Ala
            20                  25                  30

Asn Ala Gln Val Ala Lys Gly Phe Pro Ile Val Tyr Cys Ser Asp Gly
        35                  40                  45

Phe Cys Glu Leu Ala Gly Phe Ala Arg Thr Glu Val Met Gln Lys Ser
    50                  55                  60

Cys Ser Cys Lys Phe Leu Phe Gly Val Glu Thr Asn Glu Gln Leu Met
65                  70                  75                  80

Leu Gln Ile Glu Lys Ser Leu Glu Glu Lys Val Glu Phe Lys Gly Glu
                85                  90                  95

Ile Met Phe Tyr Lys Lys Asn Gly Ala Pro Phe Trp Cys Leu Leu Asp
            100                 105                 110

Ile Val Pro Ile Lys Asn Glu Lys Gly Asp Val Val Leu Phe Leu Ala
        115                 120                 125

Ser Phe Lys Asp Ile Thr Asp Thr Lys Val Lys Ile Thr Ser Glu Asp
    130                 135                 140

Lys Lys Glu Asp Arg Ala Lys Gly Arg Ser Arg Ala Gly Ser His Phe
145                 150                 155                 160
```

-continued

```
Asp Ser Ala Arg Arg Arg Ser Arg Ala Val Leu Tyr His Ile Ser Gly
            165                 170                 175
His Leu Gln Arg Arg Glu Lys Asn Lys Leu Lys Ile Asn Asn Asn Val
            180                 185                 190
Phe Val Asp Lys Pro Ala Phe Pro Glu Tyr Lys Val Ser Asp Ala Lys
            195                 200                 205
Lys Ser Lys Phe Ile Leu Leu His Phe Ser Thr Phe Lys Ala Gly Trp
            210                 215                 220
Asp Trp Leu Ile Leu Leu Ala Thr Phe Tyr Val Ala Val Thr Val Pro
225                 230                 235                 240
Tyr Asn Val Cys Phe Ile Gly Asn Glu Asp Leu Ser Thr Thr Arg Ser
                245                 250                 255
Thr Thr Val Ser Asp Ile Ala Val Glu Ile Leu Phe Ile Ile Asp Ile
            260                 265                 270
Ile Leu Asn Phe Arg Thr Thr Tyr Val Ser Lys Ser Gly Gln Val Ile
            275                 280                 285
Phe Glu Ala Arg Ser Ile Cys Ile His Tyr Val Thr Thr Trp Phe Ile
            290                 295                 300
Ile Asp Leu Ile Ala Ala Leu Pro Phe Asp Leu Leu Tyr Ala Phe Asn
305                 310                 315                 320
Val Thr Val Val Ser Leu Val His Leu Leu Lys Thr Val Arg Leu Leu
            325                 330                 335
Arg Leu Leu Arg Leu Leu Gln Lys Leu Asp Arg Tyr Ser Gln His Ser
            340                 345                 350
Thr Ile Val Leu Thr Leu Leu Met Ser Met Phe Ala Leu Leu Ala His
            355                 360                 365
Trp Met Ala Cys Ile Trp Tyr Val Ile Gly Lys Met Glu Arg Glu Asp
            370                 375                 380
Asn Ser Leu Leu Lys Trp Glu Val Gly Trp Leu His Glu Leu Gly Lys
385                 390                 395                 400
Arg Leu Glu Ser Pro Tyr Tyr Gly Asn Asn Thr Leu Gly Gly Pro Ser
            405                 410                 415
Ile Arg Ser Ala Tyr Ile Ala Ala Leu Tyr Phe Thr Leu Ser Ser Leu
            420                 425                 430
Thr Ser Val Gly Phe Gly Asn Val Ser Ala Asn Thr Asp Ala Glu Lys
            435                 440                 445
Ile Phe Ser Ile Cys Thr Met Leu Ile Gly Ala Leu Met His Ala Leu
            450                 455                 460
Val Phe Gly Asn Val Thr Ala Ile Ile Gln Arg Met Tyr Ser Arg Trp
465                 470                 475                 480
Ser Leu Tyr His Thr Arg Thr Lys Asp Leu Lys Asp Phe Ile Arg Val
            485                 490                 495
His His Leu Pro Gln Gln Leu Lys Gln Arg Met Leu Glu Tyr Phe Gln
            500                 505                 510
Thr Thr Trp Ser Val Asn Asn Gly Ile Asp Ser Asn Glu Leu Leu Lys
            515                 520                 525
Asp Phe Pro Asp Glu Leu Arg Ser Asp Ile Thr Met His Leu Asn Lys
            530                 535                 540
Glu Ile Leu Gln Leu Ser Leu Phe Glu Cys Ala Ser Arg Gly Cys Leu
545                 550                 555                 560
Arg Ser Leu Ser Leu His Ile Lys Thr Ser Phe Cys Ala Pro Gly Glu
            565                 570                 575
```

```
Tyr Leu Leu Arg Gln Gly Asp Ala Leu Gln Ala Ile Tyr Phe Val Cys
            580                 585                 590

Ser Gly Ser Met Glu Val Leu Lys Asp Ser Met Val Leu Ala Ile Leu
            595                 600                 605

Gly Lys Gly Asp Leu Ile Gly Ala Asn Leu Ser Ile Lys Asp Gln Val
            610                 615                 620

Ile Lys Thr Asn Ala Asp Val Lys Ala Leu Thr Tyr Cys Asp Leu Gln
625                 630                 635                 640

Cys Ile Ile Leu Lys Gly Leu Phe Glu Val Leu Gly Leu Tyr Pro Glu
                645                 650                 655

Tyr Ala His Lys Phe Val Glu Asp Ile Gln His Asp Leu Thr Tyr Asn
            660                 665                 670

Leu Arg Glu Gly His Glu Ser Asp Val Ile Ser Arg Leu Ser Asn Lys
            675                 680                 685

Ser Thr Val Pro Gln Ala Glu Pro Lys Gly Asn Gly Ser Ile Lys Lys
            690                 695                 700

Arg Leu Pro Ser Ile Val Glu Asp Glu Glu Glu Glu Val Glu Glu
705                 710                 715                 720

Glu Glu Thr Thr Ser Leu Ser Pro Ile Tyr Thr Arg Gly Ser Ser Val
                725                 730                 735

Ser His Ser Lys Lys Thr Gly Ser Ser Lys Ser Tyr Leu Gly Leu Ser
            740                 745                 750

Leu Lys Gln Leu Thr Ser Gly Thr Val Pro Phe His Ser Pro Ile Arg
            755                 760                 765

Val Ser Ser Ala Asn Ser Pro Lys Thr Lys Gln Glu Ala Asp Pro Pro
770                 775                 780

Asn His Gly Thr Arg Lys Glu Lys Asn Leu Lys Val Gln Leu Cys Ser
785                 790                 795                 800

Leu Gly Thr Ala Gly Thr Pro Glu Leu Ser Pro Arg Ile Val Asp Gly
                805                 810                 815

Ile Glu Asp Gly Asn Ser Ser Glu Glu Thr Gln Thr Phe Asp Phe Gly
            820                 825                 830

Ser Glu Gln Ile Arg Pro Glu Pro Arg Ile Ser Pro Ser Leu Gly Glu
            835                 840                 845

Ser Glu Ile Gly Ala Ala Phe Leu Phe Ile Lys Ala Glu Glu Thr Lys
            850                 855                 860

Gln Gln Ile Asn Lys Leu Asn Ser Glu Val Thr Thr Leu Thr Gln Glu
865                 870                 875                 880

Val Ser Gln Leu Gly Lys Asp Met Arg Ser Ile Met Gln Leu Leu Glu
                885                 890                 895

Asn Ile Leu Ser Pro Gln Gln Pro Ser Gln Phe Cys Ser Leu His Pro
            900                 905                 910

Thr Ser Ile Cys Pro Ser Arg Glu Ser Phe Gln Thr Arg Val Ser Trp
            915                 920                 925

Ser Ala His Gln Pro Cys Leu His Leu Gln Ala Asn Gly Ala His Leu
            930                 935                 940

Tyr His Gly Asn Val Thr Ser Asp Ile Trp Ser Val Asp Pro Ser Leu
945                 950                 955                 960

Val Gly Ser Asn Pro Gln Arg Thr Glu Ala His Glu Gln Ser Pro Val
                965                 970                 975

Asp Ser Glu Leu His His Ser Pro Asn Leu Ala Tyr Ser Pro Ser His
            980                 985                 990

Cys Gln Val Ile Gln Glu Gly His  Leu Gln Phe Leu Arg  Cys Ile Ser
```

-continued

```
            995                 1000                1005
Pro His Ser Asp Thr Thr Leu Thr Pro Leu Gln Ser Ile Ser Ala Thr
    1010                1015            1020

Leu Ser Ser Ser Val Cys Ser Ser Ser Glu Thr Ser Leu His Leu Val
1025                1030            1035                1040

Leu Pro Ser Arg Ser Glu Glu Gly Ser Ile Thr His Gly Pro Val Ser
                1045            1050            1055

Ser Phe Ser Leu Glu Asn Leu Pro Gly Ser Trp Asp Arg Glu Gly Met
            1060            1065            1070

Met Ser Ala Ser Thr Glu Pro Leu Glu Asn Phe Pro Val Glu Val Val
        1075            1080            1085

Thr Ser Thr Ala Asp Val Lys Asp Ser Lys Ala Ile Asn Val
    1090            1095            1100
```

ERG POTASSIUM CHANNEL

RELATED APPLICATIONS

This application is a continuation in part of U.S. patent application No.: 09/119,855, filed on Jul. 21, 1998, incorporated herein in its entirety by this reference.

BACKGROUND OF THE INVENTION

The fundamental function of a neuron is to receive, conduct, and transmit signals. Despite the varied purpose of the signals carried by different classes of neurons, the form of the signal is always the same and consists of changes in the electrical potential across the plasma membrane of the neuron. The plasma membrane of a neuron contains voltage-gated cation channels, which are responsible for generating this electrical potential (also referred to as an action potential or nerve impulse) across the plasma membrane.

One class of voltage-gated cation channels are the voltage-gated potassium channels (Kv). These include: (1) the delayed potassium channels, which repolarize the membrane after each action potential to prepare the cell to fire again; (2) the early potassium channels, which open when the membrane is depolarized and act to reduce the rate of firing at levels of stimulation which are just above the. threshold required for firing; and (3) the calcium-activated potassium channels, which act along with the voltage-gated calcium channels to decrease the response of the cell to an unchanging prolonged stimulation, a process called adaptation. In addition to being critical for action potential conduction, the voltage-gated potassium channels also play a role in neurotransmitter release. As a result of these activities, voltage-gated potassium channels are important in controlling neuronal excitability (Hille B., Ionic Channels of Excitable Membranes, Second Edition, Sunderland, Mass.: Sinauer, (1992)).

There is a surprising amount of structural and functional diversity within the voltage-gated potassium channels. This diversity is generated both by existence of multiple genes and by alternative splicing of RNA transcripts produced from the same gene. Nonetheless, the amino acid sequences of the known voltage-gated potassium channels show similarity. The Drosophila SH locus was the first potassium channel structural gene to be isolated (Kamb A. et al. (1987) *Cell* 50: 405). Since then, a number of additional potassium channel genes have been cloned from Drosophila and other organisms (Baumann A. et al. (1988) *EMBO J.* 7: 2457). One of these genes is the X-linked EAG locus, which was originally identified in Drosophil, on the basis of mutations that cause a leg-shaking phenotype (Kaplan W. D. et al. (1969) *Genetics* 61: 399). Electrophysiological studies revealed that EAG mutations caused spontaneous repetitive firing in motor axons and elevated transmitter release at the larval neuromuscular junction (Ganetzky B. et al. (1985) *Trends Neurosci.* 8:322). The striking hyperexcitability of EAG mutants demonstrates the importance of EAG channels in maintaining normal neuronal excitability in Drosophila (Ganetzky B. et al. (1983) *J. Neurogeret.* 1: 17–28).

EAG, along with m-EAG, ELK. and h-ERG define a family of potassium channel genes in Drosophila and mammals. A distinctive feature of the EAG/ERG family is the homology to cyclic nucleotide binding domains of cyclic nucleotide-gated cation channels and cyclic nucleotide-activated protein kinases (Kaupp, U. B. et al. (1991) *Trends Neurosci.* 14: 150–157). However, unlike the veirebrate cyclic nucleotide-gated cation channels, which are relatively voltage-insensitive, activation of EAG/ERG channels shows a very steep voltage dependence (Robertson, G. et al. (1993) *Biophys. J.* 64: 430). In addition, whereas cyclic nucleotide-activated cation channels show little selectivity among monovalent and divalent cations, eag is strongly selective for $K^+$ over $Na^+$. The EAG/ERG family may thus be an evolutionary link between voltage-activated potassium channels and cyclic nucleotide-gated cation channels with intermediate structural and functional properties.

SUMMARY OF THE INVENTION

The present invention is based, at least in part, on the discovery of novel ERG potassium channel family members, referred to herein as "ERG-like proteins" ("ERG-LP") nucleic acid and protein molecules. The ERG-LP molecules of the present invention are useful as targets for developing modulating agents to regulate a variety of cellular processes. Accordingly, in one aspect, this invention provides isolated nucleic acid molecules encoding ERG-LP proteins or biologically active portions thereof, as well as nucleic acid fragments suitable as primers or hybridization probes for the detection of ERG-LP-encoding nucleic acids.

In one embodiment, an ERG-LP nucleic acid molecule of the invention is at least 28%, 30%, 35%, 40%, 45%, 50%, 55%, 60%, 65%, 70%, 75%, 80%, 85%, 90%, 95% or more homologous to the nucleotide sequence (e.g., to the entire length of the nucleotide sequence) shown in SEQ ID NO:1, SEQ ID NO:3, or a complement thereof. In another embodiment, an ERG-LP nucleic acid molecule of the invention is at least 42%, 45%, 50%, 55%, 60%, 65%, 70%, 75%, 80%, 85%, 90%, 95% or more homologous to the nucleotide sequence (e.g., to the entire length of the nucleotide sequence) shown in SEQ ID NO:4, SEQ ID NO:6, SEQ ID NO:15, SEQ ID NO:17, or a complement thereof. In another embodiment, an ERG-LP nucleic acid molecule of the invention is at least 50%, 55%, 60%, 65%, 70%, 75%, 80%, 85%, 90%, 95%, or more homologous. to the nucleotide sequence (e.g., to the entire length of the nucleotide sequence) shown in SEQ ID NO:7, SEQ ID NO:9, or a complement thereof.

In a preferred embodiment, the isolated nucleic acid molecule includes the nucleotide sequence shown SEQ ID NO:1 or 3, or a complement thereof. In another embodiment, the nucleic acid molecule: includes SEQ ID NO:3 and nucleotides 1–112 of SEQ ID NO:1. In another preferred embodiment, the nucleic acid molecule has the nucleotide sequence shown in SEQ ID NO:1 or 3. In another preferred embodiment, the nucleic acid molecule includes a fragment of at least 949 nucleotides of the nucleotide sequence of SEQ ID NO:1, SEQ ID NO:3, or a complement thereof.

In another preferred embodiment, the isolated nucleic acid molecule includes the nucleotide sequence shown SEQ ID NO:4 or 6, or a complement thereof. In another embodiment, the nucleic acid molecule. includes SEQ ID NO:6 and nucleotides 1–214 of SEQ ID NO:4. In yet another embodiment, the nucleic acid molecule includes SEQ ID NO:6 and nucleotides 1844–2694 of SEQ ID NO:4. In another preferred embodiment, the nucleic acid molecule has the nucleotide sequence shown in SEQ ID NO:4 or 6. In another preferred embodiment, the nucleic acid molecule includes a fragment of at least 307 nucleotides of the nucleotide sequence of SEQ ID NO:4, SEQ ID NO:6, or a complement thereof.

In another preferred embodiment, the isolated nucleic acid molecule includes at least 200 consecutive. nucleotides, more preferably at least 400 consecutive nucleotides, more preferably at least 600 consecutive nucleotides, more preferably at least 800 consecutive nucleotides, more preferably at least 1000 consecutive nucleotides, more preferably at least 1200 consecutive nucleotides, more preferably at least 1400 consecutive nucleotides, more preferably at least 1500 consecutive nucleotides of the nucleotide sequence shown SEQ ID NO:4 or 6, or a complement thereof.

In another preferred embodiment, the isolated nucleic acid molecule includes the nucleotide sequence shown SEQ ID NO:7 or 9, or a complement thereof. In another embodiment, the nucleic acid molecule includes SEQ ID NO:9 and nucleotides 1–262 of SEQ ID NO:7. In another preferred embodiment, the nucleic acid molecule has the nucleotide sequence shown in SEQ ID NO:7 or 9. In another preferred embodiment, the nucleic acid molecule includes a fragment of at least 1114 nucleotides of the nucleotide sequence of SEQ ID NO:7, SEQ ID NO:9, or a complement thereof.

In another preferred embodiment, the isolated nucleic acid molecule includes the nucleotide sequence shown SEQ ID NO: 15 or 17, or a complement thereof. In another embodiment, the nucleic acid molecule includes SEQ ID NO:17 and nucleotides 1–195 of SEQ ID NO:15. In yet another embodiment, the nucleic acid molecule includes SEQ ID NO:17 and nucleotides 3517–5107 of SEQ ID NO:15. In another preferred embodiment, the nucleic acid molecule has the nucleotide sequence shown in SEQ ID NO:15 or 17.

In another embodiment, an ERG-LP nucleic acid molecule includes a nucleotide sequence encoding a protein having an amino acid sequence sufficiently homologous to the amino acid sequence of SEQ ID NO:2. SEQ ID NO:5, SEQ ID NO:8, or SEQ ID NO:16. In a preferred embodiment, an ERG-LP nucleic acid molecule includes a nucleotide sequence encoding a protein having an amino acid sequence at least 37%, 40%, 45%, 50%, 55%, 60%, 65%, 70%, 75%, 80%, 85%, 90%, 95% or more homologous to the amino acid sequence of SEQ ID NO:2, or SEQ ID NO:8. In another preferred embodiment, an ERG-LP nucleic acid molecule includes a nucleotide sequence encoding a protein having an amino acid sequence at least 25%, 30%, 35%, 40%, 45%, 50%, 55%, 60%, 65%, 70%, 75%, 80%, 85%, 90%, 93%, 95% or more homologous to the amino acid sequence of SEQ ID NO:5 or SEQ ID NO:16.

In another preferred embodiment, an isolated nucleic acid molecule encodes the amino acid sequence of human. or monkey ERG-LP1. In yet another preferred embodiment, the nucleic acid molecule includes a nucleotide sequence encoding a protein having the amino acid sequence of SEQ ID NO:2, or SEQ ID NO:8. In yet another preferred embodiment, the nucleic acid molecule, is at least 387 nucleotides in length and encodes a protein having an ERG-LP1 activity (,is described herein). In yet another preferred embodiment, an isolated nucleic acid molecule encodes the amino acid sequence of human ERG-LP-2. In yet another preferred emnbodiment, the nucleic acid molecule includes a nucleotide sequence encoding a protein having the amino acid sequence of SEQ ID NO:5 or SEQ ID NO:16.

Another embodiment of the invention features nucleic acid molecules, preferably ERG-LP nucleic acid molecules, which specifically detect ERG-LP nucleic acid molecules relative to nucleic acid molecules encoding non-ERG-LP proteins. For example, in one embodiment, such a nucleic acid molecule is at least 949, 950–1000, 1000–1050, 1050–1100 or more nucleotides in length and hybridizes under stringent conditions to a nucleic acid molecule comprising the nucleotide sequence shown in SEQ ID NO:1, or a complement thereof. In preferred embodiments, the nucleic acid molecules are at least 15 (e.g., contiguous) nucleotides in length and hybridize under stringent conditions to nucleotides 1082–1100, 1258–1289, 1336–1343, 1404–1430, 2190–2428, or 3107–3355 of SEQ ID NO:1. In other preferred embodiments, the nucleic acid molecules comprise nucleotides 1082–1100, 1258–1289, 1336–1343, 1404–1330, 2190–2428, or 3107–3355 of SEQ ID NO:1.

In another particularly preferred embodiment, the nucleic acid molecule comprises a fragment of at least 307, 350–400, 400–450, 450–500 or more nucleotides of the nucleotide sequence of SEQ ID NO:4, SEQ ID NO:6, SEQ ID NO:15, SEQ ID NO:17, or a complement thereof. In preferred embodiments, the nucleic acid molecules are at least 15 (e.g., contiguous) nucleotides in length and hybridize under stringent conditions to nucleotides 1–29, 442–621, 755–1013, 1170–1246, or 1463–1651 of SEQ ID NO:4. In other preferred embodiments, the nucleic acid molecules include nucleotides 1–29, 442–621, 755–1013, 1170–1246, or 1463–1651 of SEQ ID NO:4.

In other preferred embodiments, the nucleic acid molecule encodes a naturally occurring allelic variant of a polypeptide comprising the amino acid sequence of SEQ ID NO:2, wherein the nucleic acid molecule hybridizes to a nucleic acid molecule comprising SEQ ID NO:1 or SEQ ID NO:3 under stringent conditions. In yet other preferred embodiments, the nucleic acid molecule encodes a naturally occurring allelic variant of a polypeptide comprising the amino acid sequence of SEQ ID NO:5, wherein the nucleic acid molecule hybridizes to a nucleic acid molecule comprising SEQ ID NO:4 or SEQ ID NO:6 under stringent conditions. In other preferred embodiments, the nucleic acid molecule encodes a naturally occurring allelic variant of a polypeptide comprising the amino acid sequence of SEQ ID NO:8, wherein the nucleic acid molecule hybridizes to a nucleic acid molecule comprising SEQ ID NO:7 or SEQ ID NO:9 under stringent conditions. In yet other preferred embodiments, the nucleic acid molecule encodes a naturally occurring allelic variant of a polypeptide comprising the amino acid sequence of SEQ ID NO:16, wherein the nucleic acid molecule hybridizes to a nucleic acid molecule comprising SEQ ID NO:15 or SEQ ID NO:17 under stringent conditions.

Another embodiment of the invention provides an isolated nucleic acid molecule which is antisense to an ERG-LP nucleic acid molecule, e.g., the coding strand of an ERG-LP nucleic acid molecule.

Another aspect of the invention provides a vector comprising an ERG-LP nucleic acid molecule. In certain embodiments, the vector is a recombinant expression vector. In another embodiment, the invention provides a host cell containing a vector of the invention. The invention also provides a method for producing a protein, preferably an ERG-LP protein, by culturing in a suitable medium, a host cell, e.g., a mammals host cell such as a non-human mammalian cell, of the invention containing a recombinant expression vector, such that the protein is produced.

Another aspect of this invention features isolated or recombinant ERG-LP proteins and polypeptides. In one embodiment, the isolated protein, preferably an ERG-LP protein, includes at least one transmembrane domain. In another embodiment, the isolated protein, preferably an ERG-LP protein, includes a P-loop. In another embodiment, the isolated protein, preferably an ERG-LP protein, includes a cyclic nucleotide-binding domain. In another embodiment, the isolated protein, preferably an ERG-LP protein, includes transmembrane region cyclic nucleotide gated channel domain. In another embodiment, the isolated protein, preferably an ERG-LP protein, includes at least one transmembrane domain, a P-loop, a cyclic nucleotide-binding domain, and a transmembrane region cyclic nucleotide gated channel domain. In a preferred embodiment, the protein, preferably an ERG-LP protein, includes at least one transmembrane domain, a P-loop, and a cyclic nucleotide-binding domain, and has an amino acid sequence at least about 25%, 30%, 35%, 37%, 40%, 45%, 50%, 55%, 60%, 650%, 70%, 75%, 80%, 85%, 90%, 93%, 95%, or more homologous to the amino acid sequence of SEQ ID NO:2, SEQ ID NO:5, SEQ ID NO:8, or SEQ ID NO:16. In another preferred embodiment, the protein, preferably an ERG-LP protein, includes at least one transmembrane domain and plays a role in generating an electrical potential across a plasma membrane, e.g., a neuronal plasma membrane or a muscle plasma membrane. In another preferred embodiment, the protein, preferably an ERG-LP protein, includes at least one P-loop and plays a role in generating an electrical potential across a plasma membrane, e.g., a neuronal plasma membrane or a muscle plasma membrane. In another preferred embodiment, the protein, preferably an ERG-LP protein, includes at least one cyclic nucleotide-binding domain, and plays a role in generating an electrical potential across a plasma membrane, e.g., a neuronal plasma membrane or a muscle plasma membrane. In another preferred embodiment, the protein, preferably an ERG-LP protein, includes at least one transmembrane region cyclic nucleotide gated channel domain and plays a role in generating an electrical potential across a plasma membrane, e.g., a neuronal plasma membrane or a muscle plasma membrane. In another preferred embodiment, the protein, preferably an ERG-LP protein, includes at least one transmembrane domain and a P-loop, and plays a role in generating an electrical potential across a plasma membrane, e.g., a neuronal plasma membrane or a muscle plasma membrane. In another preferred embodiment, the protein, preferably an ERG-LP protein, includes at least one transmembrane domain and a cyclic nucleotide-binding domain, and plays a role in generating an electrical. potential across a plasma membrane, e.g., a neuronal plasma membrane or a muscle plasma membrane. In another preferred embodiment, the protein, preferably an ERG-LP protein, includes at least one transmembrane domain and a transmembrane region cyclic nucleotide gated channel domain, and plays a role in generating an electrical potential across a plasma membrane, e.g., a neuronal plasma membrane or a muscle plasma membrane. In another preferred embodiment, the protein, preferably an ERG-LP protein, includes at least one P-loop and a cyclic nucleotide-binding domain, and plays a role in generating, an electrical potential across a plasma membrane, e.g., a neuronal plasma membrane or a muscle plasma membrane. In another preferred embodiment, the protein, preferably in ERG-LP protein, includes at least one P-loop and a transmembrane region cyclic nucleotide gated channel domain, and plays a role in generating an electrical potential across a plasma membrane, e.g., a neuronal plasma membrane or a muscle plasma membrane. In another preferred embodiment, the protein, preferably an ERG-LP protein, includes at least one transmembrane domain, a P-loop, and a cyclic nucleotide-binding domain, and plays a role in generating an electrical potential across a plasma membrane, e.g., a neuronal plasma membrane or a muscle plasma membrane. In another preferred embodiment, the protein, preferably an ERG-LP protein, includes at least one transmembrane domain, a P-loop, and a transmembrane region cyclic nucleotide gated channel domain, and l)lays a role in generating an electrical potential across a plasma membrane, e.g., a neuronal plasma membrane or a muscle plasma membrane. In yet another preferred embodiment, the protein, preferably an ERG-LP protein, includes at least one transmembrane domain, a P-loop, and a cyclic nucleotide-binding domain, and is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, or SEQ ID NO:9.

In another preferred embodiment, the isolated protein includes at least 50 consecutive amino acids, more preferably at least 100 consecutive amino acids, more preferably at least 150 consecutive amino acids, more preferably at least 200 consecutive amino acids, more preferably at least 250 consecutive amino acids, more preferably at least 0.350 consecutive amino acids, more preferably at least 450 consecutive amino acids, more preferably at least 500 consecutive amino acids of the amino acid sequence shown SEQ ID NO:5 or 16.

In another embodiment, the invention features fragments of the proteins having the amino acid sequence of SEQ ID NO:2, SEQ ID NO:5, or SEQ ID NO:8 or SEQ ID NO:16, wherein the fragment comprises at least 15 amino acids (e.g., contiguous amino acids) of the amino acid sequence of SEQ ID NO:2, SEQ ID NO:5, SEQ ID NO:8 or SEQ ID NO:16. In another embodiment, the protein, preferably an ERG-LP protein, has the amino acid sequence of SEQ ID NO:2, SEQ ID NO:5, or SEQ ID NO:8 or SEQ ID NO:16.

In another embodiment, the invention features an isolated protein, preferably an ERG-LP protein, which is encoded by a nucleic acid molecule having a nucleotide sequence at least about 28%, 30%, 35%, 40%, 45%, 50%, 55%, 60%, 65%, 70%, 75% 80%, 85%, 90%, 95% or more homologous to a nucleotide sequence of SEQ ID NO:1, SEQ ID NO:3, or a complement thereof. In yet another embodiment, the invention features an isolated protein, preferably an ERG-LP protein, which is encoded by a nucleic acid molecule having a nucleotide sequence at least about 42%, 45%, 50%, 55%, 60%, 65%, 70%, 75%, 80%, 85%, 90%, 95% or more homologous to a nucleotide sequence of SEQ ID NO:4, SEQ ID NO:6, or a complement thereof. In yet another embodiment, the invention features an isolated protein, preferably an ERG-LP protein, which is encoded by a nucleic acid molecule having a nucleotide sequence at least about 50%, 55%, 60%, 65%, 70%, 75%, 80%, 85%, 90%, 95% or more homologous to a nucleotide sequence of SEQ ID NO:7, SEQ ID NO:9, or a complement thereof. In yet another embodiment, the invention features an isolated protein, preferably an ERG-LP protein, which is encoded by a nucleic acid molecule having a nucleotide sequence at least about 50%, 55%, 60%, 65%, 70%, 75%, 80%, 85%, 90%, 95% or more homologous to a nucleotide sequence of SEQ ID NO:15, SEQ ID NO:17, or a complement thereof. This invention further features an isolated protein, preferably an ERG-LP protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:15, SEQ ID NO:17 or a complement thereof.

The proteins of the present invention or biologically active portions thereof, can be operatively linked to a non-ERG-LP polypeptide (e.g., heterologous amino acid sequences) to form fusion proteins. The invention further features antibodies, such as monoclonal or polyclonal antibodies, that specifically bind proteins of the invention, preferably ERG-LP proteins. In addition, the ERG-LP proteins or biologically active portions thereof can be incorporated into pharmaceutical compositions, which optionally include pharmaceutically acceptable carriers.

In another aspect, the present invention provides a method for detecting the presence of an ERG-LP nucleic acid molecule, protein or polypeptide in a biological sample by contacting the biological sample with an agent capable of detecting an ERG-LP nucleic acid molecule, protein or polypeptide such that the presence of an ERG-LP nucleic acid molecule, protein or polypeptide is detected in the biological sample.

In another aspect, the present invention provides a method for detecting the presence of ERG-LP activity in a biological sample by contacting the biological sample with an agent capable of detecting an indicator of EPG-LP activity such that the presence of ERG-LP activity is detected in the biological sample.

In another aspect, the invention provides a method for modulating ERG-LP activity comprising contacting a cell capable o)f expressing ERG-LP with an agent that modulates ERG-LP activity such that ERG-LP activity in the cell is modulated. In one embodiment, the agent inhibits ERG-LP activity. In another embodiment, the agent stimulates ERG-LP activity. In one embodiment, the agent is an antibody that specifically binds to an ERG-LP protein. In another embodiment, the agent modulates expression of ERG-LP by modulating transcription of an ERG-LP gene or translation of an ERG-LP mRNA. In yet another embodiment, the agent is a nucleic acid molecule having a nucleotide sequence that is antisense to the coding strand of an ERG-LP mRNA or an ERG-LP gene.

In one embodiment, the methods of the present invention are used to treat a subject having a disorder characterized by aberrant ERG-LP protein or nucleic acid expression or activity by administering an agent which is an ERG-LP modulator to the subject. In one embodiment, the ERG-LP modulator is an ERG-LP protein. In another embodiment the ERG-LP modulator is an ERG-LP nucleic acid molecule. In yet another embodiment, the ERG-LP modulator is a peptide, peplidomimetic, or other small molecule. In a preferred embodiment, the disorder characterized by aberrant ERG-LP protein or nucleic acid expression is a CNS disorder.

The present invention also provides a diagnostic assay for identifying the presence or absence of a genetic alteration characterized by at least one of (i) aberrant modification or mutation of a gene encoding an ERG-LP protein; (ii) misregulation of the gene; and (iii) aberrant post-translational modification of an ERG-LP protein, wherein a wild-type form of the gene encodes an protein with an ERG-LP activity.

In another aspect the invention provides a method for identifying a compound that binds to or modulates the activity of an ERG-LP protein, by providing an indicator composition comprising an ERG-LP protein having ERG-LP activity, contacting the indicator composition with a test compound, and determining the effect of the test compound on ERG-LP activity in the indicator composition to identify a compound that modulates the activity of an ERG-LP protein.

Other features and advantages of the invention will be apparent from the following detailed description and claims.

BRIEF DESCRIPTION OF THE DRAWINGS

FIG. 1 depicts the cDNA sequence and predicted amino acid sequence of monkey ERG-LP1. The nucleotide sequence (corresponds to nucleic acids 1 to 3355 of SEQ ID NO:1. The amino acid sequence corresponds to amino acids 1 to 1083 of SEQ ID NO:2. The coding region without the 5' and 3' untranslated regions of the monkey ERG-LP1 (lkba251d10orf, corresponding to SEQ ID NO:2) gene is shown in SEQ ID NO:3.

FIG. 2 depicts the partial cDNA sequence and predicted amino acid sequence of human ERG-LP2. The partial nucleotide sequence corresponds to nucleic acids 1 to 2694 of SEQ ID NO:4. The partial amino acid sequence corresponds to amino acids 1 to 542 of SEQ ID NO:5. The coding region without the 5' and 3' untranslated regions of the human ERG-LP2 gene is shown in SEQ ID NO:6.

FIG. 3 depicts an alignment of the amino acid sequence of monkey ERG-LP1 with the amino acid sequence of the human. ERG protein (SEQ ID NO:10).

FIG. 4 depicts an alignment of the partial amino acid sequence of human ERG-LP2 with the amino acid sequence of the Drosophila ERK protein (SEQ ID NO:11).

FIG. 5 depicts the partial cDNA sequence and predicted amino acid sequence of human ERG-LP1. The partial nucleotide sequence corresponds to nucleic acids 1 to 1132 of SEQ ID NO:7. The partial amino acid sequence corresponds to amino acids 1 to 290 of SEQ ID NO:8. The coding region without the 5' and 3' untranslated regions of the human ERG-LP1 gene is shown in SEQ ID NO:9.

FIG. 8 depicts the cDNA sequence and predicted amino acid sequence of full length human ERG-LP2. The nucleotide sequence corresponds to nucleic acids 1 to of SEQ ID NO:15. The amino acid sequence corresponds to amino acids 1 to 1107 of SEQ ID NO:16. The coding region without the 5' untranslated regions of the human ERG-LP2 gene is shown in SEQ ID NO:17.

FIG. 10 depicts the results of a search which was performed against the HMM database and which resulted in the identification of a "transmembrane region cyclic nucleotide gated channel" domain (SEQ ID NO:22) in the human ERG-LP-2 protein (SEQ ID NO:23). A search was also performed against the Program database, which resulted in the identification of several potential additional domains in the human ERG-LP2 protein. The identified domains in the human ERG-LP2 protein correspond to SEQ ID NOs.:24, 26, 28, 30, 32, and 34. SEQ ID NO:24 corresponds to the sequence contained in SEQ ID NO:25, SEQ ID NO:26 corresponds to the sequence contained in SEQ ID NO:27, SEQ ID NO:28 corresponds to the sequence contained in SEQ ID NO:29, SEQ ID NO:30 corresponds to the sequence contained in SEQ ID NO:31, SEQ ID NO:32 corresponds to the sequence contained in SEQ ID NO:33, and SEQ ID NO:34 corresponds to the sequence contained in SEQ ID NO:35.

FIG. 11 depicts a global alignment of the full length human ERG-LP2 protein (Flhba042h05, corresponding to SEQ ID NO:16) with the the rat Relk1 protein (ratelk1, corresponding to SEQ (SEQ ID NO:36) using the the GAP program in the GCG software package, using a Blossum 62 matrix and a gap weight of 12 and a length weight of 4. The results showed a 92.552% identity between the two sequences.

FIG. 12 depicts a global alignment of the full length human ERG-LP2 protein (Flhba042h05, corresponding to SEQ ID NO:16) with the human ERG protein (human.erg, corresponding to SEQ ID NO:10) using the GAP program in the GCG software package, using a Blossum 62 matrix and a gap weight of 12 and a length weight of 4. The results showed a 40.852% identity between the two sequences.

Figure 13:
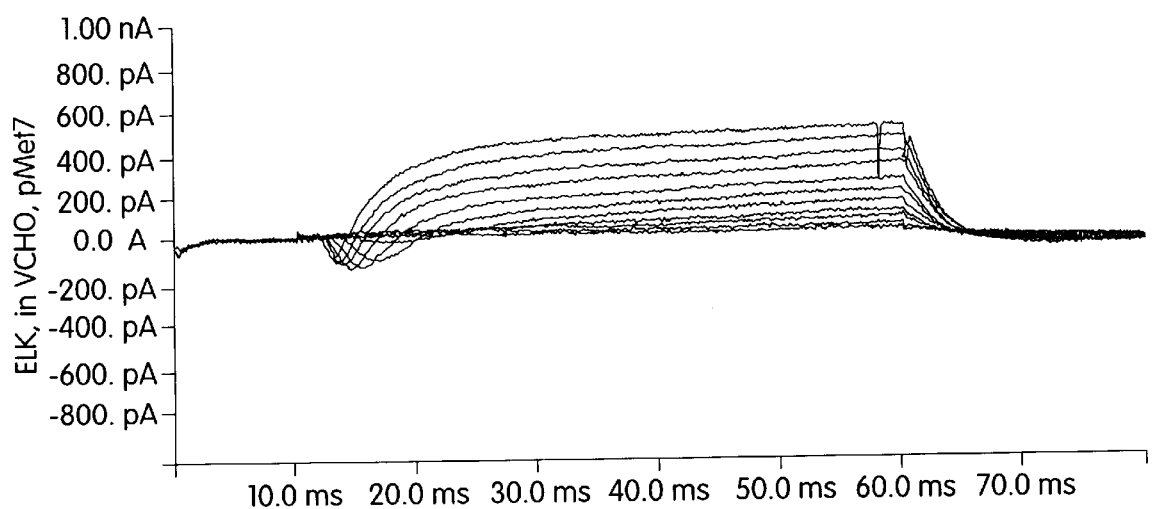
Figure 13A:
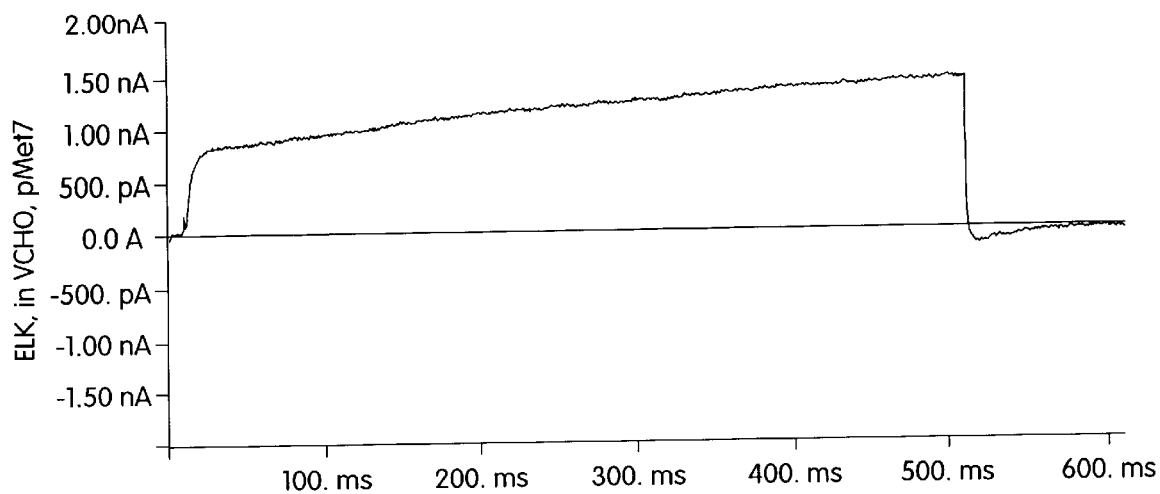
Figure 13B:
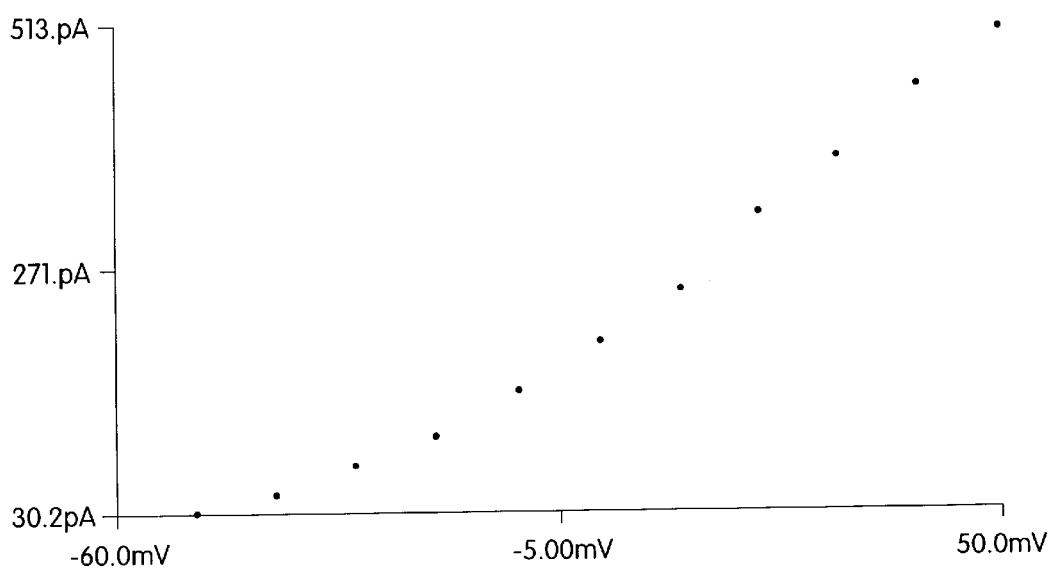

FIG. 13 depicts electrophysiology measurements taken using a single electrode patch-clamp in CHO cells transfected with monkey ERG-LP1.

DETAILED DESCRIPTION OF THE INVENTION

The present invention is based, at least in part, on the discovery of novel molecules, referred to herein as ERG-LP nucleic acid and protein molecules, which are novel members of the ERG potassium channel family. These novel molecules are capable of, for example, modulating a potassium channel mediated activity in a cell, e.g., a neuronal cell or a muscle cell.

As used herein, a "potassium channel" refers to a protein which is involved in receiving, conducting, and transmitting signals, in an electrically excitable cell, e.g., a neuronal cell or a muscle cell. Potassium channels are potassium ion selective, and can determine membrane excitability (the ability of, for example, a neuron to respond to a stimulus and convert it into an impulse), influence the resting potential of membranes, wave forms and frequencies of action potentials, and thresholds of excitation. Potassium channels are typically expressed in electrically excitable cells, e.g., neurons, muscle, endocrine, and egg cells, and may form heteromultineric structures, e.g., composed of pore-forming α and cytoplasmic β subunits. Examples of potassium channels include: (1) the voltage-gated potassium channels, (2) the ligand-gated potassium channels, e.g., cyclic nucleotide-gated potassium channels, and (3) the mechanically-gated potassium channels. Voltage-gated and ligand-gated potassium channels are ex,pressed in the brain, e.g., in brainstem monoaminergic and forebrain cholinergic neurons, where they are involved in the release of neurotransmitters, or in the dendrites of hippocampal and neocortical pyramidal cells, where they are involved in the processes of leraming and memory formation. For a detailed description of potassium channels, see Kandel E. R. et al., Principles of Neural Science, second edition, (Elsevier Science Publishing Co., Inc., N.Y. (1985)), the contents of which are incorporated herein by reference. Thus, the ERG-LP proteins can modulate potassium channel mediated activities and provide novel diagnostic targets for potassium channel associated disorders.

As used herein, a "potassium channel associated disorder" refers to a disorder, disease or condition which is characterized by a misregulation of a potassium channel mediated activity. Potassium channel associated disorders can detrimentally affect conveyance of sensory impulses from the periphery to the brain and/or conductance of motor impulses from the brain to the periphery; integration of reflexes; interpretation of sensory impulses; or emotional, intellectual (e.g., learning and memory), or motor processes. Examples of potassium channel associated disorders include neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, korsakoffs psychosis, mania, anxiety disorders, or phobic disorders; learning or memory disorders, e.g., amnesia or age-related memory loss; neurological disorders, e.g., migraine; obesity; and cardiac disorders, e.g., cardiac arrythmias.

In another embodiment, the ERG-LP molecules of the invention are capable of modulating a potassium channel mediated activity. As used herein, a "potassium channel mediated activity" refers to an activity which involves a potassium channel, e.g., a potassium channel in a neuronal cell or a muscle cell. Potassium channel mediated activities are activities involved in receiving, conducting, and transmitting signals in, for example, the nervous system. Potassium channel mediated activities include release of neurotransmitters, e.g., dopamine or norepinephrine, from cells, e.g., neuronal cells; modulation of resting potential of membranes, wave forms and frequencies of action potentials, and thresholds of excitation; and modulation of processes such as integration of sub-threshold synaptic responses and the conductance of back-propagating action potentials in, for example, neuronal cells or muscle cells. Thus, the ERG-LP proteins can have one or more of the following activities: (1) modulate the release of neurotransmitters, (2) modulate membrane excitability, (3) influence the resting potential of membranes, (4) modulate wave forms and frequencies of action potentials, (5) modulate thresholds of excitation, and (6) modulate processes which underlie learning and memory, such as integration of sub-threshold synaptic responses and the conductance of back-propagating action potentials.

One embodiment of the invention features ERG-LP nucleic acid molecules, preferably human ERG-LP molecules, e.g., human ERG-LP1 and human ERG-LP-2, or monkey ERG-LP molecules, e.g., monkey ERG-LP1, which were identified from human or monkey brain libraries. The ERG-LP nucleic acid and protein molecules of the invention are described in further detail in the following subsections.

A. The ERG-LP1 Nucleic Acid and Protein Molecules

The present invention is based, at least in part, on the discovery of novel molecules, referred to herein as ERG-LP1 protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

In one embodiment, the isolated proteins of the present invention, preferably ERG-LP1 proteins, are identified based on the presence of at least one or more of a "transmembrane domain", a "P-loop", and a "cyclic nucleotide-binding domain." As used herein, the term "transmembrane domain" includes an amino acid sequence of about 15–40 amino acid residues in length, more preferably, about 15–30 amino acid residues in length, and most preferably about 18–25 amino acid residues in length, which spans the plasma membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Annual Rev. Neuronsci.* 19: 235–63, the contents of which are incorporated herein by reference. Amino acid residues 29–45, 229–251, 306–323, 357–381, 480–504, and 618–640 of the monkey ERG-LP1 comprise transmembrane domains.

As used herein, the term "P-loop" (also known as an H5 domain) includes an amino acid sequence of about 15–25 amino acid residues in length, preferably about 18–22 amino acid residues in length, and most preferably about 20–22 amino acid residues in length, which is involved in lining the potassium channel pore. The P-loop is typically found between transmembrane domains 5 and 6 and is believed to be a major determinant of ion selectivity in potassium channels. In a preferred embodiment, a P-loop can have the following consensus sequence: (D/T)-(A/S)-(L/F)-$X_1$-$X_1$-(A/T)-$X_2$-(S/T)-(S/T)-$X_2$-T-(S/T)-V-G-$X_1$-G-(N/D)-$X_2$-X-(A/P)-X-T-X-X-X (SEQ ID NO:12), where $X_1$ can be F,Y, or W; $X_2$ can be M, I, L, or V; and X can be any amino acid. P-loops are described in, for example, Warmke et al. (1991) *Science* 252:1560–1562, and Zagotta W. N. et al., (1 996) *Annual Rev. Neuronsci.* 19:235–63, the contents of which are incorporated herein by reference. Amino acid residues 451–471 of the monkey ERG-LP1 protein comprise a P-loop.

As used herein, a "cyclic nucleotide-binding domain" includes an amino acid sequence of about 60–120 amino acid residues in length, preferably about 60–100 amino acid residues in length, and most preferably about 60–80 amino acid residues in length, which is involved in the binding of cyclic nucleotides, e.g., cGMP or cAMP. In preferred embodiments, the cyclic nucleotide binding domain can have the following consensus sequence: X-X-X-G-(E/D)-$X_1$-(I/L)-X-X-X-G-(D/S/R)-$X_{(7-10)}$-G-(S/K)-X-$X_2$-(V/I)-X-(R/K)-X-(D/G)-$X_{(7-12)}$-G-$X_{(6)}$-(D/E)-$X_{(9-15)}$-(A/T)-$X_{(2)}$-(D/A/V)-$X_{(5-10)}$) (SEQ ID NO:13) where $X_1$ can be: T, Y, L, or C and $X_2$ can be: E, A or N. Cyclic nucleotide binding domains are described in, for example, Zagotta W. N. et al., (1996) *Annual Rev. Neuronsci.* 19:235–63, the contents of which are incorporated herein by reference. Amino acid residues 601–674 of the monkey ERG-LP1 protein comprise a cyclic nucleotide binding domain.

In another embodiment, ERG-LP1 proteins include at least one or more N-glycosylation sites. Predicted N-glycosylation sites are found, for example, from about amino acids 421–424, 428–431, 436–439, 470–473 and 499–502 of SEQ ID NO:2.

In another embodiment, ERG-LP1 proteins include at least one or more glycosaminoglycan attachment sites. Predicted glycosaminoglycan attachment sites are found, for example, from about amino acids 922–925of SEQ ID NO:2.

In another embodiment, ERG-LP1 proteins include at least one protein kinase C phosphorylation site. Predicted protein kinase C phosphorylation sites are found, for example, from about amino acid residues 129–131, 150–152, 250–252, 336–338, 447–449, 477–479, 769–771, 821–823, 840–842 and 901–903 of SEQ ID NO:2.

In another embodiment, ERG-LP1 proteins include at least one casein kinase II phosphorylation site. Predicted casein kinase II phosphorylation sites are found, for example, from about amino acid residues 13–16, 20–23, 56–59, 129–132, 250–253, 262–265, 389–392, 431–434, 438–441, 475–478, 560–563, 604–607, 726–729, 733–736, 846–849, 996–999, 1034–1037, 1040–1043 and 1076–1079 of SEQ ID NO:2.

In another embodiment, ERG-LP1 proteins include at least one tyrosine kinase phosphorylation site. Predicted tyrosine kinase phosphorylation sites are found, for example, from about amino acid residues 404–411 and 517–524 of SEQ ID NO:2.

Isolated proteins of the present invention, preferably ERG-LP1 proteins, have an amino acid sequence sufficiently homologous to the amino acid sequence of SEQ ID NO:2 or SEQ ID NO:8 or are encoded by a nucleotide sequence sufficiently homologous to SEQ ID NO:1, SEQ ID NO:3, SEQ ID NO:7, or SEQ ID NO:9. As used herein, the term "sufficiently homologous" refers to a first amino acid or nucleotide sequence which contains a sufficient or minimum number of identical or equivalent (e.g., an amino acid residue-which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70–80%, or 90–95% homology and share a common functional activity are defined herein as sufficiently homologous.

As used interchangeably herein an "ERG-LP1 activity", "biological activity of ERG-LP1" or "functional activity of ERG-LP1", refers to an activity exerted by an ERG-LP1 protein, polypeptide or nucleic acid molecule on an ERG-LP1 responsive cell as determined in vivo, or in vitro, according to standard techniques. The biological activity of ERG-LP1 is described herein.

Accordingly, another embodiment of the invention features isolated ERG-LP1 proteins and polypeptides having an ERG-LP1 activity. Preferred proteins are ERG-LP1 proteins having at least one transmembrane domain, a P-loop, and a cyclic nucleotide-binding domain and, preferably, an ERG-LP1 activity. Other preferred proteins are ERG-LP1 proteins having at least one transmembrane domain and, preferably, an ERG-LP1 activity. Other preferred proteins are ERG-LP1 proteins having at least one P-loop, and, preferably, an ERG-LP1 activity. Other preferred proteins are ERG-LP1 proteins having at least one cyclic nucleotide-binding domain and, preferably, an ERG-LP1 activity. Other preferred proteins are ERG-LP1 proteins having at least one transmembrane domain, a P-loop, and, preferably, an ERG-LP1 activity. Other preferred proteins are ERG-LP1 proteins having at least one transmembrane domain, a cyclic nucleotide-binding domain and, preferably, an ERG-LP1 activity. Other preferred proteins are ERG-LP1 proteins having at least one P-loop, a cyclic nucleotide-binding domain and, preferably, an ERG-LP1 activity. Additional preferred proteins have at least one transmembrane domain, a P-loop, and a cyclic nucleotide-binding domain and are, preferably, encoded by a nucleic acid molecule having a nucleotide sequence which hybridizes under stringent hybridization conditions to a nucleic acid molecule comprising the nucleotide sequence of SEQ ID NO:1, SEQ ID NO:3, SEQ ID NO:7, or SEQ ID NO:9.

The nucleotide sequence of the isolated monkey ERG-LP1 cDNA and the predicted amino acid sequence of the monkey ERG-LP1 polypeptide are shown in FIG. 1 and in SEQ MD NOs;1 and 2, respectively. The nucleotide sequence of the isolated human ERG-LP1 cDNA and the predicted amino acid sequence of the human ERG-LP1 polypeptide are shown in FIG. 5 and in SEQ ID NOs:7 and 8, respectively.

The monkey ERG-LP1 gene, which is approximately 3355 nucleotides in length, encodes a protein having a molecular weight of approximately 124.2 kD and which is approximately 1080 amino acid residues in length. The monkey ERG-LP1 gene is expressed exclusively in the brain (expression is highest in cortical regions, hippocampus, caudate, and amygdala).

The human ERG-LP1 gene, which is approximately 1132 nucleotides in length, encodes a protein having a molecular weight of approximately 33.3 kD and which is approximately 290 amino acid residues in length. The human ERG-LP1 gene is expressed exclusively in the brain (expression is highest in cortical regions, hippocampus, caudate, and amygdala).

B. The ERG-LP2 Nucleic Acid and Protein Molecules

In another embodiment, the isolated proteins of the present invention, preferably ERG-LP2 proteins, are identified based on the presence of at least one or more of a "transmembrane domain", a "P-loop", a "cyclic nucleotide-binding domain" and a "transmembrane region cyclic nucleotide gated channel domain."

Amino acid residues 226–247, 303–327, 354–377, and 449–473 of the partial human ERG-LP2 protein (SEQ ID NO:5) comprise transmembrane domains. Amino acid residues 423–442 of the partial human ERG-LP2 protein (SEQ ID NO:5) comprise a P-loop. Amino acid residues 295 to 535 of the full length human ERG-LP2 protein (SEQ ID NO:16) comprise a transmembrane region cyclic nucleotide gated channel domain.

In another embodiment, ERG-LP2 proteins include at least one or more N-glycosylation sites. Predicted N-glycosylation sites are found, for example, from about amino acids 317–320, 406–409, 436–439, 465–468, 614–617, 684–687, 818–821and 950–953 of SEQ ID NO:16.

In another embodiment, ERG-LP2 proteins include at least one protein kinase C phosphorylation site. Predicted protein kinase C phosphorylation sites are found, for example, from about amino acid residues 63–65, 126–128, 159–161, 216–218, 250–252, 329–331, 413–415, 616–618, 683–685, 733–735, 741–743, 749–751, 771–773, 807–809, 830–832 and 1078–1080 of SEQ ID NO:16.

In another embodiment, ERG-LP2 proteins include at least one casein kinase II phosphorylation site. Predicted casein kinase II phosphorylation sites are found, for example, from about amino acid residues 10–13, 17–20, 83–86, 126–129, 138–141, 155–158, 255–258, 441–444, 547–550, 616–619, 624–627, 632–635, 689–692, 705–708, 774–777, 819–822, 1033–1036, 1045–1048 and 1092–1095 of SEQ ID NO:16.

In another embodiment, ERG-LP2 proteins include at least one tyrosine kinase phosphorylation site. Predicted tyrosine kinase phosphorylation sites are found, for example, from about amino acid residues 397–404 of SEQ ID NO:16.

In another embodiment, ERG-LP2 proteins include at least one cAMP and cGMP dependent protein kinase phosphorylation site. Predicted cAMP and cGMP dependent protein kinase phosphorylation sites are found, for example, from about amino acid residues 161–164 of SEQ ID NO:16.

Isolated proteins of the present invention, preferably ERG-LP2 proteins, have an amino acid sequence sufficiently homologous to the amino acid sequence of SEQ ID NO:5 or SEQ ID NO:16 or are encoded by a nucleotide sequence sufficiently homologous to SEQ ID NO:4, SEQ ID NO:6, SEQ ID NO:15 or SEQ ID NO:17.

As used interchangeably herein an "ERG-LP2 activity", "biological activity of ERG-LP2" or "functional activity of ERG-LP2", refers to an activity exerted by an ERG-LP2 protein, polypeptide or nucleic acid molecule on an ERG-LP2 responsive cell as determined in vivo, or in vitro, according to standard techniques. The biological activity of ERG-LP2 is described herein.

Accordingly, another embodiment of the invention features isolated ERG-LP2 proteins and polypeptides having an ERG-LP2 activity. Preferred proteins are ERG-LP2 proteins having at least one transmembrane domain, a P-loop, a cyclic nucleotide-binding domain and a transmembrane region cyclic nucleotide gated channel domain and, preferably, an ERG-LP2 activity. Additional preferred proteins have at least one transmembrane domain, a P-loop, a cyclic nucleotide-binding domain and a transmembrane region cyclic nucleotide gated channel domain and are, preferably, encoded by a nucleic acid molecule having a nucleotide sequence which hybridizes under stringent hybridization conditions to a nucleic acid molecule comprising the nucleotide sequence of SEQ ID NO:4, SEQ ID NO:6, SEQ ID NO:15 or SEQ ID NO:17.

The nucleotide sequence of the isolated partial human ERG-LP2 cDNA and the predicted amino acid sequence of the human ERG-LP2 polypeptide are shown in FIG. 2 and in SEQ ID NOs:4 and 5, respectively. The nucleotide sequence of the isolated full length human ERG-LP2 cDNA and the predicted amino acid sequence of he human ERG-LP2 polypeptide are shown in FIG. 8 and in SEQ ID NOs:15 and 16, respectively.

Various aspects of the invention are described in further detail in the following subsections:

I. Isolated Nucleic Acid Molecules

One aspect of the invention pertains to isolated nucleic acid molecules that encode ERG-LP proteins or biologically active portions thereof, as well as nucleic acid fragments sufficient for use as hybridization probes to identify ERG-LP-encoding nucleic acid molecules (e.g., ERG-LP mRNA) and fragments for use as PCR primers for the amplification or mutation of ERG-LP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ERG-LP nucleic acid molecule can contain less than about 5 kb, 4 kb, 3 kb, 2kb, 1 kb, 0.5 kb or 0.1 kb of nucleotide sequences which naturally flank the nucleic acid molecule in genomic DNA of the cell from which the nucleic acid is derived. Moreover, an "isolated"nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, or a portion thereof, can be isolated using standard molecular biology techniques and the sequence information provided herein. Using all or portion of the nucleic acid sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, as a hybridization probe, ERG-LP nucleic acid molecules can be isolated using standard hybridization and cloning techniques (e.g., as described in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO:1, SEQ ID NO:3, SEQ ID NO:4, SEQ ID NO:6, SEQ ID NO:7, SEQ ID NO:9, SEQ ID NO:15 or SEQ ID NO:17 can be isolated by the polymerase chain reaction (PCR) using synthetic oligonucleotide primers designed based upon the sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to ERG-LP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the monkey ERG-LP1 cDNA. This cDNA comprises sequences encoding the monkey ERG-LP1 protein (i.e., "the coding region", from nucleotides 113–3243), as well as 5' untranslated sequences (nucleotides 1–112). Alternatively, the nucleic acid molecule can comprise only the coding region of SEQ ID NO:1 (e.g., nucleotides 113–3243, corresponding to SEQ ID NO:3).

In another preferred embodiment, an isolated nucleic acid molecule of the invention comprises the nucleotide sequence shown in SEQ ID NO:4. The sequence of SEQ ID NO:4 corresponds to the partial human ERG-LP2 cDNA. This cDNA comprises sequences encoding the partial human ERG-LP2 protein (i.e., "the coding region", from nucleotides 215–1843), as well as 5' untranslated sequences (nucleotides 1–214) and 3' untranslated sequences (nucleotides 1844–2694). Alternatively, the nucleic acid molecule can comprise only the coding region of SEQ ID NO:4 (e.g., nucleotides 215–1843, corresponding to SEQ ID NO:6).

In yet another preferred embodiment, an isolated nucleic acid molecule of the invention comprises the nucleotide sequence shown in SEQ ID NO:7. The sequence of SEQ ID NO:7 corresponds to the human ERG-LP1 cDNA. This cDNA comprises sequences encoding the human ERG-LP1 protein (i.e., "the coding region", from nucleotides 263–1132), as well as 5' untranslated sequences (nucleotides 1–262). Alternatively, the nucleic acid molecule can comprise only the coding region of SEQ ID NO:7 (e.g., nucleotides 263–1132, corresponding to SEQ ID NO:9).

In yet another preferred embodiment, an isolated nucleic acid molecule of the invention comprises the nucleotide sequence shown in SEQ ID NO:15. The sequence of SEQ ID NO:15 corresponds to the human ERG-LP2 cDNA. This cDNA comprises sequences encoding the human ERG-LP2 protein (i.e., "the coding region", from nucleotides 196–3516), as well as 5' untranslated sequences (nucleotides 1–195). Alternatively, the nucleic acid molecule can comprise only the coding region of SEQ ID NO:15 (e.g., nucleotides 196–3516, corresponding to SEQ ID NO:17).

In another preferred embodiment, an isolated nucleic acid molecule of the invention comprises a nucleic acid molecule which is a complement of the nucleotide sequence shown in SEQ ID NO:1, SEQ ID NO:3, SEQ ID NO:4, SEQ ID NO:6, SEQ ID NO:7, SEQ ID NO:9, SEQ ID NO:15 or SEQ ID NO:17, or a portion of any of these nucleotide sequences. A nucleic acid molecule which is complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:15 or SEQ ID NO:17, is one which is sufficiently complementary to the nucleotide sequence shown in SEQ ID NO:1, SEQ ID NO:3, SEQ ID NO:4, SEQ ID NO:6, SEQ ID NO:7, SEQ ID NO:9, SEQ ID NO:15 or SEQ ID NO:17, such that it can hybridize to the nucleotide sequence shown in SEQ ID NO:1, SEQ ID NO:3, SEQ ID NO:4, SEQ ID NO:6, SEQ ID NO:7, SEQ ID NO:9, SEQ ID NO:15 or SEQ ID NO:17.

In still another preferred embodiment, an isolated nucleic acid molecule of the present invention comprises a nucleotide sequence which is at least about 28%, 30%, 35%, 40%, 45%, 50%, 55%, 60%, 65%, 70%, 75%, 80%, 85%, 90%, 95% or more homo the entire length of the nucleotide sequence shown in SEQ ID NO:1 or SEQ ID NO:3, or a portion of any of these nucleotide sequences. In yet another preferred embodiment, an isolated nucleic acid molecule of the present invention comprises a nucleotide sequence which is at least about 42%, 45%, 50%, 55%, 60%, 65%, 70%, 75%, 80%, 85%, 90% or more homologous to the entire length of the nucleotide sequence shown in SEQ ID NO:4, or SEQ ID NO:6, or a portion of any of these nucleotide sequences. In yet another preferred embodiment, an isolated nucleic acid molecule of the present invention comprises a nucleotide sequence which is at least about 50%, 55%, 60%, 65%, 70%, 75%, 80%, 85%, 90%, 95% or more homologous to the entire length of the nucleotide sequence shown in SEQ ID NO:7 or SEQ ID NO:9, or a portion of any of these nucleotide sequences. In yet another preferred embodiment, an isolated nucleic acid molecule of the present invention comprises a nucleotide sequence which is at least about 50%, 55%, 60%, 65%, 70%, 75%, 80%, 85%, 90%, 95% or more homologous to the entire length of the nucleotide sequence shown in SEQ ID NO:15 or SEQ ID NO:17, or a portion of any of these nucleotide sequences.

Moreover, the nucleic acid molecule of the invention can comprise only a portion of the nucleic acid sequence of SEQ ID NO:1, SEQ ID NO:3, SEQ ID NO:4, SEQ ID NO:6, SEQ ID NO:7, SEQ ID NO:9,SEQ ID NO:15 or SEQ ID NO:17, for example a fragment which can be used as a probe or primer or a fragment encoding a biologically active portion of an ERG-LP protein. The nucleotide sequence determined from the cloning of the ERG-LP gene allows for the generation of probes and primers designed for use in identifying and/or cloning other ERG-LP family members, as well as ERG-LP homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, of an anti-sense sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, or of a naturally occurring allelic variant or mutant of SEQ ID NO:1, SEQ ID NO:3, SEQ ID NO:4, SEQ ID NO:6, SEQ ID NO:7, SEQ ID NO:9, SEQ ID NO:15 or SEQ ID NO:17. In an exemplary embodiment, a nucleic acid molecule of the present invention comprises a nucleotide sequence which is greater than 307, 350–400, 400–450, 450–500, 500–550, 550–600, 600–650, 650–700, 700–750, 750–800, 800–850, 850–900, 949, 950–1000, or more nucleotides in length and hybridizes under stringent hybridization conditions to a nucleic acid molecule of SEQ ID NO:1, SEQ ID NO:3, SEQ ID NO:4, SEQ ID NO:6, SEQ ID NO:7, SEQ ID NO:9, SEQ ID NO:15 or SEQ ID NO:17.

Probes based on the ERG-LP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an ERG-LP protein, such as by measuring a level of an ERG-LP-encoding nucleic acid in a sample of cells from a subject e.g., detecting ERG-LP mRNA levels or determining whether a genomic ERG-LP gene has been mutated or deleted.

A nucleic acid fragment encoding a "biologically active portion of an ERG-LP protein" can be prepared by isolating a portion of the nucleotide sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, which encodes a polypeptide having an ERG-LP biological activity (the biological activities of the ERG-LP proteins are described herein), expressing the encoded portion of the ERG-LP protein (e.g., by recombinant expression in vitro) and assessing the activity of the encoded portion of the ERG-LP protein.

The invention further encompasses nucleic acid molecules that differ from the nucleotide sequence shown in SEQ ID NO:1, SEQ ID NO:3, SEQ ID NO:4, SEQ ID NO:6, SEQ ID NO:7, SEQ ID NO:9, SEQ ID NO:15 or SEQ ID NO:17, due to degeneracy of the genetic code and thus encode the same ERG-LP proteins as those encoded by the nucleotide sequence shown in SEQ ID NO:1, SEQ ID NO:3, SEQ ID NO:4, SEQ ID NO:6, SEQ ID NO:7, SEQ ID NO:9,SEQ ID NO:15 or SEQ ID NO:17. In another embodiment, an isolated nucleic acid molecule of the invention has a nucleotide sequence encoding a protein having an amino acid sequence shown in SEQ ID NO:2, SEQ ID NO:5, SEQ ID NO:8 or SEQ ID NO:16.

In addition to the ERG-LP nucleotide sequences shown in SEQ ID NO:1, SEQ ID NO:3, SEQ ID NO:4, SEQ ID NO:6, SEQ ID NO:7, SEQ ID NO:9, SEQ ID NO:15 or SEQ ID NO:17, it will be appreciated by those skilled in the art that DNA sequence polymorphisms that lead to changes in the amino acid sequences of the ERG-LP proteins may exist within a population (e.g., the human population). Such genetic polymorphism in the ERG-LP genes may exist among individuals within a population due to natural allelic variation. As used herein, the terms "gene" and "recombinant gene" refer to nucleic acid molecules comprising an open reading frame encoding an ERG-LP protein, preferably a mammalian ERG-LP protein. Such natural allelic variations can typically result in 1–5% variance in the nucleotide sequence of an ERG-LP gene. Any and all such nucleotide variations and resulting amino acid polymorphisms in ERG-LP genes that are the result of natural allelic variation and that do not alter the functional activity of an ERG-LP protein are intended to be within the scope of the invention.

Moreover, nucleic acid molecules encoding other ERG potassium channel family members (e.g., other ERG-LP family members) and thus which have a nucleotide sequence which differs from the ERG-LP sequences of SEQ ID NO:1, SEQ ID NO:3, SEQ ID NO:4, SEQ ID NO:6, SEQ ID NO:7, or SEQ ID NO:9 are intended to be within the scope of the invention. For example, another ERG-LP cDNA can be identified based on the nucleotide sequence of human ERG-LP. Moreover, nucleic acid molecules encoding ERG-LP proteins from different species, and thus which have a nucleotide sequence which differs from the ERG-LP sequences of SEQ ID NO:1, SEQ ID NO:3, SEQ ID NO:4, SEQ ID NO:6, SEQ ID NO:7, SEQ ID NO:9, SEQ ID NO:15 or SEQ ID NO:17 are intended to be within the scope of the invention. For example, a mouse ERG-LP cDNA can be identified based on the nucleotide sequence of a human ERG-LP.

Nucleic acid molecules corresponding to natural allelic variants and homologues of the ERG-LP cDNAs of the invention can be isolated based on their homology to the ERG-LP nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17. In other embodiment, the nucleic acid is at least 30, 50, 100, 150, 200, 250, 300, 307, 350, 400, 450, 500, 550, 600, 650, 700, 750, 800, 850, 900, 949, or 950 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the ERG-LP sequences that may exist in the population, the skilled artisan will further appreciate that changes can be introduced by mutation into the nucleotide sequences of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, thereby leading to changes in the amino acid sequence of the encoded ERG-LP proteins, without altering the functional ability of the ERG-LP proteins. For example, nucleotide substitutions leading to amino acid substitutions at "non-essential" amino acid residues can be made in the sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17. A "non-essential" amino acid residue is a residue that can be altered from the wild-type sequence of ERG-LP (e.g., the sequence of SEQ ID NO:2) without altering the biological activity, whereas an "iessential" amino acid residue is required for biological activity. For example, amino acid residues that are conserved among the ERG-LP proteins of the present invention, are predicted to be particularly unamenable to alteration. Furthermore, additional amino acid residues that are conserved between the ERG-LP proteins of the present invention and other members of the ERG potassium channel families are not likely to be amenable to alteration.

Accordingly, another aspect of the invention pertains to nucleic acid molecules encoding ERG-LP proteins that contain changes in amino acid residues that are not essential for activity. Such ERG-LP proteins differ in amino acid sequence from SEQ ID NO:2, SEQ ID NO:5, SEQ ID NO:8, or SEQ ID NO:16 yet retain biological activity. In one embodiment, the isolated nucleic acid molecule comprises a nucleotide sequence encoding a protein, wherein the protein comprises an amino acid sequence at least about 37%, 40%, 45%, 50%, 55%, 65%, 65%, 70%, 75%, 80%, 85%, 90%, 95% or more homologous to SEQ ID NO:2 or SEQ ID NO:8. In another embodiment, the isolated nucleic acid molecule comprises a nucleotide sequence encoding a protein, wherein the protein comprises an amino acid sequence at least about 25%, 30%, 35%, 40%, 45%, 50%, 55%, 60%, 65%, 70% 75%, 80%, 85%, 90%, 95% or more homologous to SEQ ID NO:5 or SEQ ID NO:16.

An isolated nucleic acid molecule encoding an ERG-LP protein homologous to the protein of SEQ ID NO:2, SEQ ID NO:5, SEQ ID NO:8 or SEQ ID NO:16 can be created by introducing one or more nucleotide substitutions, additions or deletions into the nucleotide sequence of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, such that one or more amino acid substitutions, additions or deletions are introduced into the encoded protein. Mutations can be introduced into SEQ ID NO:1, SEQ ID NO:3, SEQ ID NO:4, SEQ ID NO:6, SEQ ID NO:7, SEQ ID NO:9, SEQ ID NO:15 or SEQ ID NO:17 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an ERG-LP protein is preferably replaced with another amino acid residue from the same side chain family. Alternatively, in another embodiment, mutations can be introduced randomly along all or part of an ERG-LP coding sequence, such as by saturation mutagenesis, and the resultant mutants can be screened for ERG-LP biological activity to identify mutants that retain activity. Following mutagenesis of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, the encoded protein can be expressed recombinantly and the activity of the protein can be determined.

In a preferred embodiment, a mutant ERG-LP protein can be assayed for the ability to (1) interact with a non-ERG-LP protein molecule; (2) activate an ERG-LP-dependent signal transduction pathway; (3) modulate the release of neurotransmitters, (4) modulate membrane excitability, (5) influence the resting potential of membranes, wave forms and frequencies of action potentials, and thresholds of excitation, and (6) modulate processes which underlie learning and memory, such as integration of sub-threshold synaptic responses and the conductance of back-propagating action potentials.

In addition to the nucleic acid molecules encoding ERG-LP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire ERG-LP coding strand, or to only a portion thereof. In one embodiment, an antisense nucleic acid molecule is antisense to a "coding region" of the coding strand of a nucleotide sequence encoding ERG-LP. The term "coding region" refers to the region of the nucleotide sequence comprising codons which are translated into amino acid residues (e.g., the coding region of monkey ERG-LP1 corresponds to SEQ ID NO:3). In another embodiment, the antisense nucleic acid molecule is antisense to a "noncoding region" of the coding strand of a nucleotide sequence encoding ERG-LP. The term "noncoding region" refers to 5' and 3' sequences which flank the coding region that are not translated into amino acids (i.e., also referred to as 5' and 3' untranslated regions).

Given the coding strand sequences encoding ERG-LP disclosed herein (e.g., SEQ ID NO:3, SEQ ID NO:6, and SEQ ID NO:9), antisense nucleic acids of the invention can be designed according to the rules of Watson and Crick base pairing. The antisense nucleic acid molecule can be complementary to the entire coding region of ERG-LP mRNA, but more preferably is an oligonucleotide which is antisense to only a portion of the coding or noncoding region of ERG-LP mRNA. For example, the antisense oligonucleotide can be complementary to the region surrounding the translation start site of ERG-LP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcy tosine, 5-(carboxyhydroxylmethyl) uraci 1,5-carboxymethylami nomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an ERG-LP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave ERG-LP mRNA transcripts to thereby inhibit translation of ERG-LP mRNA. A ribozyme having specificity for an ERG-LP-encoding nucleic acid can be designed based upon the nucleotide sequence of an ERG-LP cDNA disclosed herein (i.e., SEQ ID NO:1, SEQ ID NO:3, SEQ ID NO:4, SEQ ID NO:6, SEQ ID NO:7, SEQ ID NO:9, SEQ ID NO:15 or SEQ ID NO:17). For example, a derivative of a Tetrahymena L-19 IVS RNA can be constructed in which the nucleotide sequence of the active site is complementary to the nucleotide sequence to be cleaved in an ERG-LP-encoding mRNA. See, e.g., Cech et al. U.S. Pat. No. 4,987,071; and Cech et al. U.S. Pat. No. 5,116,742. Alternatively, ERG-LP mRNA can be used to select a catalytic RNA having a specific ribonuclease activity from a pool of RNA molecules. See, .e.g., Bartel, D. and Szostak, J. W. (1993) *Science* 261:1411–1418.

Alternatively, ERG-LP gene expression can be inhibited by targeting nucleotide sequences complementary to the regulatory region of the ERG-LP (e.g., the ERG-LP promoter and/or enhancers) to form triple helical structures that prevent transcription of the ERG-LP gene in target cells. See generally, Helene, C. (1991) *Anticancer Drug Des.* 6(6) :569–84; Helene, C. et al. (1992) *Ann. N.Y Acad Sci.* 660:27–36; and Maher, L. J. (1992) Bioassays 14(12) :807–15.

In yet another embodiment, the ERG-LP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of ERG-LP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of ERG-LP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of ERG-LP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of ERG-LP nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res*. 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res*. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett*. 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US*. 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res*. 5:539–549). To this end, the oligonucleotide may be conjugated to another molecule, (e.g., a peptide, hybridization triggered cross-linking agent, transport agent, or hybridization-triggered cleavage agent).

II. Isolated ERG-LP Proteins and Anti-ERG-LP Antibodies

One aspect of the invention pertains to isolated ERG-LP proteins, and biologically active portions thereof, as well as polypeptide fragments suitable for use as immunogens to raise anti-ERG-LP antibodies. In one embodiment, native ERG-LP proteins can be isolated from cells or tissue sources by an appropriate purification scheme using standard protein purification techniques. In another embodiment, ERG-LP proteins are produced by recombinant DNA techniques. Alternative to recombinant expression, an ERG-LP protein or polypeptide can be synthesized chemically using standard peptide synthesis techniques.

An "isolated" or "purified" protein or biologically active portion thereof is substantially free of cellular material or other contaminating proteins from the cell or tissue source from which the ERG-LP protein is derived, or substantially free from chemical precursors or other chemicals when chemically synthesized. The language "substantially free of cellular material" includes preparations of ERG-LP protein in which the protein is separated from cellular components of the cells from which it is isolated or recombinantly produced. In one embodiment, the language "substantially free of cellular material" includes preparations of ERG-LP protein having less than about 30% (by dry weight) of non-ERG-LP protein (also referred to herein as a "contaminating protein"), more preferably less than about 20% of non-ERG-LP protein, still more preferably less than about 10% of non-ERG-LP protein, and most preferably less than about 5% non-ERG-LP protein. When the ERG-LP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of ERG-LP protein in which the protein is separated from chemical precursors or other chemicals which are involved in the synthesis of the protein. In one embodiment, the language "substantially free of chemical precursors or other chemicals" includes preparations of ERG-LP protein having less than about 30% (by dry weight) of chemical precursors or non-ERG-LP chemicals, more preferably less than about 20% chemical precursors or non-ERG-LP chemicals, still more preferably less than about 10% chemical precursors or non-ERG-LP chemicals, and most preferably less than about 5% chemical precursors or non-ERG-LP chemicals.

As used herein, a "biologically active portion" of an ERG-LP protein includes a fragment of an ERG-LP protein which participates in an interaction between an ERG-LP molecule and a non-ERG-LP molecule. Biologically active portions of an ERG-LP protein include peptides comprising amino acid sequences sufficiently homologous to or derived from the amino acid sequence of the ERG-LP protein, e.g., the amino acid sequence shown in SEQ ID NO:2, SEQ ID NO:5, SEQ ID NO:8, or SEQ ID NO:16 which include less amino acids than the full length ERG-LP proteins, and exhibit at least one activity of an ERG-LP protein. Typically, biologically active portions comprise a domain or motif with at least one activity of the ERG-LP protein, e.g., binding of a cyclic nucleotide. A biologically active portion of an ERG-LP protein can be a polypeptide which is, for example, 10, 25, 50, 100, 200 or more amino acids in length. Biologically active portions of an ERG-LP protein can be used as targets for developing agents which modulate a potassium channel mediated activity.

In one embodiment, a biologically active portion of an ERG-LP protein comprises at least one transmembrane domain. In another embodiment, a biologically active portion of an ERG-LP protein comprises at least a P-loop. In another embodiment a biologically active portion of an ERG-LP protein comprises at least a cyclic nucleotide-binding domain. In another embodiment a biologically active portion of an ERG-LP protein comprises at least a transmembrane region cyclic nucleotide gated channel domain. In yet another embodiment a biologically active portion of a ERG-LP protein comprises at least a transmembrane domain, a P-loop, a cyclic nucleotide-binding domain and a transmembrane region cyclic nucleotide gated channel domain.

It is to be understood that a preferred biologically active portion of an ERG-LP protein of the present invention may contain at least one of the above-identified structural domains. A more preferred biologically active portion of an ERG-LP protein may contain at least two of the above-identified structural domains. Moreover, other biologically active portions, in which other regions of the protein are deleted, can be prepared by recombinant techniques and evaluated for one or more of the functional activities of a native ERG-LP protein.

In a preferred embodiment, the ERG-LP protein has an amino acid sequence shown in SEQ ID NO:2, SEQ ID NO:5, SEQ ID NO:8 or SEQ ID NO:16. In other embodiments, the ERG-LP protein is substantially homologous to SEQ ID NO:2, SEQ ID NO:5, SEQ ID NO:8, or SEQ ID NO:16, and retains the functional activity of the protein of SEQ ID NO:2, SEQ ID NO:5, SEQ ID NO:8, or SEQ ID NO:16, yet differs in amino acid sequence due to natural allelic variation or mutagenesis, as described in detail in subsection I above.

Accordingly, in another embodiment, the ERG-LP protein is a protein which comprises an amino acid sequence at least about 25%, 30%, 35%, 37%, 40%, 45%, 50%, 55%, 60%, 65% 70%, 75%, 80%, 85%, 90%, 95% 96%, 97%, 98%, 99% or more homologous to SEQ ID NO:2, SEQ ID NO:5, SEQ ID NO:8 or SEQ ID NO:16.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence having 177 amino acid residues, to the ERG-LP amino acid sequence of SEQ ID NO:2, SEQ ID NO:5, SEQ ID NO:8, or SEQ ID NO:16, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithim. A preferred, non-limiting example of a mathematical algonthim utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed with the NBLAST program, score=100, wordlength=12 to obtain nucleotide sequences homologous to ERG-LP nucleic acid molecules of the invention. BLAST protein searches can be performed with the XBLAST program, score=50. wordlength=3 to obtain amino acid sequences homologous to ERG-LP protein molecules of the invention. To obtain gapped alignments for comparison purposes, Gapped BLAST can be utilized as described in Altschul et al., (1997) Nucleic Acids Res. 25(17):3389–3402. When utilizing BLAST and Gapped BLAST programs, the default parameters of the respective programs (e.g., XBLAST and NBLAST) can be used. See The website for the National Center for Biotechnology Information. Another preferred, non-limiting example of a mathematical algorithim utilized for the comparison of sequences is the algorithm of Myers and Miller, CABIOS (1989). Such an algonthm is incorporated into the ALIGN program (version 2.0) which is part of the GCG sequence alignment software package. When utilizing the ALIGN program for comparing amino acid sequences, a PAMI120 weight residue table, a gap length penalty of 12, and a gap penalty of 4 can be used.

The invention also provides ERG-LP chimeric or fusion proteins. As used herein, an ERG-LP "chimeric protein" or "fusion protein" comprises an ERG-LP polypeptide operatively linked to a non-ERG-LP polypeptide. An "ERG-LP polypeptide" refers to a polypeptide having an amino acid sequence corresponding to ERG-LP, whereas a "non-ERG-LP polypeptide" refers to a polypeptide having an amino acid sequence corresponding to a protein which is not substantially homologous to the ERG-LP protein, e.g., a protein which is different from the ERG-LP protein and which is derived from the same or a different organism. Within an ERG-LP fusion protein the ERG-LP polypeptide can correspond to all or a portion of an ERG-LP protein. In a preferred embodiment, an ERG-LP fusion protein comprises at least one biologically active portion of an ERG-LP protein. In another preferred embodiment, an ERG-LP fusion protein comprises at least two biologically active portions of an ERG-LP protein. Within the fusion protein, the term "operatively linked" is intended to indicate that the ERG-LP polypeptide and the non-ERG-LP polypeptide are fused in-frame to each other. The non-ERG-LP polypeptide can be fused to the N-terminus or C-terminus of the ERG-LP polypeptide.

For example, in one embodiment, the fusion protein is a GST-ERG-LP fusion protein in which the ERG-LP sequences are fused to the C-terminus of the GST sequences. Such fusion proteins can facilitate the purification of recombinant ERG-LP.

In another embodiment, the fusion protein is an ERG-LP protein containing a heterologous signal sequence at its N-terminus. In certain host cells (e.g., mammalian host cells), expression and/or secretion of ERG-LP can be increased through use of a heterologous signal sequence.

The ERG-LP fusion proteins of the invention can be incorporated into pharmaceutical compositions and administered to a subject in vivo. The ERG-LP fusion proteins can be used to affect the bioavailability of an ERG-LP substrate. Use of ERG-LP fusion proteins may be useful therapeutically for the treatment of CNS disorders, e.g., neurodegenerative disorders such as Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; autonomic nervous system disorders; gastrointestinal disorders including, but not limited to, esophageal disorders such as atresia and fistulas, stenosis, achalasia, esophageal rings and webs, hiatal hernia, lacerations, esophagitis, diverticula, systemic sclerosis (scleroderma), varices, esophageal tumors such as squamous cell carcinomas and adenocarcinomas, stomach disorders such as diaphragmatic hernias, pyloric stenosis, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas; pain disorders, e.g, pain response elicited during various forms of tissue injury, e.g., inflammation, infection, and ischemia, usually referred to as hyperalgesia (described in, for example, Fields, H. L. (1987) Pain, New York:McGraw-Hill), and pain associated with muscoloskeletal disorders, e.g., joint pain; tooth pain; headaches; pain associated with malignancies, or pain associated with surgery; psychiatric disorders, e.g., depression, schizophrenic disorders, korsakoffs psychosis, mania, anxiety disorders, or phobic disorders; learning or memory disorders, e.g., amnesia or age-related memory loss; neurological disorders; e.g., migraine; and obesity; and cardiovascular disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia.

Moreover, the ERG-LP-fusion proteins of the invention can be used as immunogens to produce anti-ERG-LP antibodies in a subject, to purify ERG-LP ligands and in screening assays to identify molecules which inhibit the interaction of ERG-LP with an ERG-LP substrate.

Preferably, an ERG-LP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An ERG-LP-encoding nucleic acid can be cloned into such an expression vector such that the fusion moiety is linked in-frame to the ERG-LP protein.

The present invention also pertains to variants of the ERG-LP proteins which function as either ERG-LP agonists (mimetics) or as ERG-LP antagonists. Variants of the ERG-LP proteins can be generated by mutagenesis, e.g., discrete point mutation or truncation of an ERG-LP protein. An agonist of the ERG-LP proteins can retain substantially the same, or a subset, of the biological activities of the naturally occurring form of an ERG-LP protein. An antagonist of an ERG-LP protein can inhibit one or more of the activities of the naturally occurring form of the ERG-LP protein by, for example, competitively modulating a potassium channel mediated activity of an ERG-LP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the ERG-LP protein.

In one embodiment, variants of an ERG-LP protein which function as either ERG-LP agonists (mimetics) or as ERG-LP antagonists can be identified by screening combinatorial libraries of mutants, e.g., truncation mutants, of an ERG-LP protein for ERG-LP protein agonist or antagonist activity. In one embodiment, a variegated library of ERG-LP variants is generated by combinatorial mutagenesis at the nucleic acid level and is encoded by a variegated gene library. A variegated library of ERG-LP variants can be produced by, for example, enzymatically ligating a mixture of synthetic oligonucleotides into gene sequences such that a degenerate set of potential ERG-LP sequences is expressible as individual polypeptides, or alternatively, as a set of larger fusion proteins (e.g., for phage display) containing the set of ERG-LP sequences therein. There are a variety of methods which can be used to produce libraries of potential ERG-LP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ERG-LP sequences. Methods for synthesizing degenerate oligonucleotides are known in the art (see, e.g., Narang, S. A. (1983) *Tetrahedron* 39:3; Itakura et al. (1 984) *Annu. Rev. Biochem.* 53:323; Itakura et al. (1984) *Science* 198:1056; Ike et al. (1983) *Nucleic Acid Res.* 11:477.

In addition, libraries of fragments of an ERG-LP protein coding sequence can be used to generate a variegated population of ERG-LP fragments for screening and subsequent selection of variants of an ERG-LP protein. In one embodiment, a library of coding sequence fragments can be generated by treating a double stranded PCR fragment of an ERG-LP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the ERG-LP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ERG-LP proteins. The most widely used techniques, which are amenable to high through-put analysis, for screening large gene libraries typically include cloning the gene library into replicable expression vectors, transforming appropriate cells with the-resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify ERG-LP variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated ERG-LP library. For example, a library of expression vectors can be transfected into a cell line which ordinarily synthesizes ERG-LP. The transfected cells are then cultured such that ERG-LP and a particular mutant ERG-LP are expressed and the effect of expression of the mutant on ERG-LP activity in the cells can be detected, e.g., by any of a number of enzymatic assays or by detecting the release of a neurotransmitter. Plasmid DNA can then be recovered from the cells which score for inhibition, or alternatively, potentiation of ERG-LP activity, and the individual clones further characterized.

An isolated ERG-LP protein, or a portion or fragment thereof, can be used as an immunogen to generate antibodies that bind ERG-LP using standard techniques for polyclonal and monoclonal antibody preparation. A full-length ERG-LP protein can be used or, alternatively, the invention provides antigenic peptide fragments of ERG-LP for use as immunogens. The antigenic peptide of ERG-LP comprises at least 8 amino acid residues of the amino acid sequence shown in SEQ ID NO:2, SEQ ID NO:5, SEQ ID NO:8 or SEQ ID NO:16 and encompasses an epitope of ERG-LP such that an antibody raised against the peptide forms a specific immune complex with ERG-LP. Preferably, the antigenic peptide comprises at least 10 amino acid residues, more preferably at least 15 amino acid residues, even more preferably at least 20 amino acid residues, and most preferably at least 30 amino acid residues.

Figure 6:
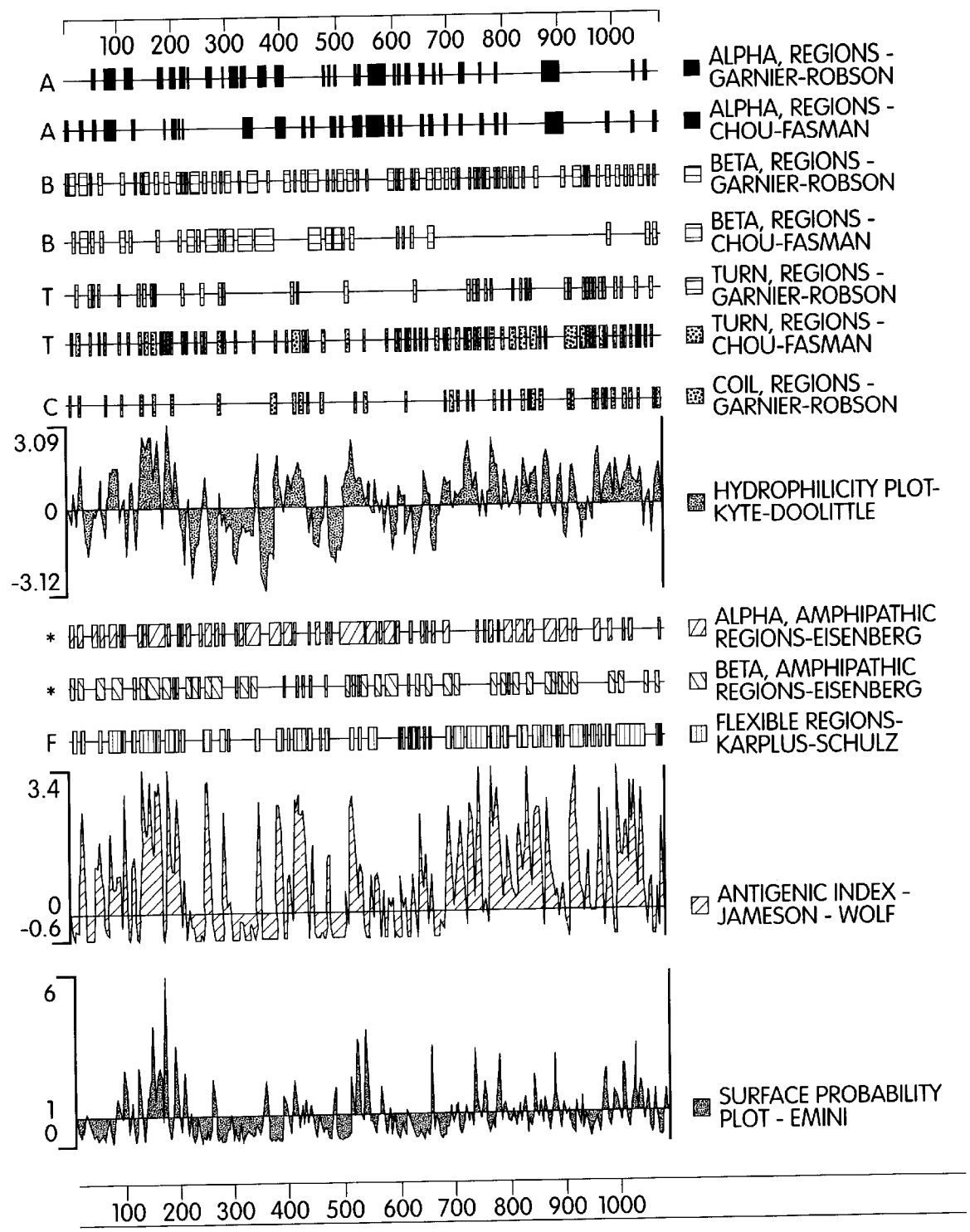
FIG. 6 depicts a structural, hydrophobicity, and antigenicity analysis of the monkey ERG-LP1 protein.
Figure 7:
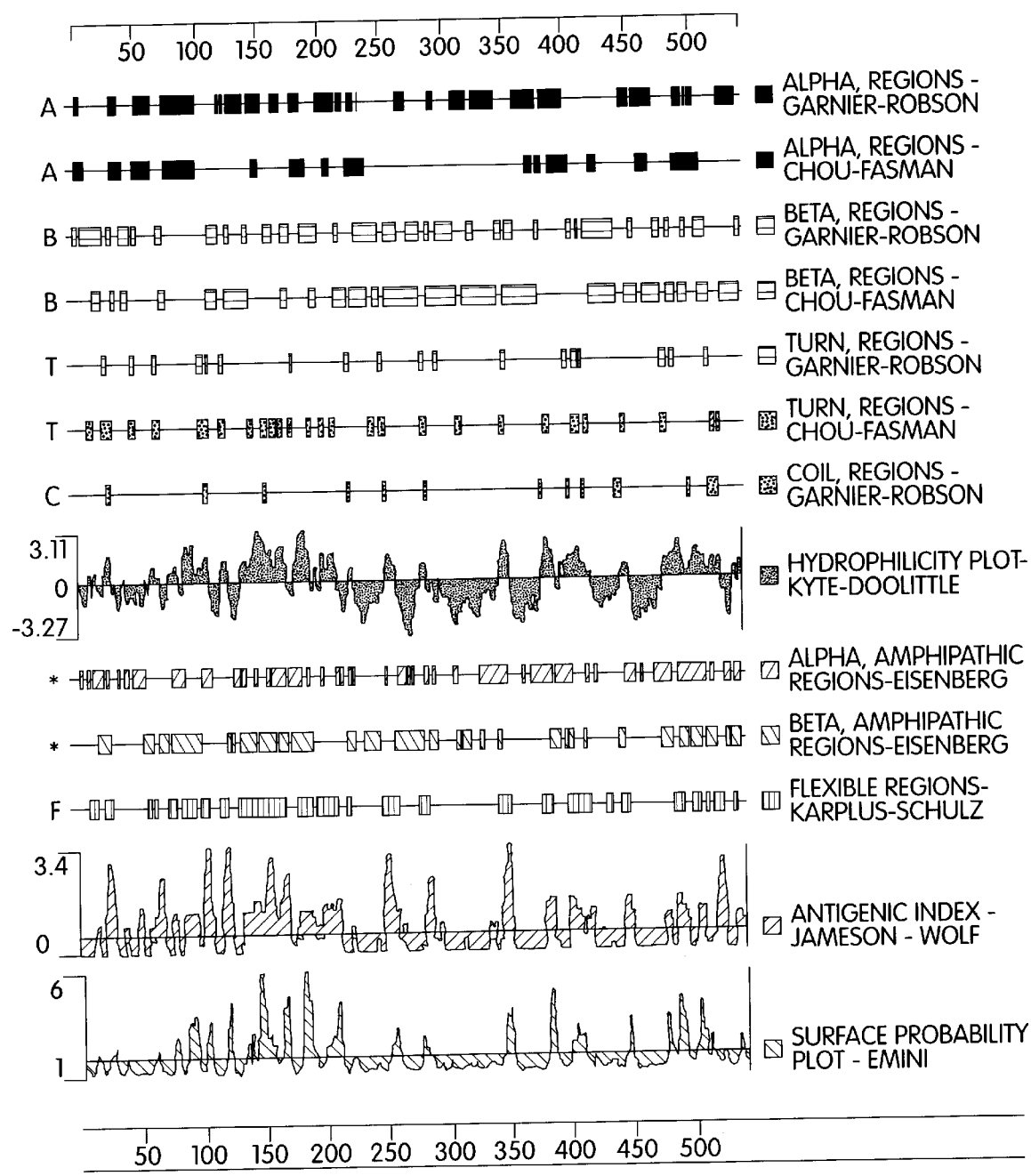
FIG. 7 depicts a structural, hydrophobicity, and antigenicity analysis of the partial human ERG-LP2 protein.
Figure 9:
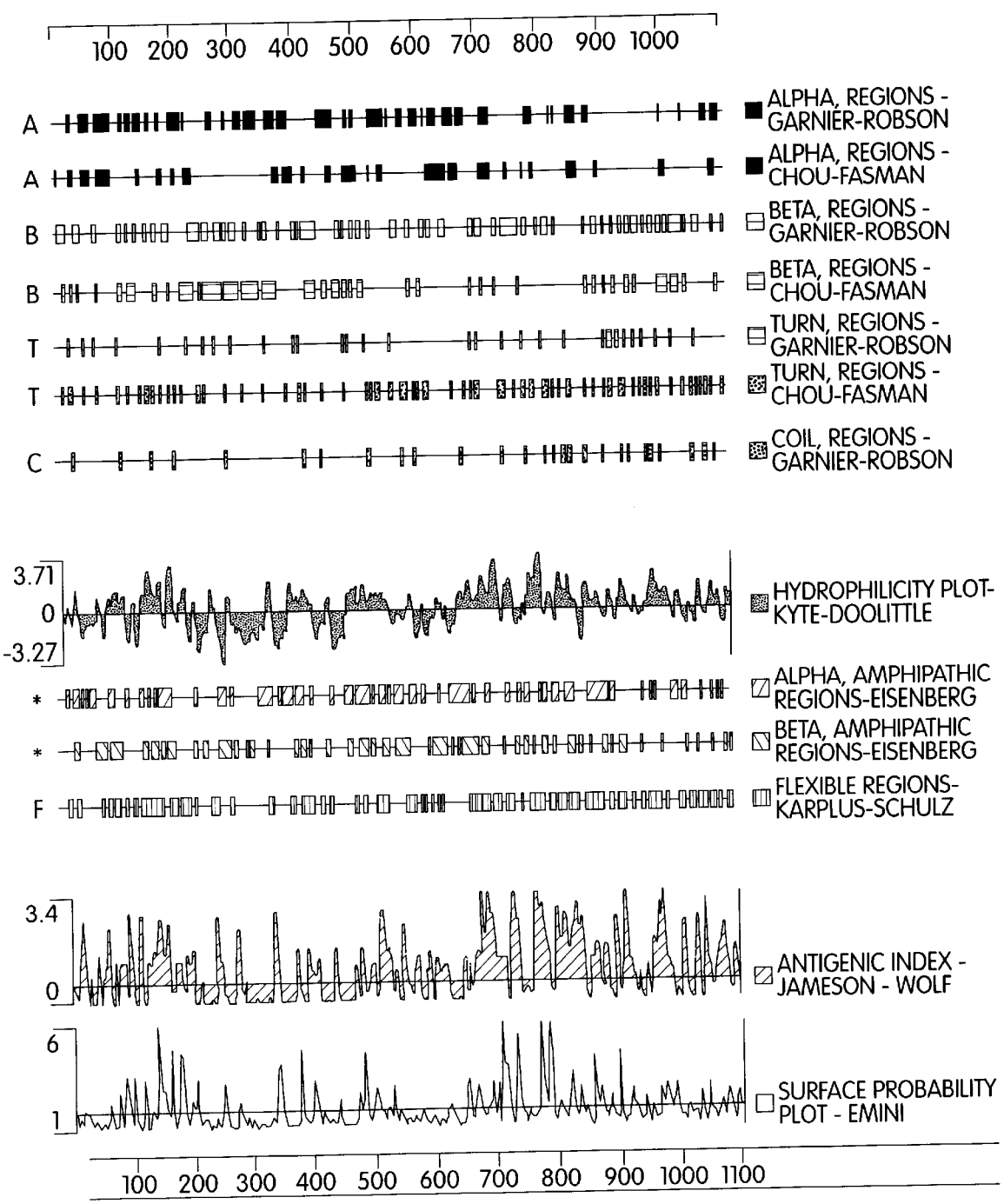
FIG. 9 depicts a structural, hydrophobicity, and antigenicity analysis of the human ERG-LP2 protein.

Preferred epitopes encompassed by the antigenic peptide are regions of ERG-LP that are located on the surface of the protein, e.g., hydrophilic regions, as well as regions with high antigenicity (see, for example, FIGS. 6, 7 and 9).

An ERG-LP immunogen typically is used to prepare antibodies by immunizing a suitable subject, (e.g., rabbit, goat, mouse or other mammal) with the immunogen. An appropriate immunogenic preparation can contain, for example, recombinantly expressed ERG-LP protein or a chemically synthesized ERG-LP polypeptide. The preparation can further include an adjuvant, such as Freund's complete or incomplete adjuvant, or similar immunostimulatory agent. Immunization of a suitable subject with an immunogenic ERG-LP preparation induces a polyclonal anti-ERG-LP antibody response.

Accordingly, another aspect of the invention pertains to anti-ERG-LP antibodies. The term "antibody" as used herein refers to immunoglobulin molecules and immunologically active portions of immunoglobulin molecules, i.e., molecules that contain an antigen binding site which specifically binds (immunoreacts with) an antigen, such as ERG-LP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind ERG-LP. The term "monoclonal antibody" or "monoclonal antibody composition", as used herein, refers to a population of antibody molecules that contain only one species of an antigen binding site capable of immunoreacting with a particular epitope of ERG-LP. A monoclonal antibody composition thus typically displays a single binding affinity for a particular ERG-LP protein with which it immunoreacts.

Polyclonal anti-ERG-LP antibodies can be prepared as described above by immunizing a suitable subject with an ERG-LP immunogen. The anti-ERG-LP antibody titer in the immunized subject can be monitored over time by standard techniques, such as with an enzyme linked immunosorbent assay (ELISA) using immobilized ERG-LP. If desired, the antibody molecules directed against ERG-LP can be isolated from the mammal (e.g., from the blood) and further purified by well known techniques, such as protein A chromatography to obtain the IgG fraction. At an appropriate time after immunization, e.g., when the anti-ERG-LP antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with an ERG-LP immunogen as described above, and the culture supernatants of the resulting hybridoma cells are screened to identify a hybridoma producing a monoclonal antibody that binds ERG-LP.

Any of the many well known protocols used for fusing lymphocytes and immortalized cell lines can be applied for the purpose of generating an anti-ERG-LP monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind ERG-LP, e.g., using a standard ELISA assay.

Alternative to preparing monoclonal antibody-secreting hybridomas, a monoclonal anti-ERG-LP antibody can be identified and isolated by screening a recombinant combinatorial immunoglobulin library (e.g., an antibody phage display library) with ERG-LP to thereby isolate immunoglobulin library members that bind ERG-LP. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-ERG-LP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173, 494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-ERG-LP antibody (e.g., monoclonal antibody) can be used to isolate ERG-LP by standard techniques, such as affinity chromatography or immunoprecipitation. An anti-ERG-LP antibody can facilitate the purification of natural ERG-LP from cells and of recombinantly produced ERG-LP expressed in host cells. Moreover, an anti-ERG-LP. antibody can be used to detect ERG-LP protein (e.g., in a cellular lysate or cell supernatant) in order to evaluate the abundance and pattern of expression of the ERG-LP protein. Anti-ERG-LP antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding an ERG-LP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Meth-*

*ods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., ERG-LP proteins, mutant forms of ERG-LP proteins, fusion proteins, and the like).

The recombinant expression vectors of the invention can be designed for expression of ERG-LP proteins in prokaryotic or eukaryotic cells. For example, ERG-LP proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Phannacia, Piscataway, N.J.) which fuse glutathione S-transferase (GST), maltose E binding protein, or protein A, respectively, to the target recombinant protein.

Purified fusion proteins can be utilized in ERG-LP activity assays, (e.g., direct assays or competitive assays described in detail below), or to generate antibodies specific for ERG-LP proteins, for example. In a preferred embodiment, an ERG-LP fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the ERG-LP expression vector is a yeast expression vector. Examples of vectors for expression in yeast S. cerivisae include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, ERG-LP proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv: Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to ERG-LP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ERG-LP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an ERG-LP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an ERG-LP protein. Accordingly, the invention further provides methods for producing an ERG-LP protein using the host cells of the invention. In one embodiment, the method comprises culturing the host cell of invention (into which a recombinant expression vector encoding an ERG-LP protein has been introduced) in a suitable medium such that an BRG-LP protein is produced. In another embodiment, the method further comprises isolating an ERG-LP protein from the medium or the host cell.

The host cells of the invention can also be used to produce non-human transgenic animals. For example, in one embodiment, a host cell of the invention is a fertilized oocyte or an embryonic stem cell into which ERG-LP-coding sequences have been introduced. Such host cells can then be used to create non-human transgenic animals in which exogenous ERG-LP sequences have been introduced into their genome or homologous recombinant animals in which endogenous ERG-LP sequences have been altered. Such animals are useful for studying the function and/or activity of an ERG-LP and for identifying and/or evaluating modulators of ERG-LP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous ERG-LP gene has been altered by homologous recombination between the endogenous gene and an exogenous DNA molecule-introduced into a cell of the animal, e.g., an embryonic cell of the animal, prior to development of the animal.

A transgenic animal of the invention can be created by introducing an ERG-LP-encoding nucleic acid into the male pronuclei of a fertilized oocyte, e.g., by microinjection, retroviral infection, and allowing the oocyte to develop in a pseudopregnant female foster animal. The ERG-LP cDNA sequence of SEQ ID NO:1 can be introduced as a transgene into the genome of a non-human animal. Alternatively, a nonhuman homologue of a human ERG-LP gene, such as a mouse or rat ERG-LP gene, can be used as a transgene. Alternatively, an ERG-LP gene homologue, such as another ERG potassium channel family member, can be isolated based on hybridization to the ERG-LP cDNA sequences of SEQ ID NO:1, SEQ ID NO:3, SEQ ID NO:4, SEQ ID NO:6, SEQ ID NO:7, SEQ ID NO:9 SEQ ID NO:15 or SEQ ID NO:17 and used as a transgene. Intronic sequences and polyadenylation signals can also be included in the transgene to increase the efficiency of expression of the transgene. A tissue-specific regulatory sequence(s) can be operably linked to an ERG-LP transgene to direct expression of an ERG-LP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of an ERG-LP transgene in its genome and/or expression of ERG-LP mRNA in tissues or cells of the animals. A transgenic founder animal can then be used to breed additional animals carrying the transgene. Moreover, transgenic animals carrying a transgene encoding an ERG-LP protein can further be bred to other transgenic animals carrying other transgenes.

To create a homologous recombinant animal, a vector is prepared which contains at least a portion of an ERG-LP gene into which a deletion, addition or substitution has been introduced to thereby alter, e.g., functionally disrupt, the ERG-LP gene. The ERG-LP gene can be a human gene (e.g., the cDNA of SEQ ID NO:6), but more preferably, is a non-human homologue of a human ERG-LP gene (e.g., a cDNA isolated by stringent hybridization with the nucleotide sequence of SEQ ID NO:4). For example, a mouse ERG-LP gene can be used to construct a homologous recombination vector suitable for altering an endogenous ERG-LP gene in the mouse genome. In a preferred embodiment, the vector is designed such that, upon homologous recombination, the endogenous ERG-LP gene is functionally disrupted (i.e., no longer encodes a functional protein; also referred to as a "knock out" vector). Alternatively, the vector can be designed such that, upon homologous recombination, the endogenous ERG-LP gene is mutated or otherwise altered but still encodes functional protein (e.g., the upstream regulatory region can be altered to thereby alter the expression of the endogenous ERG-LP protein). In the homologous recombination vector, the altered portion of the ERG-LP gene is flanked at its 5' and 3' ends by additional nucleic acid sequence of the ERG-LP gene to allow for homologous recombination to occur between the exogenous ERG-LP gene carried by the vector and an endogenous ERG-LP gene in an embryonic stem cell. The additional flanking ERG-LP nucleic acid sequence is of sufficient length for successful homologous recombination with the endogenous gene. Typically, several kilobases of flanking DNA (both at'the 5' and 3' ends) are included in the vector (see e.g., Thomas, K.R. and Capecchi, M. R. (1987) *Cell* 51:503 for a description of homologous recombination vectors). The vector is introduced into an embryonic stem cell line (e.g., by electroporation) and cells in which the introduced ERG-LP gene has homologously recombined with the endogenous ERG-LP gene are selected (see e.g., Li, E. et al. (1992) *Cell* 69:915). The selected cells are-then injected into a blastocyst of an animal (e.g., a mouse) to form aggregation chimeras (see e.g., Bradley, A. in *Teratocarcinomas and Embryonic Stem Cells. A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxp recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The ERG-LP nucleic acid molecules, fragments of ERG-LP proteins, and anti-ERG-LP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of an ERG-LP protein or an anti-ERG-LP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdernal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, an ERG-LP protein of the invention has one or more of the following activities: (1) it can modulate the release of neurotransmitters, (2) it can modulate membrane excitability, (3) it can influence the resting potential of membranes, (4) it can modulate wave forms and frequencies of action potentials, (5) it can modulate thresholds of excitation, and (6) it can modulate processes which underlie learning and memory, such as integration of sub-threshold synaptic responses and the conductance of back-propagating action potentials, and, thus, can be used to, for example, (1) modulate the release of neurotransmitters, (2) modulate membrane excitability, (3) influence the resting potential of membranes, (4) modulate wave forms and frequencies of action potentials, (5) modulate thresholds of excitation, and (6) modulate processes which underlie learning and memory, such as integration of sub-threshold synaptic responses and the conductance of back-propagating action potentials.

The isolated nucleic acid molecules of the invention can be used, for example, to express ERG-LP protein (e.g., via a recombinant expression vector in a host cell in gene therapy applications), to detect ERG-LP mRNA (e.g., in a biological sample) or a genetic alteration in an ERG-LP gene, and to modulate ERG-LP activity, as described further below. The ERG-LP proteins can be used to treat disorders characterized by insufficient or excessive production of an ERG-LP substrate or production of ERG-LP inhibitors. In addition, the ERG-LP proteins can be used to screen for naturally occurring ERG-LP substrates, to screen for drugs or compounds which modulate ERG-LP activity, as well as to treat disorders characterized by insufficient or excessive production of ERG-LP protein or production of ERG-LP protein forms which have decreased or aberrant activity compared to ERG-LP wild type protein (e.g., CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy and Jakob-Creutzfieldt disease; psychiatric disorders, e.g., depression, schizophrenic disorders, korsakoff s psychosis, mania, anxiety disorders, or phobic disorders; learning or memory disorders, e.g., amnesia or age-related memory loss; neurological disorders, e.g., migraine; obesity; autonomic nervous system disorders; gastrointestinal disorders including, but not limited to, esophageal disorders such as atresia and fistulas, stenosis, achalasia, esophageal rings and webs, hiatal hernia, lacerations, esophagitis, diverticula, systemic sclerosis (scleroderma), varices, esophageal tumors such as squamous cell carcinomas and adenocarcinomas, stomach disorders such as diaphragmatic hernias, pyloric stenosis, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas; pain disorders, e.g, pain response elicited during various forms of tissue injury, e.g., inflammation, infection, and ischemia, usually referred to as hyperalgesia (described in, for example, Fields, H. L. (1987) Pain, New York:McGraw-Hill), and pain associated with muscoloskeletal disorders, e.g., joint pain; tooth pain; headaches; pain associated with malignancies, or pain associated with surgery; and cardiovascular disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia. Moreover, the anti-ERG-LP antibodies of the invention can be used to detect and isolate ERG-LP proteins, regulate the bioavailability of ERG-LP proteins, and modulate ERG-LP activity.

A. Screening Assays

The invention provides a method (also referred to herein as a "screening assay") for identifying modulators, i.e., candidate or test compounds or agents (e.g., peptides, peptidomimetics, small molecules or other drugs) which bind to ERG-LP proteins, have a stimulatory or inhibitory effect on, for example, ERG-LP expression or ERG-LP activity, or have a stimulatory or inhibitory effect on, for example, the expression or activity of ERG-LP substrate.

In one embodiment, the invention provides assays for screening candidate or test compounds which are substrates of an ERG-LP protein or polypeptide or biologically active portion thereof. In another embodiment, the invention provides assays for screening candidate or test compounds which bind to or modulate the activity of an ERG-LP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad Sci. U.S.A. 90:6909; Erb et al. (1994) Proc. Nati. Acad Sci. USA 91:11422; Zuckemnann et al. (1994). J. Med Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al.(1994) J. Med. Chem. 37:1233.

Libraries of compounds may be presented in solution (e.g., Houghten (1992) Biotechniques 13:412–421), or on beads (Lam (1991) Nature 354:82–84), chips (Fodor (1993) Nature 364:555–556), bacteria (Ladner U.S. Pat. No. 5,223,409), spores (Ladner U.S. Pat. No. '409), plasmids (Cull et al. (1992) Proc Natl Acad Sci USA 89:1865–1869) or on phage (Scott and Smith (1990) Science 249:386–390); (Devlin (1990) Science 249:404–406); (Cwirla et al. (1990) Proc. Natl. Acad. Sci. 87:6378–6382); (Felici (1991) J. Mol. Biol. 222:301–310); (Ladner supra.).

In one embodiment, an assay is a cell-based assay in which a cell which expresses an ERG-LP protein or biologically active portion thereof is contacted with a test compound and the ability of the test compound to modulate ERG-LP activity is determined. Determining the ability of the test compound to modulate ERG-LP activity can be accomplished by monitoring, for example, the release of a neurotransmitter form a cell which expresses ERG-LP. The cell, for example, can be of mammalian origin. Determining the ability of the test compound to modulate the ability of ERG-LP to bind to a substrate can be accomplished, for example, by coupling the ERG-LP substrate with a radio-isotope or enzymatic label such that binding of the ERG-LP substrate to ERG-LP can be determined by detecting the labeled ERG-LP substrate in a complex. For example, compounds (e.g., ERG-LP substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., ERG-LP substrate) to interact with ERG-LP without the labeling of any of the interactants. For example, a microphysiometer can be used to detect the interaction of a compound with ERG-LP without the labeling of either the compound or the ERG-LP. McConnell, H. M. et al. (1992) Science 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and ERG-LP.

In another embodiment, an assay is a cell-based assay comprising contacting a cell expressing an ERG-LP target molecule (e.g., an ERG-LP substrate) with a test compound and determining the ability of the test compound to modulate (e.g. stimulate or inhibit) the activity of the ERG-LP target molecule. Determining the ability of the test compound to modulate the activity of an ERG-LP target molecule can be accomplished, for example, by determining the ability of the ERG-LP protein to bind to or interact with the ERG-LP target molecule.

Determining the ability of the ERG-LP protein or a biologically active fragment thereof, to bind to or interact with an ERG-LP target molecule can be accomplished by one of the methods described above for determining direct binding. In a preferred embodiment, determining the ability of the ERG-LP protein to bind to or interact with an ERG-LP target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which an ERG-LP protein or biologically active portion thereof is contacted with a test compound and the ability of the test compound to bind to the ERG-LP protein or biologically active portion thereof is determined. Preferred biologically active portions of the ERG-LP proteins to be used in assays of the present invention include fragments which participate in interactions with non-ERG-LP molecules, e.g., cyclic nucleotides, or fragments with high surface probability scores (see, for example, FIGS. 6 and 7). Binding of the test compound to the ERG-LP protein can be determined either directly or indirectly as described above. In a preferred embodiment, the assay includes contacting the ERG-LP protein or biologically active portion thereof with a known compound which binds ERG-LP to form an assay mixture, contacting the assay mixture with a test compound, and determining the ability of the test compound to interact with an ERG-LP protein, wherein determining the ability of the test compound to interact with an ERG-LP protein comprises determining the ability of the test compound to preferentially bind to ERG-LP or biologically active portion thereof as compared to the known compound.

In another embodiment, the assay is a cell-free assay in which an ERG-LP protein or biologically active portion thereof is contacted with a test compound and the ability of the test compound to modulate (e.g., stimulate or inhibit) the activity of the ERG-LP protein or biologically active portion thereof is determined. Determining the ability of the test compound to modulate the activity of an ERG-LP protein can be accomplished, for example, by determining the ability of the ERG-LP protein to bind to an ERG-LP target molecule by one of the methods described above for determining direct binding. Determining the ability of the ERG-LP protein to bind to an ERG-LP target molecule can also be accomplished using a technology such as real-time Biomolecular Interaction-Analysis (BIA). Sjolander, S. and Urbaniczky, C. (1991) Anal. Chem. 63:2338–2345 and Szabo et al. (1995) Curr. Opin. Struct. Biol. 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of an ERG-LP protein can be accomplished by determining the ability of the ERG-LP protein to further modulate the activity of a downstream effector of an ERG-LP target molecule. For example, the activity of the effector molecule on an appropriate target can be determined or the binding of the effector to an appropriate target can be determined as previously described.

In yet another embodiment, the cell-free assay involves contacting an ERG-LP protein or biologically active portion thereof with a known compound which binds the ERG-LP protein to form an assay mixture, contacting the assay mixture with a test compound, and determining the ability of the test compound to interact with the ERG-LP protein, wherein determining the ability of the test compound to interact with the ERG-LP protein comprises determining the ability of the ERG-LP protein to preferentially bind to or modulate the activity of an ERG-LP target molecule.

The cell-free assays of the present invention are amenable to use of both soluble and/or membrane-bound forms of isolated proteins (e.g., ERG-LP proteins or biologically active portions thereof). In the case of cell-free assays in which a membrane-bound form an isolated protein is used (e.g., a potassium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either ERG-LP or its target molecule to facilitate separation of complexed from uncomplexed forms of one or both of the proteins, as well as to accommodate automation of the assay. Binding of a test compound to an ERG-LP protein, or interaction of an ERG-LP protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can-be provided which adds a domain that allows one or both of the proteins to be bound to a matrix. For example, glutathione-S-transferase/ ERG-LP fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or ERG-LP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of ERG-LP binding or activity determined using standard techniques.

Other techniques for immobilizing proteins on matrices can also be used in the screening assays of the invention. For example, either an ERG-LP protein or an ERG-LP target molecule can be immobilized utilizing conjugation of biotin and streptavidin. Biotinylated ERG-LP protein or target molecules can be prepared from biotin-NHS (N-hydroxysuccinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with ERG-LP protein or target molecules but which do not interfere with binding of the ERG-LP protein to its target molecule can be derivatized to the wells of the plate, and unbound target or ERG-LP protein trapped in the wells by antibody conjugation. Methods for detecting such complexes, in addition to those described above for the GST-immobilized complexes, include immunodetection of complexes using antibodies reactive with the ERG-LP protein or target molecule, as well as enzyme-linked assays which rely on detecting an enzymatic activity associated with the ERG-LP protein or target molecule.

In another embodiment, modulators of ERG-LP expression are identified in a method wherein a cell is contacted with a candidate compound and the expression of ERG-LP mRNA or protein in the cell is determined. The level of expression of ERG-LP mRNA or protein in the presence of the candidate compound is compared to the level of expression of ERG-LP mRNA or protein in the absence of the candidate compound. The candidate compound can then be identified as a modulator of ERG-LP expression based on this comparison. For example, when expression of ERG-LP mRNA or protein is greater (statistically significantly greater) in the presence of the candidate compound than in its absence, the candidate compound is identified as a stimulator of ERG-LP mRNA or protein expression. Alternatively, when expression of ERG-LP mRNA or protein is less (statistically significantly less) in the presence of the candidate compound than in its absence, the candidate compound is identified as an inhibitor of ERG-LP mRNA or protein expression. The level of ERG-LP mRNA or protein expression in the cells can be determined by methods described herein for detecting ERG-LP mRNA or protein.

In yet another aspect of the invention, the ERG-LP proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO 94/10300), to identify other proteins, which bind to or interact with ERG-LP ("ERG-LP-binding proteins" or "ERG-LP-bp") and are involved in ERG-LP activity. Such ERG-LP-binding proteins are also likely to be involved in the propagation of signals by the ERG-LP proteins or ERG-LP targets as, for example, downstream elements of an ERG-LP-mediated signaling pathway. Alternatively, such ERG-LP-binding proteins are likely to be ERG-LP inhibitors.

The two-hybrid system is based on the modular nature of most transcription factors, which consist of separable DNA-binding and activation domains. Briefly, the assay utilizes two different DNA constructs. In one construct, the gene that codes for an ERG-LP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ERG-LP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the ERG-LP protein.

This invention further pertains to novel agents identified by the above-described screening assays. Accordingly, it is within the scope of this invention to further use an agent identified as described herein in an appropriate animal model. For example, an agent identified as described herein (e.g., an ERG-LP modulating agent, an antisense ERG-LP nucleic acid molecule, an ERG-LP-specific antibody, or an ERG-LP-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the ERG-LP nucleotide sequences, described herein, can be used to map the location of the ERG-LP genes on a chromosome. The mapping of the ERG-LP sequences to chromosomes is an important first step in correlating these sequences with genes associated with disease.

Briefly, ERG-LP genes can be mapped to chromosomes by preparing PCR primers (preferably 15–25 bp in length) from the ERG-LP nucleotide sequences. Computer analysis of the ERG-LP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the ERG-LP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes.

By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the ERG-LP nucleotide sequences to design oligonucleotide primers, sublocalization can be achieved with panels of fragments from specific chromosomes. Other mapping strategies which can similarly be used to map an ERG-LP sequence to its chromosome include in situ hybridization (described in Fan, Y. et al. (1990) *Proc. Natl. Acad. Sci. USA*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783–787.

Moreover, differences in the DNA sequences between individuals affected and unaffected with a disease associated with the ERG-LP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The ERG-LP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the ERG-LP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can 35 be used to obtain such identification sequences from individuals and from tissue. The ERG-LP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:4, SEQ ID NO:7, SEQ ID NO:14 or SEQ ID NO:15 can comfortably provide positive individual identification with a panel of perhaps 10 to 1,000 primers which each yield a noncoding amplified sequence of 100 bases. If predicted coding sequences, such as those in SEQ ID NO:3, SEQ ID NO:6, SEQ ID NO:9, or SEQ ID NO:17 are used, a more appropriate number of primers for positive individual identification would be 500–2,000.

If a panel of reagents from ERG-LP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial ERG-LP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:4, SEQ ID NO:7, SEQ ID NO:14 or SEQ ID NO:15 are particularly appropriate for this use as greater numbers of polymorphisms occur in the noncoding regions, making it easier to differentiate individuals using this technique. Examples of polynucleotide reagents include the ERG-LP nucleotide sequences or portions thereof, e.g., fragments derived from the noncoding regions of SEQ ID NO:1 or SEQ ID NO:4, having a length of at least 20 bases, preferably at least 30 bases.

The ERG-LP nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such ERG-LP probes can be used to identify tissue by species and/or by organ type.

In a similar fashion, these reagents, e.g., ERG-LP primers or probes can be used to screen tissue culture for contamination (i.e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining ERG-LP protein and/or nucleic acid expression as well as ERG-LP activity, in the context of a biological sample (e.g., blood, serum, cells, tissue) to thereby determine whether an individual is afflicted with a disease or disorder, or is at risk of developing a disorder, associated with aberrant ERG-LP expression or activity. The invention also provides for prognostic (or predictive) assays for determining whether an individual is at risk of developing a disorder associated with ERG-LP protein, nucleic acid expression or activity. For example, mutations in an ERG-LP gene can be assayed in a biological sample. Such assays can be used for prognostic or predictive purpose to thereby phophylactically treat an individual prior to the onset of a disorder characterized by or associated with ERG-LP protein, nucleic acid expression or activity.

Another aspect of the invention pertains to monitoring the influence of agents (e.g., drugs, compounds) on the expression or activity of ERG-LP in clinical trials.

These and other agents are described in, further detail in the following sections.

1. Diagnostic Assays

An exemplary method for detecting the presence or absence of ERG-LP protein or nucleic acid in a biological sample involves obtaining a biological sample from a test subject and contacting the biological sample with a compound or an agent capable of detecting ERG-LP protein or nucleic acid (e.g., mRNA, genomic DNA) that encodes ERG-LP protein such that the presence of ERG-LP protein or nucleic acid is detected in the biological sample. A preferred agent for detecting ERG-LP mRNA or genomic DNA is a labeled nucleic acid probe capable of hybridizing to ERG-LP mRNA or genomic DNA. The nucleic acid probe can be, for example, a full-length ERG-LP nucleic acid, such as the nucleic acid of SEQ ID NO:1, SEQ ID NO:3, SEQ ID NO:4, SEQ ID NO:6, SEQ ID NO:7, SEQ ID NO:9, SEQ ID NO:15 or SEQ ID NO:17, or a portion thereof, such as an oligonucleotide of at least 15, 30, 50, 100, 250 or 500 nucleotides in length and sufficient to specifically hybridize under stringent conditions to ERG-LP mRNA or genomic DNA. Other suitable probes for use in the diagnostic assays of the invention are described herein.

A preferred agent for detecting ERG-LP protein is an antibody capable of binding to ERG-LP protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect ERG-LP mRNA, protein, or genomic DNA in a biological sample in vitro as well as in vivo. For example, in vitro techniques for detection of ERG-LP mRNA include Northern hybridizations and in situ hybridizations. In vitro techniques for detection of ERG-LP protein include enzyme linked immunosorbent assays (ELISAs), Western blots, immunoprecipitations and immunofluorescence. In vitro techniques for detection of ERG-LP genomic DNA include Southern hybridizations. Furthermore, in vivo techniques for detection of ERG-LP protein include introducing into a subject a labeled anti-ERG-LP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting ERG-LP protein, mRNA, or genomic DNA, such that the presence of ERG-LP protein, mRNA or genomic DNA is detected in the biological sample, and comparing the presence of ERG-LP protein, mRNA or genomic DNA in the control sample with the presence of ERG-LP protein, mRNA or genomic DNA in the test sample.

The invention also encompasses kits for detecting the presence of ERG-LP in a biological sample. For example, the kit can comprise a labeled compound or agent capable of detecting ERG-LP protein or mRNA in a biological sample; means for determining the amount of ERG-LP in the sample; and means for comparing the amount of ERG-LP in the sample with a standard. The compound or agent can be packaged in a suitable container. The kit can further comprise instructions for using the kit to detect ERG-LP protein or nucleic acid.

2. Prognostic Assays

The diagnostic methods described herein can furthermore be utilized to identify subjects having or at risk of developing a disease or disorder associated with aberrant ERG-LP expression or activity. For example, the assays described herein, such as the preceding diagnostic assays or the following assays, can be utilized to identify a subject having or at risk of developing a disorder associated with a misregulation in ERG-LP protein activity or nucleic acid expression, such as a CNS disorder. Alternatively, the prognostic assays can be utilized to identify a subject having or at risk for developing a disorder associated with a misregulation in ERG-LP protein activity or nucleic acid expression, such as a CNS disorder. Thus, the present invention provides a method for identifying a disease or disorder associated with aberrant ERG-LP expression or activity in which a test sample is obtained from a subject and ERG-LP protein or nucleic acid (e.g., mRNA or genomic DNA) is detected, wherein the presence of ERG-LP protein or nucleic acid is diagnostic for a subject having or at risk of developing a disease or disorder associated with aberrant ERG-LP expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant ERG-LP expression or activity. For example, such methods can be used to determine whether a subject can be effectively treated with an agent for a CNS disorder. Thus, the present invention provides methods for determining whether a subject can be effectively treated with an agent for a disorder associated with aberrant ERG-LP expression or activity in which a test sample is obtained and ERG-LP protein or nucleic acid expression or activity is detected (e.g., wherein the abundance of ERG-LP protein or nucleic acid expression or activity is diagnostic for a subject that can be administered the agent to treat a disorder associated with aberrant ERG-LP expression or activity).

The methods of the invention can also be used to detect genetic alterations in an ERG-LP gene, thereby determining if a subject with the altered gene is at risk for a disorder characterized by misregulation in ERG-LP protein activity or nucleic acid expression, such as a CNS disorder. In preferred embodiments, the methods include detecting, in a sample of cells from the subject, the presence or absence of a genetic alteration characterized by at least one of an alteration affecting the integrity of a gene encoding an ERG-LP-protein, or the mis-expression of the ERG-LP gene. For example, such genetic alterations can be detected by ascertaining the existence of at least one of 1) a deletion of one or more nucleotides from an ERG-LP gene; 2) an addition of one or more nucleotides to an ERG-LP gene; 3) a substitution of one or more nucleotides of an ERG-LP gene, 4) a chromosomal rearrangement of an ERG-LP gene; 5) an alteration in the level of a messenger RNA transcript of an ERG-LP gene, 6) aberrant modification of an ERG-LP gene, such as of the methylation pattern of the genomic DNA, 7) the presence of a non-wild type splicing pattern of a messenger RNA transcript of an ERG-LP gene, 8) a non-wild type level of an ERG-LP-protein, 9) allelic loss of an ERG-LP gene, and 10) inappropriate post-translational modification of an ERG-LP-protein. As described herein, there are a large number of assays known in the art which can be used for detecting alterations in an ERG-LP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the ERG-LP-gene (see Abravaya et al. (1995) Nucleic Acids Res. 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to an ERG-LP gene under conditions such that hybridization and amplification of the ERG-LP-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874–1878), transcriptional amplification system (Kwoh, D. Y. et al., (1989) Proc. Natl. Acad. Sci. USA 86:1173–1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ERG-LP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in ERG-LP can be identified by hybridizing a sample and control nucleic acids, e.g., DNA or RNA, to high density arrays containing hundreds or thousands of oligonucleotides probes (Cronin, M. T. et al. (1996) Human Mutation 7: 244–255; Kozal, M. J. et al. (1996) Nature Medicine 2: 753–759). For example, genetic mutations in ERG-LP can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the ERG-LP gene and detect mutations by comparing the sequence of the sample ERG-LP with the corresponding wild-type (control) sequence. Examples of sequencing reactions include those based on techniques developed by Maxam and Gilbert ((1977) Proc. Nail. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the ERG-LP gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type ERG-LP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl Acad Sci USA 85:4397; Saleeba et al. (1 992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ERG-LP cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an ERG-LP sequence, e.g., a wild-type ERG-LP sequence, is hybridized to a cDNA or other DNA product from a test cell(s). The duplex is treated with a DNA mismatch repair enzyme, and the cleavage products, if any can be detected from electrophoresis protocols or the like. See, for example, U.S. Pat. No. 5,459,039.

In other embodiments, alterations in electrophoretic mobility will be used to identify mutations in ERG-LP genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control ERG-LP nucleic acids will be denatured and allowed to renature. The secondary-structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is antici-pated that in certain embodiments amplification may also be performed using Taq ligase for amplification (Barany (1991) *Proc. Natl. Acad Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving an ERG-LP gene.

Furthermore, any cell type or tissue in which ERG-LP is expressed may be utilized in the prognostic assays described herein.

3. Monitoring of Effects During Clinical Trials

Monitoring the influence of agents (e.g., drugs) on the expression or activity of an ERG-LP protein (e.g., the modulation of membrane excitability or resting potential) can be applied not only in basic drug screening, but also in clinical trials. For example, the effectiveness of an agent determined by a screening assay as described herein to increase ERG-LP gene expression, protein levels, or upregulate ERG-LP activity, can be monitored in clinical trials of subjects exhibiting decreased ERG-LP gene expression, protein levels, or downregulated ERG-LP activity. Alternatively, the effectiveness of an agent determined by a screening assay to decrease ERG-LP gene expression, protein levels, or downregulate ERG-LP activity, can be monitored in clinical trials of subjects exhibiting increased ERG-LP gene expression, protein levels, or upregulated ERG-LP activity. In such clinical trials, the expression or activity of an ERG-LP gene, and preferably, other genes that have been implicated in, for example, a potassium channel associated disorder can be used as a "read out" or markers of the phenotype of a particular cell.

For example, and not by way of limitation, genes, including ERG-LP, that are modulated in cells by treatment with an agent (e.g., compound, drug or small molecule) which modulates ERG-LP activity (e.g., identified in a screening assay as described herein) can be identified. Thus, to study the effect of agents on potassium channel associated disorders, for example, in a clinical trial, cells can be isolated and RNA prepared and analyzed for the levels of expression of ERG-LP and other genes implicated in the potassium channel associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of ERG-LP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of an ERG-LP protein, mRNA, or genomic DNA in the preadministration sample; (iii) obtaining one or more post-administration samples from the subject; (iv) detecting the level of expression or activity of the ERG-LP protein, mRNA, or genomic DNA in the post-administration samples; (v) comparing the level of expression or activity of the ERG-LP protein, mRNA, or genomic DNA in the pre-administration sample with the ERG-LP protein, mRNA, or genomic DNA in the post administration sample or samples; and (vi) altering the administration of the agent to the subject accordingly. For example, increased administration of the agent may be desirable to increase the expression or activity of ERG-LP to higher levels than detected, i.e., to increase the effectiveness of the agent. Alternatively, decreased administration of the agent may be desirable to decrease expression or activity of ERG-LP to lower levels than detected, i.e. to decrease the effectiveness of the agent. According to such an embodiment, ERG-LP expression or activity may be used as an indicator of the effectiveness of an agent, even in the absence of an observable phenotypic response.

C. Methods of Treatment

The present invention provides for both prophylactic and therapeutic methods of treating a subject at risk of (or susceptible to) a disorder or having a disorder associated with aberrant ERG-LP expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the ERG-LP molecules of the present invention or ERG-LP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant ERG-LP expression or activity, by administering to the subject an ERG-LP or an agent which modulates ERG-LP expression or at least one ERG-LP activity. Subjects at risk for a disease which is caused or contributed to by aberrant ERG-LP expression or activity can be identified by, for example, any or a combination of diagnostic or prognostic assays as described herein. Administration of a prophylactic agent can occur prior to the manifestation of symptoms characteristic of the ERG-LP aberrancy, such that a disease or disorder is prevented or, alternatively, delayed in its progression. Depending on the type of ERG-LP aberrancy, for example, an ERG-LP, ERG-LP agonist or ERG-LP antagonist agent can be used for treating the subject. The appropriate agent can be determined based on screening assays described herein.

2. Therapeutic Methods

Another aspect of the invention pertains to methods of modulating ERG-LP expression or activity for therapeutic purposes. Accordingly, in an exemplary embodiment, the modulatory method of the invention involves contacting a cell with an ERG-LP or agent that modulates one or more of the activities of ERG-LP protein activity associated with the cell. An agent that modulates ERG-LP protein activity can be an agent as described herein, such as a nucleic acid or a protein, a naturally-occurring target molecule of an ERG-LP protein (e.g., an ERG-LP substrate), an ERG-LP antibody, an ERG-LP agonist or antagonist, a peptidomimetic of an ERG-LP agonist or antagonist, or other small molecule. In one embodiment, the agent stimulates one or more ERG-LP activities. Examples of such stimulatory agents include active ERG-LP protein and a nucleic acid molecule encoding ERG-LP that has been introduced into the cell. In another embodiment, the agent inhibits one or more ERG-LP activities. Examples of such inhibitory agents include antisense ERG-LP nucleic acid molecules, anti-ERG-LP antibodies, and ERG-LP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of an ERG-LP protein or nucleic acid molecule. In one embodiment, the method involves administering an agent (e.g., an agent identified by a screening assay described herein), or combination of agents that modulates (e.g., upregulates or downregulates) ERG-LP expression or activity. In another embodiment, the method involves administering an ERG-LP protein or nucleic acid molecule as therapy to compensate for reduced or aberrant ERG-LP expression or activity.

Stimulation of ERG-LP activity is desirable in situations in which ERG-LP is abnormally downregulated and/or in which increased ERG-LP activity is likely to have a beneficial effect. For example, stimulation of ERG-LP activity is desirable in situations in which an ERG-LP is downregulated and/or in which increased ERG-LP activity is likely to have a beneficial effect. Likewise, inhibition of ERG-LP activity is desirable in situations in which ERG-LP is abnormally upregulated and/or in which decreased ERG-LP activity is likely to have a beneficial effect.

3. Pharmacogenomics

The ERG-LP molecules of the present invention, as well as agents, or modulators which have a stimulatory or inhibitory effect on ERG-LP activity (e.g., ERG-LP gene expression) as identified by a screening assay described herein can be administered to individuals to treat (prophylactically or therapeutically) potassium channel associated disorders (e.g, CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, korsakoff s psychosis, mania, anxiety disorders, or phobic disorders; learning or memory disorders, e.g., amnesia or age-related memory loss; neurological disorders; e.g., migraine; and obesity; autonomic nervous system disorders; gastrointestinal disorders including, but not limited to, esophageal disorders such as atresia and fistulas, stenosis, achalasia, esophageal rings and webs, hiatal hernia, lacerations, esophagitis, diverticula, systemic sclerosis (scleroderna), varices, esophageal tumors such as squamous cell carcinomas and adenocarcinomas, stomach disorders such as diaphragmatic hernias, pyloric stenosis, gastritis, acute gastric erosion and ulceration, peptic ulcers, stomach tumors such as carcinomas and sarcomas, small intestine disorders such as congenital atresia and stenosis, diverticula, Meckel's diverticulum, pancreatic rests, ischemic bowel disease, infective enterocolitis, Crohn's disease, tumors of the small intestine such as carcinomas and sarcomas, disorders of the colon such as malabsorption, obstructive lesions such as hernias, megacolon, diverticular disease, melanosis coli, ischemic injury, hemorrhoids, angiodysplasia of right colon, inflammations of the colon such as ulcerative colitis, and tumors of the colon such as polyps and sarcomas; pain disorders, e.g, pain response elicited during various forms of tissue injury, e.g., inflammation, infection, and ischemia, usually referred to as hyperalgesia (described in, for example, Fields, H. L. (1987) *Pain*, New York:McGraw-Hill), and pain associated with muscoloskeletal disorders, e.g., joint pain; tooth pain; headaches; pain associated with malignancies, or pain associated with surgery; and cardiovascular disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm,or arrhythmia.) associated with aberrant ERG-LP activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant harmacogenomics studies in determining whether to administer an ERG-LP molecule or RG-LP modulator as well as tailoring the dosage and/or therapeutic regimen of treatment with an ERG-LP molecule or ERG-LP modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11) 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., an ERG-LP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., an ERG-LP molecule or ERG-LP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with an ERG-LP molecule or ERG-LP modulator, such as a modulator identified by one of the exemplary screening assays described herein.

This invention is further illustrated by the following examples which should not be construed as limiting. The contents of Sequence Listing, figures and all references, patents and published patent applications cited throughout this application are incorporated herein by reference.

EXAMPLES

Example 1

Identification and Characterization of ERG-LP cDNAs

In this example, the identification and characterization of the genes encoding human and monkey ERG-LP1 and human ERG-LP2 are described.

Isolation of the human and monkey ERG-LP1 cDNA

The invention is based, at least in part, on the discovery of a human and a monkey gene encoding a novel protein, referred to herein as ERG-LP1. A partial cDNA sequence (jlkbc037e12) was identified in a monkey striatum library using the Sequence Explorer, which is 45% identical to the Drosophila ELK potassium channel (Accession Number U04246). Subsequently, a full length monkey clone (jlkba25d10) was identified in a monkey hippocampal library by analysis of a proprietary database using the Drosophila ELK potassium channel (Accession Number U04246) as a probe.

The sequence of the entire monkey clone was determined and found to contain an open reading frame of 1083 amino acids termed monkey "ERG-like protein 1" or ERG-LP1. The nucleoude sequence encoding the monkey ERG-LP1 protein is shown in FIG. 1 and is set forth as SEQ ID NO:1. The full length protein encoded by this nucleic acid comprises about 1083 amino acids and has the amino acid sequence shown in FIG. 1 and set forth as SEQ ID NO:2. The coding region (open reading frame) of SEQ ID NO:1 is set forth as SEQ ID NO:3.

The human ERG-LP1 was identified by searching a GenBank™ EST database. A human EST (IMAGE clone 37299) was identified wish similarity to the 5' end of the monkey jlkba25d10 clone. The sequence of the entire human clone was determined and found to contain an open reading frame of 290 amino acids termed human "ERG-like protein 1" or ERG-LP1. The nucleotide sequence encoding the human ERG-LP1 protein is shown in FIG. 5 and is set forth as SEQ ID NO:7. The partial length protein encoded by this nucleic acid comprises about 290 amino acids and has the amino acid sequence shown in FIG. 5 and set forth as SEQ ID NO:8. The coding region (open reading frame) of SEQ ID NO:7 is set forth as SEQ ID NO:9.

Isolation of the human ERG-LP2 cDNA

The invention is further based, at least in part, on the discovery of a human gene encoding a novel protein, referred to herein as ERG-LP2. The human gene was discovered by analysis of a proprietary database using the potassium channel clone Flh37299 as a probe. Clone jlhbaa042h05 from a human brain library was identified. This clone was picked, plasmid was prepared and sequenced. BlastP searching (BLAST™ searching utilizing an amino acid sequence against a protein database), using the translation product (frame 1) of this sequence, revealed homology to proteins belonging to the potassium channel superfamily, e.g., the human ERG channel and the Drosophila ELK channel.

Initial sequencing of clone jlhbaa042h05 revealed an open reading frame of 542 amino acids termed "ERG-like protein 2" or ERG-LP2. The nucleoide sequence encoding the parial human ERG-LP2 protein is shown in FIG. 2 and is set forth as SEQ ID NO:4. The protein encoded by this nucleic acid comprises about 542 amino acids and has the amino acid sequence shown in FIG. 2 and set forth as SEQ ID NO:5. The coding region (open reading frame) of SEQ ID NO:4 is set forth as SEQ ID NO:6.

Additional sequencing of clone jlhbaa042h05 revealed a larger open reading frame of 1107 amino acids comprising full length human ERG-LP2. The nucleotide sequence of clone jlhbaa042h05 encompassing the full length human ERG-LP2 protein is set forth as SEQ ID NO:14. Nucleotides 196 to 1770 of SEQ ID NO:14 comprise one exon of human ERG-LP2, nucleotides 1771 to 2618 comprise an intron, and nucleotides 2619 to 4364 comprise a second exon of human ERG-LP2. Following splicing of the ERG-LP2 nucleotide sequence of SEQ ID NO:14, the nucleotide sequence encoding the full length human ERG-LP2 protein is shown in FIG. 8 and is set forth as SEQ ID NO:15. The full length protein encoded by this nucleic acid comprises about 1107 amino acids and has the amino acid sequence shown in FIG. 8 and set forth as SEQ ID NO:16. The coding region (open reading frame) of SEQ ID NO:15 is set forth as SEQ ID NO:17.

Analysis of Monkey ERG-LP1

A BLAST search (Altschul et al. (1990) *J. Mol. Biol.* 215:403) of the nucleotide and protein sequences of monkey ERG-LP1 revealed that ERG-LP1 is similar to the Drosophila ELK potassium channel protein (Accession Number U04246) and the human ERG potassium channel protein (Accession Number U04270). The mouse Melk2 protein has also been identified as a member of the ERG potassium channel family (Trudeau et al. (1999) *J. Neuroscience*, 19:2906–2918). An alignment of monkey ERG-LP1 and the human ERG potassium channel protein is presented in FIG. 3. Hydropathy plots have identified 6 transmembrane domains and a P-loop in this protein.

Analysis of Human ERG-LP2

A BLAST search (Altschul et al. (1990) *J. Mol. Biol.* 215:403) of the partial nucleotide and protein sequences of human ERG-LP2 revealed that ERG-LP2 is similar to the rat ERG potassium channel protein (Accession Number Z96106), the Drosophila ELK potassium channel protein (Accession Number U04246), and the human ERG potassium channel protein (Accession Number U04270). Relk1 is a rat protein that is also related to the ERG potassium channel family of proteins (Shi et al. (1998) *J. Physiology*, 511:675–682). An alignment of the partial human ERG-LP2 protein and the Drosophila ELK potassium channel protein is presented in FIG. 4. An alignment of the human ERG-LP2 protein and the rat Relk1 potassium channel protein is presented in FIG. 11. Hydropathy plots have identified 6 transmembrane domains in this protein.

Tissue Distribution of ERG-LP mRNA

This Example describes the tissue distribution of ERG-LP mRNA, as determined by Northern blot hybridization, PCR and in situ hybridization.

Northern blot hybridizations with the various RNA samples were performed under standard conditions and washed under stringent conditions, i.e., 0.2×SSC at 65° C. The DNA probe was radioactively labeled with $^{32}$P-dCTP using the Prime-It kit (Stratagene, La Jolla, Calif.) according to the instructions of the supplier. Filters containing human mRNA (MultiTissue Northern I and MultiTissue Northern II from Clontech, Palo Alto, Calif.) were probed in ExpressHyb hybridization solution (Clontech) and washed at high stringency according to manufacturer's recommendations. For the monkey ERG-LP1 gene, the probe was generated by PCR from the 3' end of the gene. For the human ERG-LP2, the probe was generated from a region in the open reading frame which does not have any homology to the human ERG.

ERG-LP1 message was detected exclusively in the brain (expression was highest in cortical regions, hippocampus, caudate, and amygdala). The ERG-LP2 gene is expressed in the brain.

ERG-LP2 expression in normal human tissues was also assessed by PCR using the Taqman® system (PE Applied Biosystems) according to the manufacturer's instructions. ERG-LP2 was strongly expressed in the brain, moderately expressed in the testis and fetal kidney, and weakly expressed in the prostate, breast, liver, colon, fetal liver and fetal heart.

For in situ analysis, various tissues obtained from brains, e.g. rat or monkey brains, were first frozen on dry ice. Ten-micrometer-thick coronal sections of the tissues were postfixed with 4% formaldehyde in DEPC treated 1× phosphate-buffered saline at room temperature for 10 minutes before being rinsed twice in DEPC 1× phosphate-buffered saline and once in 0.1 M triethanolamine-HCl (pH 8.0). Following incubation in 0.25% acetic anhydride-0.1 M triethanolamine-HCl for 10 minutes, sections were rinsed in DEPC 2×SSC (1×SSC is 0.15M NaCl plus 0.015M sodium citrate). Tissue was then dehydrated through a series of ethanol washes, incubated in 100% chloroform for 5 minutes, and then rinsed in 100% ethanol for 1 minute and 95% ethanol for 1 minute and allowed to air dry.

Hybridizations were performed with $^{35}$S-radiolabeled ($5\times10^7$ cpm/ml) cRNA probes. Probes were incubated in the presence of a solution containing 600 mM NaCl, 10 mM Tris (pH 7.5), 1 mM EDTA, 0.01% sheared salmon sperm DNA, 0.01% yeast tRNA, 0.05% yeast total RNA type X1, 1×Denhardt's solution, 50% formamide, 10% dextran sulfate, 100 mM dithiothreitol, 0.1% sodium dodecyl sulfate (SDS), and 0.1% sodium thiosulfate for 18 hours at 55° C.

After hybridization, slides were washed with 2×SSC. Sections were then sequentially incubated at 37° C. in TNE (a solution containing 10 mM Tris-HCl (pH 7.6), 500 mM NaCl, and 1 mM EDTA), for 10 minutes, in TNE with 10 µg of RNase A per ml for 30 minutes, and finally in TNE for 10 minutes. Slides were then rinsed with 2×SSC at room temperature, washed with 2×SSC at 50° C. for 1 hour, washed with 0.2×SSC at 55° C. for 1 hour, and 0.2×SSC at 60° C. for 1 hour. Sections were then dehydrated rapidly through serial ethanol-0.3 M sodium acetate concentrations before being air dried and exposed to Kodak Biomax MR scientific imaging film for 24 hours and subsequently dipped in NB-2 photoemulsion and exposed at 4° C. for 7 days before being developed and counter stained.

ERG-LP1 is expressed at higher levels in different regions of monkey and rat brain, including the cortex, caudate, hippocampus and cerebellum. ERG-LP1 transcripts are absent from the spinal cord, dorsal root ganglion and superior cervical ganglion in both the monkey and rat brain.

ERG-LP2 message is expressed at high levels in the monkey brain in a subpopulation of small neurons in the dorsal root ganglion. Lower levels of expression are found in neurons within the brain, spinal cord and in sympathetic neurons of the superior cervical ganglion. The ERG-LP2 gene is also expressed in human brain. Expression of ERG-LP2 in small neurons in the dorsal root ganglion and in sympathetic neurons of the superior cervical ganglion demonstrates a role for this channel in autonomic nervous system function and the perception of pain.

Example 2

Chromosme Mapping of the ERG-LP Genes

In this example, the mapping of the chromosomal location of the genes encoding human ERG-LP1 and ERG-LP2 using PCR screening of somatic cell hybrids is described. Techniques involved in chromosome mapping are described on pages 56–58.

Oligonucleotide primers for PCR were designed based on the sequence of the monkey ERG-LP1 gene (SEQ ID NO:1) and the human ERG-LP2 gene (SEQ ID NO:4) as follows:

| | | | |
|---|---|---|---|
| ERG-LP1 | Forward: CAGAGTGAAGACAGGGTGGCG | (SEQ ID NO:18) |
| | Reverse: TTCCTTGTCCTCAGGTCTCTGC | (SEQ ID NO:19) |
| ERG-LP2 | Forward: TTTCACAATGCCAATTTGGATTGACCG | (SEQ ID NO:20) |
| | Reverse: GCAGTCTGGGGTGTTTCTGG | (SEQ ID NO:21) |

These primers were used in PCR reactions to amplify somatic cell hybrid DNA samples, in duplicate, from the Genebridge 4 Radiation Hybrid Panel. The ERG-LP gene products were analyzed on 8% acrylamide gels, post-stained with SYBR Gold (1:10,000 dilution in 1×Tris-Borate-EDTA buffer), and scanned on a Molecular Dynamics 595 Fluorimager. Radiation hybrid linkage analysis was performed using the Map Manager QTb23 software package.

The ERG-LP1 gene was found to map to human chromosome 12q11–13, between markers WI-7107 and WI-6327. The ERG-LP2 gene mapped to human chromosome 3p21.3–24.3, between markers WI-4218 and RP_LI15_1.

Example 3

Functional Expending of the Monkey ERG-LP1 Gene in Cho Cells

To express the monkey ERG-LP1 gene in CHO cells, the full length monkey ERG-LP1 gene in the pMet7 expression vector and transiently transfected into CHO cells using lipofectamine. Electrophysiological measurements were taken using a single electrode patch-clamp 48 hours after transfection. As shown in FIG. 12, with voltage steps from −60 mV to +50 mV in 10 mV increments from a holding potential of −80 mV, the CHO cells transfected with monkey ERG-LP1 displayed sustained outward currents (1–1.5 nA) with significant tail currents (250 pA). There was no evidence of inactivation during 500 msec voltage steps. The I-V curve was linear from −60 mV to +50 mV.

Example 4

Expression of Recombinant ERG-LP Protein in Bacterial Cells

In this example, ERG-LP is expressed as a recombinant glutathione-S-transferase (GST) fusion polypeptide in *E. coli* and the fusion polypeptide is isolated and characterized. Specifically, ERG-LP is fused to GST and this fusion polypeptide is expressed in *E. coli*, e.g., strain PEB 199. Expression of the GST-ERG-LP fusion protein in PEB 199 is induced with IPTG. The recombinant fusion polypeptide is purified from crude bacterial lysates of the induced PEB 199 strain by affinity chromatography on glutathione beads.

Using polyacrylamide gel electrophoretic analysis of the polypeptide purified from the bacterial lysates, the molecular weight of the resultant fusion polypeptide is determined.

Example 5

Expression of Recombinant ERG-LP Protein in COS Cells

To express the ERG-LP gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire ERG-LP protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the ERG-LP DNA sequence is amplified by PCR using two primers. The 5' primer contains the restriction site of interest followed by approximately twenty nucleotides of the ERG-LP coding sequence starting from the initiation codon; the 3' end sequence contains complementary sequences to the other restriction site of interest, a translation stop codon, the HA tag or FLAG tag and the last 20 nucleotides of the ERG-LP coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the ERG-LP gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the ERG-LP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the ERG-LP polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the ERG-LP coding sequence is cloned directly into the polylinker of the pCDNA/Amp vector using the appropriate restriction sites. The resulting plasmid is transfected into COS cells in the manner described above, and the expression of the ERG-LP polypeptide is detected by radiolabelling and immunoprecipitation using an ERG-LP specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated polypeptide comprising the amino acid sequence of SEQ ID NO:5.

2. An isolated polypepnide consisting of the amino acid sequence of SEQ ID NO:5.

3. An isolated polypeptide encoded by the nucleotide sequence of SEQ ID NO:4 or SEQ ID NO:6.

4. An isolated polypeptide comprising a fragment of the amino acid sequence of SEQ ID NO:5 wherein the fragment comprises at least 38 contiguous amino acids of SEQ ID NO:5.

5. An isolated polypeptide comprising a fragment of the amino acid sequence of SEQ ID NO:5 wherein the fragment comprises at least 50 contiguous amino acids of SEQ ID NO:5.

6. An isolated polypeptide comprising a fragment of the amino acid sequence of SEQ ID NO:5 wherein the fragment comprises at least 100 contiguous amino acids of SEQ ID NO:5.

7. An isolated polypeptide comprising a fragment of the amino acid sequence of SEQ ID NO:5 wherein the fragment comprises at least 150 contiguous amino acids of SEQ ID NO:5.

8. A naturally occurring allelic variant of a polypeptide comprising the amino acid sequence of SEQ ID NO:5, wherein the polypeptide is encoded by a nucleic acid molecule which hybridizes to the complement of a nucleic acid molecule comprising SEQ ID NO:4 or SEQ ID NO:6, followed by one or more washes in 0.2×SSC, 0.1% SDS at 50–65° C., and wherein said naturally occurring allelic variant is 4 potassium channel that modulates membrane excitability.

9. An isolated polypeptide which is encoded by a nucleic acid molecule comprising a nucleotide sequence which is at least 90% identical to the nucleotide sequence of SEQ ID NO:4 or SEQ ID NO:6, wherein said polypeptide is a potassium channel that modulates membrane excitability.

10. An isolated polypepnide comprising an amino acid sequence which is at least 90% identical to the amino acid sequence of SEQ ID NO:5, wherein said polypeptide is a potassium channel that modulates membrane excitability.

11. An isolated polypeptide comprising an amino acid sequence which is at least 93% identical to the amino acid sequence of SEQ ID NO:5, wherein said polypeptide is a potassium channel that modulates membrane excitability.

12. An isolated polypeptide comprising an amino acid sequence which is at least 95% identical to the amino acid sequence of SEQ ID NO:5, wherein said polypeptide is a potassium channel that modulates membrane excitability.

13. An isolated polypeptide comprising a fragment of the amino acid sequence of SEQ ID NO:5 wherein the fragment comprises at least 450 contiguous amino acids of SEQ ID NO:5.

14. The polypeptide of any one of claim 1–10, 11, 12 or 13 further comprising heterologous amino acid sequences.

* * * * *